(12) United States Patent
Brondyk et al.

(10) Patent No.: US 12,103,961 B2
(45) Date of Patent: Oct. 1, 2024

(54) COMPOSITIONS FOR INCREASING HALF-LIFE OF A THERAPEUTIC AGENT IN LIVESTOCK ANIMALS AND METHODS OF USE

(71) Applicant: Invetx, Inc., Boston, MA (US)

(72) Inventors: William Brondyk, Mansfield, MA (US); Juergen Horn, Marblehead, MA (US)

(73) Assignee: Invetx, Inc., Boston, MA (US)

( * ) Notice: Subject to any disclaimer, the term of this patent is extended or adjusted under 35 U.S.C. 154(b) by 38 days.

(21) Appl. No.: 17/540,044

(22) Filed: Dec. 1, 2021

(65) Prior Publication Data

US 2022/0177549 A1 Jun. 9, 2022

Related U.S. Application Data

(60) Provisional application No. 63/122,365, filed on Dec. 7, 2020.

(51) Int. Cl.
*C07K 16/00* (2006.01)

(52) U.S. Cl.
CPC .......... *C07K 16/00* (2013.01); *C07K 2317/72* (2013.01); *C07K 2317/92* (2013.01); *C07K 2317/94* (2013.01)

(58) Field of Classification Search
CPC ............ C07K 2317/72; C07K 2317/92; C07K 2317/94
USPC ...................................................... 424/133.1
See application file for complete search history.

(56) References Cited

U.S. PATENT DOCUMENTS

| | | | |
|---|---|---|---|
| 4,399,216 A | 8/1983 | Axel et al. | |
| 4,439,196 A | 3/1984 | Higuchi | |
| 4,447,224 A | 5/1984 | DeCant, Jr. et al. | |
| 4,447,233 A | 5/1984 | Mayfield | |
| 4,487,603 A | 12/1984 | Harris | |
| 4,634,665 A | 1/1987 | Axel et al. | |
| 5,179,017 A | 1/1993 | Axel et al. | |
| 5,292,658 A | 3/1994 | Cormier et al. | |
| 5,418,155 A | 5/1995 | Cormier et al. | |
| 5,683,888 A | 11/1997 | Campbell | |
| 5,741,668 A | 4/1998 | Ward et al. | |
| 5,777,079 A | 7/1998 | Tsien et al. | |
| 5,804,387 A | 9/1998 | Cormack et al. | |
| 5,874,304 A | 2/1999 | Zolotukhin et al. | |
| 5,876,995 A | 3/1999 | Bryan | |
| 5,925,558 A | 7/1999 | Tsien et al. | |
| 9,079,949 B1 * | 7/2015 | Andrien, Jr. ............. | A61P 17/06 |
| 10,626,169 B2 * | 4/2020 | Beil ........................ | A61P 21/00 |
| 11,498,953 B2 * | 11/2022 | Brondyk ................ | C07K 16/00 |
| 11,623,964 B2 * | 4/2023 | Lansing ................. | C07K 16/00 |
| | | | 424/136.1 |
| 2006/0074225 A1* | 4/2006 | Chamberlain .......... | C07K 16/44 |
| | | | 530/387.1 |
| 2013/0129727 A1 | 5/2013 | Zhang et al. | |
| 2019/0185557 A1 | 6/2019 | Igawa et al. | |
| 2020/0223938 A1 | 7/2020 | Jung et al. | |
| 2022/0009994 A1* | 1/2022 | Brondyk ................ | C07K 16/00 |
| 2022/0259282 A1* | 8/2022 | Brondyk .......... | C07K 14/70503 |
| 2023/0090405 A1* | 3/2023 | Brondyk ................ | C07K 16/00 |
| | | | 435/69.1 |

FOREIGN PATENT DOCUMENTS

| | | |
|---|---|---|
| WO | WO 1992/015673 | 9/1992 |
| WO | WO 1995/007463 | 3/1995 |
| WO | WO 1998/014605 | 4/1998 |
| WO | WO 1998/026277 | 6/1998 |
| WO | WO 1999/049019 | 9/1999 |
| WO | WO 2005/123780 | 12/2005 |
| WO | WO-2020082048 A1 | 4/2020 |
| WO | WO 2020/142625 | 7/2020 |
| WO | WO-2022109313 A1 | 5/2022 |

OTHER PUBLICATIONS

International Search Report and Written Opinion in International Appln. No. PCT/US2021/061409, mailed May 23, 2022, 12 pages.
Beniaminovitz et al., "Prevention of rejection in cardiac transplantation by blockade of the interleukin-2 receptor with a monoclonal antibody," New Engl. J. Med., Mar. 2000, 342(9):613-619.
Better et al., "*Escherichia coli* secretion of an active chimeric antibody fragment," Science, May 1998, 240(4855):1041-1043.
Booth et al., "Extending human IgG half-life using structure-guided design," MAbs, Oct. 2018, 10(7):1098-1110.
Borrok et al., "pH-dependent binding engineering reveals an FcRn affinity threshold that governs IgG recycling," J. Biol. Chem., Feb. 2015, 290(7):4282-4290, 10 pages.
Chalfie et al., "Green fluorescent protein as a marker for gene expression," Science, Feb. 1994, 263(5148):802-805.
Gearing et al., "In Vitro and In Vivo Characterization of a Fully Felinized Therapeutic Anti-Nerve Growth Factor Monoclonal Antibody for the Treatment of Pain in Cats," J Vet Intern Med, Jun. 2016, 30(4):1129-1137.
GenBank Accession No. AAA52216.1, "Ig gamma 1b chain constant region, partial [Sus scrofa]," dated Jul. 26, 2016, 1 page.
GenBank Accession No. AAA52219.1, "Ig gamma 1a chain constant region, partial [Sus scrofa]," dated Jul. 26, 2016, 1 page.
GenBank Accession No. AAA52220.1, "Ig gamma 4a chain constant region, partial [Sus scrofa]," dated Jul. 26, 2016, 1 page.
GenBank Accession No. AAC48761.1, "IgG3 heavy chain constant region, partial [Bos taurus]," dated Jul. 26, 2016, 1 page.
Genbank Accession No. AAF60956.1, "IgG Fc receptor FcRN [Bos taurus]," dated Apr. 28, 2000, 1 page.
GenBank Accession No. AAP82181.1, "immunoglobulin gamma 3 heavy chain constant region, partial [Equus caballus]," dated Jul. 25, 2016, 1 page.

(Continued)

*Primary Examiner* — Lynn A Bristol
(74) *Attorney, Agent, or Firm* — Clark & Elbing LLP

(57) ABSTRACT

Provided are compositions for increasing the half-life of a polypeptide or polypeptides in a livestock animal and methods of their use. The compositions involve variant IgG Fc regions.

28 Claims, 57 Drawing Sheets

Specification includes a Sequence Listing.

(56) References Cited

OTHER PUBLICATIONS

GenBank Accession No. AAS18414.1, "immunoglobulin gamma 7 heavy chain, partial [Equus caballus]," dated Jul. 26, 2016, 1 page.
GenBank Accession No. AAS18415.1, "immunoglobulin gamma 4 heavy chain, partial [Equus caballus]," dated Jul. 26, 2016, 1 page.
GenBank Accession No. AB699687.1, "Sus scrofa genes for immunoglobulin heavy chain constant region, clone: L342C21," dated Jan. 25, 2018, 27 pages.
GenBank Accession No. ABE68619.1, "immunoglobulin gamma 1 heavy chain constant region, partial [Bos taurus]," dated Jul. 26, 2016, 1 page.
GenBank Accession No. ABY85805.1, "immunoglobulin gamma chain 6b, partial [Sus scrofa]," dated Jul. 26, 2016, 1 page.
GenBank Accession No. ABY85806.1, "immunoglobulin gamma chain 4b, partial [Sus scrofa]," dated Jul. 26, 2016, 1 page.
GenBank Accession No. ABY85809.1, "immunoglobulin gamma chain 5a, partial [Sus scrofa]," dated Jul. 26, 2016, 1 page.
GenBank Accession No. ABY85810.1, "immunoglobulin gamma chain 3, partial [Sus scrofa]," dated Jul. 26, 2016, 1 page.
Genbank Accession No. AEM45004.1, "immunoglobulin kappa light chain constant region, partial [Bos taurus]," dated Jul. 25, 2016, 1 page.
Genbank Accession No. AHB17990.1, "immunoglobulin light chain constant region, partial [Sus scrofa]," dated Jun. 16, 2014, 1 page.
GenBank Accession No. AQT27057.1, "immunoglobulin gamma heavy chain [Bos taurus]," dated Mar. 4, 2017, 1 page.
Genbank Accession No. AY549962.1, "Ovis aries beta-2 microglobulin (B2M) mRNA, complete cds," dated Mar. 10, 2004, 1 page.
Genbank Accession No. CAA53284.1, "immunoglobulin kappa light chain [Equus caballus]," dated Jul. 18, 2003, 1 page.
GenBank Accession No. CAC44760.1, "immunoglobulin gamma 1 heavy chain constant region, partial [Equus caballus]," dated Jul. 23, 2016, 1 page.
GenBank Accession No. CAC44761.1, "immunoglobulin gamma 2 heavy chain constant region, partial [Equus caballus]," dated Jul. 23, 2016, 1 page.
GenBank Accession No. CAC86340.1, "immunoglobulin gamma 5 heavy chain constant region, partial [Equus caballus]," dated Jul. 26, 2016, 1 page.
GenBank Accession No. CAC86341.1, "immunoglobulin gamma 6 heavy chain constant region, partial [Equus caballus]," dated Jul. 26, 2016, 1 page.
Genbank Accession No. E9LK24, "FCGRT Fc gamma receptor and transporter [ Sus scrofa (pig) ]," updated Nov. 16, 2021, 4 pages.
Genbank Accession No. L13854.1, "Sus scrofa beta 2-microglobulin mRNA, complete cds," dated Feb. 10, 1994, 1 page.
Genbank Accession No. Q8HZV2, "Neonatal Fc receptor alpha chain," dated Nov. 28, 2006, 1 page.
GenBank Accession No. U03779.1, "Sus scrofa Ig gamma 2a constant region (IgG2a) mRNA, partial cds," dated Nov. 8, 1994, 1 page.
GenBank Accession No. U03780.1, "Sus scrofa Ig gamma 2b constant region (IgG2b) mRNA, partial cds," dated Nov. 8, 1994, 1 page.
GenBank Accession No. U55762, "Cloning vector pEGFP-N1, complete sequence, enhanced green fluorescent protein (egfp) and neomycin phosphotransferase genes, complete cds," Aug. 22, 2003, 3 pages.
Genbank Accession No. X69083.1, "Equus caballus mRNA for beta 2-microglobulin," dated Apr. 18, 2005, 1 page.
Genbank Accession No. X69084.1, "B.taurus mRNA for beta 2-microglobulin," dated Nov. 14, 2006, 1 page.
Genbank Accession No. X69797.1, "O.aries mRNA for immunoglobulin gammal chain secreted form," dated Jul. 14, 2016, 1 page.
Genbank Accession No. X70983.1, "O.aries mRNA for Ig gamma 2 constant region heavy chain," dated Dec. 10, 1993, 1 page.
Genbank Accession No. XP_023505908.1, "IgG receptor FcRn large subunit p51 isoform X1 [Equus caballus]," dated Jan. 23, 2018, 1 page.
Ghosh et al., "Natalizumab for active Crohn's disease," New Engl. J. Med., Jan. 2003, 348(1):24-32.
Heim et al., "Engineering green fluorescent protein for improved brightness, longer wavelengths and fluorescence resonance energy transfer," Curr. Biol., Feb. 1996, 6(2):178-182.
Hogrefe et al., "Creating randomized amino acid libraries with the QuikChange Multi Site-Directed Mutagenesis Kit," Biotechniques., Nov. 2002, 33(5):1158-1165.
Ichiki et al., "Regulation of the expression of human C epsilon germline transcript. Identification of a novel IL-4 responsive element," J. Immunol., Jun. 1993, 150(12):5408-5417.
Kaufman et al., "Amplification and expression of sequences cotransfected with a modular dihydrofolate reductase complementary dna gene," Mol. Biol., Aug. 1982, 159(4):601-621.
Lei et al., "Characterization of the Erwinia carotovora pe1B gene and its product pectate lyase," J. Bacteriol., Sep. 1987, 169(9):4379-4383.
Lipsky et al., "Infliximab and methotrexate in the treatment of rheumatoid arthritis. Anti-Tumor Necrosis Factor Trial in Rheumatoid Arthritis with Concomitant Therapy Study Group," New Engl. J. Med., Nov. 2000, 343(22):1594-1602.
Milgrom et al., "Treatment of allergic asthma with monoclonal anti-IgE antibody. rhuMAb-E25 Study Group," New Engl. J. Med., Dec. 1999, 341(26):1966-1973.
Mizushima et al., "pEF-BOS, a powerful mammalian expression vector," Nucleic Acids Res., Sep. 1990, 18(17):5322.
Mulligan et al., "Synthesis of rabbit beta-globin in cultured monkey kidney cells following infection with a SV40 beta-globin recombinant genome," Nature, Jan. 1979, 277(5692):108-114.
Nolan et al., "Fluorescence-activated cell analysis and sorting of viable mammalian cells based on beta-D-galactosidase activity after transduction of *Escherichia coli* lacZ," Proc. Natl. Acad. Sci. U.S.A., Apr. 1988, 85(8):2603-2607.
Powers et al., "Expression of single-chain Fv-Fc fusions in Pichia pastoris," J Immunol Methods., May 2001, 251(1-2):123-135.
Schwartz et al., "The antibody loci of the domestic goat (*Capra hircus*)," Immunogenetics, May 2018, 70:317-326, 10 pages.
Slamon et al., "Use of chemotherapy plus a monoclonal antibody against HER2 for metastatic breast cancer that overexpresses HER2," New Engl. J. Med., Mar. 2001, 344(11):783-792.
Stauber et al., "Development and applications of enhanced green fluorescent protein mutants," Biotechniques, Mar. 1998, 24(3):462-471.
Urlaub et al., "Isolation of Chinese hamster cell mutants deficient in dihydrofolate reductase activity," Proc. Natl. Acad. Sci. USA, Jul. 1980, 77(7):4216-4220.
Ward et al., "Binding activities of a repertoire of single immunoglobulin variable domains secreted from *Escherichia coli*," Nature, Oct. 1989, 341(6242):544-546.

* cited by examiner

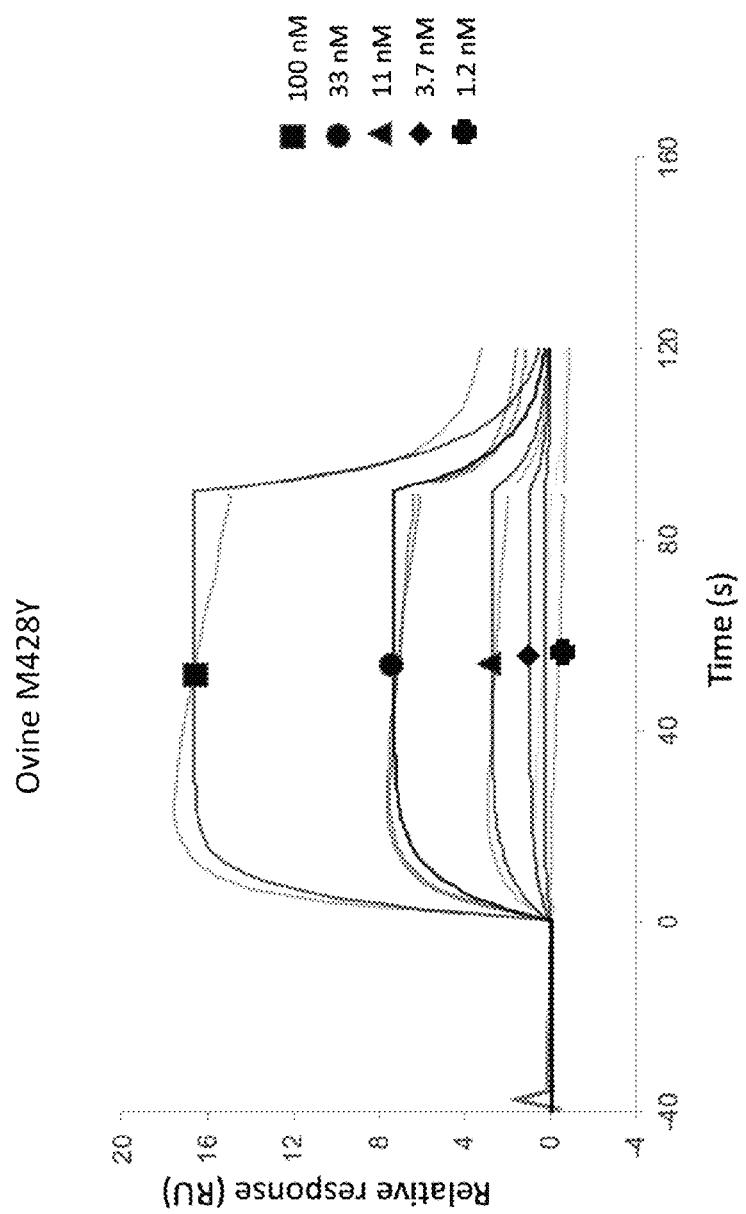

COMPOSITIONS FOR INCREASING HALF-LIFE OF A THERAPEUTIC AGENT IN LIVESTOCK ANIMALS AND METHODS OF USE

CROSS REFERENCE TO RELATED APPLICATIONS

This application claims priority to U.S. Provisional Application No. 63/122,365, filed Dec. 7, 2020, the content of which is incorporated by reference in its entirety.

FIELD

This disclosure relates generally to polypeptides (e.g., fusion polypeptides such as polypeptide-Fc region fusions; or binding molecules such as antibodies or ligand-binding portions of receptor-Fc fusions) that have increased half-life in livestock animals compared to their wild type counterparts.

SEQUENCE LISTING SUBMITTED VIA EFS-WEB

The entire content of the following electronic submission of the sequence listing via the USPTO EFS-WEB server, as authorized and set forth in MPEP § 1730 II.B.2(a), is incorporated herein by reference in its entirety for all purposes. The sequence listing is within the electronically filed text file that is identified as follows:
File Name: 47406-0017001_Sequence_Listing.txt
Date of Creation: Dec. 1, 2021
Size (bytes): 64,960 bytes

BACKGROUND

The Fc region of antibodies plays a number of functional roles, including, but not limited to, protecting the antibody from degradation through the lysosomal pathway and mediating antibody effector functions. With the increasing use of antibodies as therapeutic agents in livestock animals, there has been an enhanced focus on not just selecting an optimal Fab, but also combining it with an appropriate Fc for desired half-life and effector functions.

There is little guidance in the art relating to increasing half-life of polypeptide therapeutics (e.g., antibodies) for use in livestock animals. This disclosure remedies that failing by providing Fc region variants that improve the serum persistence of polypeptides (e.g., antibodies) in livestock animals.

SUMMARY

Provided herein are Fc (e.g., IgG Fc region variant) of livestock animals or FcRn binding fragments thereof that are useful in therapeutic polypeptides. This disclosure features polypeptides that have increased binding to FcRn of livestock animals than control polypeptides (e.g., the wild type counterpart IgG Fc regions). In some instances, these polypeptides have increased binding to FcRn livestock animals when compared to control polypeptides at pH 5.5, pH 6.0 and/or pH 6.5. In some instances, these polypeptides can, e.g., bind to FcRn of livestock animals at a higher level at acidic pH (e.g., pH 5.5, pH 6.0 or pH 6.5) than at a neutral pH (e.g., pH 7.0, 7.1, 7.2, 7.3, 7.4, or 7.5). In some instances, these polypeptides bind to FcRn of livestock animals at a higher level at pH 5.5 and/or 6.0 than at pH 7.4. This disclosure relates, in part, to polypeptides that have increased half-life in livestock animals than their wild type counterparts. For example, provided are binding molecules (e.g., antibodies or ligand-binding portions of receptors) with increased half-life relative to versions of these binding molecules not attached to the Fc regions or FcRn binding regions thereof disclosed herein. Also provided are enzyme-Fc region fusions, ligand-Fc region fusions, nanobody-Fc fusions, and peptide-Fc region fusions, wherein the fusions have increased half-life compared with their wild type counterparts. The Fc regions, in addition to having a substitution or substitutions (relative to the wild type Fc region of a livestock animal of the same species) that increase half-life, may also include other substitutions that, e.g., increase effector function, decrease effector function, increase binding to Protein A and/or decrease heterogeneity of the polypeptide (e.g., by removing one or more post-translational modifications in the Fc region). The Fc region sequences of livestock animals can be from any antibody of the livestock animal. In some instances, the Fc region sequences of the livestock animal are from an IgG, subclasses of which are described elsewhere herein.

The disclosure features a recombinant protein comprising (1) a binding domain, or a fragment thereof, that specifically binds to a ligand, or an epitope of a protein, wherein the binding domain is attached to (2) a domain comprising an Fc region (CH2+CH3 region) of a livestock animal, or an FcRn binding region thereof, as disclosed herein. In some instances, the binding domain comprises (i) the six complementarity determining regions (CDRs), for example, of a livestock animal or human/humanized antibody; (ii) a nanobody; (iii) a soluble receptor-binding domain that binds a ligand, or a ligand-binding fragment thereof and (iv) an extracellular domain of a livestock animal receptor protein.

The disclosure also provides a composition comprising: (1) a first polypeptide comprising a first Fc region (e.g., a CH2 domain, a CH3 domain, a CH2+CH3 domain) comprising a livestock animal IgG Fc region variant described herein; and (2) a second polypeptide comprising a second Fc region comprising a livestock animal IgG Fc region variant described herein. The first and second polypeptide can be associated through the first and second Fc regions. In some instances, the amino acid sequences of the first and second Fc regions are the same. In other instances, the amino acid sequences of the first and second Fc regions are different (e.g., by 1, 2, 3, 4, 5, 6, 7, 8, 9, 10, 11, 12, 13, 14, 15, 16, 17, 18, 19, 20, 21, 22, 23, 24, or 25 amino acids).

In some embodiments, the Fc region variant is an Fc variant of a porcine IgG selected from the group consisting of IgG1a, IgG1b, IgG2a, IgG2b, IgG3, IgG4a, IgG4b, IgG5a, IgG5b, IgG6a and IgG6b.

In some embodiments, the Fc region variant is an Fc variant of a bovine IgG selected from the group consisting of IgG1, IgG2 and IgG3.

In some embodiments, the Fc region variant is an Fc variant of an equine IgG selected from the group consisting of IgG1, IgG2, IgG3, IgG4, IgG5, IgG6 and IgG7.

In some embodiments, the Fc region variant is an Fc variant of an ovine IgG selected from the group consisting of IgG1, IgG2 and IgG3.

In some embodiments, the Fc region variant is an Fc variant of a caprine IgG selected from the group consisting of IgG1, IgG2 and IgG3.

Also disclosed is a fusion molecule comprising a livestock animal IgG Fc region variant disclosed herein and a polypeptide. In some instances, the livestock animal IgG Fc region variant is covalently attached to the polypeptide (e.g., through a hinge region or a linker). In some instances, the polypeptide is a ligand binding domain of a livestock animal receptor protein, an extracellular domain of a livestock animal receptor protein, or an antigen-binding domain. In some instances, the polypeptide is selected from the ligand binding domain or extracellular domain of an IL-13Rα1, or IL-13Rα2, a livestock animal erythropoietin (EPO), a livestock animal CTLA4, a livestock animal LFA3, a livestock animal VEGFR1/VEGFR3, a livestock animal IL-1R, a livestock animal GLP-1 receptor agonist, and a livestock animal thrombopoietin binding peptide. In some instances, the polypeptide is an scFv, a nanobody, or single domain antibody. In some instances, the IgG Fc region variant is a variant of a livestock animal IgG1a antibody Fc region. In some instances, the IgG Fc region variant is a variant of a livestock animal IgG1b antibody Fc region. In some instances, the IgG Fc region variant is a variant of a livestock animal IgG2 antibody Fc region.

In some aspects, the disclosure provides a polypeptide comprising an IgG Fc region variant of a livestock animal, or an FcRn-binding region thereof, wherein the polypeptide comprises an amino acid substitution at at least one position selected from the group consisting of:
  (i) a position that corresponds to amino acid position 250 of a wild type IgG of the livestock animal, wherein the amino acid substitution is selected from the group consisting of S250Q, S250E, T250Q, T250E, I250Q, I250E, A250Q, A250E, V250Q and V250E;
  (ii) a position that corresponds to amino acid position 252 of a wild type IgG of the livestock animal, wherein the amino acid substitution is selected from the group consisting of M252Y, M252W, M252F, T252Y, T252W, T252F, K252Y, K252W and K252F;
  (iii) a position that corresponds to amino acid position 254 of a wild type IgG of the livestock animal, wherein the amino acid substitution is selected from the group consisting of S254T, S254R, S254K, S254H, T254R, T254K and T254H;
  (iv) a position that corresponds to amino acid position 256 of a wild type IgG of the livestock animal, wherein the amino acid substitution is selected from the group consisting of T256A, T256D, T256E, M256A, M256D, M256E, K256A, K256D and K256E;
  (v) a position that corresponds to amino acid position 286 of a wild type IgG of the livestock animal, wherein the amino acid substitution is selected from the group consisting of S286Y, S286F, S286W, S286L, S286D, S286E, T286Y, T286F, T286W, T286L, T286D and T286E;
  (vi) a position that corresponds to amino acid position 309 of a wild type IgG of the livestock animal, wherein the amino acid substitution is selected from the group consisting of Q309V, Q309D and Q309E;
  (vii) a position that corresponds to amino acid position 311 of a wild type IgG of the livestock animal, wherein the amino acid substitution is selected from the group consisting of Q311V, Q311K, Q311R, Q311L, Q311H, E311V, E311K, E311R, E311L, E311H, K311V, K311R, K311L, K311H, D311V, D311K, D311R, D311L and D311H;
  (viii) a position that corresponds to amino acid position 426 of a wild type IgG of the livestock animal, wherein the amino acid substitution is selected from the group consisting of A426Y, A426F, A426H, V426Y, V426F, V426H, G426Y, G426F and G426H;
  (ix) a position that corresponds to amino acid position 428 of a wild type IgG of the livestock animal, wherein the amino acid substitution is selected from the group consisting of M428L, M428Y, M428F, H428L, H428Y and H428F;
  (x) a position that corresponds to amino acid position 434 of a wild type IgG of the livestock animal, wherein the amino acid substitution is selected from the group consisting of N434A, N434H, N434F, N434S, N434W, N434Y, H434A, H434F, H434S, H434W and H434Y; and (x) a position that corresponds to amino acid position 436 of a wild type IgG of the livestock animal, wherein the amino acid substitution is selected from the group consisting of Y436H, T436H, F436H and V436H;
  wherein the amino acid positions are based on EU numbering, and wherein the polypeptide has increased binding affinity to an FcRn of the livestock animal when compared to an Fc domain of the wild type IgG.

In some embodiments, the livestock animal is a porcine.

In some embodiments, the polypeptide comprises an amino acid substitution at at least one position selected from the group consisting of:
  (i) a position that corresponds to amino acid position 250 of a wild type IgG of the livestock animal, wherein the amino acid substitution is selected from the group consisting of T250Q, T250E, I250Q and I250E;
  (ii) a position that corresponds to amino acid position 252 of a wild type IgG of the livestock animal, wherein the amino acid substitution is selected from the group consisting of M252Y, M252W and M252F;
  (iii) a position that corresponds to amino acid position 254 of a wild type IgG of the livestock animal, wherein the amino acid substitution is selected from the group consisting of S254T, S254R, S254K and S254H;
  (iv) a position that corresponds to amino acid position 256 of a wild type IgG of the livestock animal, wherein the amino acid substitution is selected from the group consisting of T256A, T256D and T256E;
  (v) a position that corresponds to amino acid position 286 of a wild type IgG of the livestock animal, wherein the amino acid substitution is selected from the group consisting of T286Y, T286F, T286W, T286L, T286D and T286E;
  (vi) a position that corresponds to amino acid position 309 of a wild type IgG of the livestock animal, wherein the amino acid substitution is selected from the group consisting of Q309V, Q309D and Q309E;
  (vii) a position that corresponds to amino acid position 311 of a wild type IgG of the livestock animal, wherein the amino acid substitution is selected from the group consisting of Q311V, Q311K, Q311R, Q311L, Q311H, E311V, E311K, E311R, E311L and E311H;
  (viii) a position that corresponds to amino acid position 426 of a wild type IgG of the livestock animal, wherein the amino acid substitution is selected from the group consisting of A426Y, A426F, A426H, V426Y, V426F and V426H;
  (ix) a position that corresponds to amino acid position 428 of a wild type IgG of the livestock animal, wherein the amino acid substitution is selected from the group consisting of M428L, M428Y, M428F, H428L, H428Y and H428F;
  (x) a position that corresponds to amino acid position 434 of a wild type IgG of the livestock animal, wherein the amino acid substitution is selected from the group consisting of N434A, N434H, N434F, N434S, N434W, N434Y, H434A, H434F, H434S, H434W and H434Y; and (xi) a position that corresponds to amino acid position 436 of a wild type IgG of the livestock animal, wherein the amino acid substitution is selected from the group consisting of Y436H and T436H.

In some embodiments, the polypeptide comprises an amino acid substitution at at least one position selected from the group consisting of:
  (i) a position that corresponds to amino acid position 252 of a wild type IgG of the livestock animal, wherein the amino acid substitution is M252Y;
  (ii) a position that corresponds to amino acid position 286 of a wild type IgG of the livestock animal, wherein the amino acid substitution is T286E;
  (iii) a position that corresponds to amino acid position 309 of a wild type IgG of the livestock animal, wherein the amino acid substitution is Q309D or Q309V;
  (iv) a position that corresponds to amino acid position 311 of a wild type IgG of the livestock animal, wherein the amino acid substitution is Q311V;
  (v) a position that corresponds to amino acid position 426 of a wild type IgG of the livestock animal, wherein the amino acid substitution is A426Y;
  (vi) a position that corresponds to amino acid position 428 of a wild type IgG of the livestock animal, wherein the amino acid substitution is M428Y; and
  (vii) a position that corresponds to amino acid position 434 of a wild type IgG of the livestock animal, wherein the amino acid substitution is selected from the group consisting of N434Y.

In some embodiments, the wild type IgG Fc is a porcine IgG Fc comprising an amino acid sequence selected from the group consisting of SEQ ID NOs: 1 to 11.

In some embodiments, the livestock animal is a bovine.

In some embodiments, the polypeptide comprises an amino acid substitution at at least one position selected from the group consisting of:
  (i) a position that corresponds to amino acid position 250 of a wild type IgG of the livestock animal, wherein the amino acid substitution is selected from the group consisting of T250Q and T250E;
  (ii) a position that corresponds to amino acid position 252 of a wild type IgG of the livestock animal, wherein the amino acid substitution is selected from the group consisting of M252Y, M252W, M252F, T252Y, T252W and T252F;
  (iii) a position that corresponds to amino acid position 254 of a wild type IgG of the livestock animal, wherein the amino acid substitution is selected from the group consisting of S254T, S254R, S254K, S254H, T254R, T254K and T254H;
  (iv) a position that corresponds to amino acid position 256 of a wild type IgG of the livestock animal, wherein the amino acid substitution is selected from the group consisting of T256A, T256D and T256E;
  (v) a position that corresponds to amino acid position 286 of a wild type IgG of the livestock animal, wherein the amino acid substitution is selected from the group consisting of T286Y, T286F, T286W, T286L, T286D and T286E;
  (vi) a position that corresponds to amino acid position 309 of a wild type IgG of the livestock animal, wherein the amino acid substitution is selected from the group consisting of Q309V, Q309D and Q309E;
  (vii) a position that corresponds to amino acid position 311 of a wild type IgG of the livestock animal, wherein the amino acid substitution is selected from the group consisting of Q311V, Q311K, Q311R, Q311L and Q311H;
  (viii) a position that corresponds to amino acid position 426 of a wild type IgG of the livestock animal, wherein the amino acid substitution is selected from the group consisting of A426Y, A426F, A426H, V426Y, V426F and V426H;
  (ix) a position that corresponds to amino acid position 434 of a wild type IgG of the livestock animal, wherein the amino acid substitution is selected from the group consisting of N434A, N434H, N434F, N434S, N434W and N434Y; and
  (x) a position that corresponds to amino acid position 436 of a wild type IgG of the livestock animal, wherein the amino acid substitution is Y436H.

In some embodiments, the polypeptide comprises an amino acid substitution at at least one position selected from the group consisting of:
  (i) a position that corresponds to amino acid position 252 of a wild type IgG of the livestock animal, wherein the amino acid substitution is T252Y;
  (ii) a position that corresponds to amino acid position 309 of a wild type IgG of the livestock animal, wherein the amino acid substitution is Q309V;
  (iii) a position that corresponds to amino acid position 311 of a wild type IgG of the livestock animal, wherein the amino acid substitution is Q311V;
  (iv) a position that corresponds to amino acid position 434 of a wild type IgG of the livestock animal, wherein the amino acid substitution is selected from the group consisting of N434Y; and
  (v) a position that corresponds to amino acid position 436 of a wild type IgG of the livestock animal, wherein the amino acid substitution is selected from the group consisting of Y436H.

In some embodiments, the wild type IgG Fc is a bovine IgG Fc comprising an amino acid sequence selected from the group consisting of SEQ ID NOs: 12 to 14.

In some embodiments, the livestock animal is an equine.

In some embodiments, the polypeptide comprises an amino acid substitution at at least one position selected from the group consisting of:
  (i) a position that corresponds to amino acid position 250 of a wild type IgG of the livestock animal, wherein the amino acid substitution is selected from the group consisting of T250Q, T250E, A250Q, A250E, V250Q and V250E;
  (ii) a position that corresponds to amino acid position 252 of a wild type IgG of the livestock animal, wherein the amino acid substitution is selected from the group consisting of M252Y, M252W, M252F, K252Y, K252W and K252F;
  (iii) a position that corresponds to amino acid position 254 of a wild type IgG of the livestock animal, wherein the amino acid substitution is selected from the group consisting of S254T, S254R, S254K, S254H, T254R, T254K and T254H;
  (iv) a position that corresponds to amino acid position 256 of a wild type IgG of the livestock animal, wherein the amino acid substitution is selected from the group consisting of T256A, T256D, T256E, M256A, M256D, M256E, K256A, K256D and K256E;
  (v) a position that corresponds to amino acid position 286 of a wild type IgG of the livestock animal, wherein the amino acid substitution is selected from the group consisting of S286Y, S286F, S286W, S286L, S286D, S286E, T286Y, T286F, T286W, T286L, T286D and T286E;
(vi) a position that corresponds to amino acid position 309 of a wild type IgG of the livestock animal, wherein the amino acid substitution is selected from the group consisting of Q309V, Q309D and Q309E;
(vii) a position that corresponds to amino acid position 311 of a wild type IgG of the livestock animal, wherein the amino acid substitution is selected from the group consisting of Q311V, Q311K, Q311R, Q311L, Q311H, K311V, K311R, K311L and K311H;
(viii) a position that corresponds to amino acid position 426 of a wild type IgG of the livestock animal, wherein the amino acid substitution is selected from the group consisting of A426Y, A426F, A426H, V426Y, V426F, V426H, G426Y, G426F and G426H;
(ix) a position that corresponds to amino acid position 428 of a wild type IgG of the livestock animal, wherein the amino acid substitution is selected from the group consisting of M428L, M428Y and M428F;
(x) a position that corresponds to amino acid position 434 of a wild type IgG of the livestock animal, wherein the amino acid substitution is selected from the group consisting of N434A, N434H, N434F, N434S, N434W, N434Y, H434A, H434F, H434S, H434W and H434Y; and
(xi) a position that corresponds to amino acid position 436 of a wild type IgG of the livestock animal, wherein the amino acid substitution is selected from the group consisting of Y436H, F436H and V436H.

In some embodiments, the polypeptide comprises an amino acid substitution at at least one position selected from the group consisting of:
(i) a position that corresponds to amino acid position 252 of a wild type IgG of the livestock animal, wherein the amino acid substitution is M252Y;
(ii) a position that corresponds to amino acid position 286 of a wild type IgG of the livestock animal, wherein the amino acid substitution is T286E
(iii) a position that corresponds to amino acid position 309 of a wild type IgG of the livestock animal, wherein the amino acid substitution is Q309V;
(iv) a position that corresponds to amino acid position 311 of a wild type IgG of the livestock animal, wherein the amino acid substitution is Q311V;
(v) a position that corresponds to amino acid position 426 of a wild type IgG of the livestock animal, wherein the amino acid substitution is G426Y; and
(vi) a position that corresponds to amino acid position 434 of a wild type IgG of the livestock animal, wherein the amino acid substitution is selected from the group consisting of N434Y.

In some embodiments, the wild type IgG Fc is an equine IgG Fc comprising an amino acid sequence selected from the group consisting of SEQ ID NOs: 15 to 21.

In some embodiments, the livestock animal is an ovine.

In some embodiments, the polypeptide comprises an amino acid substitution at at least one position selected from the group consisting of:
(i) a position that corresponds to amino acid position 250 of a wild type IgG of the livestock animal, wherein the amino acid substitution is selected from the group consisting of S250Q, S250E, T250Q and T250E;
(ii) a position that corresponds to amino acid position 252 of a wild type IgG of the livestock animal, wherein the amino acid substitution is selected from the group consisting of M252Y, M252W, M252F, T252Y, T252W and T252F;
(iii) a position that corresponds to amino acid position 254 of a wild type IgG of the livestock animal, wherein the amino acid substitution is selected from the group consisting of S254R, S254K, S254H, T254R, T254K and T254H;
(iv) a position that corresponds to amino acid position 256 of a wild type IgG of the livestock animal, wherein the amino acid substitution is selected from the group consisting of T256A, T256D and T256E;
(v) a position that corresponds to amino acid position 286 of a wild type IgG of the livestock animal, wherein the amino acid substitution is selected from the group consisting of T286Y, T286F, T286W, T286L, T286D and T286E;
(vi) a position that corresponds to amino acid position 309 of a wild type IgG of the livestock animal, wherein the amino acid substitution is selected from the group consisting of Q309V, Q309D and Q309E;
(vii) a position that corresponds to amino acid position 311 of a wild type IgG of the livestock animal, wherein the amino acid substitution is selected from the group consisting of Q311V, Q311K, Q311R, Q311L, Q311H, D311V, D311K, D311R, D311L and D311H;
(viii) a position that corresponds to amino acid position 426 of a wild type IgG of the livestock animal, wherein the amino acid substitution is selected from the group consisting of V426Y, V426F and V426H;
(ix) a position that corresponds to amino acid position 428 of a wild type IgG of the livestock animal, wherein the amino acid substitution is selected from the group consisting of M428L, M428Y and M428F;
(x) a position that corresponds to amino acid position 434 of a wild type IgG of the livestock animal, wherein the amino acid substitution is selected from the group consisting of N434A, N434H, N434F, N434S, N434W and N434Y; and
(xi) a position that corresponds to amino acid position 436 of a wild type IgG of the livestock animal, wherein the amino acid substitution is Y436H.

In some embodiments, the wild type IgG Fc is an ovine IgG Fc comprising an amino acid sequence selected from the group consisting of SEQ ID NOs: 22 to 24.

In some embodiments, the polypeptide comprises an amino acid substitution at at least one position selected from the group consisting of:
(i) a position that corresponds to amino acid position 252 of a wild type IgG of the livestock animal, wherein the amino acid substitution is T252Y;
(ii) a position that corresponds to amino acid position 309 of a wild type IgG of the livestock animal, wherein the amino acid substitution is Q309V;
(iii) a position that corresponds to amino acid position 311 of a wild type IgG of the livestock animal, wherein the amino acid substitution is Q311V;
(iv) a position that corresponds to amino acid position 428 of a wild type IgG of the livestock animal, wherein the amino acid substitution is selected from the group consisting of M428Y; and
(v) a position that corresponds to amino acid position 434 of a wild type IgG of the livestock animal, wherein the amino acid substitution is selected from the group consisting of N434Y.

In some embodiments, the wild type IgG Fc is an ovine IgG Fc comprising an amino acid sequence selected from the group consisting of SEQ ID NOs: 22 to 24.

In some embodiments, the livestock animal is a caprine.

In some embodiments, the polypeptide comprises an amino acid substitution at at least one position selected from the group consisting of:
  (i) a position that corresponds to amino acid position 250 of a wild type IgG of the livestock animal, wherein the amino acid substitution is selected from the group consisting of S250Q, S250E, T250Q and T250E;
  (ii) a position that corresponds to amino acid position 252 of a wild type IgG of the livestock animal, wherein the amino acid substitution is selected from the group consisting of M252Y, M252W, M252F, T252Y, T252W and T252F;
  (iii) a position that corresponds to amino acid position 254 of a wild type IgG of the livestock animal, wherein the amino acid substitution is selected from the group consisting of S254R, S254K, S254H, T254R, T254K and T254H;
  (iv) a position that corresponds to amino acid position 256 of a wild type IgG of the livestock animal, wherein the amino acid substitution is selected from the group consisting of T256A, T256D, T256E, K256A, K256D and K256E;
  (v) a position that corresponds to amino acid position 286 of a wild type IgG of the livestock animal, wherein the amino acid substitution is selected from the group consisting of T286Y, T286F, T286W, T286L, T286D and T286E;
  (vi) a position that corresponds to amino acid position 309 of a wild type IgG of the livestock animal, wherein the amino acid substitution is selected from the group consisting of Q309V, Q309D and Q309E;
  (vii) a position that corresponds to amino acid position 311 of a wild type IgG of the livestock animal, wherein the amino acid substitution is selected from the group consisting of Q311V, Q311K, Q311R, Q311L, Q311H, K311V, K311R, K311L, K311H, D311V, D311K, D311R, D311L and D311H;
  (viii) a position that corresponds to amino acid position 426 of a wild type IgG of the livestock animal, wherein the amino acid substitution is selected from the group consisting of A426Y, A426F, A426H, V426Y, V426F and V426H;
  (ix) a position that corresponds to amino acid position 428 of a wild type IgG of the livestock animal, wherein the amino acid substitution is selected from the group consisting of M428L, M428Y and M428F;
  (x) a position that corresponds to amino acid position 434 of a wild type IgG of the livestock animal, wherein the amino acid substitution is selected from the group consisting of N434A, N434H, N434F, N434S, N434W and N434Y; and
  (xi) a position that corresponds to amino acid position 436 of a wild type IgG of the livestock animal, wherein the amino acid substitution is Y436H.

In some embodiments, the wild type IgG Fc is a caprine IgG Fc comprising an amino acid sequence selected from the group consisting of SEQ ID NOs: 25 to 27.

In some embodiments, the polypeptide comprises at two or more of the at least one amino acid substitutions, wherein the two or more amino acid substitutions are at different positions, and wherein the polypeptide has increased binding affinity to an FcRn of the livestock animal when compared to (a) an Fc domain of the wild type IgG of the livestock animal, and (b) a polypeptide comprising only one of the two or more amino acid substitutions.

In some embodiments, the polypeptide further comprises a binding domain. In some embodiments, the binding domain comprises (i) six complementarity determining regions (CDRs) of an immunoglobulin molecule; (ii) a ligand binding domain of a receptor protein of the livestock animal, (iii) a nanobody, or (iv) an extracellular domain of a receptor protein of the livestock animal.

In some embodiments, the binding domain specifically binds to an antigen selected from the group consisting of NGF, TrKA, ADAMTS, IL-1, IL-2, IL-4, IL-4R, Angiotensin type 1 (AT1) receptor, Angiotensin type 2 (AT2) receptor, IL-5, IL-12, IL-13, IL-31, IL-33, CD3, CD20, CD47, CD52, and complement system complex.

In some embodiments, a specific binding between a binding domain (e.g., a binding domain of an antibody) and an antigen is represented by a $K_D$ value. $K_D$ is the ratio of the antibody dissociation rate ($k_{off}$) to the antibody association rate ($k_{on}$) of the antibody. The $K_D$ values can be determined by measuring the $k_{on}$ and $k_{off}$ rates of a specific antibody/antigen interaction and then using a ratio of these values to calculate the $K_D$ value. The smaller the $K_D$ value the greater the affinity of the antibody (or a binding domain thereof) for its target.

In some embodiments, the $K_D$ value for a specific binding ranges from about $10^{-6}$ to about $10^{-12}$ (e.g., $10^{-6}$, $10^{-7}$, $10^{-8}$, $10^{-9}$, $10^{-10}$, $10^{-11}$, or $10^{-12}$).

In some embodiments, the polypeptide further comprises a protein selected from the group consisting of EPO, CTLA4, LFA3, VEGFR1/VEGFR3, IL-1R, IL-4R, GLP-1 receptor agonist, and Thrombopoietin binding peptide.

In some embodiments, the polypeptide binds to an FcRn of the livestock animal at a higher level at an acidic pH than at a neutral pH.

In some embodiments, the polypeptide binds to an FcRn of the livestock animal at a higher level at pH 5.5 than at pH 7.4.

In some embodiments, the polypeptide binds to an FcRn of the livestock animal at a higher level at pH 6.0 than at pH 7.4.

Also disclosed herein is a pharmaceutical composition comprising (i) the polypeptide as described herein, and (ii) a pharmaceutically acceptable excipient.

The present disclosure also extends to a nucleic acid or nucleic acids encoding the polypeptide as described herein.

In another aspect disclosed herein, there is provided an expression vector or expression vectors comprising the nucleic acid or nucleic acids as described herein. The present disclosure also extends to a host cell comprising the nucleic acid or nucleic acids disclosed herein or the expression vector or expression vectors disclosed herein.

Also disclosed herein is a method of making a polypeptide, the method comprising:
  (a) providing a nucleic acid or nucleic acids as disclosed herein;
  (b) expressing the nucleic acid or nucleic acids in a host cell culture, thereby producing the polypeptide; and
  (c) collecting the polypeptide produced in (b) from the host cell culture.

In some embodiments, the method further comprises formulating the polypeptide as a pharmaceutical formulation.

The present disclosure also extends to a method of treating a disease or disorder in a livestock animal in need thereof, the method comprising administering an effective amount of a composition comprising the pharmaceutical composition as disclosed herein to the livestock animal.

The present disclosure also extends to a method of preventing a disease or disorder in a livestock animal in need thereof, the method comprising administering an effective amount of a composition comprising the pharmaceutical composition as disclosed herein to the livestock animal.

In some embodiments, the disease or disorder is an allergy, chronic pain, acute pain, an inflammatory disease, an autoimmune disease, an endocrine disease, a gastrointestinal disease, a cardiovascular disease, a renal disease, a fertility related disorder, an infectious disease or a cancer.

In some embodiments, the disease or disorder is atopic dermatitis, allergic dermatitis, osteoarthritic pain, arthritis, anemia, or obesity.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description and from the claims.

BRIEF DESCRIPTION OF THE DRAWINGS

FIGS. 7A-7J show the sensorgrams of kinetic binding data for the ovine IgG variants and wild-type.

DETAILED DESCRIPTION

Figure 1:
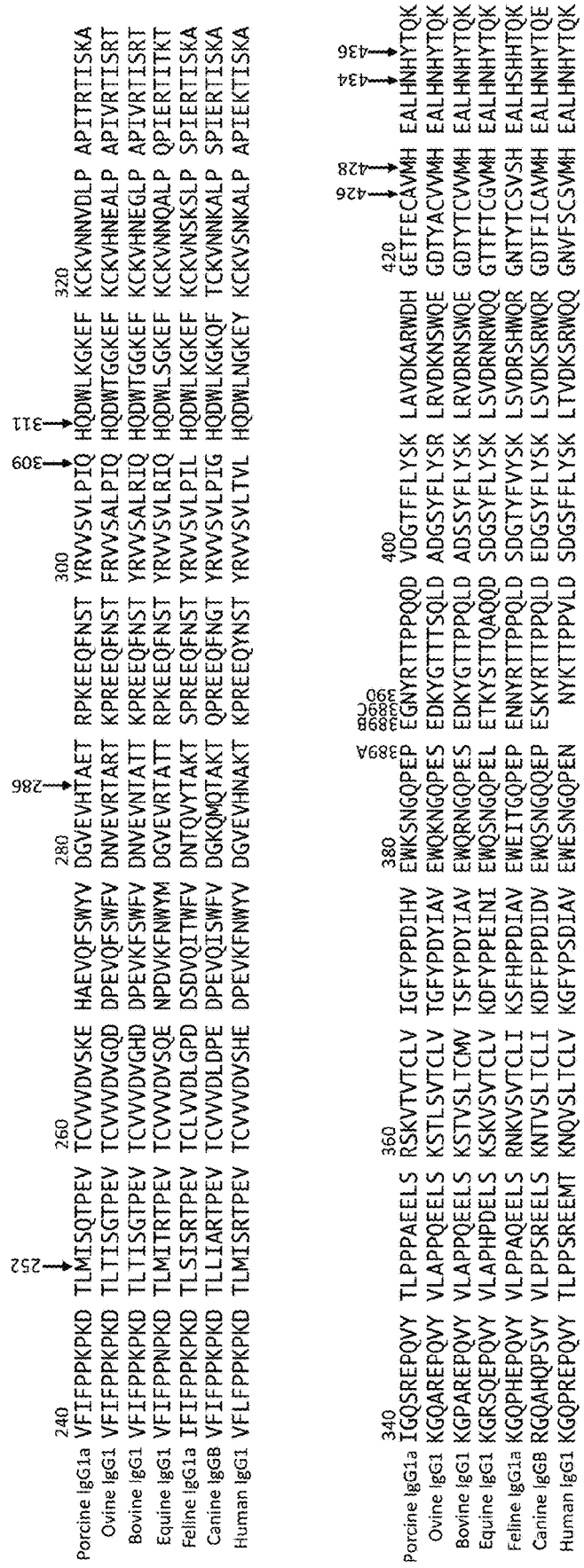
FIG. 1 shows the alignment of the amino acid sequences of the wild-type Fc regions of porcine IgG1a, ovine IgG1, bovine IgG1, equine IgG1, feline IgG1a, canine IgGB and human IgG1. These sequences are assigned SEQ ID NOs.: 30-36, respectively.
Figure 2C:
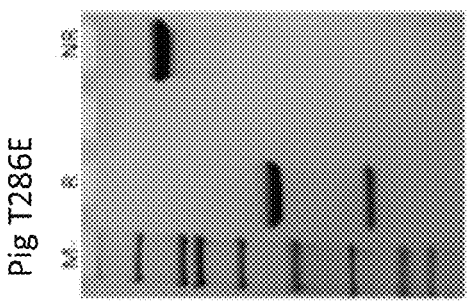
FIGS. 2A-2J show the purity of the porcine antibodies with the Fc variants determined by scanning densitometry of Coomassie blue-stained SDS/PAGE gels. The purity of each antibody was >90%.
Figure 2C:
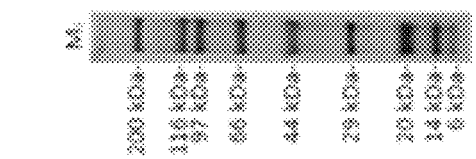
Figure 2B:
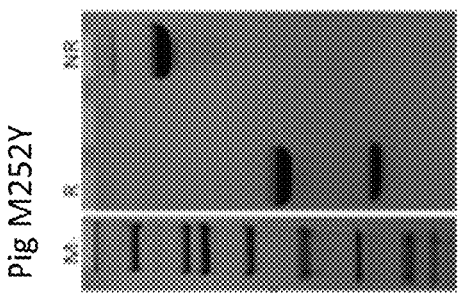
Figure 2B:
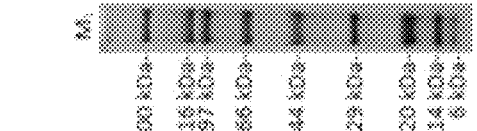
Figure 2A:
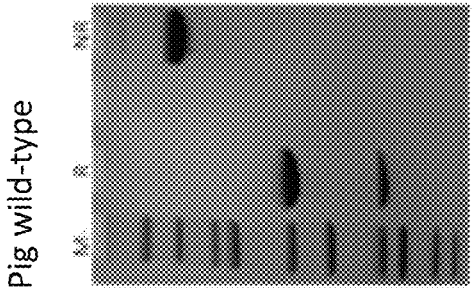
Figure 2A:
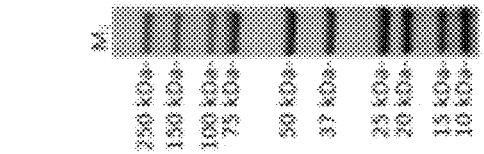
Figure 2F:
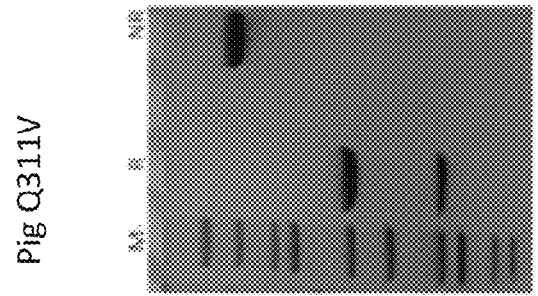
Figure 2E:
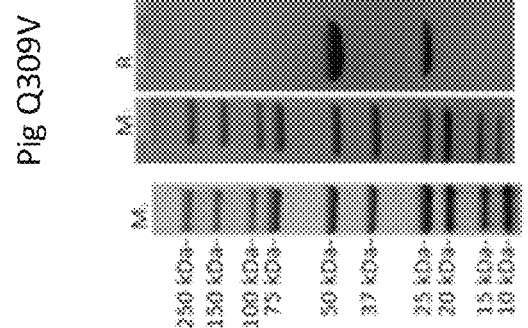
Figure 2D:
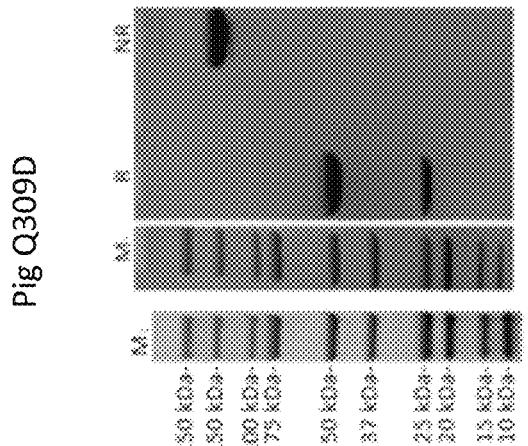
Figures 2G, 2H, 2I:
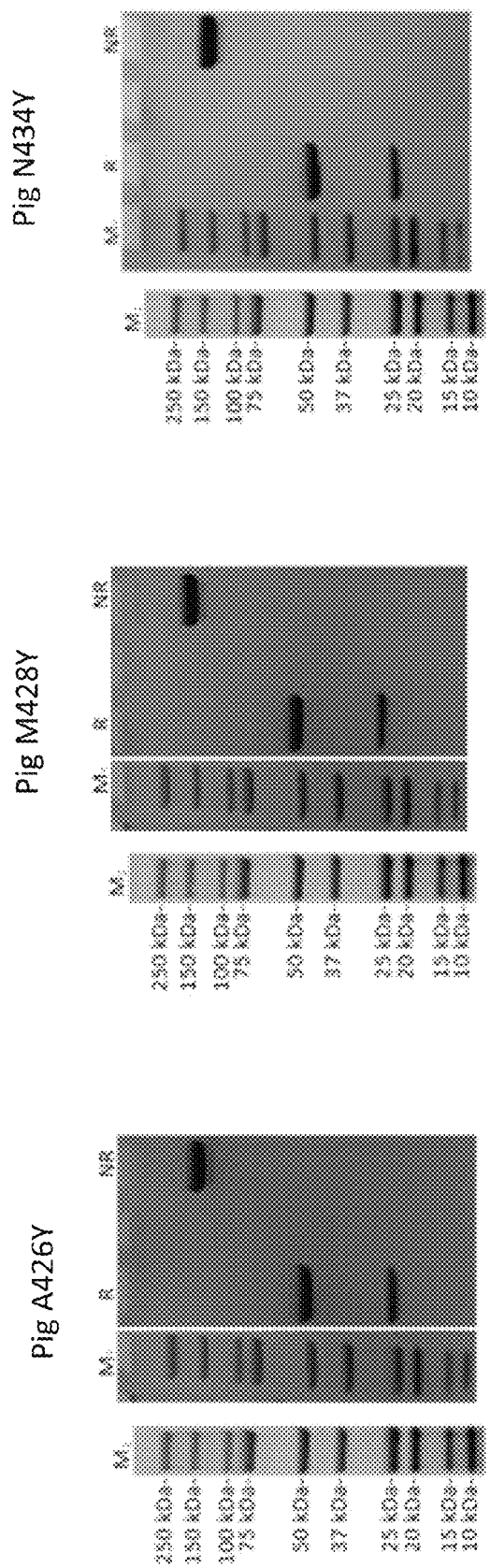
Figure 2J:
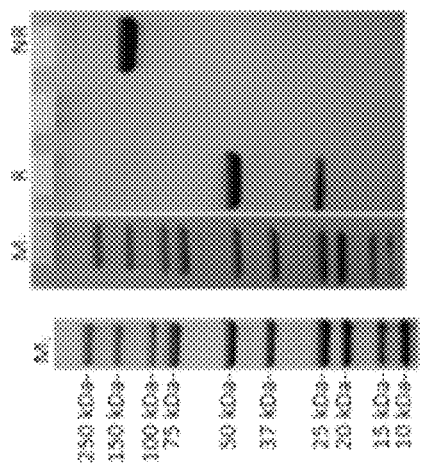
Figures 3A, 3B, 3C:
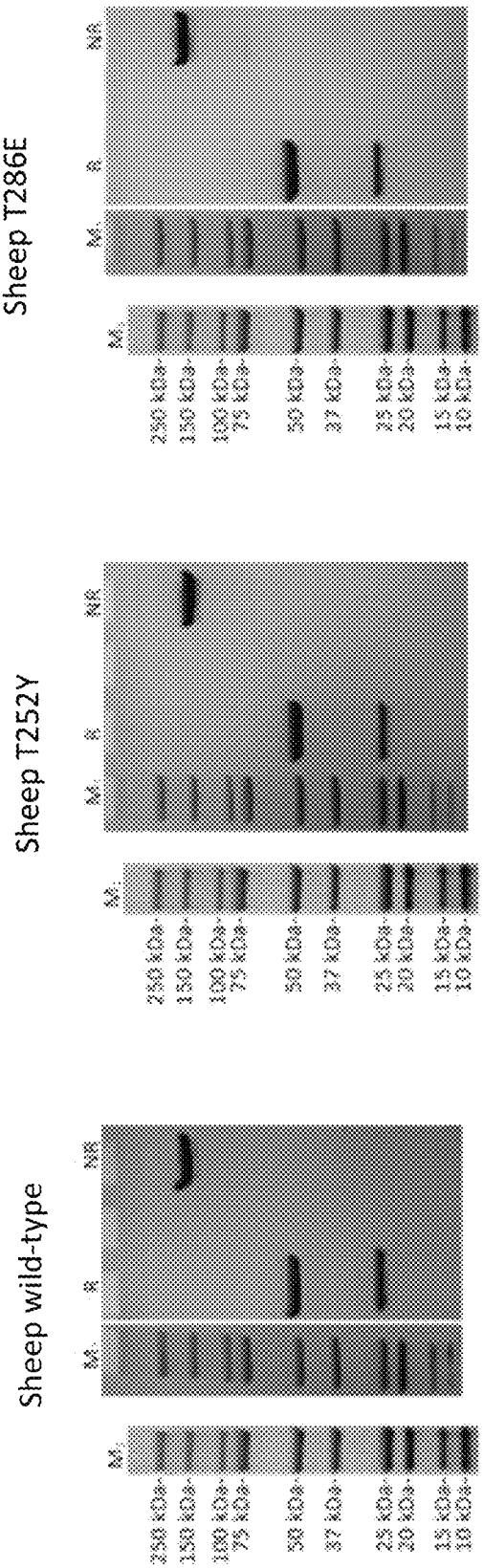
FIGS. 3A-3J show the purity of the ovine antibodies with the Fc variants determined by scanning densitometry of Coomassie blue-stained SDS/PAGE gels. The purity of each antibody was >90%.
Figure 3F:
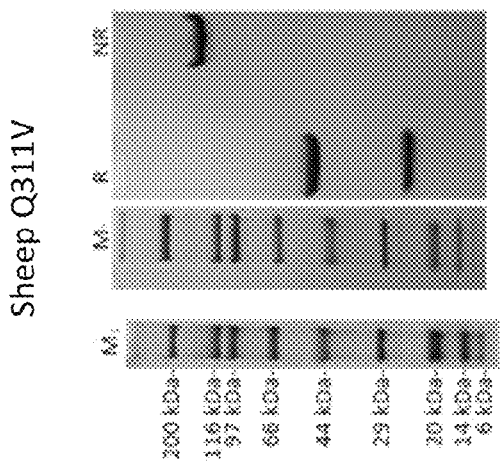
Figure 3E:
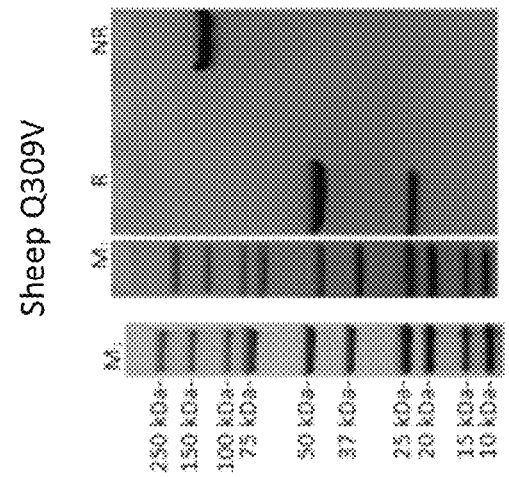
Figure 3D:
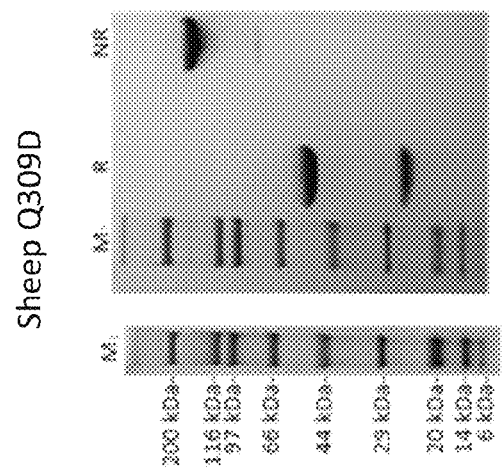
Figures 3G, 3H, 3I:
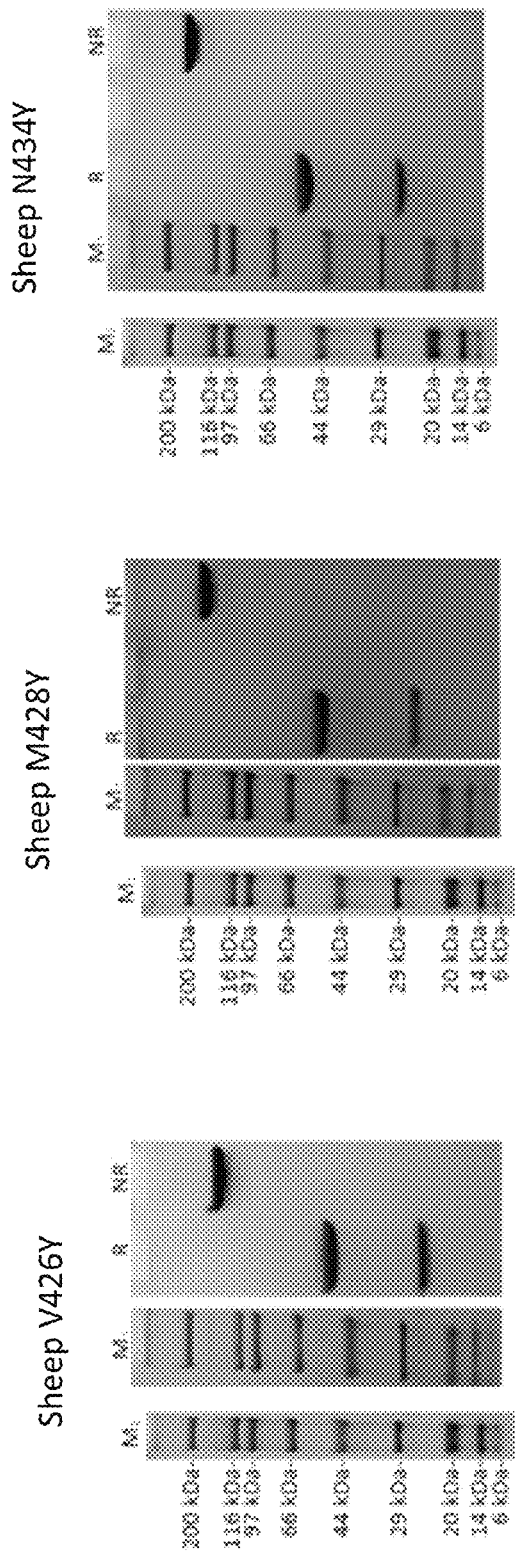
Figure 3J:
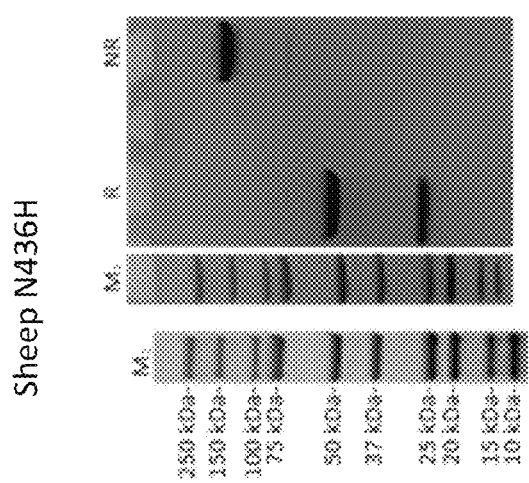
Figures 4A, 4B, 4C:
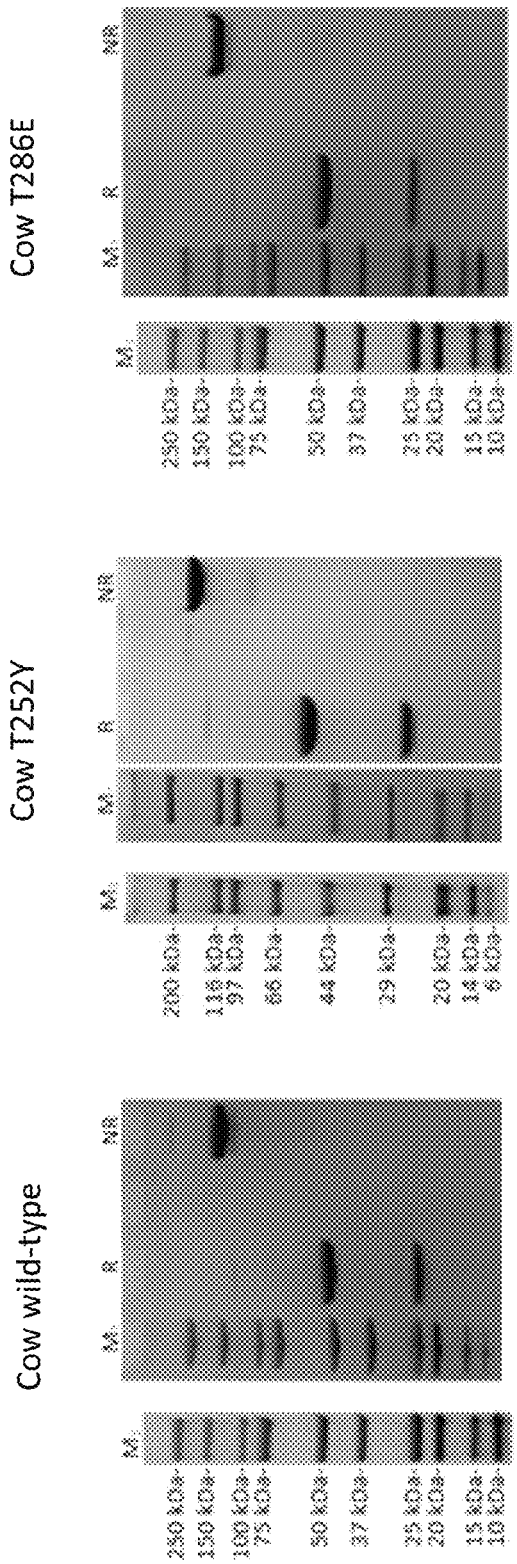
FIGS. 4A-4J show the purity of the bovine antibodies with the Fc variants determined by scanning densitometry of Coomassie blue-stained SDS/PAGE gels. The purity of each antibody was >90%.
Figure 4F:
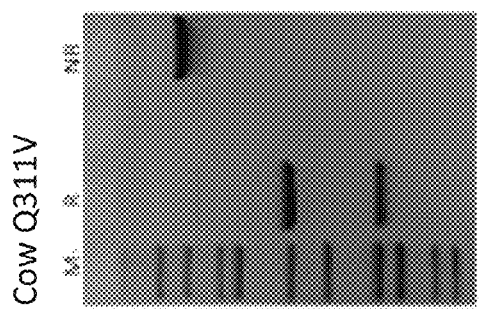
Figure 4E:
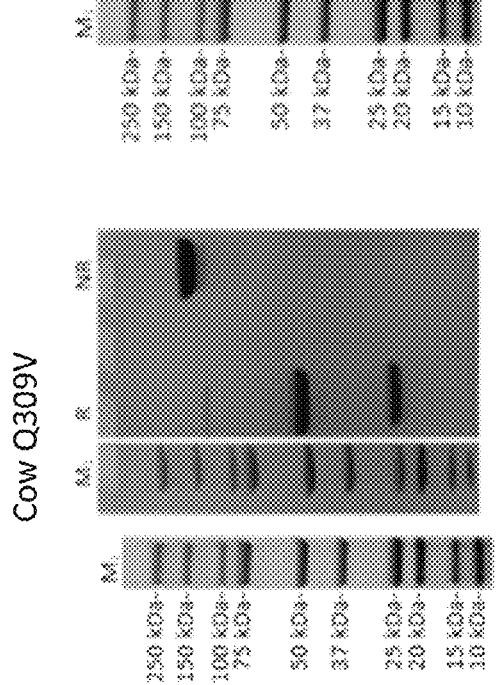
Figure 4D:
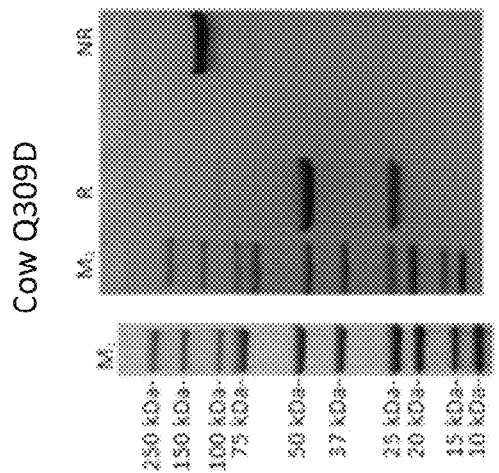
Figure 4I:
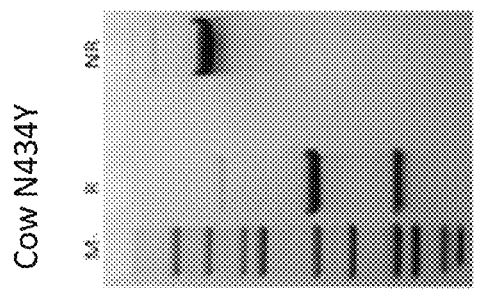
Figure 4I:
Figure 4H:
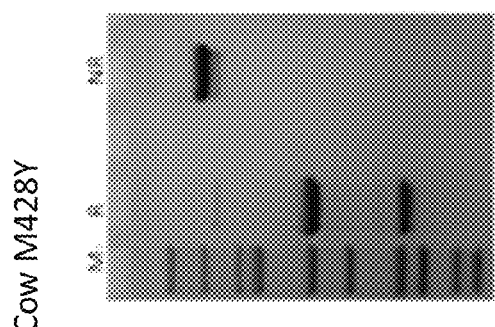
Figure 4H:
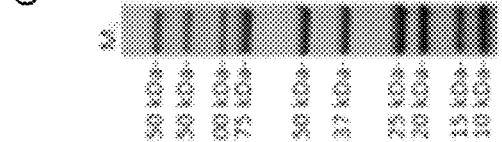
Figure 4G:
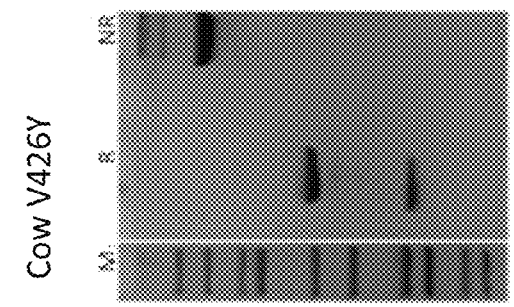
Figure 4G:
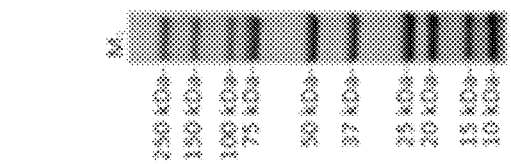
Figure 4J:
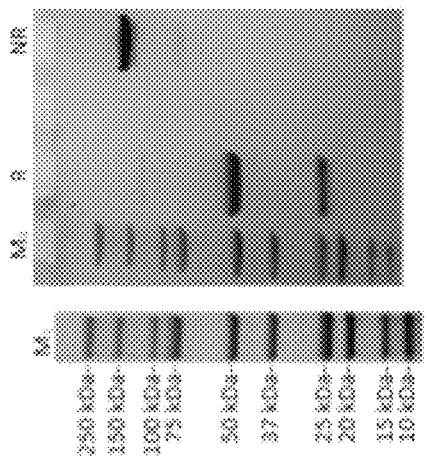
Figure 5C:
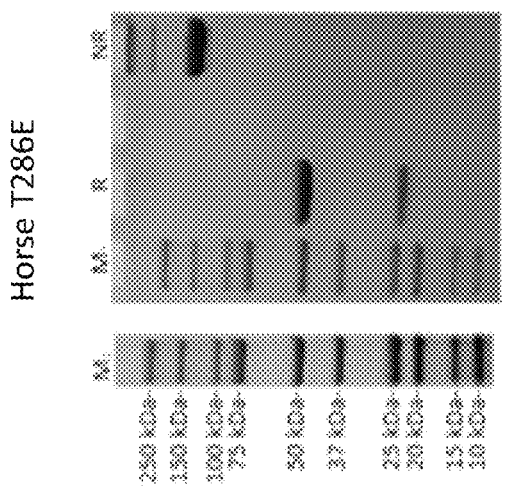
FIGS. 5A-5J show the purity of the equine antibodies with the Fc variants determined by scanning densitometry of Coomassie blue-stained SDS/PAGE gels. The purity of each antibody was >90%.
Figure 5B:
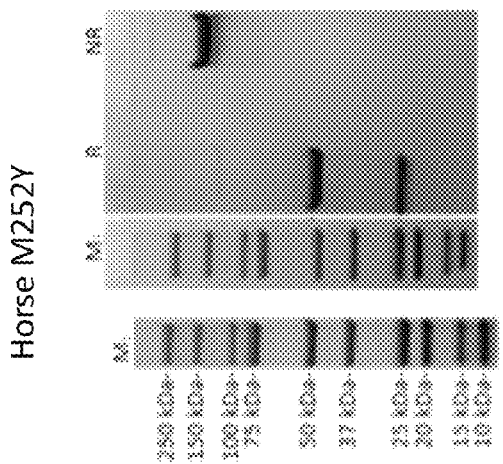
Figure 5A:
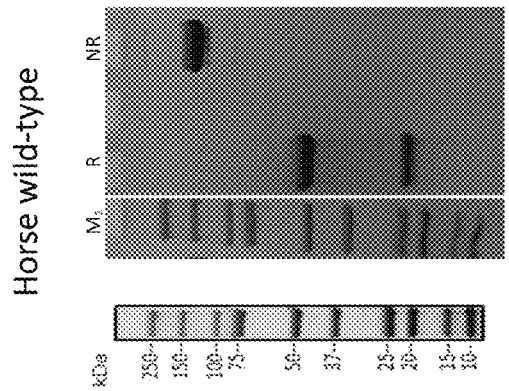
Figure 5F:
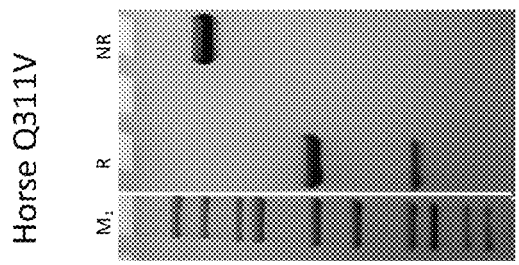
Figure 5E:
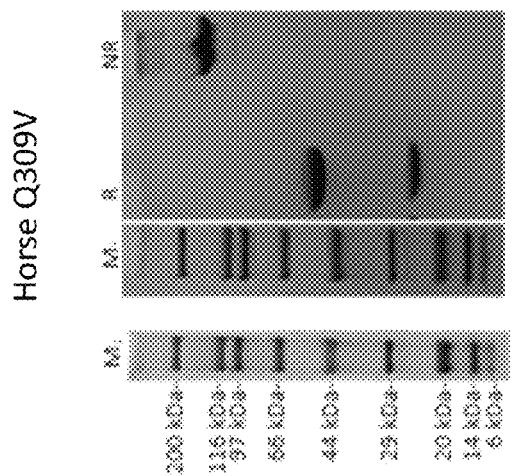
Figure 5D:
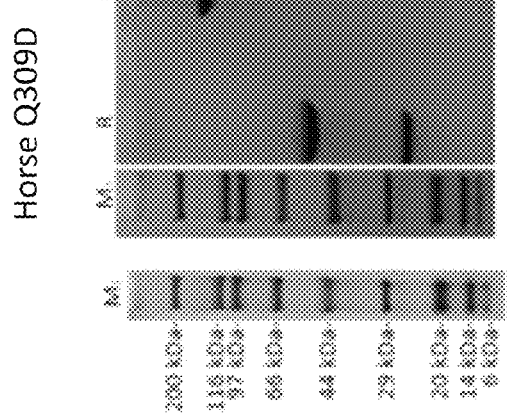
Figures 5G, 5H, 5I:
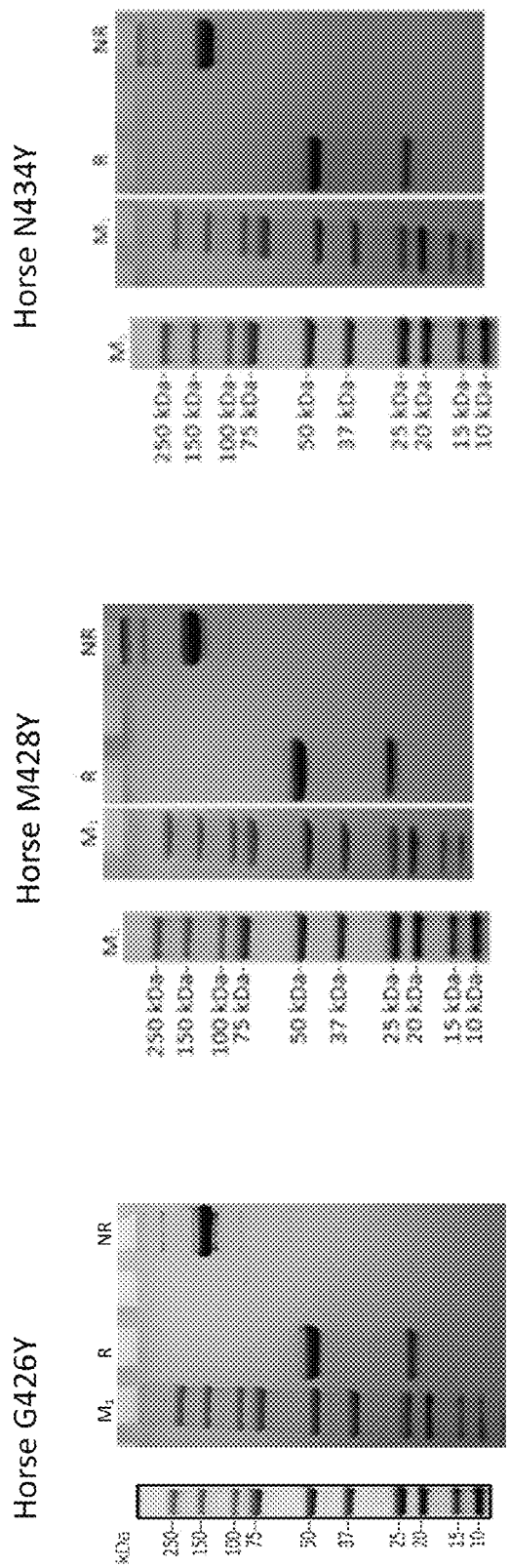
Figure 5J:
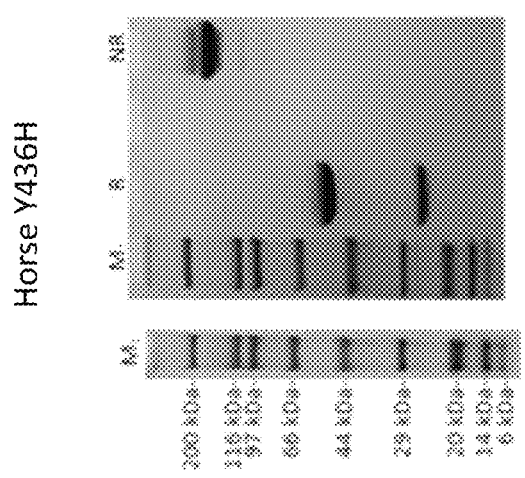
Figure 6A:
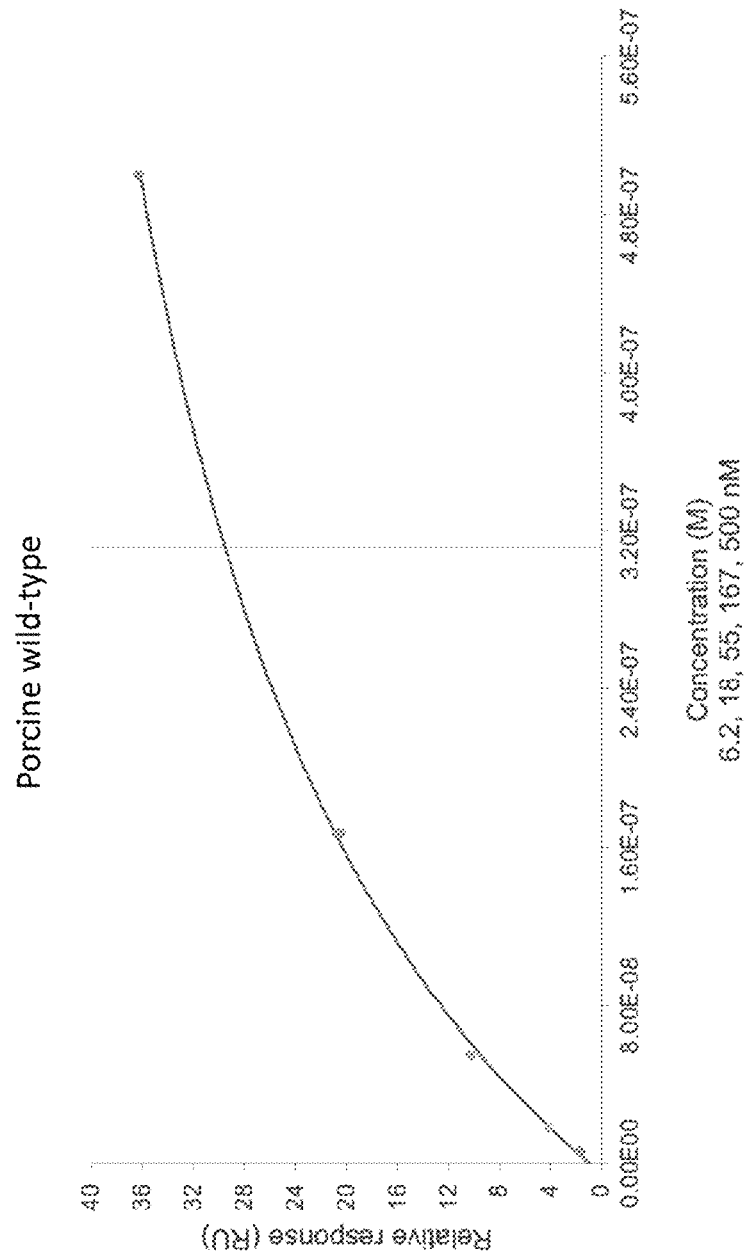
FIGS. 6A-6J show the sensorgrams of kinetic binding data for the porcine IgG variants and wild-type.
Figure 6B:
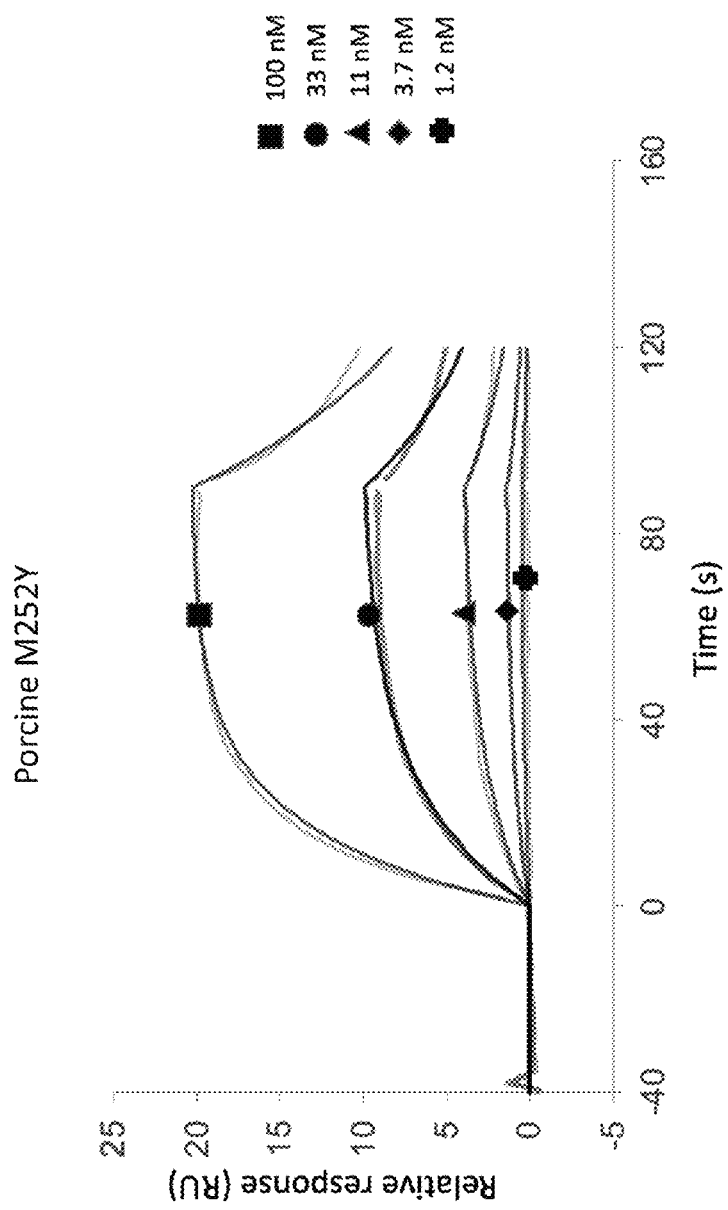
Figure 6C:
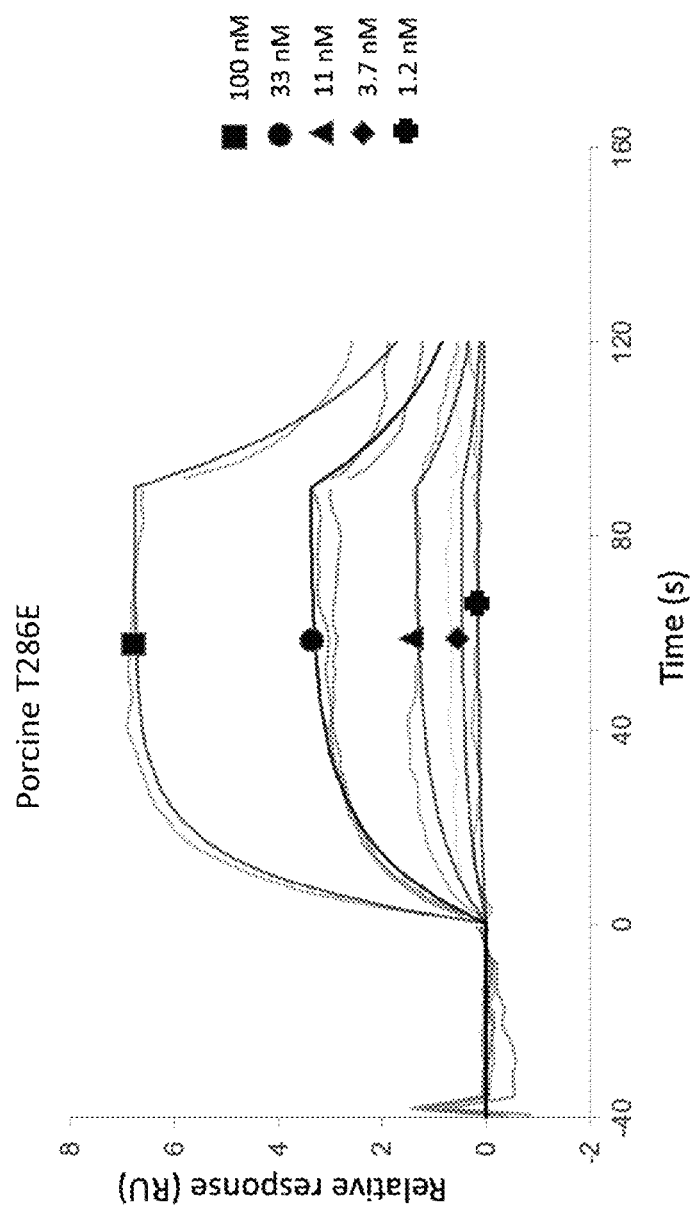
Figure 6D:
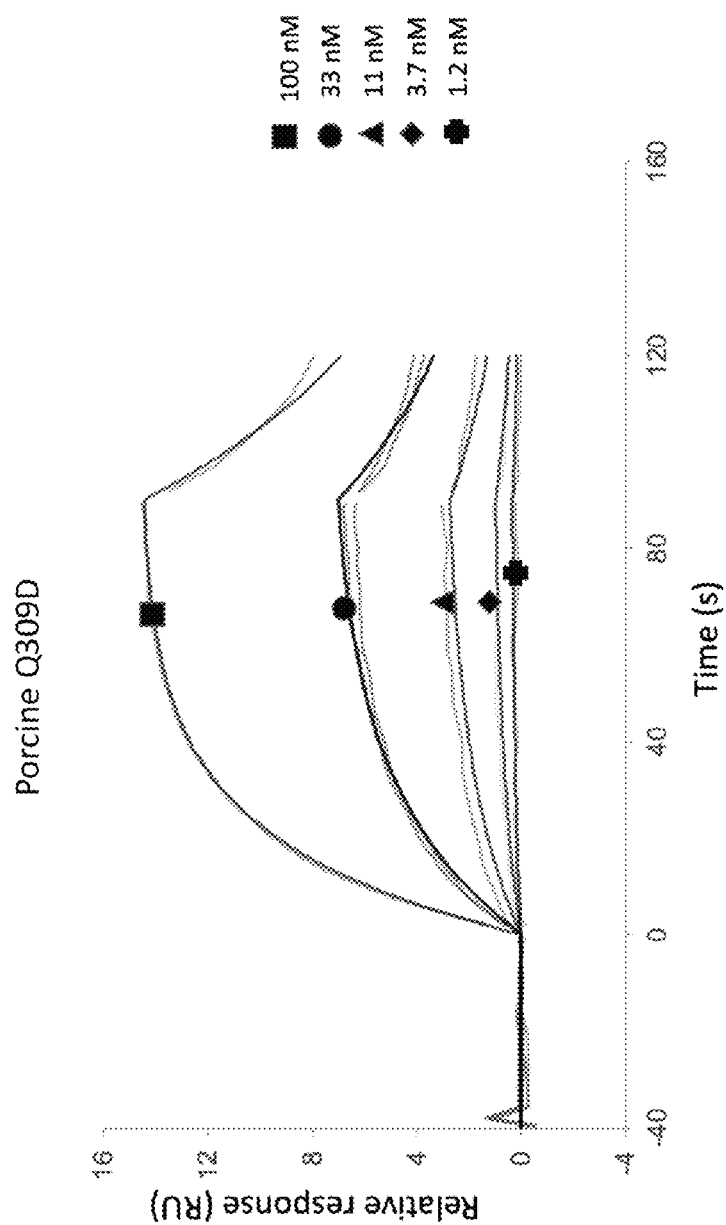
Figure 6E:
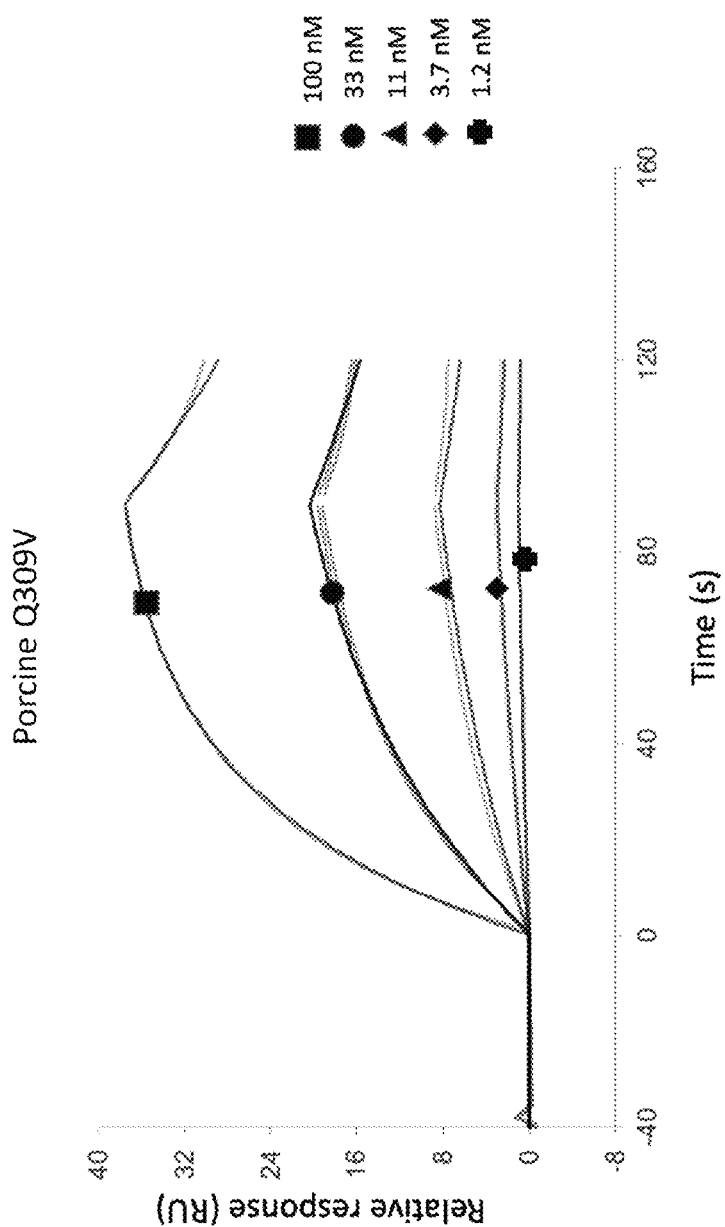
Figure 6F:
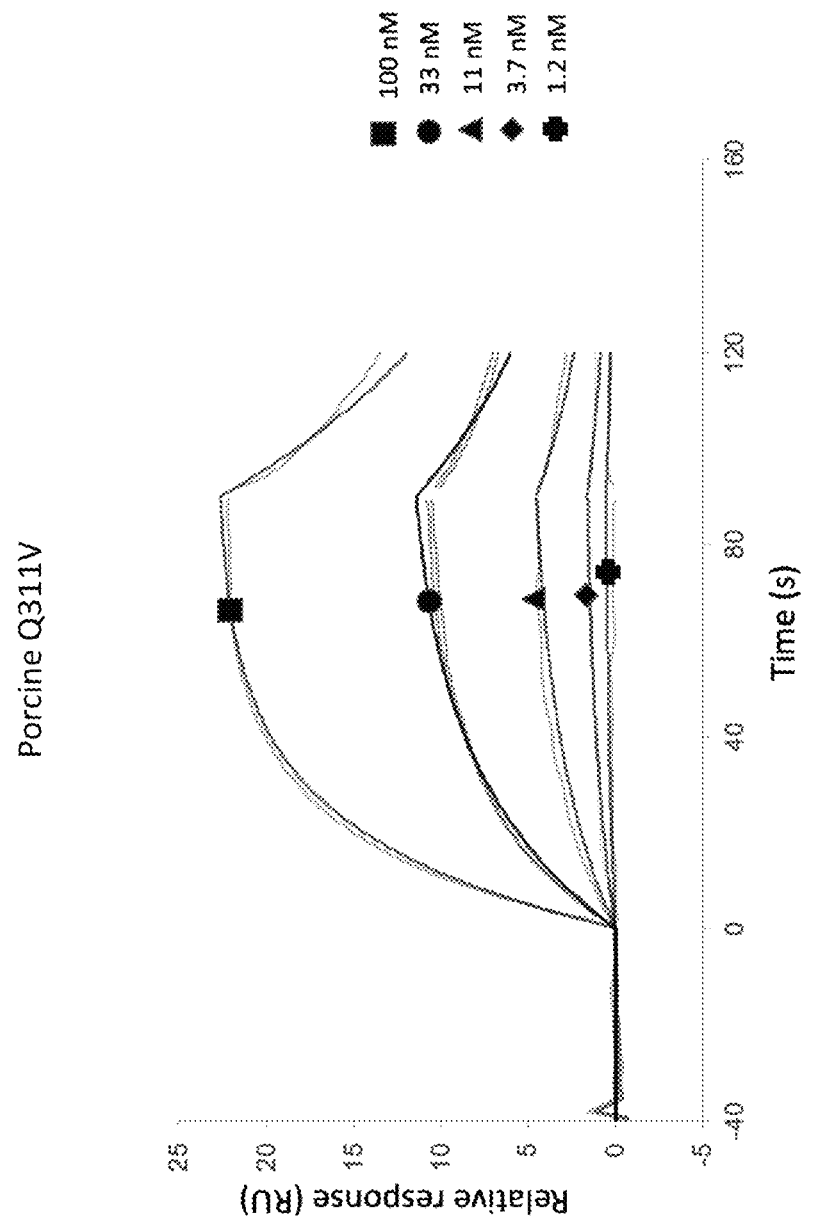
Figure 6G:
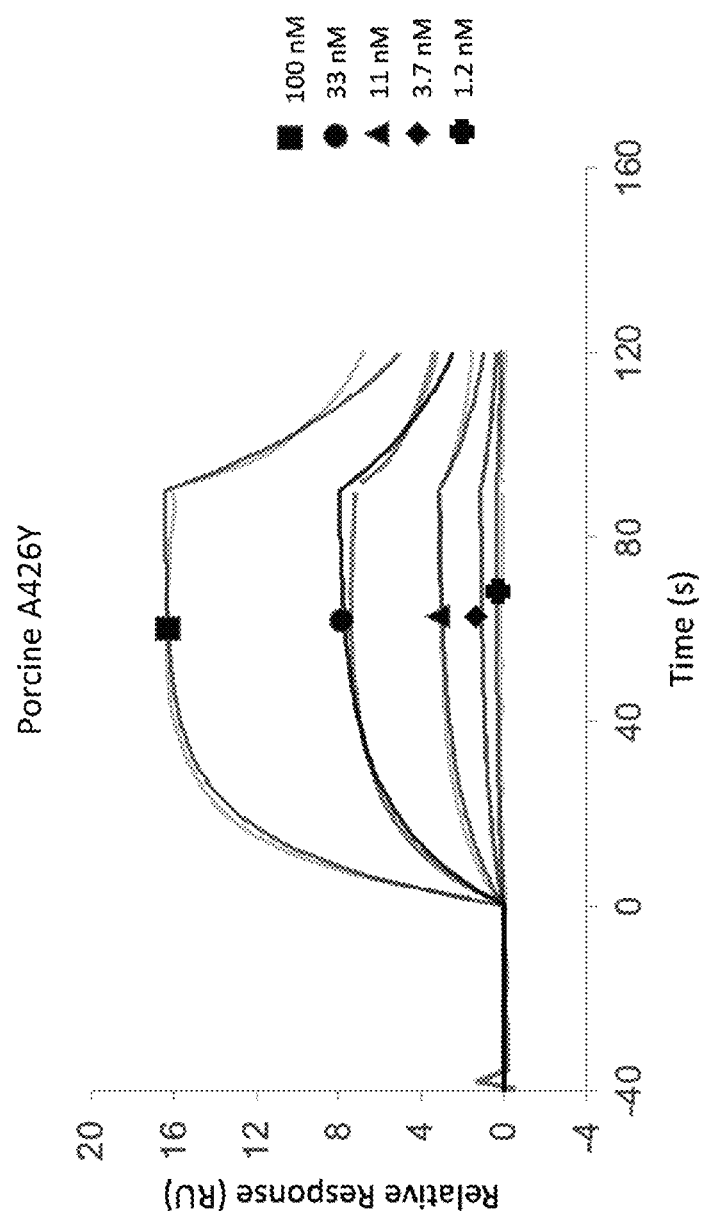
Figure 6H:
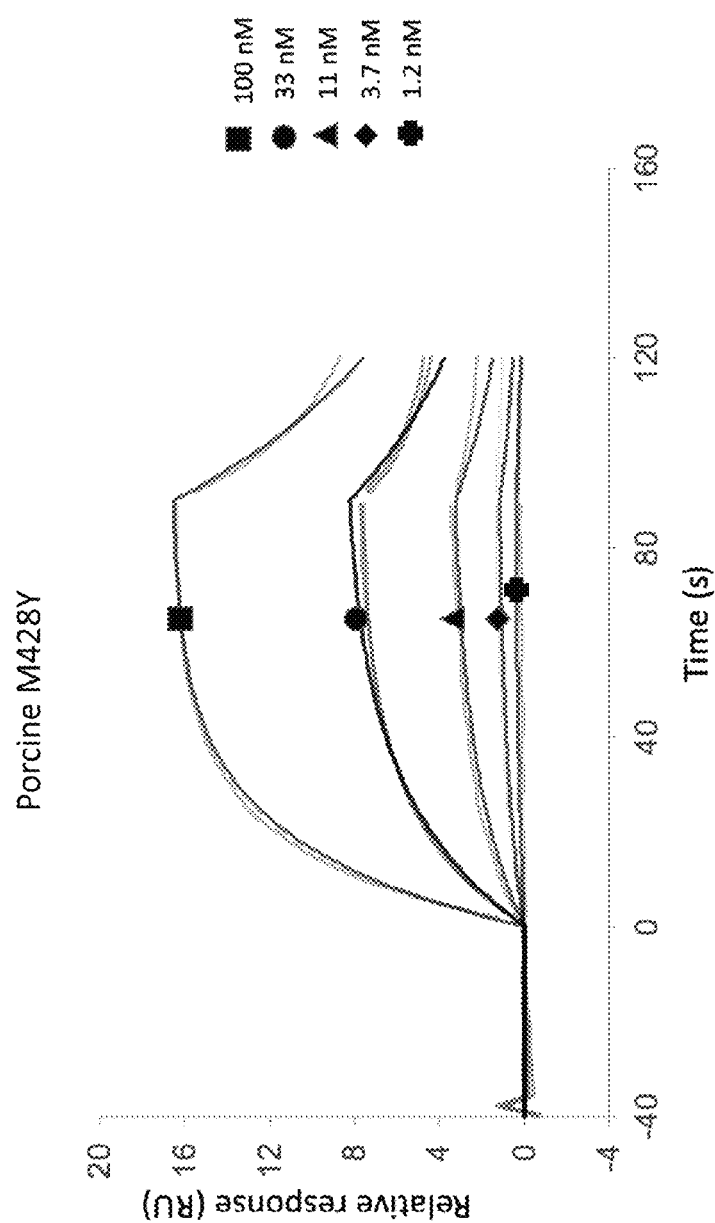
Figure 6I:
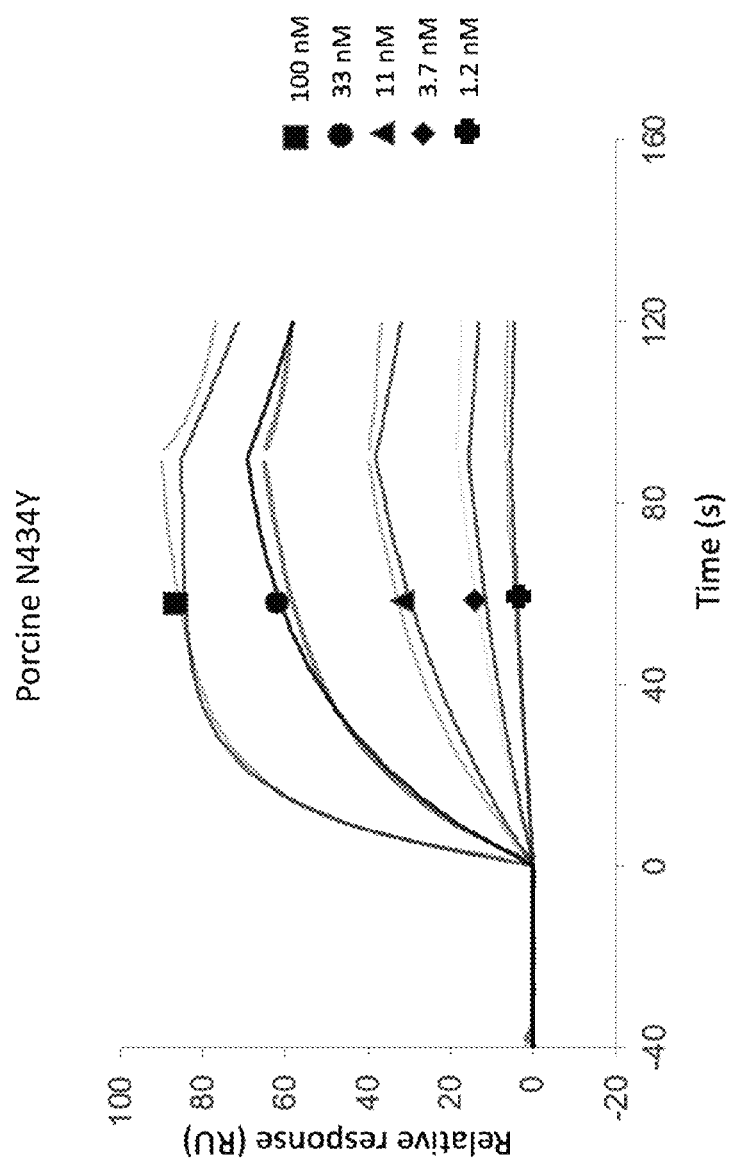
Figure 6J:
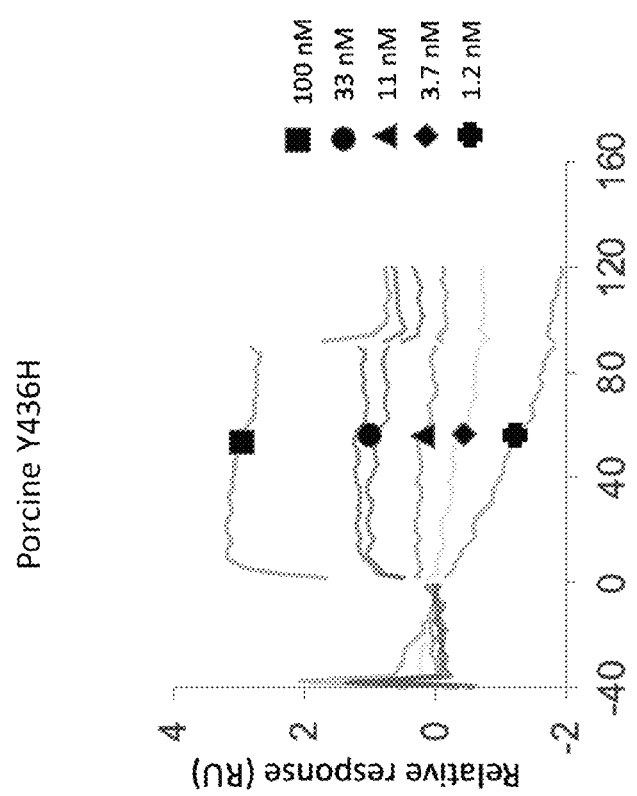
Figure 7A:
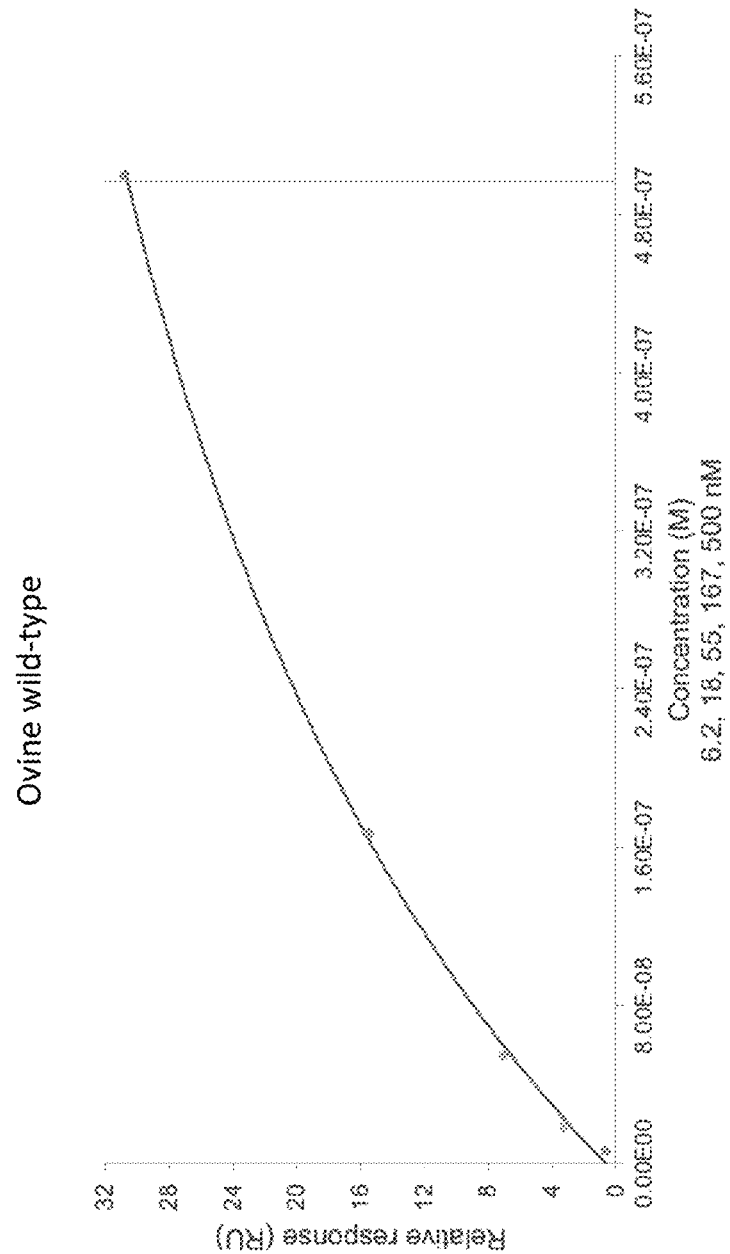
Figure 7B:
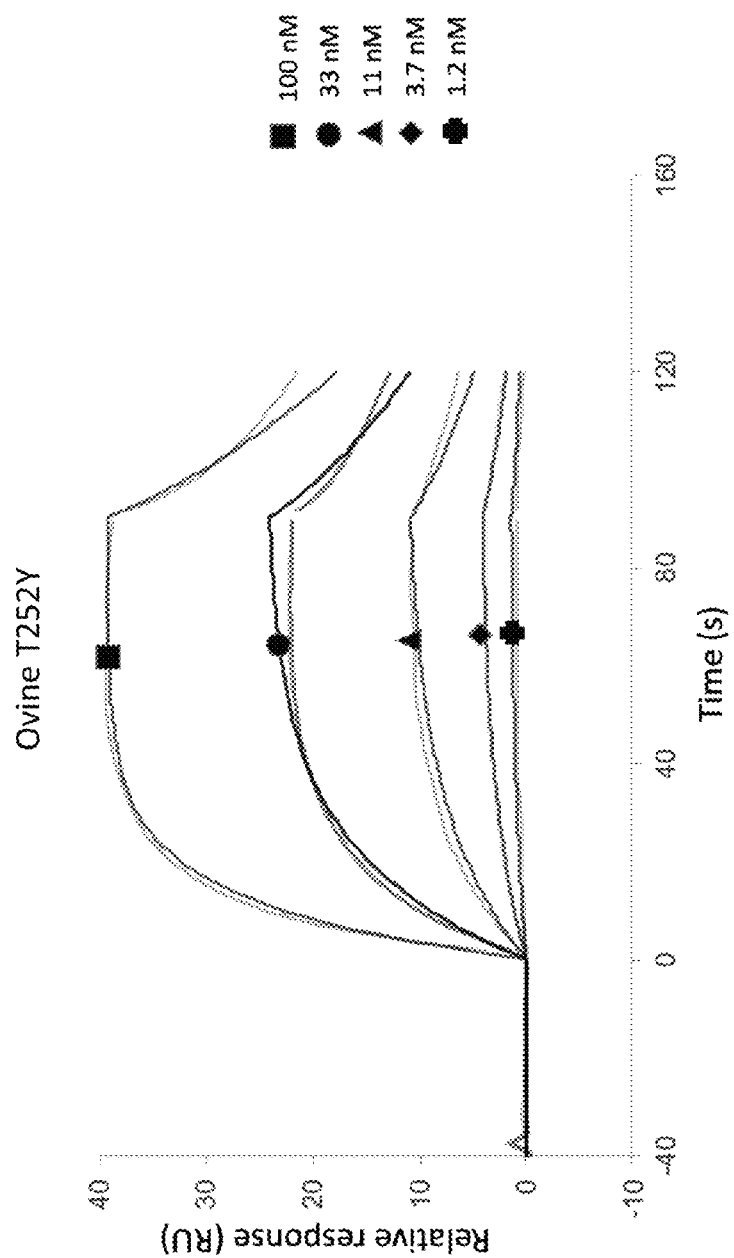
Figure 7C:
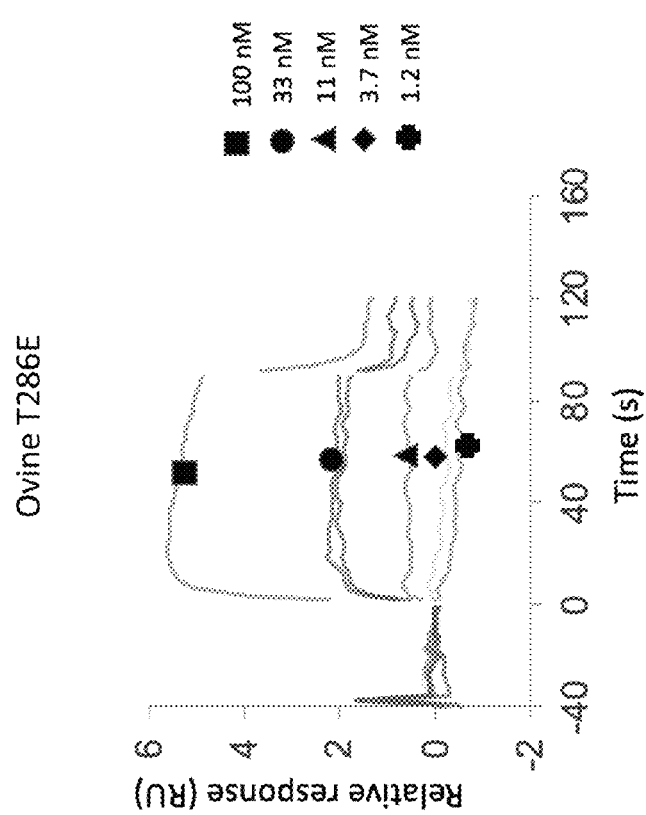
Figure 7D:
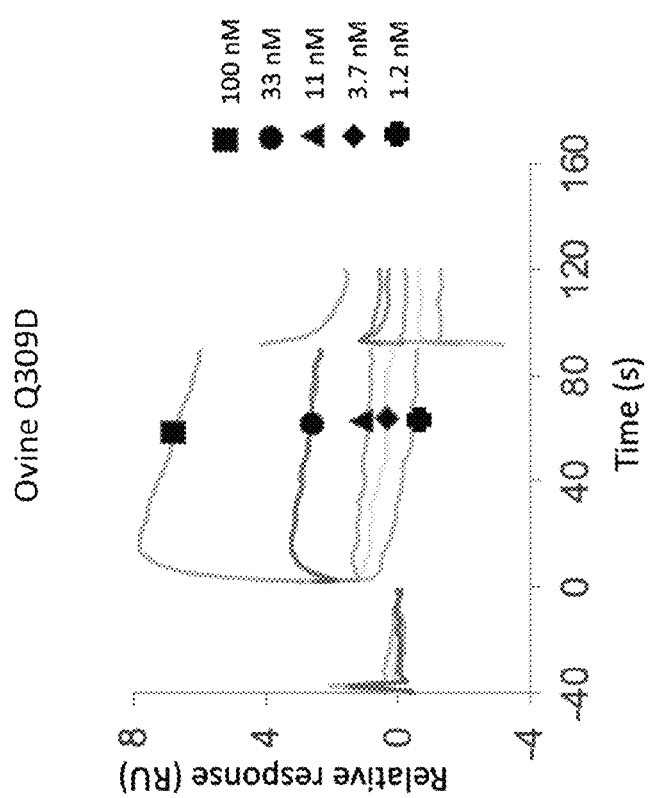
Figure 7E:
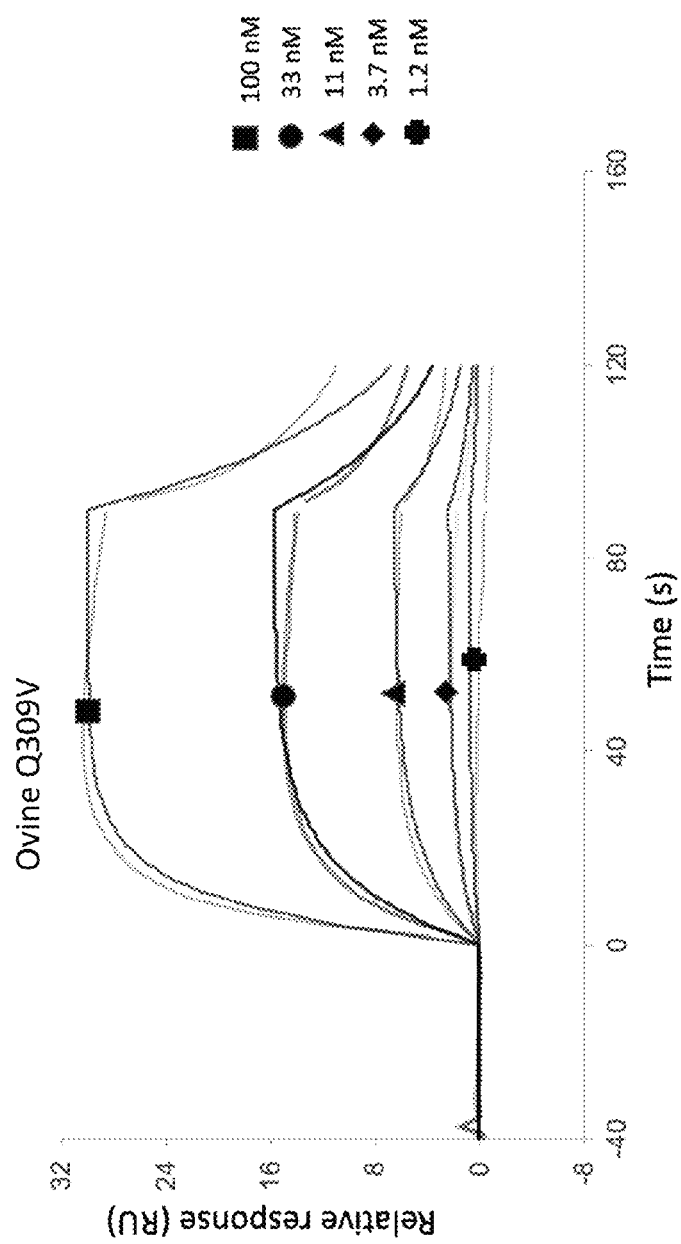
Figure 7F:
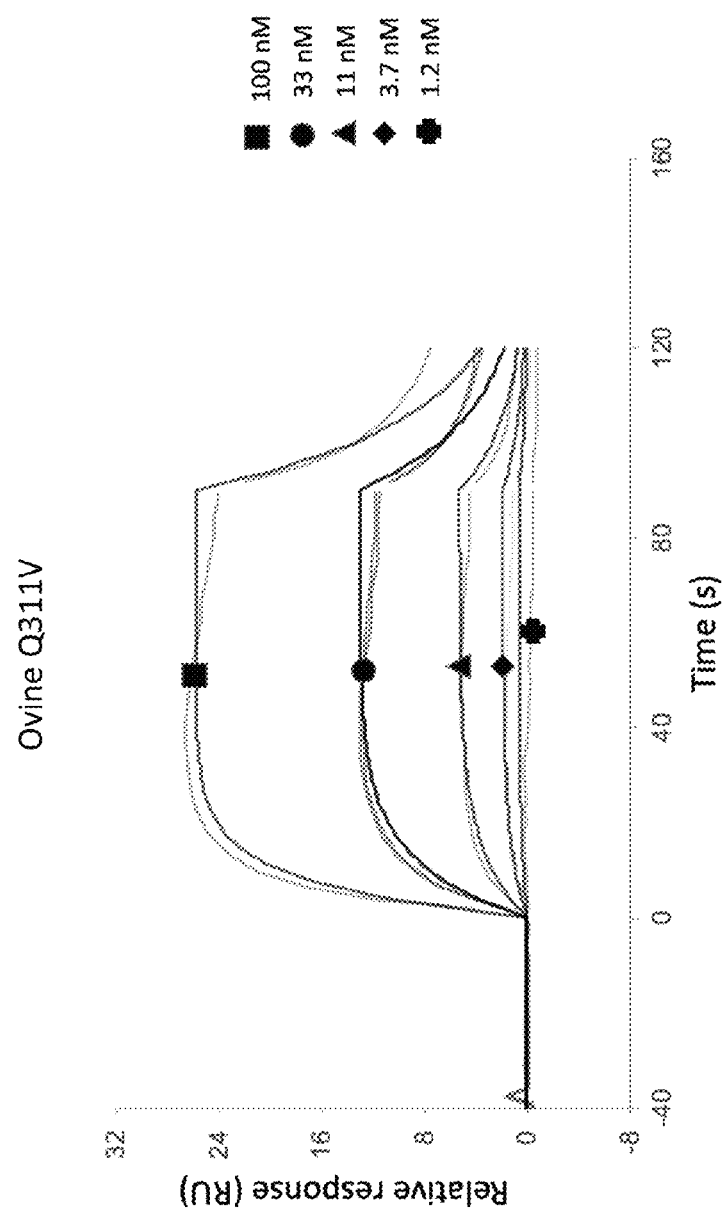
Figure 7G:
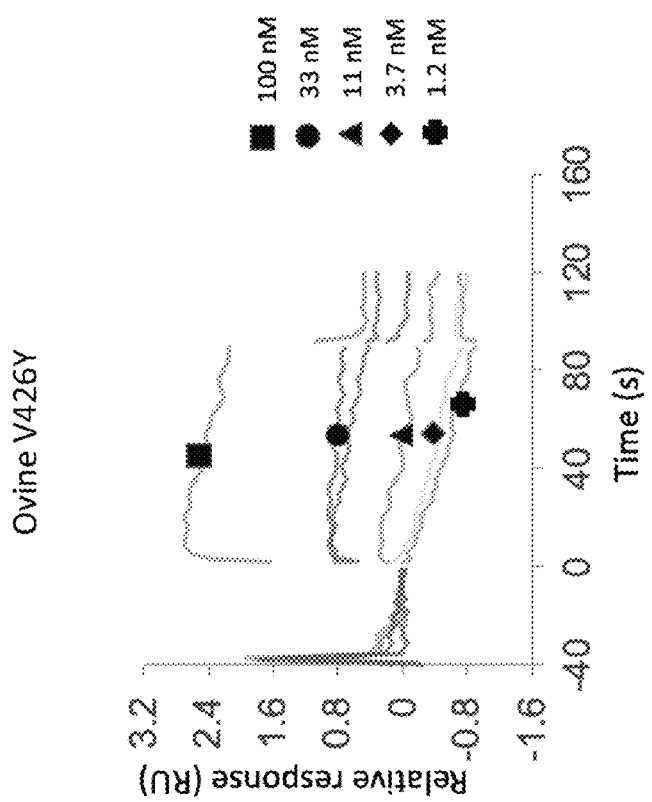
Figure 7I:
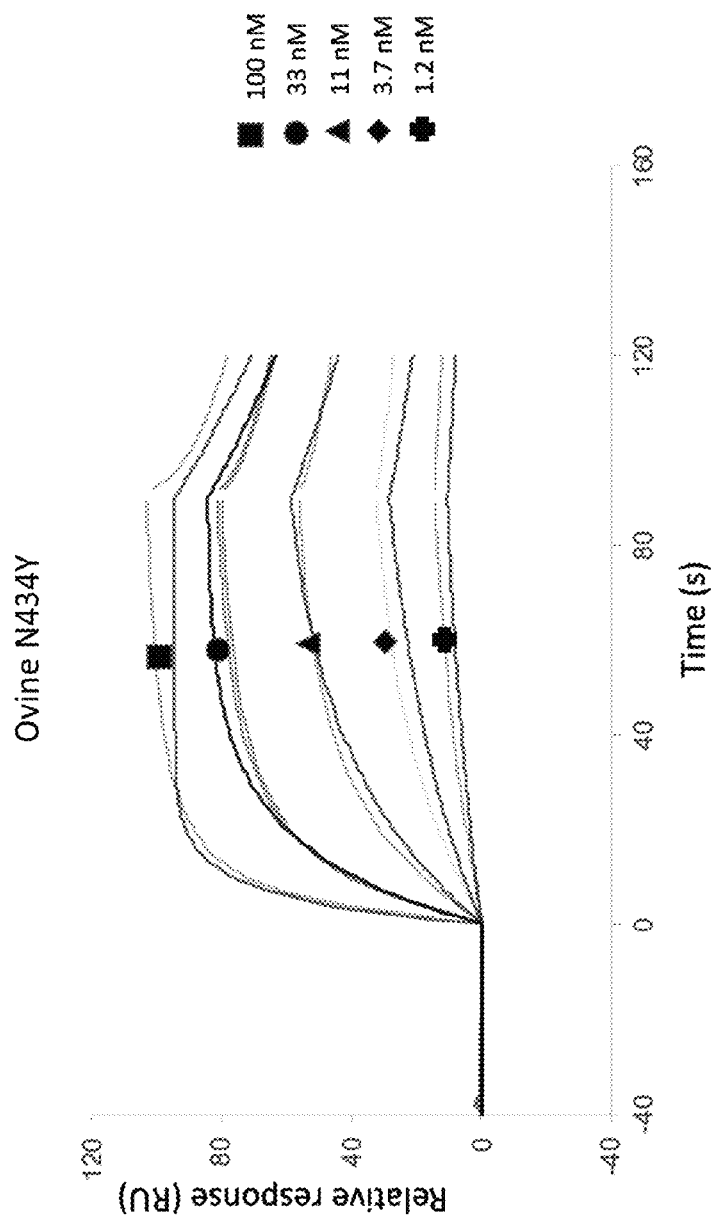
Figure 7J:
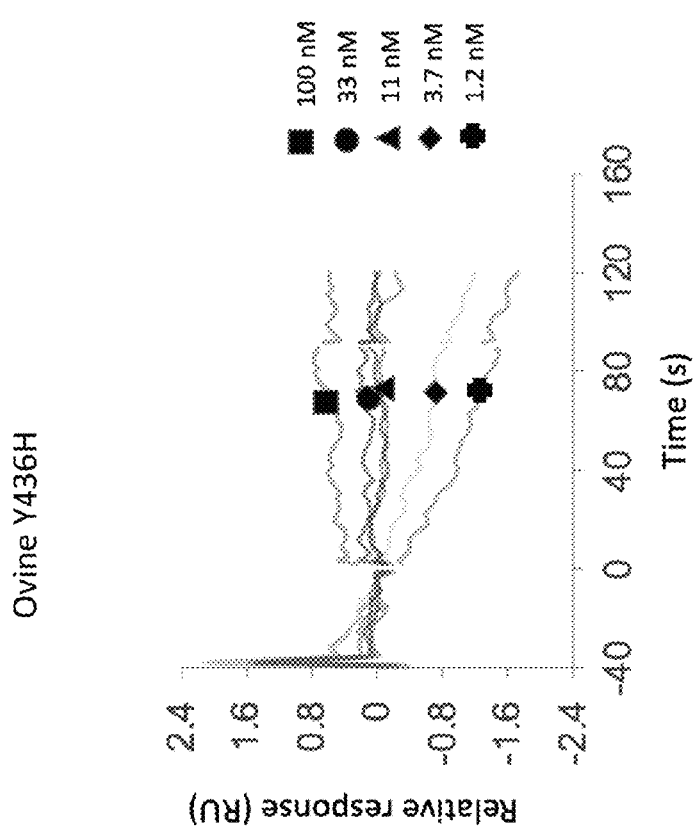
Figure 8A:
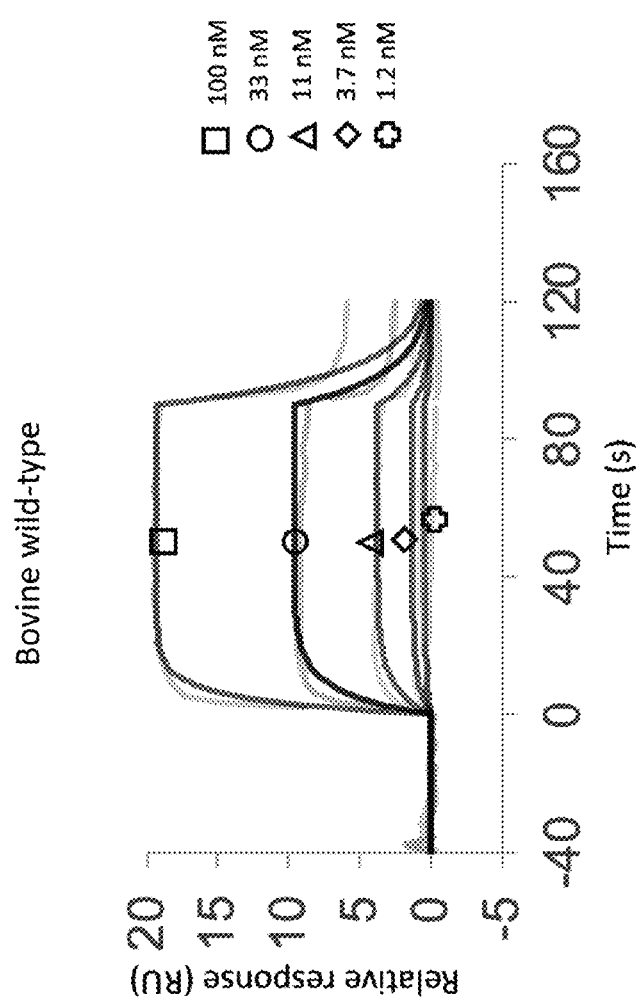
FIGS. 8A-8J show the sensorgrams of kinetic binding data for the bovine IgG variants and wild-type.
Figure 8B:
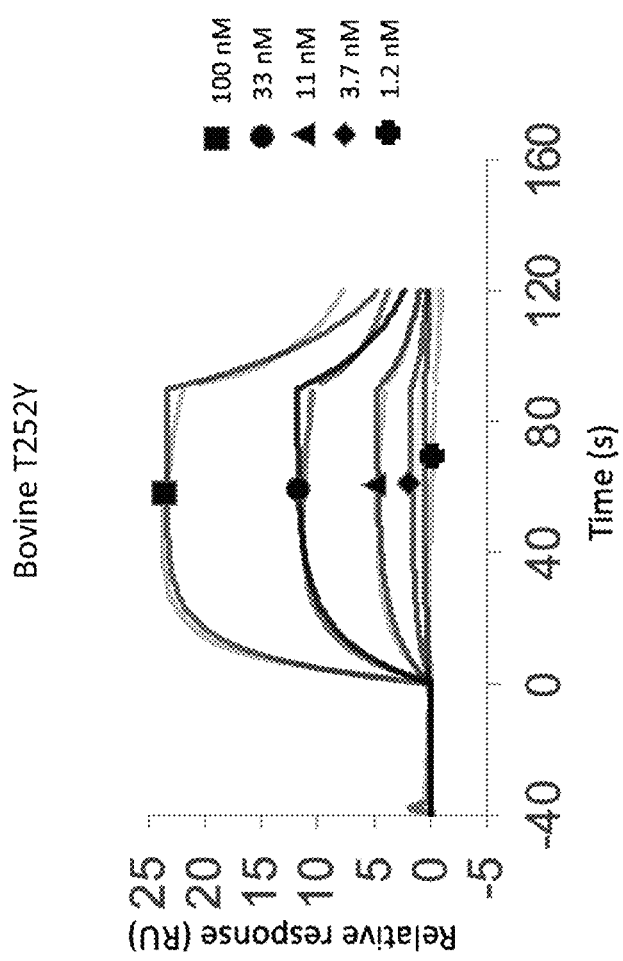
Figure 8C:
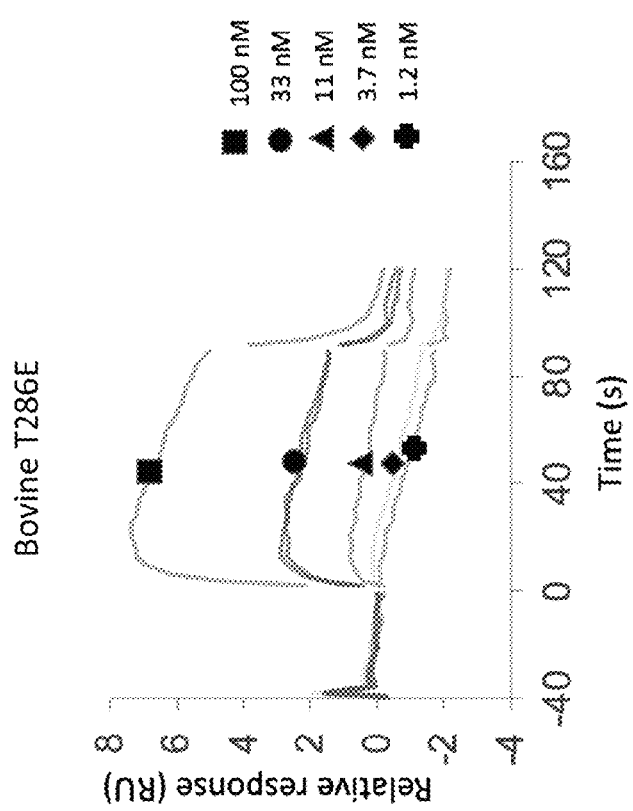
Figure 8D:
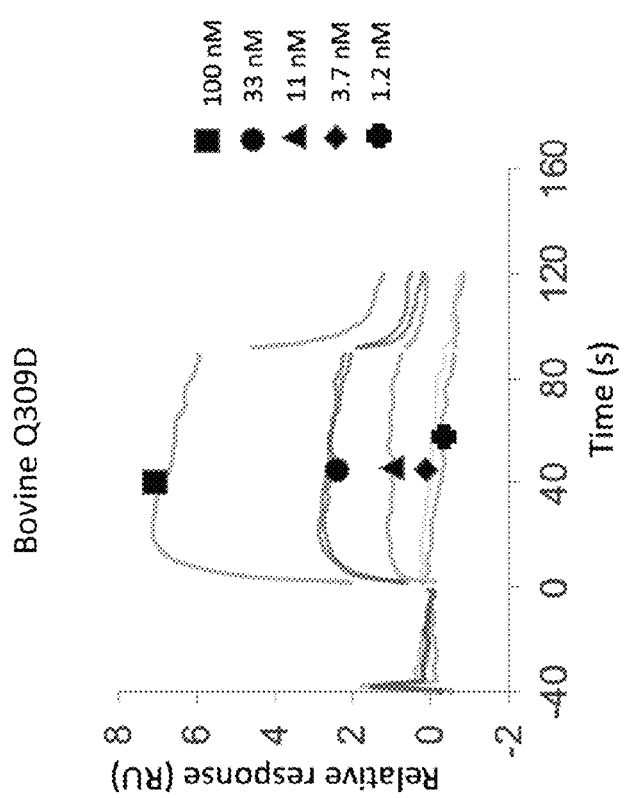
Figure 8E:
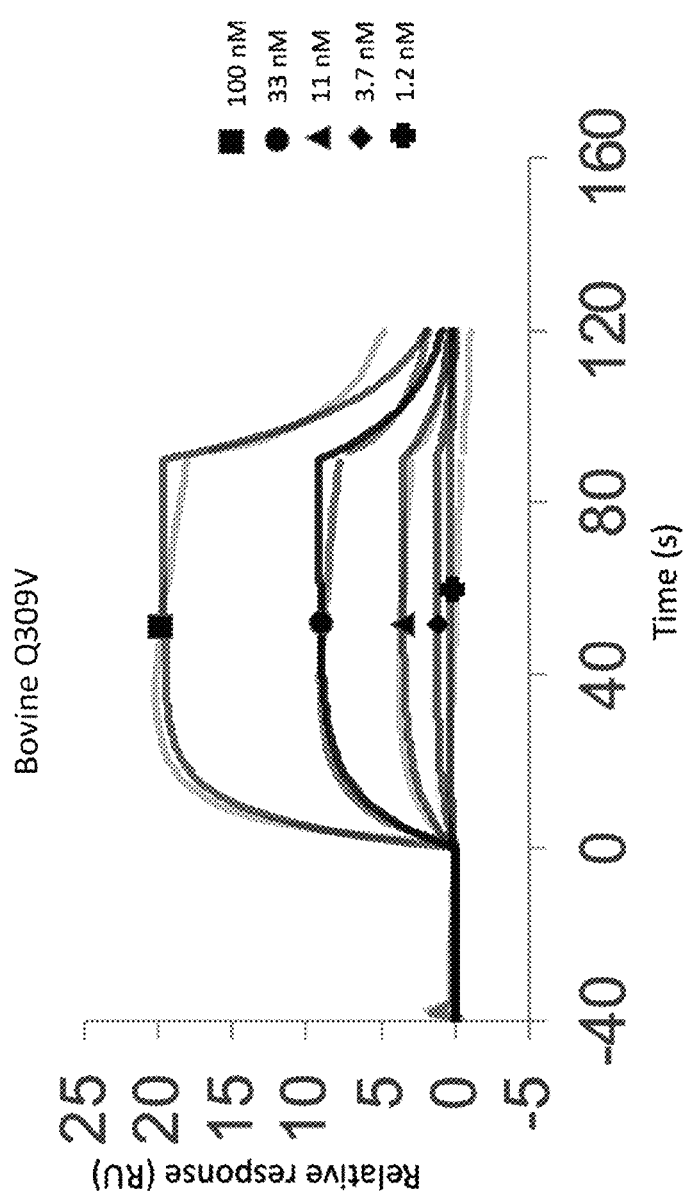
Figure 8F:
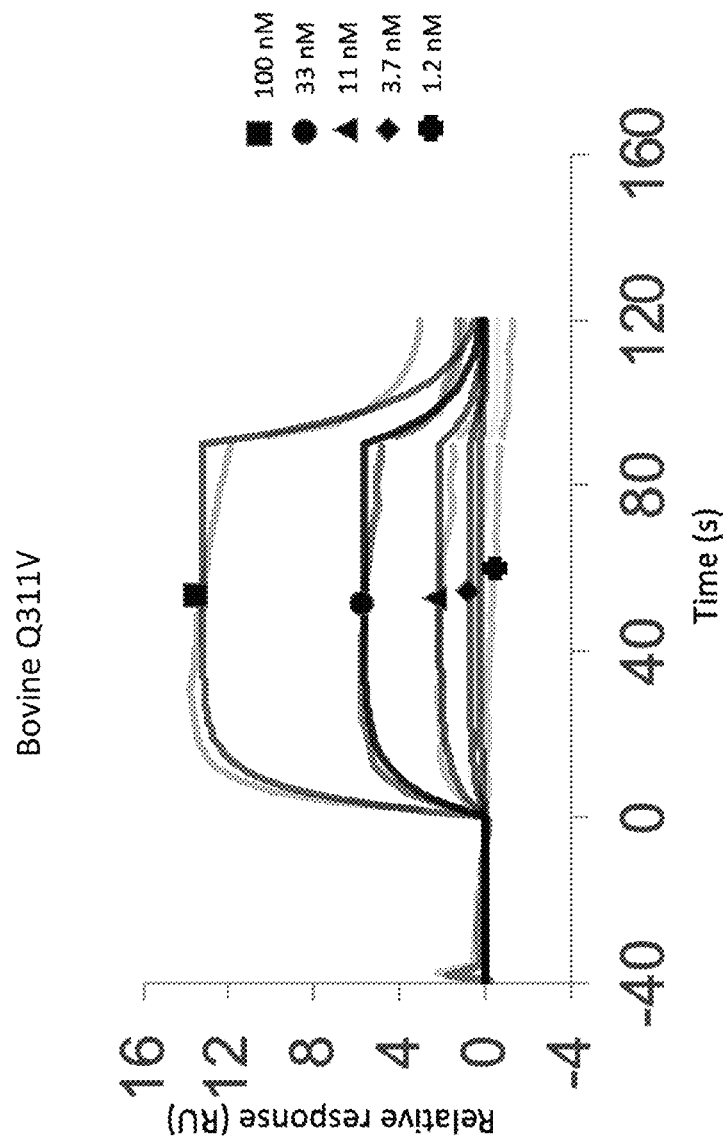
Figure 8G:
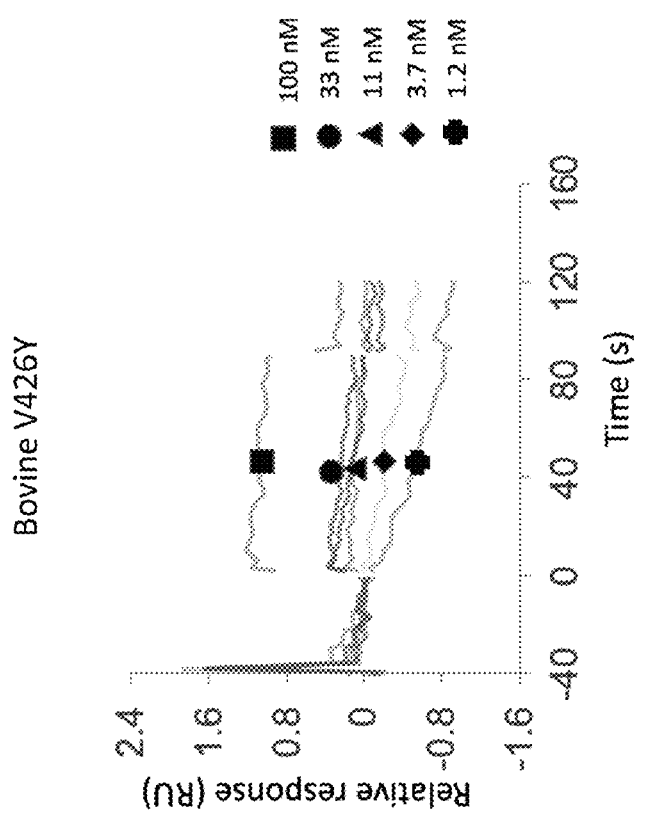
Figure 8H:
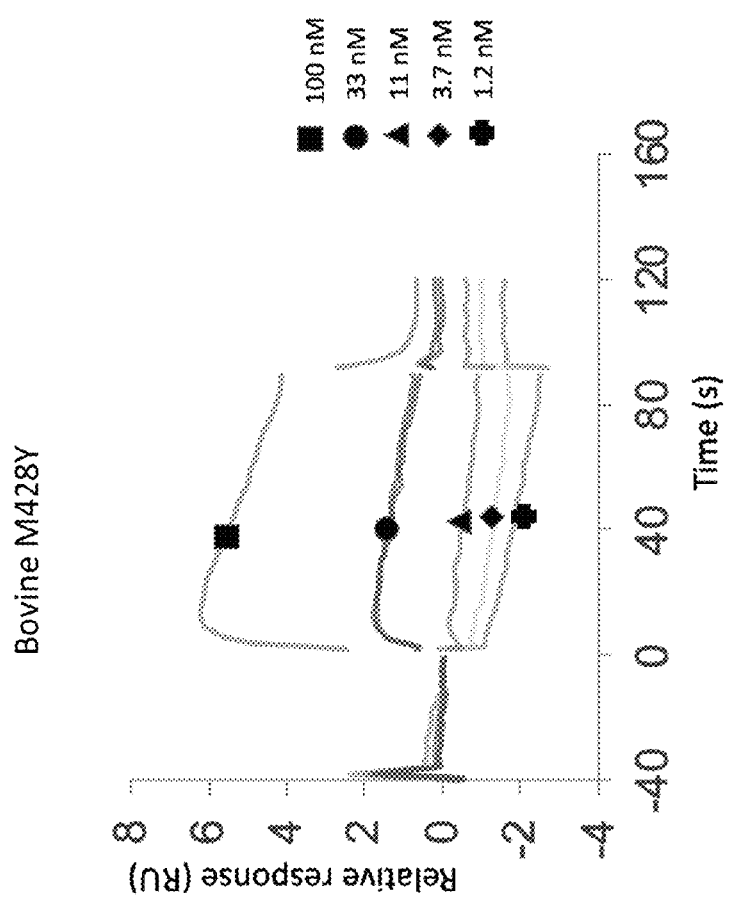
Figure 8I:
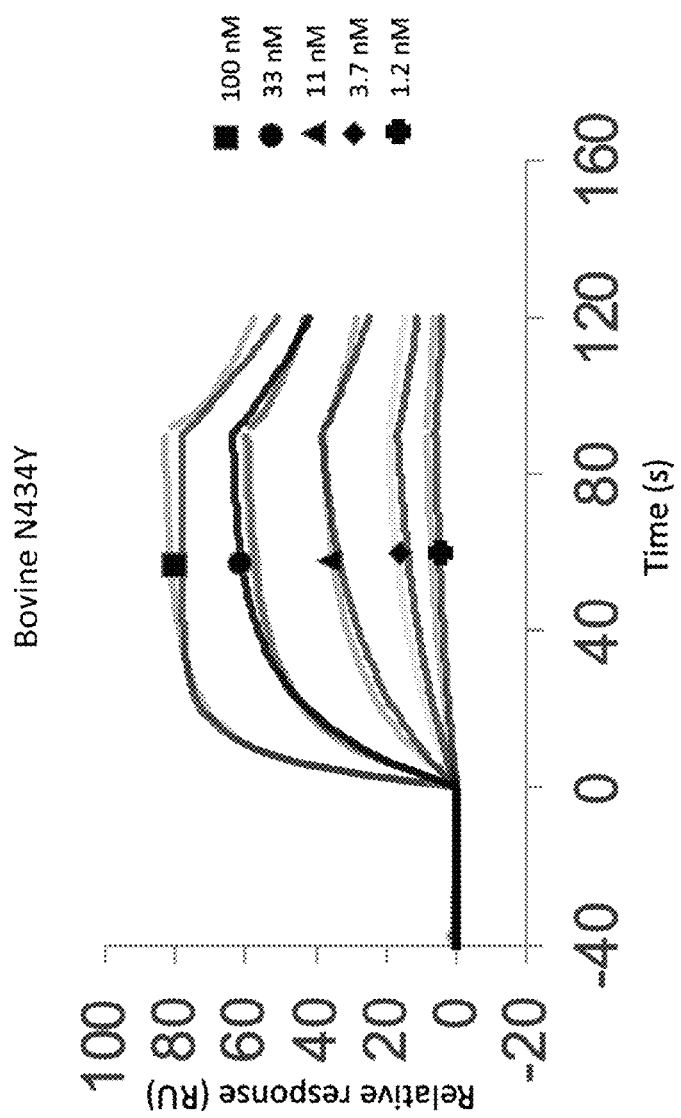
Figure 8J:
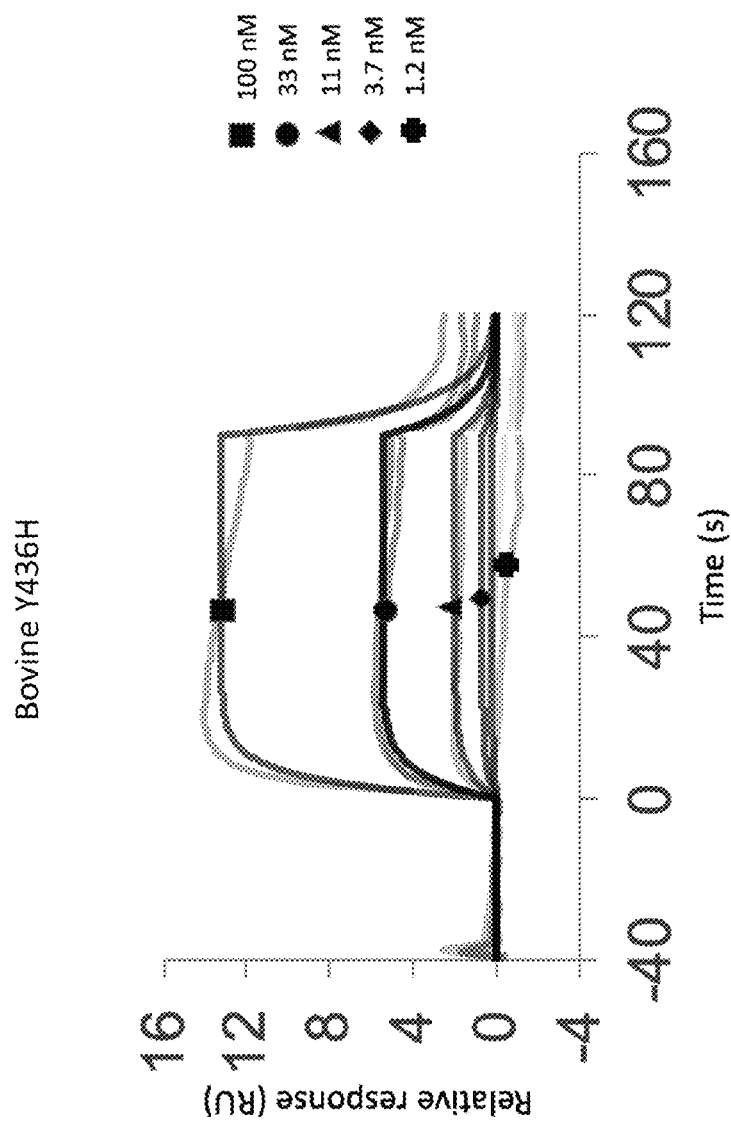
Figure 9A:
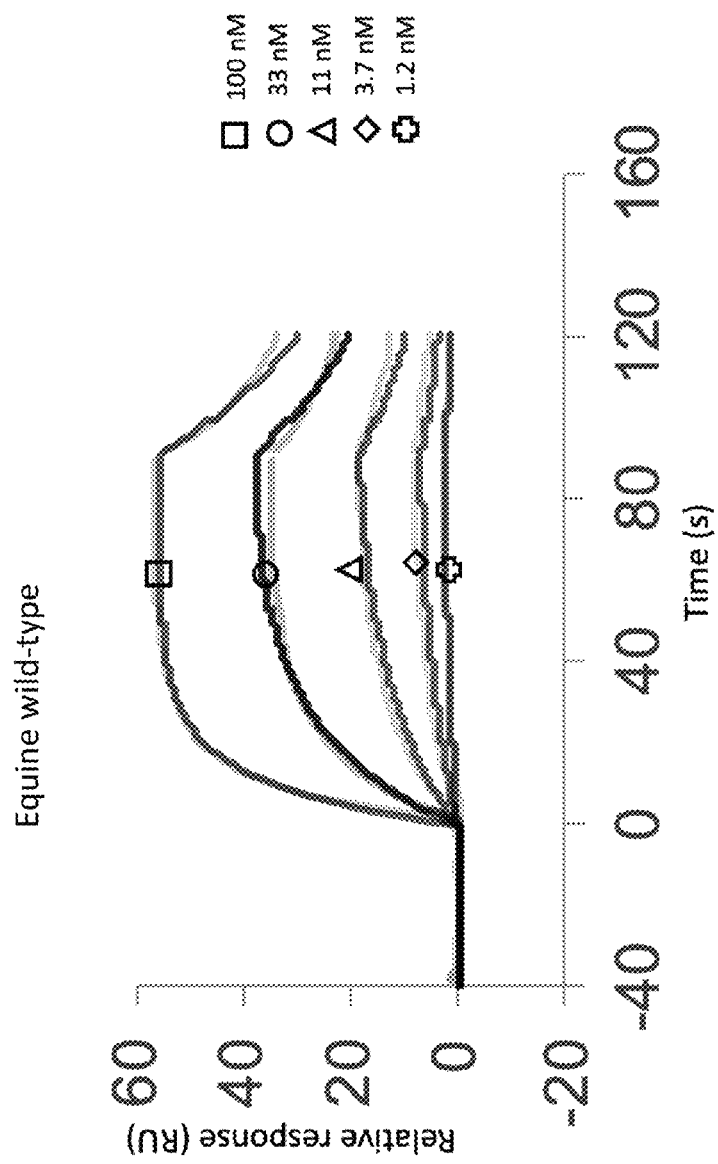
FIGS. 9A-9J show the sensorgrams of kinetic binding data for the equine IgG variants and wild-type.
Figure 9B:
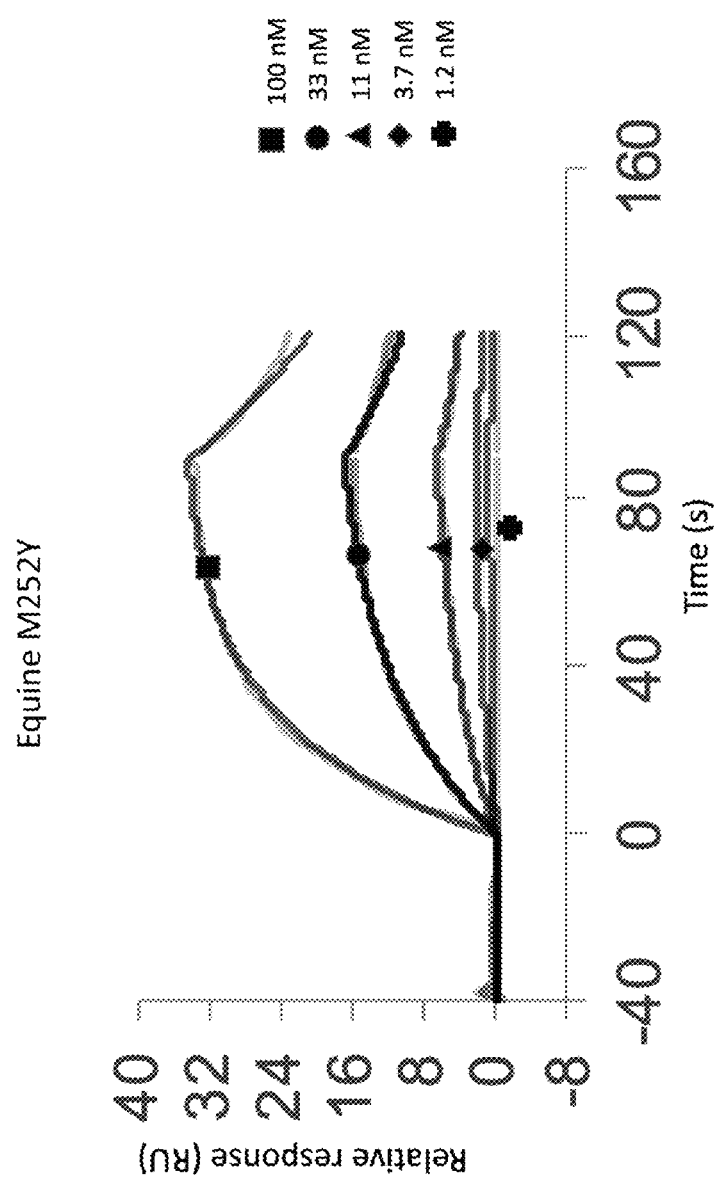
Figure 9C:
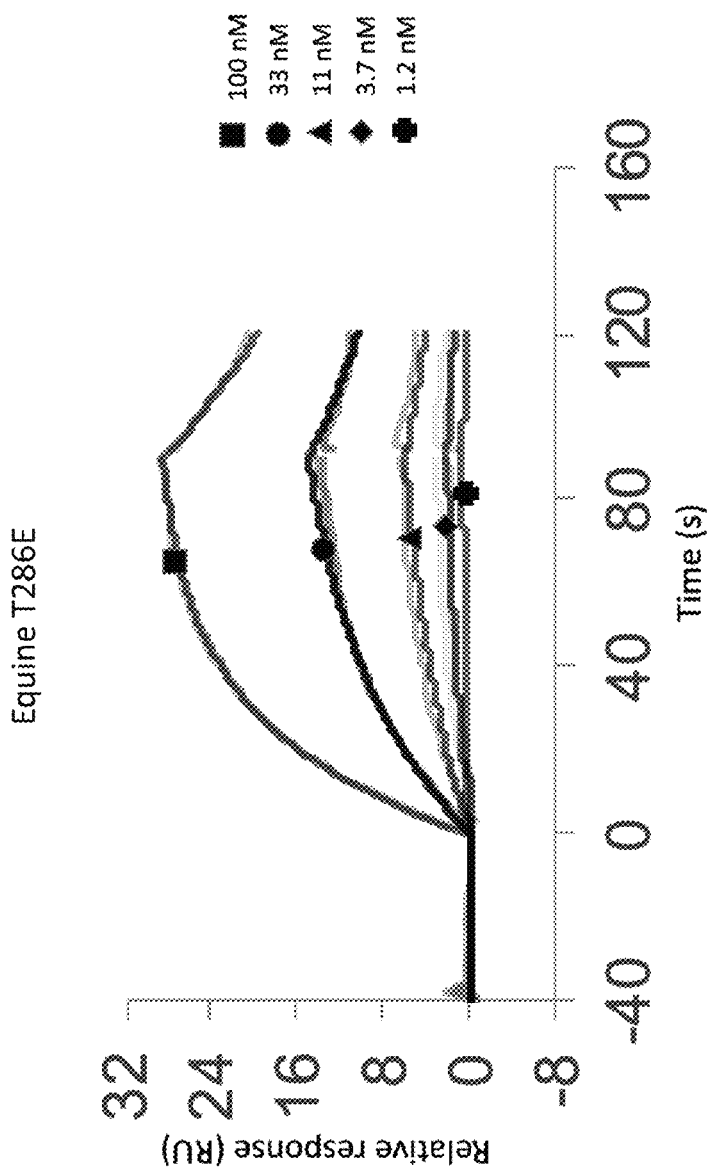
Figure 9D:
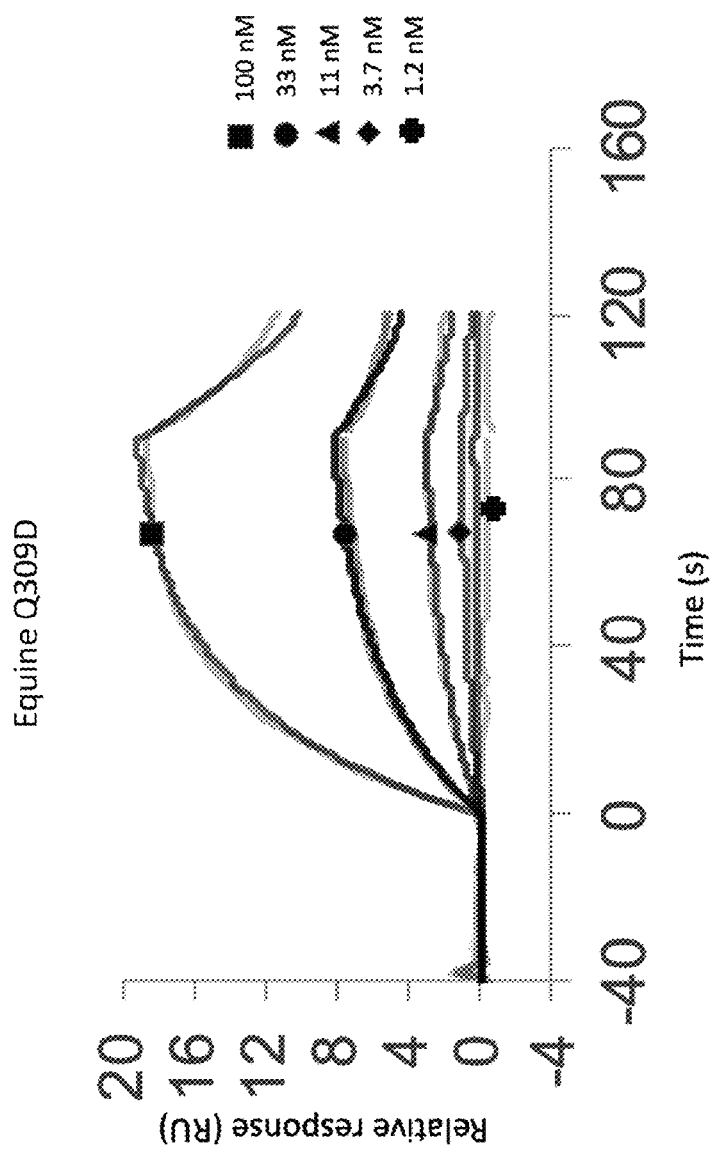
Figure 9E:
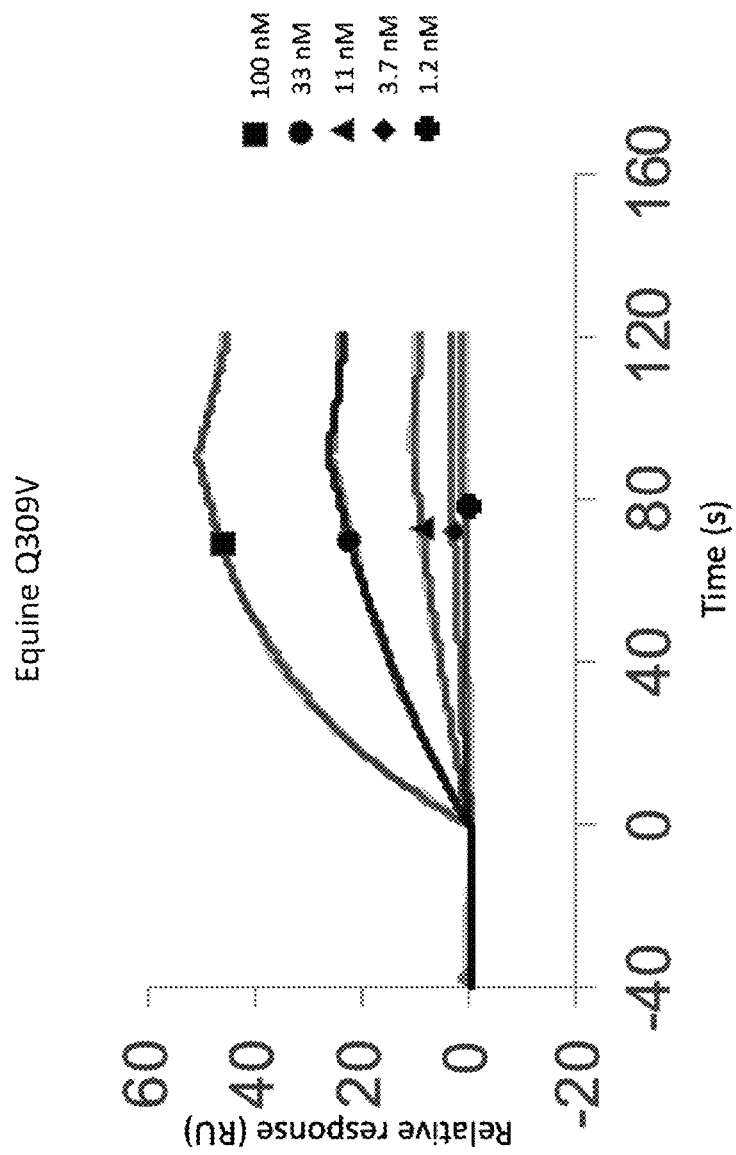
Figure 9F:
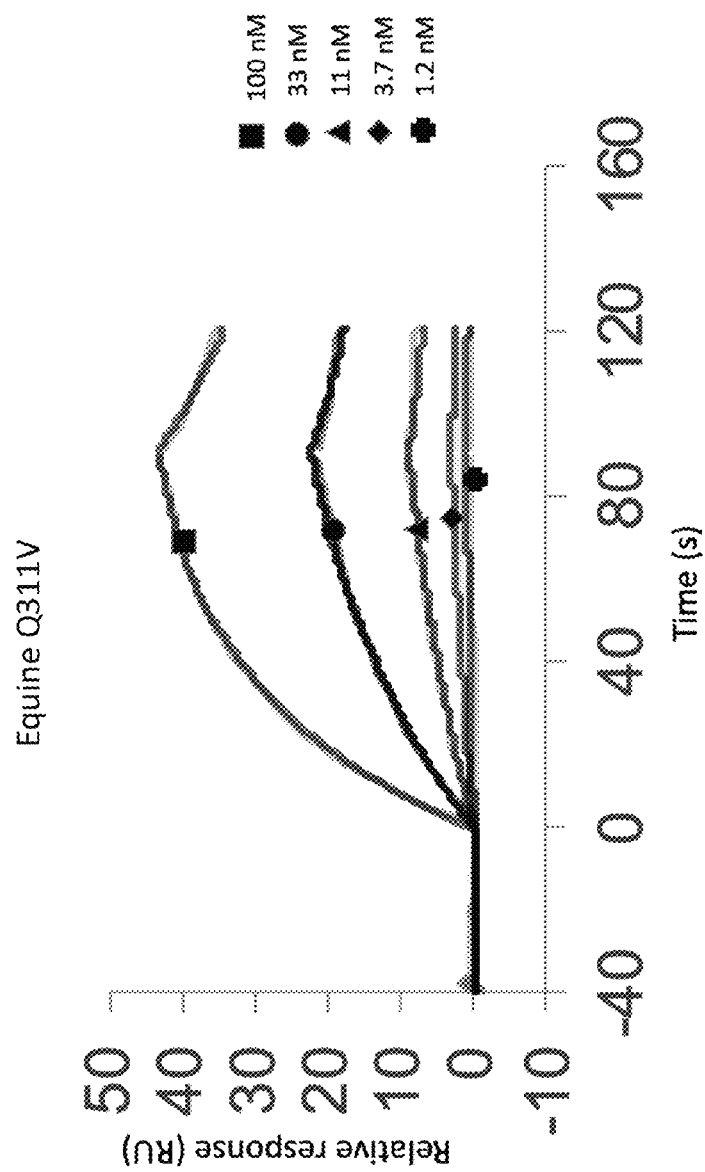
Figure 9G:
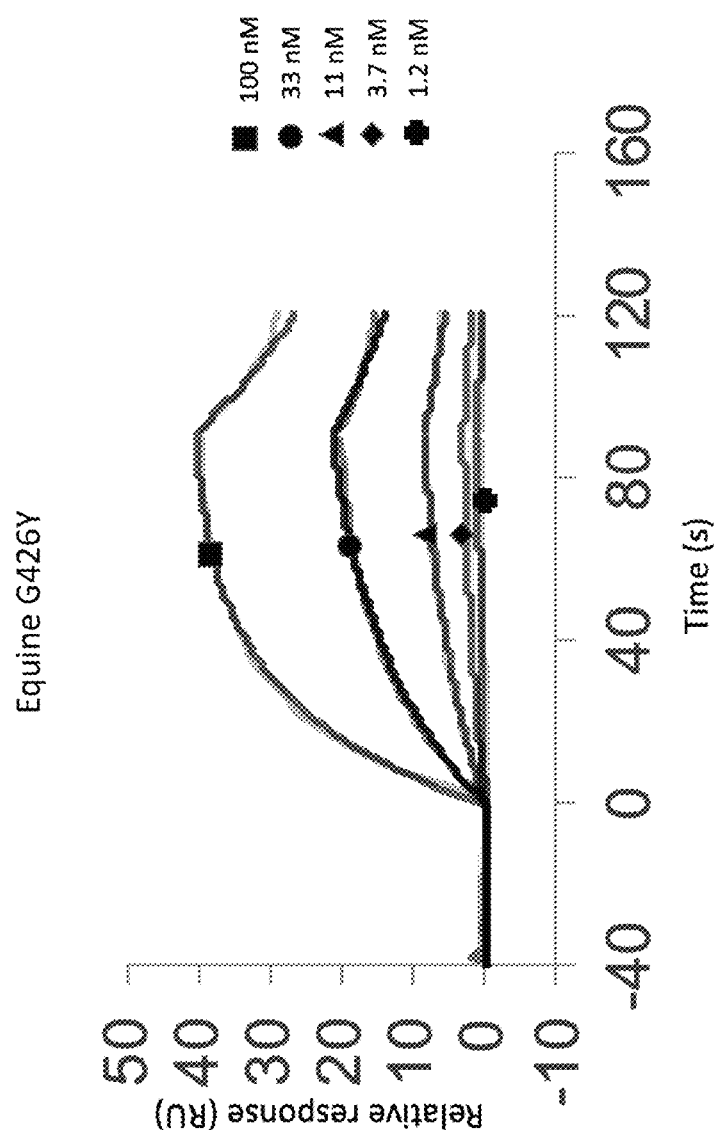
Figure 9H:
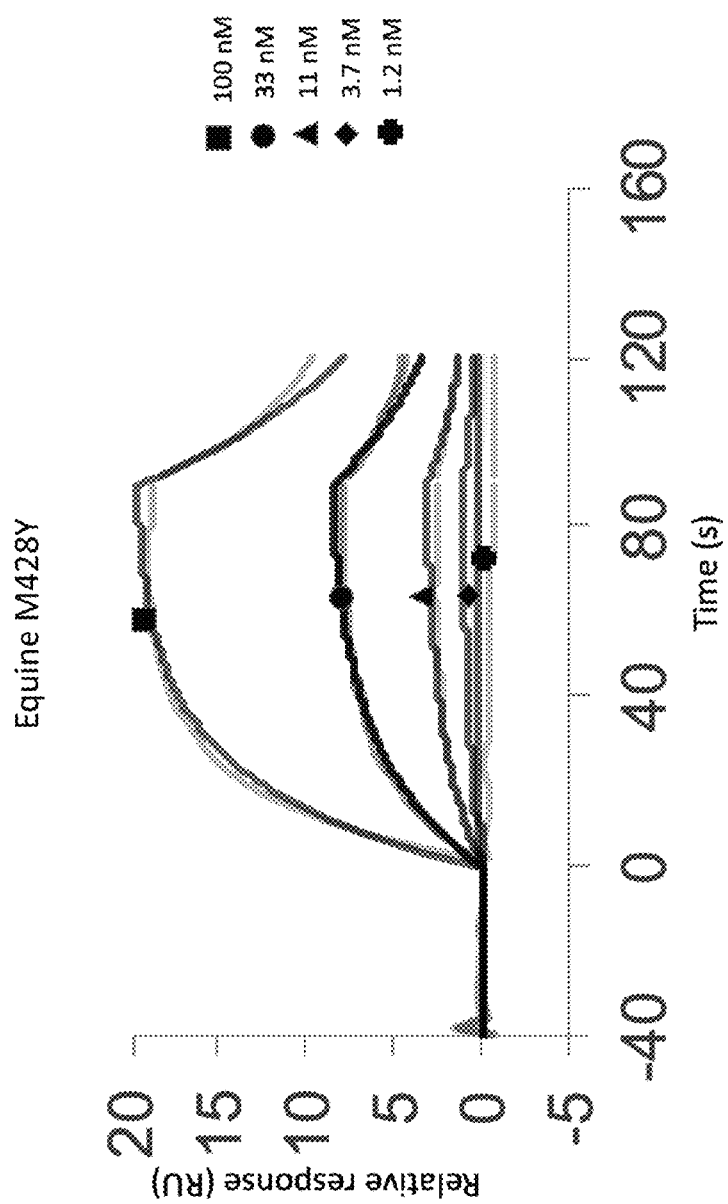
Figure 9I:
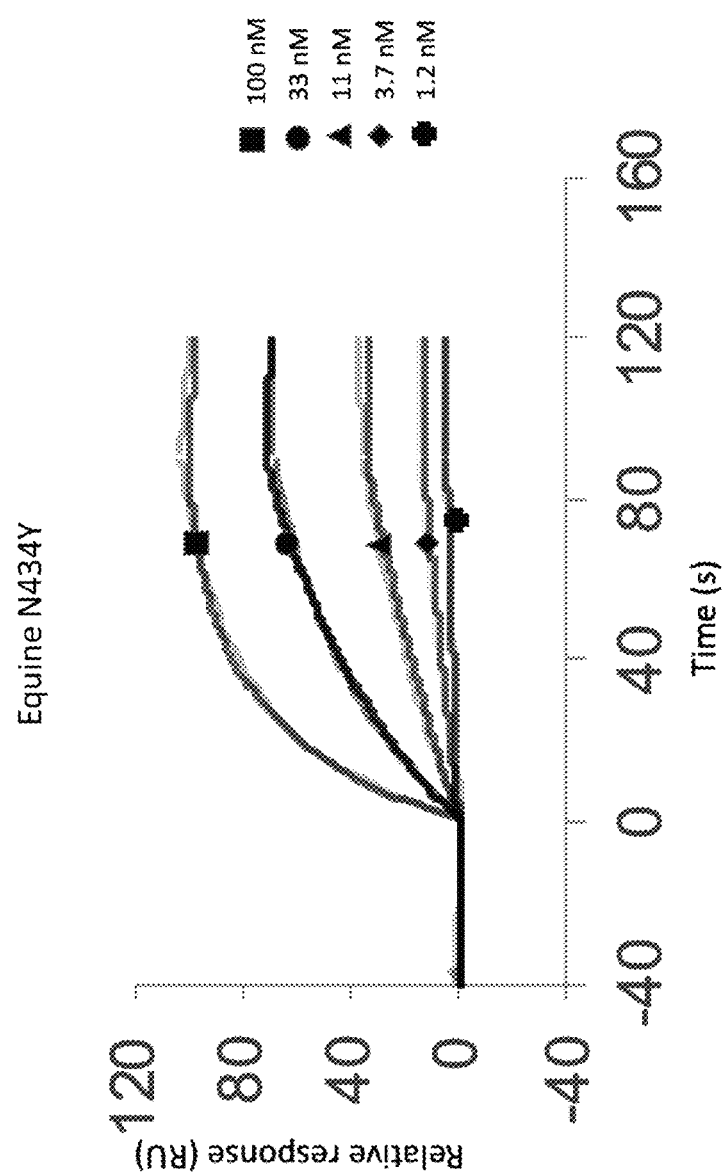
Figure 9J:
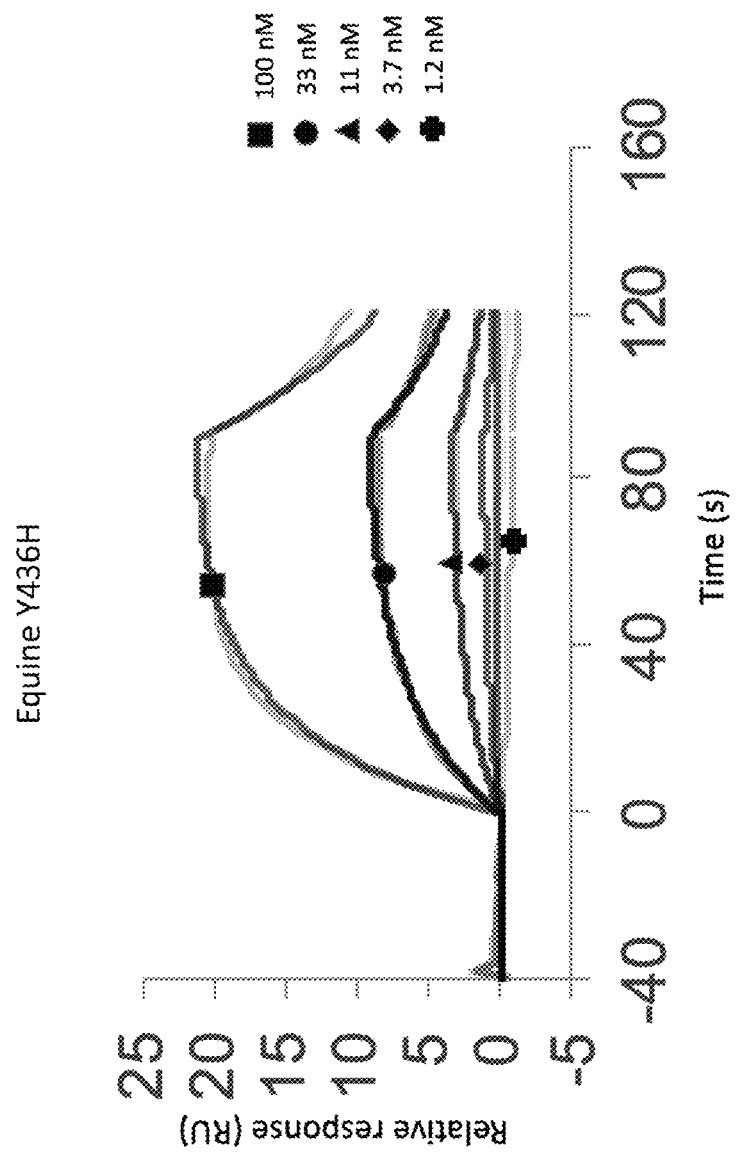

With the increasing use of polypeptide (e.g., antibodies, ligand-binding domains of receptors, enzymes, ligands, peptides) as therapeutics for the prevention and treatment of a wide variety of diseases that affect livestock animals, it is important to develop polypeptides with extended half-life, especially for the prevention or treatment of chronic diseases in which a polypeptide must be administered repetitively.

Accordingly, this disclosure features immunoglobulin Fc regions of livestock animals or FcRn-binding regions thereof comprising mutations that enhance the half-life of the polypeptide or polypeptides comprising these sequences in the livestock animal. Also disclosed are polypeptides comprising these domains and methods of their use. These peptides can be used for various therapeutic and diagnostic purposes.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated. All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

The term "about," as used herein when referring to a measurable value such as an amount or concentration and the like, is meant to encompass variations of 20%, 10%, 5%, 1%, 0.5%, or even 0.1% of the specified amount.

Porcine Antibodies

Pigs typically have eleven IgG heavy chains referred to as IgG1a, IgG1b, IgG2a, IgG2b, IgG3, IgG4a, IgG4b, IgG5a, IgG5b, IgG6a and IgG6b. These heavy chains represent eleven different subclasses of porcine IgG. The amino acid and DNA sequences for these heavy chains are available from the GENBANK® database. Illustrative examples of the amino acid sequences of the CH2 and CH3 domains of each of the eleven porcine IgG heavy chain Fc regions are shown below (CH2 domains are underlined), and the GENBANK® accession number (for the amino acid sequence or mRNA sequence from which the amino acid sequence is derived) of each heavy chain Fc region is indicated:

Porcine (*Sus scrofa*) IgG Fc sequences

IgG1a (GenBank®® AAA52219.1)
(SEQ ID NO: 1)
GCEVAGPSVFIFPPKPKDTLMISQTPEVTCVVVDVSKEHAEVQFSWYVDGV

EVHTAETRPKEEQFNSTYRVVSVLPIQHQDWLKGKEFKCKVNNVDLPAPIT

RTISKAIGQSREPQVYTLPPPAEELSRSKVTVTCLVIGFYPPDIHVEWKSN

GQPEPEGNYRTTPPQQDVDGTFFLYSKLAVDKARWDHGETFECAVMHEALH

NHYTQKSISKTQGK

IgG1b (GenBank® AAA52216.1)
(SEQ ID NO: 2)
GCEVAGPSVFIFPPKPKDTLMISQTPEVTCVVVDVSKEHAEVQFSWYVDGV

EVHTAETRPKEEQFNSTYRVVSVLPIQHQDWLKGKEFKCKVNNVDLPAPIT

RTISKAIGQSREPQVYTLPPPAEELSRSKVTLTCLVIGFYPPDIHVEWKSN

GQPEPENTYRTTPPQQDVDGTFFLYSKLAVDKARWDHGDKFECAVMHEALH

NHYTQKSISKTQGK

IgG2a (GenBank® U03779)
(SEQ ID NO: 3)
ACESPGPSVFIFPPKPKDTLMISRTPQVTCVVVDVSQENPEVQFSWYVDGV

EVHTAQTRPKEEQFNSTYRVVSVLPIQHQDWLNGKEFKCKVNNKDLPAPIT

RIISKAKGQTREPQVYTLPPHAEELSRSKVSITCLVIGFYPPDIDVEWQRN

GQPEPEGNYRTTPPQQDVDGTYFLYSKFSVDKASWQGGGIFQCAVMHEALH

NHYTQKSISKTPGK

IgG2b (GenBank® U03780)
(SEQ ID NO: 4)
ACESPGPSVFIFPPKPKDTLMISRTPQVTCVVVDVSQENPEVQFSWYVDGV

EVHTAQTRPKEEQFNSTYRVVSVLPIQHQDWLNGKEFKCKVNNKDLPAPIT

RIISKAKGQTREPQVYTLPPHAEELSRSKVSITCLVIGFYPPDIDVEWQRN

GQPEPEGNYRTTPPQQDVDGTYFLYSKFSVDKASWQGGGIFQCAVMHEALH

NHYTQKSISKTPGK

IgG3 (GenBank® ABY85810.1)
(SEQ ID NO: 5)
AAEVLGAPSVFLFPPKPKDILMISRTPKVTCVVVDVSQEEAEVQFSWYVDG

VQLYTAQTRPMEEQFNSTYRVVSVLPIQHQDWLKGKEFKCKVNNKDLLSPI

TRTISKATGPSRVPQVYTLPPAWEELSKSKVSITCLVTGFYPPDIDVEWQS

NGQQEPEGNYRTTPPQQDVDGTYFLYSKLAVDKVRWQRGDLFQCAVMHEAL

HNHYTQKSISKTQGK

IgG4a (GenBank® AAA52220.1)
(SEQ ID NO: 6)
ACEGPGPSAFIFPPKPKDTLMISRTPKVTCVVVDVSQENPEVQFSWYVDGV

EVHTAQTRPKEEQFNSTYRVVSVLPIQHQDWLNGKEFKCKVNNKDLPAPIT

RIISKAKGQTREPQVYTLPPPTEELSRSKVTLTCLVTGFYPPDIDVEWQRN

GQPEPEGNYRTTPPQQDVDGTYFLYSKLAVDKASWQRGDTFQCAVMHEALH

NHYTQKSIFKTPGK

IgG4b (GenBank® ABY85806.1)
(SEQ ID NO: 7)
ACEGPGPSAFIFPPKPKDTLMISRTPKVTCVVVDVSQENPEVQFSWYVDGV

EVHTAQTRPKEEQFNSTYRVVSVLLIQHQDWLNGKEFKCKVNNKDLPAPIT

RIISKAKGQTREPQVYTLPPPTEELSRSKVTLTCLVTGFYPPDIDVEWQRN

GQPEPEGNYRTTPPQQDVDGTYFLYSKLAVDKASWQRGDTFQCAVMHEALH

NHYT

IgG5a (GenBank® ABY85809.1)
(SEQ ID NO: 8)
GCEVAGPSVFIFPPKPKDILMISRTPEVTCVVVDVSKEHAEVQFSWYVDGE

EVHTAETRPKEEQFNSTYRVVSVLPIQHEDWLKGKEFECKVNNEDLPGPIT

RTISKAKGVVRSPEVYTLPPPAEELSKSIVTLTCLVKSIFPPPFIHVEWKIN

GKPEPENAYRTTPPQEDEDRTYFLYSKLAVDKARWDHGETFECAVMHEALH

NHYTQKSISKTQGK

IgG5b (GenBank® AB699687)
(SEQ ID NO: 9)
ICPVAGPSVFIFPPKPKDILMISRTPEVTCVVVDVSKEHAEVQFSWYVDGE

EVHTAETRPKEEQFNSTYRVVSVLPIQHEDWLKGKEFECKVNNEDLPGPIT

RTISKAKGVVRSPEVYTLPPPAEELSKSIVTLTCLVKSFFPPPFIHVEWKIN

GKPEPENAYRTTPPQEDEDGTYFLYSKFSVEKFRWHSGGIHCAVMHEALHN

HYTEKSVSQTPGK

IgG6a (GenBank® AB699687)
(SEQ ID NO: 10)
ACEGPGPSAFIFPPKPKDTLMISRTPKVTCVVVDVSQENPEVQFSWYVDGV

EVHTAQTRPKEEQFNSTYRVVSVLPIQHQDWLNGKEFKCKVNNKDLPAPIT

RIISKAKGQTREPQVYTLPPPTEELSRSKLSVTCLITGFYPPDIDVEWQRN

GQPEPEGNYRTTPPQQDVDGTYFLYSKLAVDKASWQRGDPFQCAVMHEALH

NHYTQKSIFKTPGN

IgG6b (GenBank® ABY85805.1)
(SEQ ID NO: 11)
ACEGNGPSVFIFPPKPKDTLMISRTPEVTCVVVDVSQENPEVQFSWYVDGE

EVHTAETRPKEEQFNSTYRVVSVLPIQHQDWLKGKEFECKVNNKDLPAPIT

RIISKAKGPSREPQVYTLSPSAEELSRSKVSITCLVTGFYPPDIDVEWKSN

GQPEPEGNYRSTPPQEDEDGTYFLYSKLAVDKARLQSGGIHCAVMHEALHN

HYTQKSISKT

The CH2 region of a porcine antibody comprises or consists of amino acids 231 to 340 (according to EU numbering) of a porcine IgG antibody. It is to be understood that the CH2 region may include one to six (e.g., 1, 2, 3, 4, 5, 6) additional amino acids or deletions at their N and/or C-terminus.

The CH3 region of a porcine antibody comprises or consists of amino acids 341 to 447 (according to EU numbering) of a porcine IgG antibody. It is to be understood that the CH3 region may include one to six (e.g., 1, 2, 3, 4, 5, 6) additional amino acids or deletions at their N and/or C-terminus.

The Fc region of a porcine IgG antibody comprises or consists of amino acids 231 to 447 (according to EU numbering) of a porcine IgG antibody.

Table 1 below compares the amino acid sequences of the CH2 and CH3 domains of human IgG1, canine IgGB and feline IgG1a with each of the eleven porcine IgG isotypes, based on EU numbering:

TABLE 1

| | | | | CH2 Domain | | | | | | | | | |
|---|---|---|---|---|---|---|---|---|---|---|---|---|---|
| EU number | Human IgG1 | Canine IgGB | Feline IgG1a | Pig IgG1a | Pig IgG1b | Pig IgG2a | Pig IgG2b | Pig IgG3 | Pig IgG4a | Pig IgG4b | Pig IgG5a | Pig IgG5b | Pig IgG6a | Pig IgG6b |
| 231 | A | A | P | | | | | A | | | | | | |
| 232 | P | P | P | G | G | A | A | A | A | A | G | I | A | A |
| 233 | E | E | E | C | C | C | C | E | C | C | C | C | C | C |
| 234 | L | M | M | E | E | E | E | V | E | E | E | P | E | E |
| 235 | L | L | L | V | V | S | S | L | G | G | V | V | G | G |

TABLE 1-continued

| | | | | | | | | | | | | | | |
|---|---|---|---|---|---|---|---|---|---|---|---|---|---|
| 236 | G | G | G | A | A | P | P | G | P | P | A | A | P | N |
| 237 | G | G | G | G | G | G | G | A | G | G | G | G | G | N |
| 238 | P | P | P | P | P | P | P | P | P | P | P | P | P | P |
| 239 | S | S | S | S | S | S | S | S | S | S | S | S | S | S |
| 240 | V | V | I | V | V | V | V | V | A | A | V | V | A | V |
| 241 | F | F | F | F | F | F | F | F | F | F | F | F | F | F |
| 242 | L | I | I | I | I | I | I | L | I | I | I | I | I | I |
| 243 | F | F | F | F | F | F | F | F | F | F | F | F | F | F |
| 244 | P | P | P | P | P | P | P | P | P | P | P | P | P | P |
| 245 | P | P | P | P | P | P | P | P | P | P | P | P | P | P |
| 246 | K | K | K | K | K | K | K | K | K | K | K | K | K | K |
| 247 | P | P | P | P | P | P | P | P | P | P | P | P | P | P |
| 248 | K | K | K | K | K | K | K | K | K | K | K | K | K | K |
| 249 | D | D | D | D | D | D | D | D | D | D | D | D | D | D |
| 250 | T | T | T | T | T | T | T | I | T | T | I | I | T | T |
| 251 | L | L | L | L | L | L | L | L | L | L | L | L | L | L |
| 252 | M | L | S | M | M | M | M | M | M | M | M | M | M | M |
| 253 | I | I | I | I | I | I | I | I | I | I | I | I | I | I |
| 254 | S | A | S | S | S | S | S | S | S | S | S | S | S | S |
| 255 | R | R | R | Q | Q | R | R | R | R | R | R | R | R | R |
| 256 | T | T | T | T | T | T | T | T | T | T | T | T | T | T |
| 257 | P | P | P | P | P | P | P | P | P | P | P | P | P | P |
| 258 | E | E | E | E | E | Q | Q | K | K | K | E | E | K | E |
| 259 | V | V | V | V | V | V | V | V | V | V | V | V | V | V |
| 260 | T | T | T | T | T | T | T | T | T | T | T | T | T | T |
| 261 | C | C | C | C | C | C | C | C | C | C | C | C | C | C |
| 262 | V | V | L | V | V | V | V | V | V | V | V | V | V | V |
| 263 | V | V | V | V | V | V | V | V | V | V | V | V | V | V |
| 264 | V | V | V | V | V | V | V | V | V | V | V | V | V | V |
| 265 | D | D | D | D | D | D | D | D | D | D | D | D | D | D |
| 266 | V | L | L | V | V | V | V | V | V | V | V | V | V | V |
| 267 | S | D | G | S | S | S | S | S | S | S | S | S | S | S |
| 268 | H | P | P | K | K | Q | Q | Q | Q | K | K | Q | Q |
| 269 | E | E | D | E | E | E | E | E | E | E | E | E | E |
| 270 | D | D | D | H | H | N | N | E | N | N | H | H | N | N |
| 271 | P | P | S | A | A | P | P | A | P | P | A | A | P | P |
| 272 | E | E | D | E | E | E | E | E | E | E | E | E | E | E |
| 273 | V | V | V | V | V | V | V | V | V | V | V | V | V | V |
| 274 | K | Q | Q | Q | Q | Q | Q | Q | Q | Q | Q | Q | Q | Q |
| 275 | F | I | I | F | F | F | F | F | F | F | F | F | F | F |
| 276 | N | S | T | S | S | S | S | S | S | S | S | S | S | S |
| 277 | W | W | W | W | W | W | W | W | W | W | W | W | W | W |
| 278 | Y | F | F | Y | Y | Y | Y | Y | Y | Y | Y | Y | Y | Y |
| 279 | V | V | V | V | V | V | V | V | V | V | V | V | V | V |
| 280 | D | D | D | D | D | D | D | D | D | D | D | D | D | D |
| 282 | G | G | N | T | V | V | V | V | V | V | V | E | E | V | E |
| 283 | E | Q | Q | E | E | E | E | Q | E | E | E | E | E | E |
| 284 | V | M | V | V | V | V | V | L | V | V | V | V | V | V |
| 285 | H | Q | Y | H | H | H | H | Y | H | H | H | H | H | H |
| 286 | N | T | T | T | T | T | T | T | T | T | T | T | T | T |
| 287 | A | A | A | A | A | A | A | A | A | A | A | A | A | A |
| 288 | K | K | K | E | E | Q | Q | Q | Q | Q | E | E | Q | E |
| 289 | T | T | T | T | T | T | T | T | T | T | T | T | T | T |
| 290 | K | Q | S | R | R | R | R | R | R | R | R | R | R | R |
| 291 | P | P | P | P | P | P | P | P | P | P | P | P | P | P |
| 292 | R | R | R | K | K | K | M | K | K | K | K | K | K |
| 293 | E | E | E | E | E | E | E | E | E | E | E | E | E | E |
| 294 | E | E | E | E | E | E | E | E | E | E | E | E | E | E |
| 295 | Q | Q | Q | Q | Q | Q | Q | Q | Q | Q | Q | Q | Q | Q |
| 296 | Y | F | F | F | F | F | F | F | F | F | F | F | F | F |
| 297 | N | N | N | N | N | N | N | N | N | N | N | N | N | N |
| 298 | S | G | S | S | S | S | S | S | S | S | S | S | S | S |
| 299 | T | T | T | T | T | T | T | T | T | T | T | T | T | T |
| 300 | Y | Y | Y | Y | Y | Y | Y | Y | Y | Y | Y | Y | Y | Y |
| 301 | R | R | R | R | R | R | R | R | R | R | R | R | R | R |
| 302 | V | V | V | V | V | V | V | V | V | V | V | V | V | V |
| 303 | V | V | V | V | V | V | V | V | V | V | V | V | V | V |
| 304 | S | S | S | S | S | S | S | S | S | S | S | S | S | S |
| 305 | V | V | V | V | V | V | V | V | V | V | V | V | V | V |
| 306 | L | L | L | L | L | L | L | L | L | L | L | L | L | L |
| 307 | T | P | P | P | P | P | P | P | P | L | P | P | P | P |
| 308 | V | I | I | I | I | I | I | I | I | I | I | I | I | I |
| 309 | L | G | L | Q | Q | Q | Q | Q | Q | Q | Q | Q | Q | Q |
| 310 | H | H | H | H | H | H | H | H | H | H | H | H | H | H |
| 311 | Q | Q | Q | Q | Q | Q | Q | Q | Q | Q | E | E | Q | Q |
| 312 | D | D | D | D | D | D | D | D | D | D | D | D | D | D |
| 313 | W | W | W | W | W | W | W | W | W | W | W | W | W | W |
| 314 | L | L | L | L | L | L | L | L | L | L | L | L | L | L |
| 315 | N | K | K | K | K | N | N | K | N | N | K | K | N | K |

TABLE 1-continued

| EU number | Human IgG1 | Canine IgGB | Feline IgG1a | Pig IgG1a | Pig IgG1b | Pig IgG2a | Pig IgG2b | Pig IgG3 | Pig IgG4a | Pig IgG4b | Pig IgG5a | Pig IgG5b | Pig IgG6a | Pig IgG6b |
|---|---|---|---|---|---|---|---|---|---|---|---|---|---|---|
| 316 | G | G | G | G | G | G | G | G | G | G | G | G | G | G |
| 317 | K | K | K | K | K | K | K | K | K | K | K | K | K | K |
| 318 | E | Q | E | E | E | E | E | E | E | E | E | E | E | E |
| 319 | Y | F | F | F | F | F | F | F | F | F | F | F | F | F |
| 320 | K | T | K | K | K | K | K | K | K | K | E | E | K | E |
| 321 | C | C | C | C | C | C | C | C | C | C | C | C | C | C |
| 322 | K | K | K | K | K | K | K | K | K | K | K | K | K | K |
| 323 | V | V | V | V | V | V | V | V | V | V | V | V | V | V |
| 324 | S | N | N | N | N | N | N | N | N | N | N | N | N | N |
| 325 | N | N | S | N | N | N | N | N | N | N | N | N | N | N |
| 326 | K | K | K | V | V | K | K | K | K | E | E | K | K | K |
| 327 | A | A | S | D | D | D | D | D | D | D | D | D | D | D |
| 328 | L | L | L | L | L | L | L | L | L | L | L | L | L | L |
| 329 | P | P | P | P | P | P | P | L | P | P | P | P | P | P |
| 330 | A | S | S | A | A | A | A | S | A | A | G | G | A | A |
| 331 | P | P | P | P | P | P | P | P | P | P | P | P | P | P |
| 332 | I | I | I | I | I | I | I | I | I | I | I | I | I | I |
| 333 | E | E | E | T | T | T | T | T | T | T | T | T | T | T |
| 334 | K | R | R | R | R | R | R | R | R | R | R | R | R | R |
| 335 | T | T | T | T | T | I | I | T | I | I | T | T | I | I |
| 336 | I | I | I | I | I | I | I | I | I | I | I | I | I | I |
| 337 | S | S | S | S | S | S | S | S | S | S | S | S | S | S |
| 338 | K | K | K | K | K | K | K | K | K | K | K | K | K | K |
| 339 | A | A | A | A | A | A | A | A | A | A | A | A | A | A |
| 340 | K | R | K | I | I | K | K | T | K | K | K | K | K | K |

CH3 Domain

| EU number | Human IgG1 | Canine IgGB | Feline IgG1a | Pig IgG1a | Pig IgG1b | Pig IgG2a | Pig IgG2b | Pig IgG3 | Pig IgG4a | Pig IgG4b | Pig IgG5a | Pig IgG5b | Pig IgG6a | Pig IgG6b |
|---|---|---|---|---|---|---|---|---|---|---|---|---|---|---|
| 341 | G | G | G | G | G | G | G | G | G | G | G | G | G | G |
| 342 | Q | Q | Q | Q | Q | Q | Q | P | Q | Q | V | V | Q | P |
| 343 | P | A | P | S | S | T | T | S | T | T | V | V | T | S |
| 344 | R | H | H | R | R | R | R | R | R | R | R | R | R | R |
| 345 | E | Q | E | E | E | E | E | V | E | E | S | S | E | E |
| 346 | P | P | P | P | P | P | P | P | P | P | P | P | P | P |
| 347 | Q | S | Q | Q | Q | Q | Q | Q | Q | Q | E | E | Q | Q |
| 348 | V | V | V | V | V | V | V | V | V | V | V | V | V | V |
| 349 | Y | Y | Y | Y | Y | Y | Y | Y | Y | Y | Y | Y | Y | Y |
| 350 | T | V | V | T | T | T | T | T | T | T | T | T | T | T |
| 351 | L | L | L | L | L | L | L | L | L | L | L | L | L | L |
| 352 | P | P | P | P | P | P | P | P | P | P | P | P | P | S |
| 353 | P | P | P | P | P | P | P | P | P | P | P | P | P | P |
| 354 | S | S | A | P | P | H | H | A | P | P | P | P | P | S |
| 355 | R | R | Q | A | A | A | A | W | T | T | A | A | T | A |
| 356 | D | E | E | E | E | E | E | E | E | E | E | E | E | E |
| 357 | E | E | E | E | E | E | E | E | E | E | E | E | E | E |
| 358 | L | L | L | L | L | L | L | L | L | L | L | L | L | L |
| 359 | T | S | S | S | S | S | S | S | S | S | S | S | S | S |
| 360 | K | K | R | R | R | R | R | K | R | R | K | K | R | R |
| 361 | N | N | N | S | S | S | S | S | S | S | S | S | S | S |
| 362 | Q | T | K | K | K | K | K | K | K | K | I | I | K | K |
| 363 | V | V | V | V | V | V | V | V | V | V | V | V | L | V |
| 364 | S | S | S | T | T | S | S | S | T | T | T | T | S | S |
| 365 | L | L | V | V | L | I | I | I | L | L | L | L | V | I |
| 366 | T | T | T | T | T | T | T | T | T | T | T | T | T | T |
| 367 | C | C | C | C | C | C | C | C | C | C | C | C | C | C |
| 368 | L | L | L | L | L | L | L | L | L | L | L | L | L | L |
| 369 | V | I | I | V | V | V | V | V | V | V | V | V | I | V |
| 370 | K | K | K | I | I | I | I | T | T | T | K | K | T | T |
| 371 | G | D | S | G | G | G | G | G | G | G | S | S | G | G |
| 372 | F | F | F | F | F | F | F | F | F | F | I | I | F | F |
| 373 | Y | F | H | Y | Y | Y | Y | Y | Y | Y | F | F | Y | Y |
| 374 | P | P | P | P | P | P | P | P | P | P | P | P | P | P |
| 375 | S | P | P | P | P | P | P | P | P | P | P | P | P | P |
| 376 | D | D | D | D | D | D | D | D | D | D | F | F | D | D |
| 377 | I | I | I | I | I | I | I | I | I | I | I | I | I | I |
| 378 | A | D | A | H | H | D | D | D | D | D | H | H | D | D |
| 379 | V | V | V | V | V | V | V | V | V | V | V | V | V | V |
| 380 | E | E | E | E | E | E | E | E | E | E | E | E | E | E |
| 381 | W | W | W | W | W | W | W | W | W | W | W | W | W | W |
| 382 | E | Q | E | K | K | Q | Q | Q | Q | Q | K | K | Q | K |
| 383 | S | S | I | S | S | R | R | S | R | R | I | I | R | S |
| 384 | N | N | T | N | N | N | N | N | N | N | N | N | N | N |
| 385 | G | G | G | G | G | G | G | G | G | G | G | G | G | G |
| 386 | Q | Q | Q | Q | Q | Q | Q | Q | Q | Q | K | K | Q | Q |
| 387 | P | Q | P | P | P | P | P | Q | P | P | P | P | P | P |
| 388 | E | E | E | E | E | E | E | E | E | E | E | E | E | E |
| 389(a) | N | P | P | P | P | P | P | P | P | P | P | P | P | P |

TABLE 1-continued

| Pos | 1 | 2 | 3 | 4 | 5 | 6 | 7 | 8 | 9 | 10 | 11 | 12 | 13 |
|---|---|---|---|---|---|---|---|---|---|---|---|---|---|
| 389b | E | E | E | E | E | E | E | E | E | E | E | E | E |
| 389c |   | S | N | G | N | G | G | G | G | G | N | N | G | G |
| 390 | N | K | N | N | T | N | N | N | N | N | A | A | N | N |
| 391 | Y | Y | Y | Y | Y | Y | Y | Y | Y | Y | Y | Y | Y |
| 392 | K | R | R | R | R | R | R | R | R | R | R | R | R |
| 393 | T | T | T | T | T | T | T | T | T | T | T | T | S |
| 394 | T | T | T | T | T | T | T | T | T | T | T | T | T |
| 395 | P | P | P | P | P | P | P | P | P | P | P | P | P |
| 396 | P | P | P | P | P | P | P | P | P | P | P | P | P |
| 397 | V | Q | Q | Q | Q | Q | Q | Q | Q | Q | Q | Q | Q |
| 398 | L | L | L | Q | Q | Q | Q | Q | Q | Q | E | E | Q | E |
| 399 | D | D | D | D | D | D | D | D | D | D | D | D | D |
| 400 | S | E | S | V | V | V | V | V | V | V | E | E | V | E |
| 401 | D | D | D | D | D | D | D | D | D | D | D | D | D |
| 402 | G | G | G | G | G | G | G | G | G | G | R | G | G | G |
| 403 | S | S | T | T | T | T | T | T | T | T | T | T | T | T |
| 404 | F | Y | Y | F | F | Y | Y | Y | Y | Y | Y | Y | Y | Y |
| 405 | F | F | F | F | F | F | F | F | F | F | F | F | F |
| 406 | L | L | V | L | L | L | L | L | L | L | L | L | L |
| 407 | Y | Y | Y | Y | Y | Y | Y | Y | Y | Y | Y | Y | Y |
| 408 | S | S | S | S | S | S | S | S | S | S | S | S | S |
| 409 | K | K | K | K | K | K | K | K | K | K | K | K | K |
| 410 | L | L | L | L | L | F | F | L | L | L | F | L | L |
| 411 | T | S | S | A | A | S | S | A | A | A | S | A | A |
| 412 | V | V | V | V | V | V | V | V | V | V | V | V | V |
| 413 | D | D | D | D | D | D | D | D | D | D | E | D | D |
| 414 | K | K | R | K | K | K | K | K | K | K | K | K | K |
| 415 | S | S | S | A | A | A | A | V | A | A | F | A | A |
| 416 | R | R | H | R | S | S | R | S | S | R | S | S | R |
| 417 | W | W | W | W | W | W | W | W | W | W | W | W | L |
| 418 | Q | Q | Q | D | D | Q | Q | Q | Q | Q | D | H | Q | Q |
| 419 | Q | R | R | H | H | G | G | R | R | R | H | S | R | S |
| 420 | G | G | G | G | G | G | G | G | G | G | G | G | G |
| 421 | N | D | N | E | D | G | G | D | D | D | E | G | D | G |
| 422 | V | T | T | T | K | I | I | L | T | T | T | I | P | I |
| 423 | F | F | Y | F | F | F | F | F | F | F | F | H | F | H |
| 424 | S | I | T | E | E | Q | Q | Q | Q | Q | E |   | Q | C |
| 425 | C | C | C | C | C | C | C | C | C | C | C | C | A |
| 426 | S | A | S | A | A | A | A | A | A | A | A | A | V |
| 427 | V | V | V | V | V | V | V | V | V | V | V | V | M |
| 428 | M | M | S | M | M | M | M | M | M | M | M | M | H |
| 429 | H | H | H | H | H | H | H | H | H | H | H | H | E |
| 430 | E | E | E | E | E | E | E | E | E | E | E | E | A |
| 431 | A | A | A | A | A | A | A | A | A | A | A | A | L |
| 432 | L | L | L | L | L | L | L | L | L | L | L | L | H |
| 433 | H | H | H | H | H | H | H | H | H | H | H | H | N |
| 434 | N | N | S | N | N | N | N | N | N | N | N | N | H |
| 435 | H | H | H | H | H | H | H | H | H | H | H | H | Y |
| 436 | Y | Y | H | Y | Y | Y | Y | Y | Y | Y | Y | Y | T |
| 437 | T | T | T | T | T | T | T | T |   | T | T | T | Q |
| 438 | Q | Q | Q | Q | Q | Q | Q | Q | Q |   | Q | E | Q | K |
| 439 | K | E | K | K | K | K | K | K | K |   | K | K | K | S |
| 440 | S | S | S | S | S | S | S | S | S |   | S | S | S | I |
| 441 | L | L | L | I | I | I | I | I | I |   | I | V | I | S |
| 442 | S | S | T | S | S | S | S | S | F |   | S | S | F | K |
| 443 | L | H | Q | K | K | K | K | K | K |   | K | Q | K | T |
| 444 | S | S | S | T | T | T | T | T |   |   | T | T | T |   |
| 445 | P | P | P | Q | Q | P | P | Q | P |   | Q | P | P |   |
| 446 | G | G | G | G | G | G | G | G | G |   | G | G | G |   |
| 447 | K | K | K | K | K | K | K | K | K |   | K | K | N |

Substitutions in porcine IgG Fc that Improve Half-Life

Increased serum persistence is a beneficial property for therapeutic polypeptides. This disclosure features substitutions in wild type porcine IgG1a, IgG1b, IgG2a, IgG2b, IgG3, IgG4a, IgG4b, IgG5a, IgG5b, IgG6a and IgG6b Fc regions that enhance the half-life of a polypeptide or polypeptides comprising these Fc regions in a pig relative to a control polypeptide or control polypeptides, wherein the control polypeptide or control polypeptides are identical to the polypeptide or polypeptides except for having the corresponding wild type porcine IgG Fc region in place of the IgG Fc region variant. The substitutions to increase half-life may be made in one or more of a porcine CH2 region, a porcine CH3 region, or in the context of a porcine Fc (e.g., a CH2+CH3) region.

The present disclosure provides a polypeptide comprising a porcine IgG Fc region variant, or a porcine FcRn-binding region thereof, wherein the polypeptide comprises an amino acid substitution at at least one (e.g., 1, 2, 3, 4, 5, 6, 7, 8, 9, 10 or 11) position selected from the group consisting of:

(i) a position that corresponds to amino acid position 250 of a wild type porcine IgG, wherein the amino acid substitution is selected from the group consisting of T250Q, T250E, 1250Q and 1250E;
  (ii) a position that corresponds to amino acid position 252 of a wild type porcine IgG, wherein the amino acid substitution is selected from the group consisting of M252Y, M252W and M252F;
  (iii) a position that corresponds to amino acid position 254 of a wild type porcine IgG, wherein the amino acid substitution is selected from the group consisting of S254T, S254R, S254K and S254H;

(iv) a position that corresponds to amino acid position 256 of a wild type porcine IgG, wherein the amino acid substitution is selected from the group consisting of T256A, T256D and T256E;

(v) a position that corresponds to amino acid position 286 of a wild type porcine IgG, wherein the amino acid substitution is selected from the group consisting of T286Y, T286F, T286W, T286L, T286D and T286E;

(vi) a position that corresponds to amino acid position 309 of a wild type porcine IgG, wherein the amino acid substitution is selected from the group consisting of Q309V, Q309D and Q309E;

(vii) a position that corresponds to amino acid position 311 of a wild type porcine IgG, wherein the amino acid substitution is selected from the group consisting of Q311V, Q311K, Q311R, Q311L, Q311H, E311V, E311K, E311R, E311L and E311H;

(viii) a position that corresponds to amino acid position 426 of a wild type porcine IgG, wherein the amino acid substitution is selected from the group consisting of A426Y, A426F, A426H, V426Y, V426F and V426H;

(ix) a position that corresponds to amino acid position 428 of a wild type porcine IgG, wherein the amino acid substitution is selected from the group consisting of M428L, M428Y, M428F, H428L, H428Y and H428F;

(x) a position that corresponds to amino acid position 434 of a wild type porcine IgG, wherein the amino acid substitution is selected from the group consisting of N434A, N434H, N434F, N434S, N434W, N434Y, H434A, H434F, H434S, H434W and H434Y; and (xi) a position that corresponds to amino acid position 436 of a wild type porcine IgG, wherein the amino acid substitution is selected from the group consisting of Y436H and T436H.

wherein the amino acid positions are based on EU numbering, and wherein the polypeptide has increased binding affinity to bovine FcRn when compared to an Fc domain of the wild type porcine IgG.

In some embodiments, the polypeptide comprises an amino acid substitution at at least one (e.g., 1, 2, 3, 4, 5, 6, or 7) position selected from the group consisting of:

(i) a position that corresponds to amino acid position 252 of a wild type IgG of the livestock animal, wherein the amino acid substitution is M252Y;

(ii) a position that corresponds to amino acid position 286 of a wild type IgG of the livestock animal, wherein the amino acid substitution is T286E;

(iii) a position that corresponds to amino acid position 309 of a wild type IgG of the livestock animal, wherein the amino acid substitution is Q309D or Q309V;

(iv) a position that corresponds to amino acid position 311 of a wild type IgG of the livestock animal, wherein the amino acid substitution is Q311V;

(v) a position that corresponds to amino acid position 426 of a wild type IgG of the livestock animal, wherein the amino acid substitution is A426Y;

(vi) a position that corresponds to amino acid position 428 of a wild type IgG of the livestock animal, wherein the amino acid substitution is M428Y; and (vii) a position that corresponds to amino acid position 434 of a wild type IgG of the livestock animal, wherein the amino acid substitution is selected from the group consisting of N434Y.

In some embodiments, the polypeptide has increased binding affinity to porcine FcRn at a pH of about 5.0 to about 6.5 (e.g., about 5.5 or about 6.0) when compared to an Fc domain of the wild type porcine IgG at the same pH.

In some embodiments, the polypeptide comprises an amino acid sequence that is at least 80% (e.g., at least 85%, 90%, 92%, 94%, 95%, 96%, 97%, 98%, or 99%) identical to an amino acid sequence selected from the group consisting of SEQ ID NOs: 1 to 11.

In some instances, this disclosure provides a porcine IgG CH2 domain variant comprising an amino acid sequence that is at least 75%, at least 80%, at least 85%, at least 90%, at least 95%, at least 96%, at least 97%, at least 98% or at least 99% identical to the CH2 domains shown in any one of SEQ ID NOs.:1 to 11. Also provided are porcine IgG CH2 domain variants comprising an amino acid sequence that varies from any one of the CH2 domains shown in SEQ ID NOs.:1 to 11 by 1 to 15 (e.g., by 1, 2, 3, 4, 5, 6, 7, 8, 9, 10, 11, 12, 13, 14, or 15) amino acids.

In some instances, this disclosure features a porcine IgG CH3 domain variant comprising an amino acid sequence that is at least 75%, at least 80%, at least 85%, at least 90%, at least 95%, at least 96%, at least 97% or at least 98% or at least 99%, identical to the amino acid sequence of the CH3 domain shown in any one of SEQ ID NOs.:1 to 11. Also featured are porcine IgG CH3 domain variants comprising an amino acid sequence that varies from any one of the CH3 domain sequences shown in any one of SEQ ID NOs.:1 to 11 by 1 to 15 (e.g., by 1, 2, 3, 4, 5, 6, 7, 8, 9, 10, 11, 12, 13, 14, or 15) amino acids.

In some instances, this disclosure features a porcine IgG Fc region variant comprising an amino acid sequence that is at least 75%, at least 80%, at least 85%, at least 90%, at least 95%, at least 96%, at least 97%, at least 98% or at least 99% identical to the amino acid sequence set forth in any one of SEQ ID NOs.:1 to 11. Also disclosed are porcine IgG Fc region variants comprising an amino acid sequence that varies from any one of SEQ ID NOs.:1 to 11 by 1 to 20 (e.g., by 1, 2, 3, 4, 5, 6, 7, 8, 9, 10, 11, 12, 13, 14, 15, 16, 17, 18, 19, or 20) amino acids.

In some embodiments, provided are a polypeptide or polypeptides comprising a porcine IgG Fc CH2 domain variant, the CH2 domain variant comprising an amino acid sequence that is at least 75%, at least 80%, at least 85%, at least 90%, at least 95%, at least 96%, at least 97%, at least 98% or at least 99%, identical to the amino acid sequence of the CH2 domain shown in any one of SEQ ID NOs.:1 to 11.

In some embodiments, featured are a polypeptide or polypeptides comprising a porcine IgG Fc CH3 domain variant, the CH3 domain variant comprising an amino acid sequence that is at least 75%, at least 80%, at least 85%, at least 90%, at least 95%, at least 96%, at least 97%, at least 98% or at least 99% identical to the amino acid sequence of the CH3 domain shown in any one of SEQ ID NOs.:1 to 11.

In some embodiments, featured are a polypeptide or polypeptides comprising a porcine IgG Fc region variant, the Fc region variant comprising an amino acid sequence that is at least 75%, at least 80%, at least 85%, at least 90%, at least 95%, at least 96%, at least 97%, at least 98% or at least 99% identical to the amino acid sequence set forth in any one of SEQ ID NOs.:1 to 11.

Bovine Antibodies

Bovine typically have three IgG heavy chains referred to as IgG1, IgG2, and IgG3. These heavy chains represent three different subclasses of bovine IgG. The amino acid and DNA sequences for these heavy chains are available from the GenBank® database. Illustrative examples of the amino acid sequences of the CH2 and CH3 domains of each of the three bovine IgG heavy chain Fc regions are shown below (CH2 domains are underlined), and the GenBank® accession number (for the amino acid sequence or mRNA sequence from which the amino acid sequence is derived) of each heavy chain Fc region is indicated:
Bovine *Bos Taurus*

IgG1 (GenBank® ABE68619.1)
(SEQ ID NO: 12)
PPELPGGPSVFIFPPKPKDTLTISGTPEVTCVVVDVGHDDPEVKFSWFVDN

VEVNTATTKPREEQFNSTYRVVSALRIQHQDWTGGKEFKCKVHNEGLPAPI

VRTISRTKGPAREPQVYVLAPPQEELSKSTVSLTCMVTSFYPDYIAVEWQR

NGQPESEDKYGTTPPQLDADSSYFLYSKLRVDRNSWQEGDTYTCVVMHEAL

HNHYTQKSTSKSA

IgG2 (GenBank® AQT27057.1)
(SEQ ID NO: 13)
CVREPSVFIFPPKPKDTLMITGTPEVTCVVVNVGHDNPEVQFSWFVDDVEV

HTARTKPREEQFNSTYRVVSALPIQHQDWTGGKEFKCKVNIKGLSASIVRI

ISRSKGPAREPQVYVLDPPKEELSKSTVSVTCMVIGFYPEDVDVEWQRDRQ

TESEDKYRTTPPQLDADRSYFLYSKLRVDRNSWQRGGTYTCVVMHEALHNH

YMQKSTSKSAGK

IgG3 (GenBank® AAC48761.1)
(SEQ ID NO: 14)
EPLGGLSVFIFPPKPKDTLTISGTPEVTCVVVDVGQDDPEVQFSWFVDDVE

VHTARTKPREEQFNSTYRVVSALRIQHQDWLQGKEFKCKVNNKGLPAPIVR

TISRTKGQAREPQVYVLAPPREELSKSTLSLTCLITGFYPEEIDVEWQRNG

QPESEDKYHTTAPQLDADGSYFLYSKLRVNKSSWQEGDHYTCAVMHEALRN

HYKEKSISRSPGK

The CH2 region of a bovine antibody comprises or consists of amino acids 231 to 340 (according to EU numbering) of a bovine IgG antibody. It is to be understood that the CH2 region may include one to six (e.g., 1, 2, 3, 4, 5, 6) additional amino acids or deletions at their N and/or C-terminus.

The CH3 region of a bovine antibody comprises or consists of amino acids 341 to 447 (according to EU numbering) of a bovine IgG antibody. It is to be understood that the CH3 region may include one to six (e.g., 1, 2, 3, 4, 5, 6) additional amino acids or deletions at their N and/or C-terminus.

The Fc region of a bovine IgG antibody comprises or consists of amino acids 231 to 447 (according to EU numbering) of a bovine IgG antibody.

Table 2 below compares the amino acid sequences of the CH2 and CH3 domains of human IgG1, canine IgGB and feline IgG1a with each of the three bovine IgG isotypes, based on EU numbering:

TABLE 2

| | CH2 Domain | | | | | |
|---|---|---|---|---|---|---|
| EU number | Human IgG1 | Canine IgGB | Feline IgG1a | Bovine IgG1 | Bovine IgG2 | Bovine IgG3 |
| 231 | A | A | P | P | | |
| 232 | P | P | P | P | | |
| 233 | E | E | E | E | | E |
| 234 | L | M | M | L | | P |
| 235 | L | L | L | P | | L |

TABLE 2-continued

| 236 | G | G | G | G | | G |
|---|---|---|---|---|---|---|
| 237 | G | G | G | G | | G |
| 238 | P | P | P | P | P | L |
| 239 | S | S | S | S | S | S |
| 240 | V | V | I | V | V | V |
| 241 | F | F | F | F | F | F |
| 242 | L | I | I | I | I | I |
| 243 | F | F | F | F | F | F |
| 244 | P | P | P | P | P | P |
| 245 | P | P | P | P | P | P |
| 246 | K | K | K | K | K | K |
| 247 | P | P | P | P | P | P |
| 248 | K | K | K | K | K | K |
| 249 | D | D | D | D | D | D |
| 250 | T | T | T | T | T | T |
| 251 | L | L | L | L | L | L |
| 252 | M | L | S | T | M | T |
| 253 | I | I | I | I | I | I |
| 254 | S | A | S | S | T | S |
| 255 | R | R | R | G | G | G |
| 256 | T | T | T | T | T | T |
| 257 | P | P | P | P | P | P |
| 258 | E | E | E | E | E | E |
| 259 | V | V | V | V | V | V |
| 260 | T | T | T | T | T | T |
| 261 | C | C | C | C | C | C |
| 262 | V | V | L | V | V | V |
| 263 | V | V | V | V | V | V |
| 264 | V | V | V | V | V | V |
| 265 | D | D | D | D | N | D |
| 266 | V | L | L | V | V | V |
| 267 | S | D | G | G | G | G |
| 268 | H | P | P | H | H | Q |
| 269 | E | E | D | D | D | D |
| 270 | D | D | D | D | N | D |
| 271 | P | P | S | P | P | P |
| 272 | E | E | D | E | E | E |
| 273 | V | V | V | V | V | V |
| 274 | K | Q | Q | K | Q | Q |
| 275 | F | I | I | F | F | F |
| 276 | N | S | T | S | S | S |
| 277 | W | W | W | W | W | W |
| 278 | Y | F | F | F | F | F |
| 279 | V | V | V | V | V | V |
| 280 | D | D | D | D | D | D |
| 282 | G | G | N | N | D | D |
| 282 | V | K | T | V | V | V |
| 283 | E | Q | Q | E | E | E |
| 284 | V | M | V | V | V | V |
| 285 | H | Q | Y | N | H | H |
| 286 | N | T | T | T | T | T |
| 287 | A | A | A | A | A | A |
| 288 | K | K | K | T | R | R |
| 289 | T | T | T | T | T | T |
| 290 | K | Q | S | K | K | K |
| 291 | P | P | P | P | P | P |
| 292 | R | R | R | R | R | R |
| 293 | E | E | E | E | E | E |
| 294 | E | E | E | E | E | E |
| 295 | Q | Q | Q | Q | Q | Q |
| 296 | Y | F | F | F | F | F |
| 297 | N | N | N | N | N | N |
| 298 | S | G | S | S | S | S |
| 299 | T | T | T | T | T | T |
| 300 | Y | Y | Y | Y | Y | Y |
| 301 | R | R | R | R | R | R |
| 302 | V | V | V | V | V | V |
| 303 | V | V | V | V | V | V |
| 304 | S | S | S | S | S | S |
| 305 | V | V | V | A | A | A |
| 306 | L | L | L | L | L | L |
| 307 | T | P | P | R | P | R |
| 308 | V | I | I | I | I | I |
| 309 | L | G | L | Q | Q | Q |
| 310 | H | H | H | H | H | H |
| 311 | Q | Q | Q | Q | Q | Q |
| 312 | D | D | D | D | D | D |
| 313 | W | W | W | W | W | W |
| 314 | L | L | L | T | T | L |
| 315 | N | K | K | G | G | Q |

TABLE 2-continued

| EU number | Human IgG1 | Canine IgGB | Feline IgG1a | Bovine IgG1 | Bovine IgG2 | Bovine IgG3 |
|---|---|---|---|---|---|---|
| 316 | G | G | G | G | G | G |
| 317 | K | K | K | K | K | K |
| 318 | E | Q | E | E | E | E |
| 319 | Y | F | F | F | F | F |
| 320 | K | T | K | K | K | K |
| 321 | C | C | C | C | C | C |
| 322 | K | K | K | K | K | K |
| 323 | V | V | V | V | V | V |
| 324 | S | N | N | H | N | N |
| 325 | N | N | S | N | I | N |
| 326 | K | K | K | E | K | K |
| 327 | A | A | S | G | G | G |
| 328 | L | L | L | L | L | L |
| 329 | P | P | P | P | S | P |
| 330 | A | S | S | A | A | A |
| 331 | P | P | P | P | S | P |
| 332 | I | I | I | I | I | I |
| 333 | E | E | E | V | V | V |
| 334 | K | R | R | R | R | R |
| 335 | T | T | T | T | I | T |
| 336 | I | I | I | I | I | I |
| 337 | S | S | S | S | S | S |
| 338 | K | K | K | R | R | R |
| 339 | A | A | A | T | S | T |
| 340 | K | R | K | K | K | K |

CH3 Domain

| EU number | Human IgG1 | Canine IgGB | Feline IgG1a | Bovine IgG1 | Bovine IgG2 | Bovine IgG3 |
|---|---|---|---|---|---|---|
| 341 | G | G | G | G | G | G |
| 342 | Q | Q | Q | P | P | Q |
| 343 | P | A | P | A | A | A |
| 344 | R | H | H | R | R | R |
| 345 | E | Q | E | E | E | E |
| 346 | P | P | P | P | P | P |
| 347 | Q | S | Q | Q | Q | Q |
| 348 | V | V | V | V | V | V |
| 349 | Y | Y | Y | Y | Y | Y |
| 350 | T | V | V | V | V | V |
| 351 | L | L | L | L | L | L |
| 352 | P | P | P | A | D | A |
| 353 | P | P | P | P | P | P |
| 354 | S | S | A | P | P | P |
| 355 | R | R | Q | Q | K | R |
| 356 | D | E | E | E | E | E |
| 357 | E | E | E | E | E | E |
| 358 | L | L | L | L | L | L |
| 359 | T | S | S | S | S | S |
| 360 | K | K | R | K | K | K |
| 361 | N | N | N | S | S | S |
| 362 | Q | T | K | T | T | T |
| 363 | V | V | V | V | V | L |
| 364 | S | S | S | S | S | S |
| 365 | L | L | V | L | V | L |
| 366 | T | T | T | T | T | T |
| 367 | C | C | C | C | C | C |
| 368 | L | L | L | M | M | L |
| 369 | V | I | I | V | V | I |
| 370 | K | K | K | T | I | T |
| 371 | G | D | S | S | G | G |
| 372 | F | F | F | F | F | F |
| 373 | Y | F | H | Y | Y | Y |
| 374 | P | P | P | P | P | P |
| 375 | S | P | P | D | E | E |
| 376 | D | D | D | Y | D | E |
| 377 | I | I | I | I | V | I |
| 378 | A | D | A | A | D | D |
| 379 | V | V | V | V | V | V |
| 380 | E | E | E | E | E | E |
| 381 | W | W | W | W | W | W |
| 382 | E | Q | E | Q | Q | Q |
| 383 | S | S | I | R | R | R |
| 384 | N | N | T | N | D | N |
| 385 | G | G | G | G | R | G |
| 386 | Q | Q | Q | Q | Q | Q |
| 387 | P | Q | P | P | T | P |
| 388 | E | E | E | E | E | E |
| 389(a) | N | P | P | S | S | S |
| 389b |  | E | E | E | E | E |
| 389c |  | S | N | D | D | D |
| 390 | N | K | N | K | K | K |
| 391 | Y | Y | Y | Y | Y | Y |
| 392 | K | R | R | G | R | H |
| 393 | T | T | T | T | T | T |
| 394 | T | T | T | T | T | T |
| 395 | P | P | P | P | P | A |
| 396 | P | P | P | P | P | P |
| 397 | V | Q | Q | Q | Q | Q |
| 398 | L | L | L | L | L | L |
| 399 | D | D | D | D | D | D |
| 400 | S | E | S | A | A | A |
| 401 | D | D | D | D | D | D |
| 402 | G | G | G | S | R | G |
| 403 | S | S | T | S | S | S |
| 404 | F | Y | Y | Y | Y | Y |
| 405 | F | F | F | F | F | F |
| 406 | L | L | V | L | L | L |
| 407 | Y | Y | Y | Y | Y | Y |
| 408 | S | S | S | S | S | S |
| 409 | K | K | K | K | K | K |
| 410 | L | L | L | L | L | L |
| 411 | T | S | S | R | R | R |
| 412 | V | V | V | V | V | V |
| 413 | D | D | D | D | D | N |
| 414 | K | K | R | R | R | K |
| 415 | S | S | S | N | N | S |
| 416 | R | R | H | S | S | S |
| 417 | W | W | W | W | W | W |
| 418 | Q | Q | Q | Q | Q | Q |
| 419 | Q | R | R | E | R | E |
| 420 | G | G | G | G | G | G |
| 421 | N | D | N | D | G | D |
| 422 | V | T | T | T | T | H |
| 423 | F | F | Y | Y | Y | Y |
| 424 | S | I | T | T | T | T |
| 425 | C | C | C | C | C | C |
| 426 | S | A | S | V | V | A |
| 427 | V | V | V | V | V | V |
| 428 | M | M | S | M | M | M |
| 429 | H | H | H | H | H | H |
| 430 | E | E | E | E | E | E |
| 431 | A | A | A | A | A | A |
| 432 | L | L | L | L | L | L |
| 433 | H | H | H | H | H | R |
| 434 | N | N | S | N | N | N |
| 435 | H | H | H | H | H | H |
| 436 | Y | Y | H | Y | Y | Y |
| 437 | T | T | T | T | M | K |
| 438 | Q | Q | Q | Q | Q | E |
| 439 | K | E | K | K | K | K |
| 440 | S | S | S | S | S | S |
| 441 | L | L | L | T | T | I |
| 442 | S | S | T | S | S | S |
| 443 | L | H | Q | K | K | R |
| 444 | S | S | S | S | S | S |
| 445 | P | P | P | A | A | P |
| 446 | G | G | G | G | G | G |
| 447 | K | K | K | K | K | K |

Substitutions in Bovine IgG Fc that Improve Half-Life

Increased serum persistence is a beneficial property for therapeutic polypeptides. This disclosure features substitutions in wild type bovine IgG1, IgG2 and IgG3 Fc regions that enhance the half-life of a polypeptide or polypeptides comprising these Fc regions in a bovine relative to a control polypeptide or control polypeptides, wherein the control polypeptide or control polypeptides are identical to the polypeptide or polypeptides except for having the corresponding wild type bovine IgG Fc region in place of the IgG Fc region variant. The substitutions to increase half-life may be made in one or more of a bovine CH2 domain, a bovine CH3 domain, or in the context of a bovine Fc (e.g., a CH2+CH3) region.

The present disclosure provides a polypeptide comprising a bovine IgG Fc region variant, or a bovine FcRn-binding region thereof, wherein the polypeptide comprises an amino acid substitution at at least one (e.g., 1, 2, 3, 4, 5, 6, 7, 8, 9, 10 or 11) position selected from the group consisting of:
  (i) a position that corresponds to amino acid position 250 of a wild type bovine IgG, wherein the amino acid substitution is selected from the group consisting of T250Q and T250E;
  (ii) a position that corresponds to amino acid position 252 of a wild type bovine IgG, wherein the amino acid substitution is selected from the group consisting of M252Y, M252W, M252F, T252Y, T252W and T252F;
  (iii) a position that corresponds to amino acid position 254 of a wild type bovine IgG, wherein the amino acid substitution is selected from the group consisting of S254T, S254R, S254K, S254H, T254R, T254K and T254H;
  (iv) a position that corresponds to amino acid position 256 of a wild type bovine IgG, wherein the amino acid substitution is selected from the group consisting of T256A, T256D and T256E;
  (v) a position that corresponds to amino acid position 286 of a wild type bovine IgG, wherein the amino acid substitution is selected from the group consisting of T286Y, T286F, T286W, T286L, T286D and T286E;
  (vi) a position that corresponds to amino acid position 309 of a wild type bovine IgG, wherein the amino acid substitution is selected from the group consisting of Q309V, Q309D and Q309E;
  (vii) a position that corresponds to amino acid position 311 of a wild type bovine IgG, wherein the amino acid substitution is selected from the group consisting of Q311V, Q311K, Q311R, Q311L and Q311H;
  (viii) a position that corresponds to amino acid position 426 of a wild type bovine IgG, wherein the amino acid substitution is selected from the group consisting of A426Y, A426F, A426H, V426Y, V426F and V426H;
  (ix) a position that corresponds to amino acid position 434 of a wild type bovine IgG, wherein the amino acid substitution is selected from the group consisting of N434A, N434H, N434F, N434S, N434W and N434Y; and
  (x) a position that corresponds to amino acid position 436 of a wild type bovine IgG, wherein the amino acid substitution is Y436H, wherein the amino acid positions are based on EU numbering, and wherein the polypeptide has increased binding affinity to bovine FcRn when compared to an Fc domain of the wild type bovine IgG.

In some embodiments, the polypeptide comprises an amino acid substitution at at least one (e.g., 1, 2, 3, 4, or 5) position selected from the group consisting of:
  (i) a position that corresponds to amino acid position 252 of a wild type IgG of the livestock animal, wherein the amino acid substitution is T252Y;
  (ii) a position that corresponds to amino acid position 309 of a wild type IgG of the livestock animal, wherein the amino acid substitution is Q309V;
  (iii) a position that corresponds to amino acid position 311 of a wild type IgG of the livestock animal, wherein the amino acid substitution is Q311V;
  (iv) a position that corresponds to amino acid position 434 of a wild type IgG of the livestock animal, wherein the amino acid substitution is selected from the group consisting of N434Y; and
  (v) a position that corresponds to amino acid position 436 of a wild type IgG of the livestock animal, wherein the amino acid substitution is selected from the group consisting of Y436H.

In some embodiments, the polypeptide has increased binding affinity to bovine FcRn at a pH of about 5.0 to about 6.5 (e.g., about 5.5 or about 6.0) when compared to an Fc domain of the wild type bovine IgG at the same pH.

In some embodiments, the polypeptide comprises an amino acid sequence that is at least 80% (e.g., at least 85%, 90%, 92%, 94%, 95%, 96%, 97%, 98%, or 99%) identical to an amino acid sequence selected from the group consisting of SEQ ID NOs: 12 to 14.

In some instances, this disclosure provides a bovine IgG CH2 domain variant comprising an amino acid sequence that is at least 75%, at least 80%, at least 85%, at least 90%, at least 95%, at least 96%, at least 97%, at least 98% or at least 99% identical to the CH2 domains shown in any one of SEQ ID NOs.:12 to 14. Also provided are bovine IgG CH2 domain variants comprising an amino acid sequence that varies from any one of the CH2 domains shown in SEQ ID NOs.:12 to 14 by 1 to 15 (e.g., by 1, 2, 3, 4, 5, 6, 7, 8, 9, 10, 11, 12, 13, 14, or 15) amino acids.

In other instances, this disclosure features a bovine IgG CH3 domain variant comprising an amino acid sequence that is at least 75%, at least 80%, at least 85%, at least 90%, at least 95%, at least 96%, at least 97% or at least 98% or at least 99%, identical to the amino acid sequence of the CH3 domain shown in any one of SEQ ID NOs.:12 to 14. Also featured are bovine IgG CH3 domain variants comprising an amino acid sequence that varies from any one of the CH3 domain sequences shown in any one of SEQ ID NOs.:12 to 14 by 1 to 15 (e.g., by 1, 2, 3, 4, 5, 6, 7, 8, 9, 10, 11, 12, 13, 14, or 15) amino acids.

In certain instances, this disclosure features a bovine IgG Fc region variant comprising an amino acid sequence that is at least 75%, at least 80%, at least 85%, at least 90%, at least 95%, at least 96%, at least 97%, at least 98% or at least 99% identical to the amino acid sequence set forth in any one of SEQ ID NOs.:12 to 14. Also disclosed are bovine IgG Fc region variants comprising an amino acid sequence that varies from any one of SEQ ID NOs.:12 to 14 by 1 to 20 (e.g., by 1, 2, 3, 4, 5, 6, 7, 8, 9, 10, 11, 12, 13, 14, 15, 16, 17, 18, 19, or 20) amino acids.

In some embodiments, provided are a polypeptide or polypeptides comprising a bovine IgG Fc CH2 domain variant, the CH2 domain variant comprising an amino acid sequence that is at least 75%, at least 80%, at least 85%, at least 90%, at least 95%, at least 96%, at least 97%, at least 98% or at least 99%, identical to the amino acid sequence of the CH2 domain shown in any one of SEQ ID NOs.:12 to 14.

In some embodiments, featured are a polypeptide or polypeptides comprising a bovine IgG Fc CH3 domain variant, the CH3 domain variant comprising an amino acid sequence that is at least 75%, at least 80%, at least 85%, at least 90%, at least 95%, at least 96%, at least 97%, at least 98% or at least 99% identical to the amino acid sequence of the CH3 domain shown in any one of SEQ ID NOs.:12 to 14.

In some embodiments, featured are a polypeptide or polypeptides comprising a bovine IgG Fc region variant, the Fc region variant comprising an amino acid sequence that is at least 75%, at least 80%, at least 85%, at least 90%, at least 95%, at least 96%, at least 97%, at least 98% or at least 99% identical to the amino acid sequence set forth in any one of SEQ ID NOs.:12 to 14.

Equine Antibodies

Equine typically have seven IgG heavy chains referred to as IgG1, IgG2, IgG3, IgG4, IgG5, IgG6 and IgG7. These heavy chains represent seven different subclasses of equine IgG. The amino acid and DNA sequences for these heavy chains are available from the GenBank® database. Illustrative examples of the amino acid sequences of the CH2 and CH3 domains of each of the seven equine IgG heavy chain Fc regions are shown below (CH2 domains are underlined), and the GenBank® accession number (for the amino acid sequence or mRNA sequence from which the amino acid sequence is derived) of each heavy chain Fc region is indicated:

Horse Equus caballus

IgG1 (GenBank® CAC44760.1)
(SEQ ID NO: 15)
APELLGGPSVFIFPPNPKDTLMITRTPEVTCVVVDVSQENPDVKFNWYMDG

VEVRTATTRPKEEQFNSTYRVVSVLRIQHQDWLSGKEFKCKVNNQALPQPI

ERTITKTKGRSQEPQVYVLAPHPDELSKSKVSVTCLVKDFYPPEINIEWQS

NGQPELETKYSTTQAQQDSDGSYFLYSKLSVDRNRWQQGTTFTCGVMHEAL

HNHYTQKNVSKNPGK

IgG2 (GenBank® CAC44761.1)
(SEQ ID NO: 16)
GPSVFIFPPNPKDALMISRTPVVTCVVVNLSDQYPDVQFSWYVDNTEVHSA

ITKQREAQFNSTYRVVSVLPIQHQDWLSGKEFKCSVTNVGVPQPISRAISR

GKGPSRVPQVYVLPPHPDELAKSKVSVTCLVKDFYPPDISVEWQSNRWPEL

EGKYSTTPAQLDGDGSYFLYSKLSLETSRWQQVESFTCAVMHEALHNHFTK

TDISESLGK

IgG3 (GenBank® AAP82181.1)
(SEQ ID NO: 17)
APELLGGPSVFIFPPKPKDVLMITRMPEVTCLVVDVSHDSSDVLFTWYVDG

TEVKTAKTMPNEEQNNSTYRVVSVLRIQHQDWLNGKKFKCKVNNQALPAPV

ERTISKATGQTRVPQVYVLAPHPDELSKNKVSVTCLVKDFYPTDITVEWQS

NEHPEPEGKYRTTEAQKDSDGSYFLYSKLTVEKDRWQQGTTFTCVVMHEAL

HNHVMQKNISKNPGK

IgG4 (GenBank® AA518415.1)
(SEQ ID NO: 18)
ECLQVGPSVFIFPPKPKDVLMISRTPTVTCVVVDVGHDFPDVQFNWYVDGV

ETHTATTEPKQEQFNSTYRVVSVLPIQHKDWLSGKEFKCKVNNKALPAPVE

RTISKPTGQPREPQVYVLAPHRDELSKNKVSVTCLVKDFYPTDIDIEWKSN

GQPEPETKYSTTPAQLDSDGSYFLYSKLTVETNRWQQGTTFTCAVMHEALH

NHYTEKSVSKSPGK

IgG5 (GenBank® CAC86340.1)
(SEQ ID NO: 19)
APELPGGPSVFIFPPKPKDVLKISRKPEVTCVVVDLGHDDPDVQFTWFVDG

VETHTATTEPKEEQFNSTYRVVSVLPIQHQDWLSGKEFKCSVTNKALPAPV

ERTTSKAKGQLRVPQVYVLAPHPDELAKNTVSVTCLVKDFYPPEIDVEWQS

NEHPEPEGKYSTTPAQLNSDGSYFLYSKLSVETSRWKQGESFTCGVMHEAV

ENHYTQKNVSHSPGK

IgG6 (GenBank® CAC86341.1)
(SEQ ID NO: 20)
DSKFLGRPSVFIFPPNPKDTLMISRTPEVTCVVVDVSQENPDVKFNWYVDG

VEAHTATTKAKEKQDNSTYRVVSVLPIQHQDWRRGKEFKCKVNNRALPAPV

ERTITKAKGELQDPKVYILAPHREEVTKNTVSVTCLVKDFYPPDINVEWQS

NEEPEPEVKYSTTPAQLDGDGSYFLYSKLTVETDRWEQGESFTCVVMHEAI

RHTYRQKSITNFPGK

IgG7 (GenBank® AAS18414.1)
(SEQ ID NO: 21)
ECLSVGPSVFIFPPKPKDVLMISRTPTVTCVVVDVGHDFPDVQFNWYVDGV

ETHTATTEPKQEQNNSTYRVVSILAIQHKDWLSGKEFKCKVNNQALPAPVQ

KTISKPTGQPREPQVYVLAPHRDELSKNKVSVTCLVKDFYPTDIDIEWKSN

GQPEPETKYSTTPAQLDSDGSYFLYSKLTVETNRWQQGTTFTCAVMHEALH

NHYTEKSVSKSPGK

The CH2 region of an equine antibody comprises or consists of amino acids 231 to 340 (according to EU numbering) of an equine IgG antibody. It is to be understood that the CH2 region may include one to six (e.g., 1, 2, 3, 4, 5, 6) additional amino acids or deletions at their N and/or C-terminus.

The CH3 region of an equine antibody comprises or consists of amino acids 341 to 447 (according to EU numbering) of an equine IgG antibody. It is to be understood that the CH3 region may include one to six (e.g., 1, 2, 3, 4, 5, 6) additional amino acids or deletions at their N and/or C-terminus.

The Fc region of an equine IgG antibody comprises or consists of amino acids 231 to 447 (according to EU numbering) of an equine IgG antibody.

Table 3 below compares the amino acid sequences of the CH2 and CH3 domains of human IgG1, canine IgGB and feline IgG1a with each of the seven equine IgG isotypes, based on EU numbering:

TABLE 3

| EU number | Human IgG1 | Canine IgGB | Feline IgG1a | Horse IgG1 | Horse IgG2 | Horse IgG3 | Horse IgG4 | Horse IgG5 | Horse IgG6 | Horse IgG7 |
|---|---|---|---|---|---|---|---|---|---|---|
| CH2 Domain ||||||||||| 
| 231 | A | A | P | A |   | A |   | A | D |   |
| 232 | P | P | P | P |   | P | E | P | S | E |
| 233 | E | E | E | E |   | E | C | E | K | C |
| 234 | L | M | M | L |   | L | L | L | F | L |
| 235 | L | L | L | L |   | L | Q | P | L | S |
| 236 | G | G | G | G |   | G | V | G | G | V |
| 237 | G | G | G | G | G | G | G | G | R | G |
| 238 | P | P | P | P | P | P | P | P | P | P |
| 239 | S | S | S | S | S | S | S | S | S | S |

TABLE 3-continued

| EU number | Human IgG1 | Canine IgGB | Feline IgG1a | Horse IgG1 | Horse IgG2 | Horse IgG3 | Horse IgG4 | Horse IgG5 | Horse IgG6 | Horse IgG7 |
|---|---|---|---|---|---|---|---|---|---|---|
| 240 | V | V | I | V | V | V | V | V | V | V |
| 241 | F | F | F | F | F | F | F | F | F | F |
| 242 | L | I | I | I | I | I | I | I | I | I |
| 243 | F | F | F | F | F | F | F | F | F | F |
| 244 | P | P | P | P | P | P | P | P | P | P |
| 245 | P | P | P | P | P | P | P | P | P | P |
| 246 | K | K | K | N | N | K | K | K | N | K |
| 247 | P | P | P | P | P | P | P | P | P | P |
| 248 | K | K | K | K | K | K | K | K | K | K |
| 249 | D | D | D | D | D | D | D | D | D | D |
| 250 | T | T | T | T | A | V | V | V | T | V |
| 251 | L | L | L | L | L | L | L | L | L | L |
| 252 | M | L | S | M | M | M | M | K | M | M |
| 253 | I | I | I | I | I | I | I | I | I | I |
| 254 | S | A | S | T | S | T | S | S | S | S |
| 255 | R | R | R | R | R | R | R | R | R | R |
| 256 | T | T | T | T | T | M | T | K | T | T |
| 257 | P | P | P | P | P | P | P | P | P | P |
| 258 | E | E | E | E | V | E | T | E | E | T |
| 259 | V | V | V | V | V | V | V | V | V | V |
| 260 | T | T | T | T | T | T | T | T | T | T |
| 261 | C | C | C | C | C | C | C | C | C | C |
| 262 | V | V | L | V | V | L | V | V | V | V |
| 263 | V | V | V | V | V | V | V | V | V | V |
| 264 | V | V | V | V | V | V | V | V | V | V |
| 265 | D | D | D | D | N | D | D | D | D | D |
| 266 | V | L | L | V | L | V | V | L | V | V |
| 267 | S | D | G | S | S | S | G | G | S | G |
| 268 | H | P | P | Q | D | H | H | H | Q | H |
| 269 | E | E | D | E | Q | D | D | D | E | D |
| 270 | D | D | D | N | Y | S | F | D | N | F |
| 271 | P | P | S | P | P | S | P | P | P | P |
| 272 | E | E | D | D | D | D | D | D | D | D |
| 273 | V | V | V | V | V | V | V | V | V | V |
| 274 | K | Q | Q | K | Q | L | Q | Q | K | Q |
| 275 | F | I | I | F | F | F | F | F | F | F |
| 276 | N | S | T | N | S | T | N | T | N | N |
| 277 | W | W | W | W | W | W | W | W | W | W |
| 278 | Y | F | F | Y | Y | Y | Y | F | Y | Y |
| 279 | V | V | V | M | V | V | V | V | V | V |
| 280 | D | D | D | D | D | D | D | D | D | D |
| 282 | G | G | N | G | N | G | G | G | G | G |
| 282 | V | K | T | V | T | T | V | V | V | V |
| 283 | E | Q | Q | E | E | E | E | E | E | E |
| 284 | V | M | V | V | V | V | T | T | A | T |
| 285 | H | Q | Y | R | H | K | H | H | H | H |
| 286 | N | T | T | T | S | T | T | T | T | T |
| 287 | A | A | A | A | A | A | A | A | A | A |
| 288 | K | K | K | T | I | K | T | T | T | T |
| 289 | T | T | T | T | T | T | T | T | T | T |
| 290 | K | Q | S | R | K | M | E | E | K | E |
| 291 | P | P | P | P | Q | P | P | P | A | P |
| 292 | R | R | R | K | R | N | K | K | K | K |
| 293 | E | E | E | E | E | E | Q | E | E | Q |
| 294 | E | E | E | E | A | E | E | E | K | E |
| 295 | Q | Q | Q | Q | Q | Q | Q | Q | Q | Q |
| 296 | Y | F | F | F | F | N | F | F | D | N |
| 297 | N | N | N | N | N | N | N | N | N | N |
| 298 | S | G | S | S | S | S | S | S | S | S |
| 299 | T | T | T | T | T | T | T | T | T | T |
| 300 | Y | Y | Y | Y | Y | Y | Y | Y | Y | Y |
| 301 | R | R | R | R | R | R | R | R | R | R |
| 302 | V | V | V | V | V | V | V | V | V | V |
| 303 | V | V | V | V | V | V | V | V | V | V |
| 304 | S | S | S | S | S | S | S | S | S | S |
| 305 | V | V | V | V | V | V | V | V | V | I |
| 306 | L | L | L | L | L | L | L | L | L | L |
| 307 | T | P | P | R | P | R | P | P | P | A |
| 308 | V | I | I | I | I | I | I | I | I | I |
| 309 | L | G | L | Q | Q | Q | Q | Q | Q | Q |
| 310 | H | H | H | H | H | H | H | H | H | H |
| 311 | Q | Q | Q | Q | Q | Q | K | Q | Q | K |
| 312 | D | D | D | D | D | D | D | D | D | D |
| 313 | W | W | W | W | W | W | W | W | W | W |
| 314 | L | L | L | L | L | L | L | L | R | L |
| 315 | N | K | K | S | S | N | S | S | R | S |
| 316 | G | G | G | G | G | G | G | G | G | G |

TABLE 3-continued

| EU number | Human IgG1 | Canine IgGB | Feline IgG1a | Horse IgG1 | Horse IgG2 | Horse IgG3 | Horse IgG4 | Horse IgG5 | Horse IgG6 | Horse IgG7 |
|---|---|---|---|---|---|---|---|---|---|---|
| 317 | K | K | K | K | K | K | K | K | K | K |
| 318 | E | Q | E | E | E | K | E | E | E | E |
| 319 | Y | F | F | F | F | F | F | F | F | F |
| 320 | K | T | K | K | K | K | K | K | K | K |
| 321 | C | C | C | C | C | C | C | C | C | C |
| 322 | K | K | K | K | S | K | K | S | K | K |
| 323 | V | V | V | V | V | V | V | V | V | V |
| 324 | S | N | N | N | T | N | N | T | N | N |
| 325 | N | N | S | N | N | N | N | N | N | N |
| 326 | K | K | K | Q | v | Q | K | K | R | Q |
| 327 | A | A | S | A | G | A | A | A | A | A |
| 328 | L | L | L | L | V | L | L | L | L | L |
| 329 | P | P | P | P | P | P | P | P | P | P |
| 330 | A | S | S | Q | Q | A | A | A | A | A |
| 331 | P | P | P | P | P | P | P | P | P | P |
| 332 | I | I | I | I | I | V | V | V | V | V |
| 333 | E | E | E | E | S | E | E | E | E | Q |
| 334 | K | R | R | R | R | R | R | R | R | K |
| 335 | T | T | T | T | A | T | T | T | T | T |
| 336 | I | I | I | I | I | I | I | T | I | I |
| 337 | 5 | 5 | 5 | T | S | S | S | S | T | S |
| 338 | K | K | K | K | R | K | K | K | K | K |
| 339 | A | A | A | T | G | A | P | A | A | P |
| 340 | K | R | K | K | K | T | T | K | K | T |
| | | | | CH3 Domain | | | | | | |
| 341 | G | G | G | G | G | G | G | G | G | G |
| 342 | Q | Q | Q | R | P | Q | Q | Q | E | Q |
| 343 | P | A | P | S | S | T | P | L | L | P |
| 344 | R | H | H | Q | R | R | R | R | Q | R |
| 345 | E | Q | E | E | V | V | E | V | D | E |
| 346 | P | P | P | P | P | P | P | P | P | P |
| 347 | Q | s | Q | Q | Q | Q | Q | Q | K | Q |
| 348 | V | V | V | V | V | V | V | V | V | V |
| 349 | Y | Y | Y | Y | Y | Y | Y | Y | Y | Y |
| 350 | T | V | V | V | V | V | V | V | I | V |
| 351 | L | L | L | L | L | L | L | L | L | L |
| 352 | P | P | P | A | P | A | A | A | A | A |
| 353 | P | P | P | P | P | P | P | P | P | P |
| 354 | S | S | A | H | H | H | H | H | H | H |
| 355 | R | R | Q | P | P | P | R | P | R | R |
| 356 | D | E | E | D | D | D | D | D | E | D |
| 357 | E | E | E | E | E | E | E | E | E | E |
| 358 | L | L | L | L | L | L | L | L | V | L |
| 359 | T | S | S | S | A | S | S | A | T | S |
| 360 | K | K | R | K | K | K | K | K | K | K |
| 361 | N | N | N | S | S | N | N | N | N | N |
| 362 | Q | T | K | K | K | K | K | T | T | K |
| 363 | V | V | V | V | V | V | V | V | V | V |
| 364 | S | S | S | S | S | S | S | S | S | S |
| 365 | L | L | V | V | V | V | V | V | V | V |
| 366 | T | T | T | T | T | T | T | T | T | T |
| 367 | C | C | C | C | C | C | C | C | C | C |
| 368 | L | L | L | L | L | L | L | L | L | L |
| 369 | V | V | I | V | V | V | V | V | V | V |
| 370 | K | K | K | K | K | K | K | K | K | K |
| 371 | G | D | S | D | D | D | D | D | D | D |
| 372 | F | F | F | F | F | F | F | F | F | F |
| 373 | Y | F | H | Y | Y | Y | Y | Y | Y | Y |
| 374 | P | P | P | P | P | P | P | P | P | P |
| 375 | S | P | P | P | P | T | T | P | P | T |
| 376 | D | D | D | E | D | D | D | E | D | D |
| 377 | I | I | I | I | I | I | I | I | I | I |
| 378 | A | D | A | N | S | T | D | D | N | D |
| 379 | V | V | V | I | V | V | I | V | V | I |
| 380 | E | E | E | E | E | E | E | E | E | E |
| 381 | W | W | W | W | W | W | W | W | W | W |
| 382 | E | Q | E | Q | Q | Q | K | Q | Q | K |
| 383 | S | S | I | S | S | S | S | S | S | S |
| 384 | N | N | T | N | N | N | N | N | N | N |
| 385 | G | G | G | G | R | E | G | E | E | G |
| 386 | Q | Q | Q | Q | W | H | Q | H | E | Q |
| 387 | P | Q | P | P | P | P | P | P | P | P |
| 388 | E | E | E | E | E | E | E | E | E | E |
| 389(a) | N | P | P | L | L | P | P | P | P | P |
| 389h | | E | E | E | E | E | E | E | E | E |
| 389c | | S | N | T | G | G | T | G | V | T |

TABLE 3-continued

| EU number | Human IgG1 | Canine IgGB | Feline IgG1a | Horse IgG1 | Horse IgG2 | Horse IgG3 | Horse IgG4 | Horse IgG5 | Horse IgG6 | Horse IgG7 |
|---|---|---|---|---|---|---|---|---|---|---|
| 390 | N | K | N | K | K | K | K | K | K | K |
| 391 | Y | Y | Y | Y | Y | Y | Y | Y | Y | Y |
| 392 | K | R | R | S | S | R | S | S | S | S |
| 393 | T | T | T | T | T | T | T | T | T | T |
| 394 | T | T | T | T | T | T | T | T | T | T |
| 395 | P | P | P | Q | P | E | P | P | P | P |
| 396 | P | P | P | A | A | A | A | A | A | A |
| 397 | V | Q | Q | Q | Q | Q | Q | Q | Q | Q |
| 398 | L | L | L | Q | L | K | L | L | L | L |
| 399 | D | D | D | D | D | D | D | N | D | D |
| 400 | S | E | S | S | G | S | S | S | G | S |
| 401 | D | D | D | D | D | D | D | D | D | D |
| 402 | G | G | G | G | G | G | G | G | G | G |
| 403 | S | S | T | S | S | S | S | S | S | S |
| 404 | F | Y | Y | Y | Y | Y | Y | Y | Y | Y |
| 405 | F | F | F | F | F | F | F | F | F | F |
| 406 | L | L | V | L | L | L | L | L | L | L |
| 407 | Y | Y | Y | Y | Y | Y | Y | Y | Y | Y |
| 408 | S | S | S | S | S | S | S | S | S | S |
| 409 | K | K | K | K | K | K | K | K | K | K |
| 410 | L | L | L | L | L | L | L | L | L | L |
| 411 | T | S | S | S | S | S | T | S | T | T |
| 412 | V | V | V | V | L | V | V | V | V | V |
| 413 | D | D | D | D | E | E | E | E | E | E |
| 414 | K | K | R | R | T | K | T | T | T | T |
| 415 | S | S | S | N | S | D | N | S | D | N |
| 416 | R | R | H | R | R | R | R | R | R | R |
| 417 | W | W | W | W | W | W | W | W | W | W |
| 418 | Q | Q | Q | Q | Q | Q | Q | K | E | Q |
| 419 | Q | R | R | Q | Q | Q | Q | Q | Q | Q |
| 420 | G | G | G | G | V | G | G | G | G | G |
| 421 | N | D | N | T | E | T | T | E | E | T |
| 422 | V | T | T | T | S | T | T | S | S | T |
| 423 | F | F | Y | F | F | F | F | F | F | F |
| 424 | S | I | T | T | T | T | T | T | T | T |
| 425 | C | C | C | C | C | C | C | C | C | C |
| 426 | S | A | S | G | A | V | A | G | V | A |
| 427 | V | V | V | V | V | V | V | V | V | V |
| 428 | M | M | S | M | M | M | M | M | M | M |
| 429 | H | H | H | H | H | H | H | H | H | H |
| 430 | E | E | E | E | E | E | E | E | E | E |
| 431 | A | A | A | A | A | A | A | A | A | A |
| 432 | L | L | L | L | L | L | L | V | I | L |
| 433 | H | H | H | H | H | H | H | E | R | H |
| 434 | N | N | S | N | N | N | N | N | H | N |
| 435 | H | H | H | H | H | H | H | H | T | H |
| 436 | Y | Y | H | Y | F | V | Y | Y | Y | Y |
| 437 | T | T | T | T | T | M | T | T | R | T |
| 438 | Q | Q | Q | Q | K | Q | E | Q | Q | E |
| 439 | K | E | K | K | T | K | K | K | K | K |
| 440 | S | S | S | N | D | N | S | N | S | S |
| 441 | L | L | L | V | I | I | V | V | I | V |
| 442 | S | S | T | S | S | S | S | S | T | S |
| 443 | L | H | Q | K | E | K | K | H | N | K |
| 444 | S | S | S | N | S | N | S | S | F | S |
| 445 | P | P | P | P | L | P | P | P | P | P |
| 446 | G | G | G | G | G | G | G | G | G | G |
| 447 | K | K | K | K | K | K | K | K | K | K |

Substitutions in Equine IgG Fc that Improve Half-Life

Increased serum persistence is a beneficial property for therapeutic polypeptides. This disclosure features substitutions in wild type equine IgG1, IgG2, IgG3, IgG4, IgG5, IgG6 and IgG7 Fc regions that enhance the half-life of a polypeptide or polypeptides comprising these Fc regions in an equine relative to a control polypeptide or control polypeptides, wherein the control polypeptide or control polypeptides are identical to the polypeptide or polypeptides except for having the corresponding wild type equine IgG Fc region in place of the IgG Fc region variant. The substitutions to increase half-life may be made in one or more of an equine CH2 domain, an equine CH3 domain, or in the context of an equine Fc (e.g., a CH2+CH3) region.

The present disclosure provides a polypeptide comprising an equine IgG Fc region variant, or an equine FcRn-binding region thereof, wherein the polypeptide comprises an amino acid substitution at at least one (e.g., 1, 2, 3, 4, 5, 6, 7, 8, 9, 10 or 11) position selected from the group consisting of:

(i) a position that corresponds to amino acid position 250 of a wild type equine IgG, wherein the amino acid substitution is selected from the group consisting of T250Q, T250E, A250Q, A250E, V250Q and V250E;

(ii) a position that corresponds to amino acid position 252 of a wild type equine IgG, wherein the amino acid substitution is selected from the group consisting of M252Y, M252W, M252F, K252Y, K252W and K252F;

(iii) a position that corresponds to amino acid position 254 of a wild type equine IgG, wherein the amino acid substitution is selected from the group consisting of S254T, S254R, S254K, S254H, T254R, T254K and T254H;

(iv) a position that corresponds to amino acid position 256 of a wild type equine IgG, wherein the amino acid substitution is selected from the group consisting of T256A, T256D, T256E, M256A, M256D, M256E, K256A, K256D and K256E;

(v) a position that corresponds to amino acid position 286 of a wild type equine IgG, wherein the amino acid substitution is selected from the group consisting of S286Y, S286F, S286W, S286L, S286D, S286E, T286Y, T286F, T286W, T286L, T286D and T286E;

(vi) a position that corresponds to amino acid position 309 of a wild type equine IgG, wherein the amino acid substitution is selected from the group consisting of Q309V, Q309D and Q309E;

(vii) a position that corresponds to amino acid position 311 of a wild type equine IgG, wherein the amino acid substitution is selected from the group consisting of Q311V, Q311K, Q311R, Q311L, Q311H, K311V, K311R, K311L and K311H;

(viii) a position that corresponds to amino acid position 426 of a wild type equine IgG, wherein the amino acid substitution is selected from the group consisting of A426Y, A426F, A426H, V426Y, V426F, V426H, G426Y, G426F and G426H;

(ix) a position that corresponds to amino acid position 428 of a wild type equine IgG, wherein the amino acid substitution is selected from the group consisting of M428L, M428Y and M428F;

(x) a position that corresponds to amino acid position 434 of a wild type equine IgG, wherein the amino acid substitution is selected from the group consisting of N434A, N434H, N434F, N434S, N434W, N434Y, H434A, H434F, H434S, H434W and H434Y; and (xi) a position that corresponds to amino acid position 436 of a wild type equine IgG, wherein the amino acid substitution is selected from the group consisting of Y436H, F436H and V436H, wherein the amino acid positions are based on EU numbering, and wherein the polypeptide has increased binding affinity to equine FcRn when compared to an Fc domain of the wild type equine IgG.

In some embodiments, the polypeptide comprises an amino acid substitution at at least one (e.g., 1, 2, 3, 4, 5, or 6) position selected from the group consisting of:

(i) a position that corresponds to amino acid position 252 of a wild type IgG of the livestock animal, wherein the amino acid substitution is M252Y;

(ii) a position that corresponds to amino acid position 286 of a wild type IgG of the livestock animal, wherein the amino acid substitution is T286E (iii) a position that corresponds to amino acid position 309 of a wild type IgG of the livestock animal, wherein the amino acid substitution is Q309V;

(iv) a position that corresponds to amino acid position 311 of a wild type IgG of the livestock animal, wherein the amino acid substitution is Q311V;

(v) a position that corresponds to amino acid position 426 of a wild type IgG of the livestock animal, wherein the amino acid substitution is G426Y; and (vi) a position that corresponds to amino acid position 434 of a wild type IgG of the livestock animal, wherein the amino acid substitution is selected from the group consisting of N434Y.

In some embodiments, the polypeptide has increased binding affinity to equine FcRn at a pH of about 5.0 to about 6.5 (e.g., about 5.5 or about 6.0) when compared to an Fc domain of the wild type equine IgG at the same pH.

In some embodiments, the polypeptide comprises an amino acid sequence that is at least 80% (e.g., at least 85%, 90%, 92%, 94%, 95%, 96%, 97%, 98%, or 99%) identical to an amino acid sequence selected from the group consisting of SEQ ID NOs: 15 to 21.

In some instances, this disclosure provides an equine IgG CH2 domain variant comprising an amino acid sequence that is at least 75%, at least 80%, at least 85%, at least 90%, at least 95%, at least 96%, at least 97%, at least 98% or at least 99% identical to the CH2 domains shown in any one of SEQ ID NOs.:15 to 21. Also provided are equine IgG CH2 domain variants comprising an amino acid sequence that varies from any one of the CH2 domains shown in SEQ ID NOs.:15 to 21 by 1 to 15 (e.g., by 1, 2, 3, 4, 5, 6, 7, 8, 9, 10, 11, 12, 13, 14, or 15) amino acids.

In some instances, this disclosure features an equine IgG CH3 domain variant comprising an amino acid sequence that is at least 75%, at least 80%, at least 85%, at least 90%, at least 95%, at least 96%, at least 97% or at least 98% or at least 99%, identical to the amino acid sequence of the CH3 domain shown in any one of SEQ ID NOs.:15 to 21. Also featured are equine IgG CH3 domain variants comprising an amino acid sequence that varies from any one of the CH3 domain sequences shown in any one of SEQ ID NOs.:15 to 21 by 1 to 15 (e.g., by 1, 2, 3, 4, 5, 6, 7, 8, 9, 10, 11, 12, 13, 14, or 15) amino acids.

In some instances, this disclosure features an equine IgG Fc region variant comprising an amino acid sequence that is at least 75%, at least 80%, at least 85%, at least 90%, at least 95%, at least 96%, at least 97%, at least 98% or at least 99% identical to the amino acid sequence set forth in any one of SEQ ID NOs.:15 to 21. Also disclosed are equine IgG Fc region variants comprising an amino acid sequence that varies from any one of SEQ ID NOs.:15 to 21 by 1 to 20 (e.g., by 1, 2, 3, 4, 5, 6, 7, 8, 9, 10, 11, 12, 13, 14, 15, 16, 17, 18, 19, or 20) amino acids.

In some embodiments, provided are a polypeptide or polypeptides comprising an equine IgG Fc CH2 domain variant, the CH2 domain variant comprising an amino acid sequence that is at least 75%, at least 80%, at least 85%, at least 90%, at least 95%, at least 96%, at least 97%, at least 98% or at least 99%, identical to the amino acid sequence of the CH2 domain shown in any one of SEQ ID NOs.:15 to 21.

In some embodiments, featured are a polypeptide or polypeptides comprising an equine IgG Fc CH3 domain variant, the CH3 domain variant comprising an amino acid sequence that is at least 75%, at least 80%, at least 85%, at least 90%, at least 95%, at least 96%, at least 97%, at least 98% or at least 99% identical to the amino acid sequence of the CH3 domain shown in any one of SEQ ID NOs.:15 to 21.

In some embodiments, featured are a polypeptide or polypeptides comprising an equine IgG Fc region variant, the Fc region variant comprising an amino acid sequence that is at least 75%, at least 80%, at least 85%, at least 90%, at least 95%, at least 96%, at least 97%, at least 98% or at least 99% identical to the amino acid sequence set forth in any one of SEQ ID NOs.:15 to 21.

Ovine Antibodies

Ovine typically have three IgG heavy chains referred to as IgG1, IgG2 and IgG3. These heavy chains represent three different subclasses of ovine IgG. The amino acid and DNA sequences for these heavy chains are available from the GENBANK database. Illustrative examples of the amino acid sequences of the CH2 and CH3 domains of each of the three ovine IgG heavy chain Fc regions are shown below (CH2 domains are underlined), and the GenBank accession number (for the amino acid sequence or mRNA sequence from which the amino acid sequence is derived) of each heavy chain Fc region is indicated:

Sheep *Ovis aries*

```
IgG1 (GENBANK ® X69797)
                                      (SEQ ID NO: 22)
PELPGGPSVFIFPPKPKDTLTISGTPEVTCVVVDVGQDDPEVQFSWFVDN

VEVRTARTKPREEQFNSTFRVVSALPIQHQDWTGGKEFKCKVHNEALPAP

IVRTISRTKGQAREPQVYVLAPPQEELSKSTLSVTCLVTGFYPDYIAVEW

QKNGQPESEDKYGTTTSQLDADGSYFLYSRLRVDKNSWQEGDTYACVVMH

EALHNHYTQKSISKPPGK

IgG2 (GENBANK ® X70983)
                                      (SEQ ID NO: 23)
VSRPSVFIFPPKPKDSLMITGTPEVTCVVVDVGQGDPEVQFSWFVDNVEV

RTARTKPREEQFNSTFRVVSALPIQHDHWTGGKEFKCKVHSKGLPAPIVR

TISRAKGQAREPQVYVLAPPQEELSKSTLSVTCLVTGFYPDYIAVEWQRA

RQPESEDKYGTTTSQLDADGSYFLYSRLRVDKSSWQRGDTYACVVMHEAL

HNHYTQKSISKPPGK

IgG3 (Schwartz et al, 2018, Immunogenetics, 70:
317)
                                      (SEQ ID NO: 24)
PEPLGGLSVFIFPPKPKDTLTISGTPEVTCVVVDVGQDDPEVQFSWFVDN

VEVRTARTKPREEQFNSTFRVVSALPIQHQDWLRGKEIKCKVHNKGLPAP

IVRTISRTKGQAREPQVYVLAPPQEELSKSTLSVTCLVTGFYPDYIAVEW

QKNGQPESEDKYGTTTSQLDADGSYFLYSRLRVDKNSWQEGDTYACVVMH

EALHNHYTQKSISKPPGK
```

The CH2 region of an ovine antibody comprises or consists of amino acids 231 to 340 (according to EU numbering) of an ovine IgG antibody. It is to be understood that the CH2 region may include one to six (e.g., 1, 2, 3, 4, 5, 6) additional amino acids or deletions at their N and/or C-terminus.

The CH3 region of an ovine antibody comprises or consists of amino acids 341 to 447 (according to EU numbering) of an ovine IgG antibody. It is to be understood that the CH3 region may include one to six (e.g., 1, 2, 3, 4, 5, 6) additional amino acids or deletions at their N and/or C-terminus.

The Fc region of an ovine IgG antibody comprises or consists of amino acids 231 to 447 (according to EU numbering) of an ovine IgG antibody.

Table 4 below compares the amino acid sequences of the CH2 and CH3 domains of human IgG1, canine IgGB and feline IgG1a with each of the three ovine IgG isotypes, based on EU numbering:

TABLE 4

| EU number | Human IgG1 | Canine IgGB | Feline IgG1a | Sheep IgG1 | Sheep IgG2 | Sheep IgG3 |
|---|---|---|---|---|---|---|
| | | | CH2 Domain | | | |
| 231 | A | A | P | | | |
| 232 | P | P | P | P | | P |
| 233 | E | E | E | E | | E |
| 234 | L | M | M | L | | P |
| 235 | L | L | L | P | V | L |
| 236 | G | G | G | G | S | G |
| 237 | G | G | G | G | R | G |
| 238 | P | P | P | P | P | L |
| 239 | S | S | S | S | S | S |
| 240 | V | V | I | V | V | V |
| 241 | F | F | F | F | F | F |
| 242 | L | I | I | I | I | I |
| 243 | F | F | F | F | F | F |
| 244 | P | P | P | P | P | P |
| 245 | P | P | P | P | P | P |
| 246 | K | K | K | K | K | K |
| 247 | P | P | P | P | P | P |
| 248 | K | K | K | K | K | K |
| 249 | D | D | D | D | D | D |
| 250 | T | T | T | T | S | T |
| 251 | L | L | L | L | L | L |
| 252 | M | L | S | T | M | T |
| 253 | I | I | I | I | I | I |
| 254 | S | A | S | S | T | S |
| 255 | R | R | R | G | G | G |
| 256 | T | T | T | T | T | T |
| 257 | P | P | P | P | P | P |
| 258 | E | E | E | E | E | E |
| 259 | V | V | V | V | V | V |
| 260 | T | T | T | T | T | T |
| 261 | C | C | C | C | C | C |
| 262 | V | V | L | V | V | V |
| 263 | V | V | V | V | V | V |
| 264 | V | V | V | V | V | V |
| 265 | D | D | D | D | D | D |
| 266 | V | L | L | V | V | V |
| 267 | S | D | G | G | G | G |
| 268 | H | P | P | Q | Q | Q |
| 269 | E | E | D | D | G | D |
| 270 | D | D | D | D | D | D |
| 271 | P | P | S | P | P | P |
| 272 | E | E | D | E | E | E |
| 273 | V | V | V | V | V | V |
| 274 | K | Q | Q | Q | Q | Q |
| 275 | F | I | I | F | F | F |
| 276 | N | S | T | S | S | S |
| 277 | W | W | W | W | W | W |
| 278 | Y | F | F | F | F | F |
| 279 | V | V | V | V | V | V |
| 280 | D | D | D | D | D | D |
| 282 | G | G | N | N | N | N |
| 282 | V | K | T | V | V | V |
| 283 | E | Q | Q | E | E | E |
| 284 | V | M | V | V | V | V |
| 285 | H | Q | Y | R | R | R |
| 286 | N | T | T | T | T | T |
| 287 | A | A | A | A | A | A |
| 288 | K | K | K | R | R | R |
| 289 | T | T | T | T | T | T |
| 290 | K | Q | S | K | K | K |
| 291 | P | P | P | P | P | P |
| 292 | R | R | R | R | R | R |
| 293 | E | E | E | E | E | E |
| 294 | E | E | E | E | E | E |
| 295 | Q | Q | Q | Q | Q | Q |
| 296 | Y | F | F | F | F | F |
| 297 | N | N | N | N | N | N |
| 298 | S | G | S | S | S | S |
| 299 | T | T | T | T | T | T |
| 300 | Y | Y | Y | F | F | F |
| 301 | R | R | R | R | R | R |
| 302 | V | V | V | V | V | V |
| 303 | V | V | V | V | V | V |
| 304 | S | S | S | S | S | S |
| 305 | V | V | V | A | A | A |

TABLE 4-continued

| EU number | Human IgG1 | Canine IgGB | Feline IgG1a | Sheep IgG1 | Sheep IgG2 | Sheep IgG3 |
|---|---|---|---|---|---|---|
| 306 | L | L | L | L | L | L |
| 307 | T | P | P | P | P | P |
| 308 | V | I | I | I | I | I |
| 309 | L | G | L | Q | Q | Q |
| 310 | H | H | H | H | H | H |
| 311 | Q | Q | Q | Q | D | Q |
| 312 | D | D | D | D | H | D |
| 313 | W | W | W | W | W | W |
| 314 | L | L | L | T | T | L |
| 315 | N | K | K | G | G | R |
| 316 | G | G | G | G | G | G |
| 317 | K | K | K | K | K | K |
| 318 | E | Q | E | E | E | E |
| 319 | Y | F | F | F | F | I |
| 320 | K | T | K | K | K | K |
| 321 | C | C | C | C | C | C |
| 322 | K | K | K | K | K | K |
| 323 | V | V | V | V | V | V |
| 324 | S | N | N | H | H | H |
| 325 | N | N | S | N | S | N |
| 326 | K | K | K | E | K | K |
| 327 | A | A | S | A | G | G |
| 328 | L | L | L | L | L | L |
| 329 | P | P | P | P | P | P |
| 330 | A | S | S | A | A | A |
| 331 | P | P | P | P | P | P |
| 332 | I | I | I | I | I | I |
| 333 | E | E | E | V | V | V |
| 334 | K | R | R | R | R | R |
| 335 | T | T | T | T | T | T |
| 336 | I | I | I | I | I | I |
| 337 | S | S | S | S | S | S |
| 338 | K | K | K | R | R | R |
| 339 | A | A | A | T | A | T |
| 340 | K | R | K | K | K | K |
| CH3 Domain | | | | | | |
| 341 | G | G | G | G | G | G |
| 342 | Q | Q | Q | Q | Q | Q |
| 343 | P | A | P | A | A | A |
| 344 | R | H | H | R | R | R |
| 345 | E | Q | E | E | E | E |
| 346 | P | P | P | P | P | P |
| 347 | Q | s | Q | Q | Q | Q |
| 348 | V | V | V | V | V | V |
| 349 | Y | Y | Y | Y | Y | Y |
| 350 | T | V | V | V | V | V |
| 351 | L | L | L | L | L | L |
| 352 | P | P | P | A | A | A |
| 353 | P | P | P | P | P | P |
| 354 | S | S | A | P | P | P |
| 355 | R | R | Q | Q | Q | Q |
| 356 | D | E | E | E | E | E |
| 357 | E | E | E | E | E | E |
| 358 | L | L | L | L | L | L |
| 359 | T | S | S | S | S | S |
| 360 | K | K | R | K | K | K |
| 361 | N | N | N | S | S | S |
| 362 | Q | T | K | T | T | T |
| 363 | V | V | V | L | L | L |
| 364 | S | S | S | S | S | S |
| 365 | L | L | V | V | V | V |
| 366 | T | T | T | T | T | T |
| 367 | C | C | C | C | C | C |
| 368 | L | L | L | L | L | L |
| 369 | V | I | I | V | V | V |
| 370 | K | K | K | T | T | T |
| 371 | G | D | S | G | G | G |
| 372 | F | F | F | F | F | F |
| 373 | Y | F | H | Y | Y | Y |
| 374 | P | P | P | P | P | P |
| 375 | S | P | P | D | D | D |
| 376 | D | D | D | Y | D | Y |
| 377 | I | I | I | I | I | I |
| 378 | A | D | A | A | A | A |
| 379 | V | V | V | V | V | V |
| 380 | E | E | E | E | E | E |
| 381 | W | W | W | W | W | W |
| 382 | E | Q | E | Q | Q | Q |
| 383 | S | S | I | K | R | K |
| 384 | N | N | T | N | A | N |
| 385 | G | G | G | G | R | G |
| 386 | Q | Q | Q | Q | Q | Q |
| 387 | P | Q | P | P | P | P |
| 388 | E | E | E | E | E | E |
| 389(a) | N | P | P | S | S | S |
| 389b |  | E | E | E | E | E |
| 389c |  | S | N | D | D | D |
| 390 | N | K | N | K | K | K |
| 391 | Y | Y | Y | Y | Y | Y |
| 392 | K | R | R | G | G | G |
| 393 | T | T | T | T | T | T |
| 394 | T | T | T | T | T | T |
| 395 | P | P | P | T | T | T |
| 396 | P | P | P | S | S | S |
| 397 | v | Q | Q | Q | Q | Q |
| 398 | L | L | L | L | L | L |
| 399 | D | D | D | D | D | D |
| 400 | S | E | S | A | A | A |
| 401 | D | D | D | D | D | D |
| 402 | G | G | G | G | G | G |
| 403 | S | S | T | S | S | S |
| 404 | F | Y | Y | Y | Y | Y |
| 405 | F | F | F | F | F | F |
| 406 | L | L | V | L | L | L |
| 407 | Y | Y | Y | Y | Y | Y |
| 408 | 5 | 5 | 5 | 5 | 5 | 5 |
| 409 | K | K | K | R | R | R |
| 410 | L | L | L | L | L | L |
| 411 | T | S | S | R | R | R |
| 412 | V | V | V | V | V | V |
| 413 | D | D | D | D | D | D |
| 414 | K | K | R | K | K | K |
| 415 | S | S | S | N | S | N |
| 416 | R | R | H | S | S | S |
| 417 | W | W | W | W | W | W |
| 418 | Q | Q | Q | Q | Q | Q |
| 419 | Q | R | R | E | R | E |
| 420 | G | G | G | G | G | G |
| 421 | N | D | N | D | D | D |
| 422 | V | T | T | T | T | T |
| 423 | F | F | Y | Y | Y | Y |
| 424 | S | I | T | A | A | A |
| 425 | C | C | C | C | C | C |
| 426 | S | C | S | V | V | V |
| 427 | V | V | V | V | V | V |
| 428 | M | M | S | M | M | M |
| 429 | H | H | H | H | H | H |
| 430 | E | E | E | E | E | E |
| 431 | A | A | A | A | A | A |
| 432 | L | L | L | L | L | L |
| 433 | H | H | H | H | H | H |
| 434 | N | N | S | N | N | N |
| 435 | H | H | H | H | H | H |
| 436 | Y | Y | H | Y | Y | Y |
| 437 | T | T | T | T | T | T |
| 438 | Q | Q | Q | Q | Q | Q |
| 439 | K | E | K | K | K | K |
| 440 | S | S | S | S | S | S |
| 441 | L | L | L | I | I | I |
| 442 | S | S | T | S | S | S |
| 443 | L | H | Q | K | K | K |
| 444 | S | S | S | P | P | P |
| 445 | P | P | P | P | P | P |
| 446 | G | G | G | G | G | G |
| 447 | K | K | K | K | K | K |

Substitutions in Ovine IgG Fc that Improve Half-Life

Increased serum persistence is a beneficial property for therapeutic polypeptides. This disclosure features substitutions in wild type ovine IgG1, IgG2 and IgG3 Fc regions that enhance the half-life of a polypeptide or polypeptides comprising these Fc regions in an ovine relative to a control polypeptide or control polypeptides, wherein the control polypeptide or control polypeptides are identical to the polypeptide or polypeptides except for having the corresponding wild type ovine IgG Fc region in place of the IgG Fc region variant. The substitutions to increase half-life may be made in one or more of an ovine CH2 domain, an ovine CH3 domain, or in the context of an ovine Fc (e.g., a CH2+CH3) region.

The present disclosure provides a polypeptide comprising an ovine IgG Fc region variant, or an ovine FcRn-binding region thereof, wherein the polypeptide comprises an amino acid substitution at at least one (e.g., 1, 2, 3, 4, 5, 6, 7, 8, 9, 10 or 11) position selected from the group consisting of:
- (i) a position that corresponds to amino acid position 250 of a wild type ovine IgG, wherein the amino acid substitution is selected from the group consisting of S250Q, S250E, T250Q and T250E;
- (ii) a position that corresponds to amino acid position 252 of a wild type ovine IgG, wherein the amino acid substitution is selected from the group consisting of M252Y, M252W, M252F, T252Y, T252W and T252F;
- (iii) a position that corresponds to amino acid position 254 of a wild type ovine IgG wherein the amino acid substitution is selected from the group consisting of S254R, S254K, S254H, T254R, T254K and T254H;
- (iv) a position that corresponds to amino acid position 256 of a wild type ovine IgG, wherein the amino acid substitution is selected from the group consisting of T256A, T256D and T256E;
- (v) a position that corresponds to amino acid position 286 of a wild type ovine IgG, wherein the amino acid substitution is selected from the group consisting of T286Y, T286F, T286W, T286L, T286D and T286E;
- (vi) a position that corresponds to amino acid position 309 of a wild type ovine IgG, wherein the amino acid substitution is selected from the group consisting of Q309V, Q309D and Q309E;
- (vii) a position that corresponds to amino acid position 311 of a wild type ovine IgG, wherein the amino acid substitution is selected from the group consisting of Q311V, Q311K, Q311R, Q311L, Q311H, D311V, D311K, D311R, D311L and D311H;
- (viii) a position that corresponds to amino acid position 426 of a wild type ovine IgG, wherein the amino acid substitution is selected from the group consisting of V426Y, V426F and V426H;
- (ix) a position that corresponds to amino acid position 428 of a wild type ovine IgG, wherein the amino acid substitution is selected from the group consisting of M428L, M428Y and M428F;
- (x) a position that corresponds to amino acid position 434 of a wild type ovine IgG, wherein the amino acid substitution is selected from the group consisting of N434A, N434H, N434F, N434S, N434W and N434Y; and
- (xi) a position that corresponds to amino acid position 436 of a wild type ovine IgG, wherein the amino acid substitution is Y436H, wherein the amino acid positions are based on EU numbering, and wherein the polypeptide has increased binding affinity to ovine FcRn when compared to an Fc domain of the wild type ovine IgG.

In some embodiments, the polypeptide comprises an amino acid substitution at at least one (e.g., 1, 2, 3, 4, or 5) position selected from the group consisting of:
- (i) a position that corresponds to amino acid position 252 of a wild type IgG of the livestock animal, wherein the amino acid substitution is T252Y;
- (ii) a position that corresponds to amino acid position 309 of a wild type IgG of the livestock animal, wherein the amino acid substitution is Q309V;
- (iii) a position that corresponds to amino acid position 311 of a wild type IgG of the livestock animal, wherein the amino acid substitution is Q311V;
- (iv) a position that corresponds to amino acid position 428 of a wild type IgG of the livestock animal, wherein the amino acid substitution is selected from the group consisting of M428Y; and
- (v) a position that corresponds to amino acid position 434 of a wild type IgG of the livestock animal, wherein the amino acid substitution is selected from the group consisting of N434Y.

In some embodiments, the polypeptide has increased binding affinity to ovine FcRn at a pH of about 5.0 to about 6.5 (e.g., about 5.5 or about 6.0) when compared to an Fc domain of the wild type ovine IgG at the same pH.

In some embodiments, the polypeptide comprises an amino acid sequence that is at least 80% (e.g., at least 85%, 90%, 92%, 94%, 95%, 96%, 97%, 98%, or 99%) identical to an amino acid sequence selected from the group consisting of SEQ ID NOs: 22 to 24.

In some instances, this disclosure provides an ovine IgG CH2 domain variant comprising an amino acid sequence that is at least 75%, at least 80%, at least 85%, at least 90%, at least 95%, at least 96%, at least 97%, at least 98% or at least 99% identical to the CH2 domains shown in any one of SEQ ID NOs.:22 to 24. Also provided are ovine IgG CH2 domain variants comprising an amino acid sequence that varies from any one of the CH2 domains shown in SEQ ID NOs.:22 to 24 by 1 to 15 (e.g., by 1, 2, 3, 4, 5, 6, 7, 8, 9, 10, 11, 12, 13, 14, or 15) amino acids.

In some instances, this disclosure features an ovine IgG CH3 domain variant comprising an amino acid sequence that is at least 75%, at least 80%, at least 85%, at least 90%, at least 95%, at least 96%, at least 97% or at least 98% or at least 99%, identical to the amino acid sequence of the CH3 domain shown in any one of SEQ ID NOs.:22 to 24. Also featured are ovine IgG CH3 domain variants comprising an amino acid sequence that varies from any one of the CH3 domain sequences shown in any one of SEQ ID NOs.:22 to 24 by 1 to 15 (e.g., by 1, 2, 3, 4, 5, 6, 7, 8, 9, 10, 11, 12, 13, 14, or 15) amino acids.

In some instances, this disclosure features an ovine IgG Fc region variant comprising an amino acid sequence that is at least 75%, at least 80%, at least 85%, at least 90%, at least 95%, at least 96%, at least 97%, at least 98% or at least 99% identical to the amino acid sequence set forth in any one of SEQ ID NOs.:22 to 24. Also disclosed are ovine IgG Fc region variants comprising an amino acid sequence that varies from any one of SEQ ID NOs.:22 to 24 by 1 to 20 (e.g., by 1, 2, 3, 4, 5, 6, 7, 8, 9, 10, 11, 12, 13, 14, 15, 16, 17, 18, 19, or 20) amino acids.

In some embodiments, provided are a polypeptide or polypeptides comprising an ovine IgG Fc CH2 domain variant, the CH2 domain variant comprising an amino acid sequence that is at least 75%, at least 80%, at least 85%, at least 90%, at least 95%, at least 96%, at least 97%, at least 98% or at least 99%, identical to the amino acid sequence of the CH2 domain shown in any one of SEQ ID NOs.:22 to 24.

In some embodiments, featured are a polypeptide or polypeptides comprising an ovine IgG Fc CH3 domain variant, the CH3 domain variant comprising an amino acid sequence that is at least 75%, at least 80%, at least 85%, at least 90%, at least 95%, at least 96%, at least 97%, at least 98% or at least 99% identical to the amino acid sequence of the CH3 domain shown in any one of SEQ ID NOs.:22 to 24.

In some embodiments, featured are a polypeptide or polypeptides comprising an ovine IgG Fc region variant, the Fc region variant comprising an amino acid sequence that is at least 75%, at least 80%, at least 85%, at least 90%, at least 95%, at least 96%, at least 97%, at least 98% or at least 99% identical to the amino acid sequence set forth in any one of SEQ ID NOs.:22 to 24.

Caprine Antibodies

Caprine typically have three IgG heavy chains referred to as IgG1, IgG2 and IgG3. These heavy chains represent three different subclasses of caprine IgG. The amino acid and DNA sequences for these heavy chains are available from the GENBANK® database. Illustrative examples of the amino acid sequences of the CH2 and CH3 domains of each of the three caprine IgG heavy chain Fc regions are shown below (CH2 domains are underlined):

Goat *Capra hircus*

IgG1 (Schwartz et al, 2018, Immunogenetics, 70:317)
(SEQ ID NO: 25)
<u>PELPGGPSVFIFPPKPKDTLTISGKPEVTCVVVDVGQDDPEVQFSWFVDNV</u>

<u>EVHTARTKPREEQFNSTFRVVSALPIQHQDWTGGKEFKCKVHNEGLPAPIV</u>

<u>RTISRTKGQAREPQVYVLAPPQEELSKSTLSVTCLVTGFYPDYIAVEWQRN</u>

GQPESEDKYGTTTSQLDADGSYFLYSRLRVNKSSWQEGDTYACVVMHEALH

NHYTQKSISKPPGK

IgG2 (Schwartz et al, 2018, Immunogenetics, 70:317)
(SEQ ID NO: 26)
<u>VRGPSVFIFPPKPKDSLMITGTPEVTCVVVDVGQDDPEVQFSWFVDNVEVH</u>

<u>TARTKPREEQFNSTFRVVSALPIQHDHWTGGKEFKCKVNNKALPAPIVRTI</u>

<u>SRDKGQAREPQVYVLAPPQEELSKSTLSVTCLVTGFYPDYIAVEWQRARQP</u>

ESEDKYGTTTSQLDADGSYFLYSRLRVDKSSWQEGDTYACVVMHEALHNHY

TQKSISKPPGK

IgG3 (Schwartz et al, 2018, Immunogenetics, 70:317)
(SEQ ID NO: 27)
<u>PEPLGGLSVFIFPPKPKDTLTISGTPEVTCVVVDVGQDDPEVQFSWFMDNV</u>

<u>EVHTARTTPREEQFNSTFRVVSALPIQHKDWLQGKEFKCKVHNEGLPAPII</u>

<u>RTISRAKGQAREPQVYVLAPPREELSKSTLSVTCLITGFYPEEVDVEWQRD</u>

GQPESEDKYHTAPPQLDADGSYFLYSRLRVNKSSWQEGDTYTCAVMHEALR

NHYKEKSISKSPGK

The CH2 region of a caprine antibody comprises or consists of amino acids 231 to 340 (according to EU numbering) of a caprine IgG antibody. It is to be understood that the CH2 region may include one to six (e.g., 1, 2, 3, 4, 5, 6) additional amino acids or deletions at their N and/or C-terminus.

The CH3 region of a caprine antibody comprises or consists of amino acids 341 to 447 (according to EU numbering) of a caprine IgG antibody. It is to be understood that the CH3 region may include one to six (e.g., 1, 2, 3, 4, 5, 6) additional amino acids or deletions at their N and/or C-terminus.

The Fc region of a caprine IgG antibody comprises or consists of amino acids 231 to 447 (according to EU numbering) of a caprine IgG antibody.

Table 5 below compares the amino acid sequences of the CH2 and CH3 domains of human IgG1, canine IgGB and feline IgG1a with each of the three caprine IgG isotypes, based on EU numbering:

TABLE 5

| EU number | Human IgG1 | Canine IgGB | Feline IgG1a | Goat IgG1 | Goat IgG2 | Goat IgG3 |
|---|---|---|---|---|---|---|
| CH2 Domain ||||||| 
| 231 | A | A | P | | | |
| 232 | P | P | P | P | | P |
| 233 | E | E | E | E | | E |
| 234 | L | M | M | L | | P |
| 235 | L | L | L | P | V | L |
| 236 | G | G | G | G | R | G |
| 237 | G | G | G | G | G | G |
| 238 | P | P | P | P | P | L |
| 239 | S | S | S | S | S | S |
| 240 | V | V | I | V | V | V |
| 241 | F | F | F | F | F | F |
| 242 | L | I | I | I | I | I |
| 243 | F | F | F | F | F | F |
| 244 | P | P | P | P | P | P |
| 245 | P | P | P | P | P | P |
| 246 | K | K | K | K | K | K |
| 247 | P | P | P | P | P | P |
| 248 | K | K | K | K | K | K |
| 249 | D | D | D | D | D | D |
| 250 | T | T | T | T | S | T |
| 251 | L | L | L | L | L | L |
| 252 | M | L | S | T | M | T |
| 253 | I | I | I | I | I | I |
| 254 | S | A | S | S | T | S |
| 255 | R | R | R | G | G | G |
| 256 | T | T | T | K | T | T |
| 257 | P | P | P | P | P | P |
| 258 | E | E | E | E | E | E |
| 259 | V | V | V | V | V | V |
| 260 | T | T | T | T | T | T |
| 261 | C | C | C | C | C | C |
| 262 | V | V | L | V | V | V |
| 263 | V | V | V | V | V | V |
| 264 | V | V | V | V | V | V |
| 265 | D | D | D | D | D | D |
| 266 | V | L | L | V | V | V |
| 267 | S | D | G | G | G | G |
| 268 | H | P | P | Q | Q | Q |
| 269 | E | E | D | D | D | D |
| 270 | D | D | D | D | D | D |
| 271 | P | P | S | P | P | P |
| 272 | E | E | D | E | E | E |
| 273 | V | V | V | V | V | V |
| 274 | K | Q | Q | Q | Q | Q |
| 275 | F | I | I | F | F | F |
| 276 | N | S | T | S | S | S |
| 277 | W | W | W | W | W | W |
| 278 | Y | F | F | F | F | F |
| 279 | V | V | V | V | V | M |
| 280 | D | D | D | D | D | D |
| 282 | G | G | N | N | N | N |
| 282 | V | K | T | V | V | V |
| 283 | E | Q | Q | E | E | E |
| 284 | V | M | V | V | V | V |
| 285 | H | Q | Y | H | H | H |
| 286 | N | T | T | T | T | T |
| 287 | A | A | A | A | A | A |
| 288 | K | K | K | R | R | R |
| 289 | T | T | T | T | T | T |
| 290 | K | Q | S | K | K | T |
| 291 | P | P | P | P | P | P |
| 292 | R | R | R | R | R | R |
| 293 | E | E | E | E | E | E |
| 294 | E | E | E | E | E | E |
| 295 | Q | Q | Q | Q | Q | Q |
| 296 | Y | F | F | F | F | F |
| 297 | N | N | N | N | N | N |
| 298 | S | G | S | S | S | S |
| 299 | T | T | T | T | T | T |

TABLE 5-continued

| EU number | Human IgG1 | Canine IgGB | Feline IgGla | Goat IgG1 | Goat IgG2 | Goat IgG3 |
|---|---|---|---|---|---|---|
| 300 | Y | Y | Y | F | F | F |
| 301 | R | R | R | R | R | R |
| 302 | V | V | V | V | V | V |
| 303 | V | V | V | V | V | V |
| 304 | S | S | S | S | S | S |
| 305 | V | V | V | A | A | A |
| 306 | L | L | L | L | L | L |
| 307 | T | P | P | P | P | P |
| 308 | V | I | I | I | I | I |
| 309 | L | G | L | Q | Q | Q |
| 310 | H | H | H | H | H | H |
| 311 | Q | Q | Q | Q | D | K |
| 312 | D | D | D | D | H | D |
| 313 | W | W | W | W | W | W |
| 314 | L | L | L | T | T | L |
| 315 | N | K | K | G | G | Q |
| 316 | G | G | G | G | G | G |
| 317 | K | K | K | K | K | K |
| 318 | E | Q | E | E | E | E |
| 319 | Y | F | F | F | F | F |
| 320 | K | T | K | K | K | K |
| 321 | C | C | C | C | C | C |
| 322 | K | K | K | K | K | K |
| 323 | V | V | V | V | V | V |
| 324 | S | N | N | H | N | H |
| 325 | N | N | S | N | N | N |
| 326 | K | K | K | E | K | E |
| 327 | A | A | S | G | A | G |
| 328 | L | L | L | L | L | L |
| 329 | P | P | P | P | P | P |
| 330 | A | S | S | A | A | A |
| 331 | P | P | P | P | P | P |
| 332 | I | I | I | I | I | I |
| 333 | E | E | E | V | V | I |
| 334 | K | R | R | R | R | R |
| 335 | T | T | T | T | T | T |
| 336 | I | I | I | I | I | I |
| 337 | S | S | S | S | S | S |
| 338 | K | K | K | R | R | R |
| 339 | A | A | A | T | D | A |
| 340 | K | R | K | K | K | K |
| CH3 Domain | | | | | | |
| 341 | G | G | G | G | G | G |
| 342 | Q | Q | Q | Q | Q | Q |
| 343 | P | A | P | A | A | A |
| 344 | R | H | H | R | R | R |
| 345 | E | Q | E | E | E | E |
| 346 | P | P | P | P | P | P |
| 347 | Q | s | Q | Q | Q | Q |
| 348 | V | V | V | V | V | V |
| 349 | Y | Y | Y | Y | Y | Y |
| 350 | T | V | V | V | V | V |
| 351 | L | L | L | L | L | L |
| 352 | P | P | P | A | A | A |
| 353 | P | P | P | P | P | P |
| 354 | S | S | A | P | P | P |
| 355 | R | R | Q | Q | Q | R |
| 356 | D | E | E | E | E | E |
| 357 | E | E | E | E | E | E |
| 358 | L | L | L | L | L | L |
| 359 | T | S | S | S | S | S |
| 360 | K | K | R | K | K | K |
| 361 | N | N | N | S | S | S |
| 362 | Q | T | K | T | T | T |
| 363 | V | V | V | L | L | L |
| 364 | S | S | S | S | S | S |
| 365 | L | L | V | V | V | V |
| 366 | T | T | T | T | T | T |
| 367 | C | C | C | C | C | C |
| 368 | L | L | L | L | L | L |
| 369 | V | I | I | V | V | I |
| 370 | K | K | K | T | T | T |
| 371 | G | D | S | G | G | G |
| 372 | F | F | F | F | F | F |
| 373 | Y | F | H | Y | Y | Y |
| 374 | P | P | P | P | P | P |
| 375 | S | P | P | D | D | E |
| 376 | D | D | D | Y | Y | E |
| 377 | I | I | I | I | I | V |
| 378 | A | D | A | A | A | D |
| 379 | V | V | V | V | V | V |
| 380 | E | E | E | E | E | E |
| 381 | W | W | W | W | W | W |
| 382 | E | Q | E | Q | Q | Q |
| 383 | S | S | I | R | R | R |
| 384 | N | N | T | N | A | D |
| 385 | G | G | G | G | R | G |
| 386 | Q | Q | Q | Q | Q | Q |
| 387 | P | Q | P | P | P | P |
| 388 | E | E | E | E | E | E |
| 389(a) | N | P | P | S | S | S |
| 389b |  | E | E | E | E | E |
| 389c |  | S | N | D | D | D |
| 390 | N | K | N | K | K | K |
| 391 | Y | Y | Y | Y | Y | Y |
| 392 | K | R | R | G | G | H |
| 393 | T | T | T | T | T | T |
| 394 | T | T | T | T | T | A |
| 395 | P | P | P | T | T | P |
| 396 | P | P | P | S | S | P |
| 397 | v | Q | Q | Q | Q | Q |
| 398 | L | L | L | L | L | L |
| 399 | D | D | D | D | D | D |
| 400 | S | E | S | A | A | A |
| 401 | D | D | D | D | D | D |
| 402 | G | G | G | G | G | G |
| 403 | S | S | T | S | S | S |
| 404 | F | Y | Y | Y | Y | Y |
| 405 | F | F | F | F | F | F |
| 406 | L | L | V | L | L | L |
| 407 | Y | Y | Y | Y | Y | Y |
| 408 | S | S | S | S | S | S |
| 409 | K | K | K | R | R | R |
| 410 | L | L | L | L | L | L |
| 411 | T | S | S | R | R | R |
| 412 | V | V | V | V | V | V |
| 413 | D | D | D | N | D | N |
| 414 | K | K | R | K | K | K |
| 415 | S | S | S | S | S | S |
| 416 | R | R | H | S | S | S |
| 417 | W | W | W | W | W | W |
| 418 | Q | Q | Q | Q | Q | Q |
| 419 | Q | R | R | E | E | E |
| 420 | G | G | G | G | G | G |
| 421 | N | D | N | D | D | D |
| 422 | V | T | T | T | T | T |
| 423 | F | F | Y | Y | Y | Y |
| 424 | S | I | T | A | A | T |
| 425 | C | C | C | C | C | C |
| 426 | S | A | S | V | V | A |
| 427 | V | V | V | V | V | V |
| 428 | M | M | S | M | M | M |
| 429 | H | H | H | H | H | H |
| 430 | E | E | E | E | E | E |
| 431 | A | A | A | A | A | A |
| 432 | L | L | L | L | L | L |
| 433 | H | H | H | H | H | R |
| 434 | N | N | S | N | N | N |
| 435 | H | H | H | H | H | H |
| 436 | Y | Y | H | Y | Y | Y |
| 437 | T | T | T | T | T | K |
| 438 | Q | Q | Q | Q | Q | E |
| 439 | K | E | K | K | K | K |
| 440 | S | S | S | S | S | S |
| 441 | L | L | L | I | I | I |
| 442 | S | S | T | S | S | S |
| 443 | L | H | Q | K | K | K |
| 444 | S | S | S | P | P | S |
| 445 | P | P | P | P | P | P |
| 446 | G | G | G | G | G | G |
| 447 | K | K | K | K | K | K |

Substitutions in Caprine IgG Fc that Improve Half-Life

Increased serum persistence is a beneficial property for therapeutic polypeptides. This disclosure features substitutions in wild type caprine IgG1, IgG2 and IgG3 Fc regions that enhance the half-life of a polypeptide or polypeptides comprising these Fc regions in a caprine relative to a control polypeptide or control polypeptides, wherein the control polypeptide or control polypeptides are identical to the polypeptide or polypeptides except for having the corresponding wild type caprine IgG Fc region in place of the IgG Fc region variant. The substitutions to increase half-life may be made in one or more of a caprine CH2 domain, a caprine CH3 domain, or in the context of a caprine Fc (e.g., a CH2+CH3) region.

The present disclosure provides a polypeptide comprising a caprine IgG Fc region variant, or a caprine FcRn-binding region thereof, wherein the polypeptide comprises an amino acid substitution at at least one (e.g., 1, 2, 3, 4, 5, 6, 7, 8, 9, 10 or 11) position selected from the group consisting of:

(i) a position that corresponds to amino acid position 250 of a wild type caprine IgG, wherein the amino acid substitution is selected from the group consisting of S250Q, S250E, T250Q and T250E;
(ii) a position that corresponds to amino acid position 252 of a wild type caprine IgG, wherein the amino acid substitution is selected from the group consisting of M252Y, M252W, M252F, T252Y, T252W and T252F;
(iii) a position that corresponds to amino acid position 254 of a wild type caprine IgG, wherein the amino acid substitution is selected from the group consisting of S254R, S254K, S254H, T254R, T254K and T254H;
(iv) a position that corresponds to amino acid position 256 of a wild type caprine IgG, wherein the amino acid substitution is selected from the group consisting of T256A, T256D, T256E, K256A, K256D and K256E;
(v) a position that corresponds to amino acid position 286 of a wild type caprine IgG, wherein the amino acid substitution is selected from the group consisting of T286Y, T286F, T286W, T286L, T286D and T286E;
(vi) a position that corresponds to amino acid position 309 of a wild type caprine IgG, wherein the amino acid substitution is selected from the group consisting of Q309V, Q309D and Q309E;
(vii) a position that corresponds to amino acid position 311 of a wild type caprine IgG, wherein the amino acid substitution is selected from the group consisting of Q311V, Q311K, Q311R, Q311L, Q311H, K311V, K311R, K311L, K311H, D311V, D311K, D311R, D311L and D311H;
(viii) a position that corresponds to amino acid position 426 of a wild type caprine IgG wherein the amino acid substitution is selected from the group consisting of A426Y, A426F, A426H, V426Y, V426F and V426H;
(ix) a position that corresponds to amino acid position 428 of a wild type caprine IgG, wherein the amino acid substitution is selected from the group consisting of M428L, M428Y and M428F;
(x) a position that corresponds to amino acid position 434 of a wild type caprine IgG, wherein the amino acid substitution is selected from the group consisting of N434A, N434H, N434F, N434S, N434W and N434Y; and
(xi) a position that corresponds to amino acid position 436 of a wild type caprine IgG,
wherein the amino acid substitution is Y436H, wherein the amino acid positions are based on EU numbering, and wherein the polypeptide has increased binding affinity to caprine FcRn when compared to an Fc domain of the wild type caprine IgG.

In some embodiments, the polypeptide has increased binding affinity to caprine FcRn at a pH of about 5.0 to about 6.5 (e.g., about 5.5 or about 6.0) when compared to an Fc domain of the wild type caprine IgG at the same pH.

In some embodiments, the polypeptide comprises an amino acid sequence that is at least 80% (e.g., at least 85%, 90%, 92%, 94%, 95%, 96%, 97%, 98%, or 99%) identical to an amino acid sequence selected from the group consisting of SEQ ID NOs: 25 to 27.

In some instances, this disclosure provides a caprine IgG CH2 domain variant comprising an amino acid sequence that is at least 75%, at least 80%, at least 85%, at least 90%, at least 95%, at least 96%, at least 97%, at least 98% or at least 99% identical to the CH2 domains shown in any one of SEQ ID NOs.:25 to 27. Also provided are caprine IgG CH2 domain variants comprising an amino acid sequence that varies from any one of the CH2 domains shown in SEQ ID NOs.:25 to 27 by 1 to 15 (e.g., by 1, 2, 3, 4, 5, 6, 7, 8, 9, 10, 11, 12, 13, 14, or 15) amino acids.

In some instances, this disclosure features a caprine IgG CH3 domain variant comprising an amino acid sequence that is at least 75%, at least 80%, at least 85%, at least 90%, at least 95%, at least 96%, at least 97% or at least 98% or at least 99%, identical to the amino acid sequence of the CH3 domain shown in any one of SEQ ID NOs.:25 to 27. Also featured are caprine IgG CH3 domain variants comprising an amino acid sequence that varies from any one of the CH3 domain sequences shown in any one of SEQ ID NOs.:25 to 27 by 1 to 15 (e.g., by 1, 2, 3, 4, 5, 6, 7, 8, 9, 10, 11, 12, 13, 14, or 15) amino acids.

In some instances, this disclosure features a caprine IgG Fc region variant comprising an amino acid sequence that is at least 75%, at least 80%, at least 85%, at least 90%, at least 95%, at least 96%, at least 97%, at least 98% or at least 99% identical to the amino acid sequence set forth in any one of SEQ ID NOs.:25 to 27. Also disclosed are caprine IgG Fc region variants comprising an amino acid sequence that varies from any one of SEQ ID NOs.:25 to 27 by 1 to 20 (e.g., by 1, 2, 3, 4, 5, 6, 7, 8, 9, 10, 11, 12, 13, 14, 15, 16, 17, 18, 19, or 20) amino acids.

In some embodiments, provided are a polypeptide or polypeptides comprising a caprine IgG Fc CH2 domain variant, the CH2 domain variant comprising an amino acid sequence that is at least 75%, at least 80%, at least 85%, at least 90%, at least 95%, at least 96%, at least 97%, at least 98% or at least 99%, identical to the amino acid sequence of the CH2 domain shown in any one of SEQ ID NOs.:25 to 27.

In some embodiments, featured are a polypeptide or polypeptides comprising a caprine IgG Fc CH3 domain variant, the CH3 domain variant comprising an amino acid sequence that is at least 75%, at least 80%, at least 85%, at least 90%, at least 95%, at least 96%, at least 97%, at least 98% or at least 99% identical to the amino acid sequence of the CH3 domain shown in any one of SEQ ID NOs.:25 to 27.

In some embodiments, featured are a polypeptide or polypeptides comprising a caprine IgG Fc region variant, the Fc region variant comprising an amino acid sequence that is at least 75%, at least 80%, at least 85%, at least 90%, at least 95%, at least 96%, at least 97%, at least 98% or at least 99% identical to the amino acid sequence set forth in any one of SEQ ID NOs.:25 to 27.

The present disclosure extends to a polypeptide or polypeptides in which the amino acid substitutions are made on either one or both of a CH2 domain and a CH3 domain. In some instances, the substitutions on the CH2 domain and/or the CH3 domain are identical. In some instances, the substitutions on the CH2 domain and/or the CH3 domain are not identical. In some instances, the Fc region includes one or more additional substitutions that increase or decrease effector function and/or improve product heterogeneity.

Other Substitutions that can be Combined with the Half-Life Enhancing Substitutions The development of a therapeutic polypeptide/protein (e.g., a monoclonal antibody) is a complex process that entails coordination of a complex set of activities to generate the desired polypeptide/protein. These include optimization of the specificity, affinity, functional activity, expression level in engineered cell lines, long-term stability, elimination or enhancement of effector functions and development of commercially viable manufacturing and purification methods. This disclosure encompasses any additional substitution that facilitates any one or more of the above goals.

In some embodiments, substitutions are introduced to a wild type IgG Fc region of the livestock animal to enhance binding to Protein A so as to facilitate purification by protein A chromatography. Such substitutions will be familiar to persons skilled in the art and may be at one or more (e.g., 1, 2, 3, 4, 5, 6, or 7) positions of the IgG.

In some embodiments, additional amino acid substitutions can be made to alter binding affinity to FcRn as compared to a parent polypeptide or a wild-type polypeptide (e.g., to increase or reduce binding affinity with FcRn).

In some embodiments, the polypeptide comprises a hinge region of an antibody of the livestock animal. In some embodiments, modifications can be made to the hinge region of the antibody of the livestock animal to increase half-life. Such modifications will be known to persons skilled in the art.

Polypeptides Comprising the IgG Fc Variants

The disclosure encompasses any polypeptide that may benefit from having an increased half-life in a livestock animal. To increase half-life these polypeptides are designed to include an Fc region variant (e.g., a CH2 region, a CH3 region, a CH2+CH3 region) disclosed above.

Exemplary polypeptides include, but are not limited to, whole antibodies, scFvs, nanobodies, ligand-binding portions of a receptor, cytokines, growth factors, enzymes, and peptides. For example, a CH3 domain variant disclosed above may be attached to an scFv nanobody, ligand-binding portion of a receptor (e.g., the ligand-binding portion of IL-13Rα1 or IL-13Rα2), a cytokine, a growth factor, an enzyme, or a peptide. As used herein, the terms "nanobody", "VHH", "VHH antibody fragment" and "single domain antibody" are used interchangeably herein to denote the variable domain of the single heavy chain of antibodies of the type of those found in Camelidae, which are typically found in nature to lack light chains. Suitable nanobodies will be familiar to persons skilled in the art, illustrated examples of which include nanobodies of camels, dromedaries, llamas and alpacas. Alternatively, an Fc region variant disclosed above may be attached to these polypeptides. In another embodiment, an antibody from the livestock animal is modified to include an Fc region variant disclosed herein.

In some embodiments, the polypeptides of this disclosure include an antibody hinge region. The hinge region may be placed between the antigen or ligand-binding domain of the polypeptide and the Fc region variant. In some instances, the hinge region is attached to the C-terminus of a cytokine, a growth factor, an enzyme, or a peptide and the hinge region is attached to the N-terminus of the Fc region variant. Suitable hinge region sequences will be familiar to persons skilled in the art.

The hinge region, if used, in a polypeptide of this disclosure may include zero to six (i.e., 0, 1, 2, 3, 4, 5, or 6) amino acid substitutions relative to an amino acid sequence of the native hinge region. In some instances, the hinge region used in a recombinant protein of this disclosure is at least 80%, at least 85%, at least 90%, at least 95%, at least 96%, at least 97%, at least 98%, at least 99%, or 100% identical to an amino acid sequence of the native hinge region.

The polypeptide or polypeptides of this disclosure may comprise a binding domain. The binding domain can specifically bind to a protein, subunit, domain, motif, and/or epitope of a selected target described herein. In some embodiments, the polypeptide or polypeptides (e.g., fusion polypeptide) can comprise a protein, wherein the protein is a therapeutic protein described herein. In some embodiments, the target (e.g., for the target of the binding domain) or the therapeutic protein (e.g., for the fusion polypeptide) is selected from the group consisting of: 17-IA, 4-1BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAMS, ADAM9, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, IgE, Angiotensin type 1 (AT1) receptor, Angiotensin type 2 (AT2) receptor, ARC, ART, Artemin, anti-Id, ASPARTIC, Atrial natriuretic factor, av/b3 integrin, Ax1, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CA125, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/Z/P, CBL, CC1, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 proteins), CD34, CD38, CD40, CD40L, CD44, CD45, CD46, CD47, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, *Clostridium botulinum* toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, Decay accelerating factor, des(1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, Enkephalinase, eNOS, Eot, eotaxinl, EpCAM, Ephrin B2/EphB4, EPO, ERCC, E-selectin, ET-1, Factor IIa, Factor VII, Factor VIIIc, Factor IX, fibroblast activation protein (FAP), Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, GLP1, GLP2, Glucagon, Glut 4, glycoprotein IIb/IIIa (GP IIb/IIIa), GM-CSF, gp130, gp72, GRO, GnRH, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, High molecular weight melanoma-associated antigen (HMW-MAA), HIV gp120, HIV IIIB gp120 V3 loop, HLA, HLA-DR, HM1.24, HMFG PEM, HRG, Hrk, cardiac myosin, cytomegalovirus (CMV), growth hormone (GH), HVEM, 1-309, IAP, ICAM, ICAM-1, ICAM-3, ICE, ICOS, IFNg, Ig, IgA receptor, IgE, IGF, IGF binding proteins, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-17, IL-18, IL-18R, IL-21, IL-22, IL-23, IL-25, IL-31, IL-33, interleukin receptor (e.g., IL-1R, IL-2R, IL-4R, IL-5R, IL-6R, IL-8R, IL-9R, IL-10R, IL-12R, IL-13R, IL-15R, IL-17R, IL-18R, IL-21R, IL-22R, IL-23R, IL-25R, IL-31R, IL-33R), interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta1, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein L1, Kallikrein L2, Kallikrein L3, Kallikrein L4, KC, KDR, Keratinocyte Growth Factor (KGF), laminin 5, LAMP, LAP, LAP (TGF-1), Latent TGF-1, Latent TGF-1 bp1, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC(HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, Muellerian-inhibitin substance, Mug, MuSK, NAIP, NAP, NAV 1.7, NCAD, N-Cadherin, NCA 90, NCAM, NCAM, Neprilysin, Neurotrophin-3, -4, or -6, Neurturin, Neuronal growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, Parathyroid hormone, PARC, PARP, PBR, PBSF, PCAD, P-Cadherin, PCNA, PD1, PDL1, PDGF, PDGF, PDK-1, PECAM, PEM, PF4, PGE, PGF, PGI2, PGJ2, PIN, PLA2, placental alkaline phosphatase (PLAP), P1GF, PLP, PP14, Proinsulin, Prorelaxin, Protein C, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, S100, SCF/KL, SDF-1, SERINE, Serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptors (e.g., T-cell receptor alpha/beta), TdT, TECK, TEM1, TEM5, TEM7, TEM8, TERT, testicular PLAP-like alkaline phosphatase, TfR, TGF, TGF-alpha, TGF-beta, TGF-beta Pan Specific, TGF-beta R1 (ALK-5), TGF-beta R11, TGF-beta RIIb, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFc, TNF-R1, TNF-RII, TNFRSF10A (TRAIL R1Apo-2, DR4), TNFRSF10B (TRAIL R2DR5, KILLER, TRICK-2A, TRICK-B), TNFRSF10C (TRAIL R3DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF R1CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3M68, TR6), TNFRSF7 (CD27), TNFRSF8 (CD30), TNFRSF9 (4-1BB CD137, ILA), TNFRSF21 (DR6), TNFRSF22 (DCTRAIL R2 TNFRH2), TNFRST23 (DCTRAIL R1TNFRH1), TNFRSF25 (DR3Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3Ligand), TNFSF13 (APRIL TALL2), TNFSF13B (BAFF BLYS, TALL1, THANK, TNFSF20), TNFSF14 (LIGHT HVEM Ligand, LTg), TNFSF15 (TL1A/VEGI), TNFSF18 (GITR Ligand AITR Ligand, TL6), TNFSF1A (TNF-a Conectin, DIF, TNFSF2), TNFSF1B (TNF-b LTa, TNFSF1), TNFSF3 (LTb TNFC, p33), TNFSF4 (OX40 Ligand gp34, TXGP1), TNFSF5 (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk (e.g., TrkA), TROP-2, TSG, TSLP, tumor-associated antigen CA 125, tumor-associated antigen expressing Lewis Y related carbohydrate, TWEAK, TXB2, Ung, UPAR, uPAR-1, Urokinase, VCAM, VCAM-1, VECAD, VE-Cadherin, VE-cadherin-2, VEFGR-1 (fit-1), VEGF, VEGFR, VEGFR-3 (flt-4), VEGI, VIM, Viral antigens, VLA, VLA-1, VLA-4, VNR integrin, von Willebrands factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9B, WNT10A, WNT10B, WNT11, WNT16, XCL1, XCL2, XCR1, XCR1, XEDAR, XIAP, XPD, and receptors for hormones and growth factor.

In some embodiments, the binding domain specifically binds to one or more therapeutic targets or antigens in the livestock animal, such as, but are not limited to, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAMS, ADAM9, ADAMTS, ADAMTS4, ADAMTS5, ANG, Ang, Angiotensin type 1 (AT1) receptor, Angiotensin type 2 (AT2) receptor, Atrial natriuretic factor, av/b3 integrin, b-ECGF, CD19, CD20, CD30, CD34, CD40, CD40L, CD47, COX, CTLA-4, EGFR (ErbB-1), EPO, Follicle stimulating hormone, GDF-8 (Myostatin), GLP1, GLP2, GnRH, Growth hormone releasing factor, IgE, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-17, IL-18, IL-18R, IL-21, IL-22, IL-23, IL-25, IL-31, IL-33, interleukin receptor (e.g., IL-1R, IL-2R, IL-4R, IL-5R, IL-6R, IL-8R, IL-9R, IL-10R, IL-12R, IL-13R, IL-15R, IL-17R, IL-18R, IL-21R, IL-22R, IL-23R, IL-25R, IL-31R, IL-33R), LAP (TGF-1), Latent TGF-1, Latent TGF-1 bp1, LFA-1, Neuronal growth factor (NGF), NGFR, NGF-beta, OX40L, OX40R, PD1, PDL1, TGF, TGF-alpha, TGF-beta, TGF-beta Pan Specific, TGF-beta R1 (ALK-5), TGF-beta RIb, TGF-beta RIIb, TGF-beta RIII, TGF-beta1, TGF-beta2, TGF-beta3, TGF-beta4, TGF-beta5, TNF, TNF-alpha, TNF-alpha beta, TNF-beta2, TNFc, TNF-RI, TNF-RII, TNFRSF16 (NGFR p75NTR), TNFRSF9 (4-1BB CD137, ILA), VEFGR-1 (flt-1), VEGF, VEGFR, and VEGFR-3 (flt-4).

In some embodiments, the polypeptide or polypeptides can comprise a protein, wherein the protein is a therapeutic protein, e.g., EPO, CTLA4, LFA3, VEGFR1/VEGFR3, IL-1R, IL-4R, GLP-1 receptor agonist, or Thrombopoietin binding peptide. In some embodiments, the therapeutic protein is ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAMS, ADAM9, ADAMTS, ADAMTS4, ADAMTS5, ANG, Ang, Angiotensin type 1 (AT1) receptor, Angiotensin type 2 (AT2) receptor, Atrial natriuretic factor, av/b3 integrin, b-ECGF, CD19, CD20, CD30, CD34, CD40, CD40L, CD47, COX, CTLA-4, EGFR (ErbB-1), EPO, Follicle stimulating hormone, GDF-8 (Myostatin), GLP1, GLP2, GnRH, Growth hormone releasing factor, IgE, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-17, IL-18, IL-18R, IL-21, IL-22, IL-23, IL-25, IL-31, IL-33, interleukin receptor (e.g., IL-1R, IL-2R, IL-4R, IL-5R, IL-6R, IL-8R, IL-9R, IL-10R, IL-12R, IL-13R, IL-15R, IL-17R, IL-18R, IL-21R, IL-22R, IL-23R, IL-25R, IL-31R, IL-33R), LAP (TGF-1), Latent TGF-1, Latent TGF-1 bp1, LFA-1, Neuronal growth factor (NGF), NGFR, NGF-beta, OX40L, OX40R, PD1, PDL1, TGF, TGF-alpha, TGF-beta, TGF-beta Pan Specific, TGF-beta R1 (ALK-5), TGF-beta R11, TGF-beta RIIb, TGF-beta RIII, TGF-beta1, TGF-beta2, TGF-beta3, TGF-beta4, TGF-beta5, TNF, TNF-alpha, TNF-alpha beta, TNF-beta2, TNFc, TNF-RI, TNF-RII, TNFRSF16 (NGFR p75NTR), TNFRSF9 (4-1BB CD137, ILA), VEFGR-1 (flt-1), VEGF, VEGFR, or VEGFR-3 (flt-4).

Pharmaceutical Compositions

To prepare pharmaceutical or sterile compositions of a polypeptide or polypeptides described herein, the polypeptide or polypeptides can be admixed with a pharmaceutically acceptable carrier or excipient. (See, e.g., Remington's Pharmaceutical Sciences and U.S. Pharmacopeia: National Formulary, Mack Publishing Company, Easton, Pa. (1984)).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.). In some embodiments, the polypeptide or polypeptides of the present invention are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the polypeptide compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). In particular aspects, a polypeptide or polypeptides exhibiting high therapeutic indices are desirable. The data obtained from these cell culture assays and animal studies can be used in formulating a range of dosage for use in the livestock animal. The dosage of such compounds lies preferably within a range of circulating concentrations that include the $ED_{50}$ with little or no toxicity. The dosage may vary within this range depending upon the dosage form employed and the route of administration.

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial. In some embodiments, the polypeptide or polypeptides can be administered by an invasive route such as by injection. In further embodiments, the polypeptide or polypeptides is administered intravenously, subcutaneously, intramuscularly, intraarterially, intratumorally, or by inhalation, aerosol delivery.

The pharmaceutical compositions disclosed herein may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

Alternatively or additionally, one may also administer the polypeptide or polypeptides in a local manner, for example, via injection of the antibody directly into an arthritic joint or pathogen-induced lesion characterized by immunopathology, often in a depot or sustained release formulation. Furthermore, one may administer the polypeptide or polypeptides in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

The administration regimen depends on several factors, including, without limitation, the age, weight, and physical condition of the livestock animal to be or being treated, the serum or tissue turnover rate of the therapeutic antibody, the level of symptoms, the immunogenicity of the therapeutic polypeptide or polypeptides, and the accessibility of the target cells in the biological matrix. In some implementations, the administration regimen delivers sufficient therapeutic polypeptide or polypeptides to effect improvement in the target disease state, while simultaneously minimizing undesired side effects. Accordingly, the amount of biologic delivered depends in part on the particular therapeutic polypeptide or polypeptides and the severity of the condition being treated. Guidance in selecting appropriate doses of therapeutic antibodies is available (see, e.g., Wawrzynczak Antibody Therapy, Bios Scientific Pub. Ltd, Oxfordshire, U K (1996); Milgrom et al. New Engl. J. Med. 341:1966-1973 (1999); Slamon et al. New Engl. J. Med. 344:783-792 (2001); Beniaminovitz et al. New Engl. J. Med. 342:613-619 (2000); Ghosh et al. New Engl. J. Med. 348:24-32 (2003); Lipsky et al. New Engl. J. Med. 343:1594-1602 (2000)).

Determination of the appropriate dose of the polypeptide or polypeptides is made by one skilled in the art, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.
Nucleic Acids, Vectors, Host Cells, and Methods of Making The disclosure also encompasses nucleic acid or nucleic acids encoding the polypeptide or polypeptides described herein, a vector or vectors comprising the nucleic acid or nucleic acids, and host cells comprising the nucleic acid or nucleic acids or the vector or vectors.

The polypeptide or polypeptides described herein may be produced in bacterial or eukaryotic cells. Some polypeptides, e.g., Fab's, can be produced in bacterial cells, e.g., *E. coli* cells. Polypeptides can also be produced in eukaryotic cells such as transformed cell lines (e.g., CHO, 293E, COS, 293T, Hela). In addition, polypeptides (e.g., scFv's) can be expressed in a yeast cell such as *Pichia* (see, e.g., Powers et al., J Immunol Methods. 251:123-35 (2001)), *Hanseula*, or *Saccharomyces*. To produce the antibody of interest, a polynucleotide or polynucleotides encoding the polypeptide or polypeptides is/are constructed, introduced into an expression vector or expression vectors, and then expressed in suitable host cells. To improve expression, the nucleotide sequences of the genes can be recoded without changing (or minimally changing—e.g., removal of a C-terminal residue of the heavy or light chain) the amino acid sequence. The areas for potential recoding include those associated with translation initiation, codon usage, and possible unintended mRNA splicing. Polynucleotides encoding an Fc region variant described herein would be readily envisioned by the ordinarily skilled artisan.

Standard molecular biology techniques can be used to prepare the recombinant expression vector(s), transfect the host cells, select for transformants, culture the host cells, and recover the polypeptide (e.g., antibody).

If the polypeptide or polypeptides is to be expressed in bacterial cells (e.g., *E. coli*), the expression vector should have characteristics that permit amplification of the vector in the bacterial cells. Additionally, when *E. coli* such as JM109, DH5α, HB101, or XL1-Blue is used as a host, the vector must have a promoter, for example, a lacZ promoter (Ward et al., 341:544-546 (1989), araB promoter (Better et al., Science, 240:1041-1043 (1988)), or T7 promoter that can allow efficient expression in *E. coli*. Examples of such vectors include, for example, M13-series vectors, pUC-series vectors, pBR322, pBluescript, pCR-Script, pGEX-5X-1 (Pharmacia), "QIA$_{EXPRESS}$®  system" (QIAGEN), pEGFP, and pET (when this expression vector is used, the host is preferably BL21 expressing T7 RNA polymerase). The expression vector may contain a signal sequence for antibody secretion. For production into the periplasm of *E. coli*, the pelB signal sequence (Lei et al., J. Bacteriol., 169:4379 (1987)) may be used as the signal sequence for antibody secretion. For bacterial expression, calcium chloride methods or electroporation methods may be used to introduce the expression vector into the bacterial cell.

If the polypeptide or polypeptides is to be expressed in animal cells such as CHO, COS, and NIH3T3 cells, the expression vector includes a promoter necessary for expression in these cells, for example, an SV40 promoter (Mulligan et al., Nature, 277:108 (1979)) (e.g., early simian virus 40 promoter), MMLV-LTR promoter, EF1α promoter (Mizushima et al., Nucleic Acids Res., 18:5322 (1990)), or CMV promoter (e.g., human cytomegalovirus immediate early promoter). In addition to the nucleic acid sequence encoding the Fc region variant, the recombinant expression vectors may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017). For example, typically the selectable marker gene confers resistance to drugs, such as G418, hygromycin, or methotrexate, on a host cell into which the vector has been introduced. Examples of vectors with selectable markers include pMAM, pDR2, pBK-RSV, pBK-CMV, pOPRSV, and pOP13.

In some embodiments, the polypeptide or polypeptides are produced in mammalian cells. Exemplary mammalian host cells for expressing polypeptide or polypeptides include Chinese Hamster Ovary (CHO cells) (including dhfr- CHO cells, described in Urlaub and Chasin (1980) Proc. Natl. Acad. Sci. USA 77:4216-4220, used with a DHFR selectable marker, e.g., as described in Kaufman and Sharp (1982) Mol. Biol. 159:601 621), human embryonic kidney 293 cells (e.g., 293, 293E, 293T), COS cells, NIH3T3 cells, lymphocytic cell lines, e.g., NSO myeloma cells and SP2 cells, and a cell from a transgenic animal, e.g., a transgenic mammal. For example, the cell is a mammary epithelial cell.

In an exemplary system for antibody expression, a recombinant expression vector encoding both the antibody heavy chain and the antibody light chain of the antibody is introduced into dhfr- CHO cells by calcium phosphate-mediated transfection. Within the recombinant expression vector, the antibody heavy and light chain genes are each operatively linked to enhancer/promoterregulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and the antibody is recovered from the culture medium.

Methods of Treatment

The polypeptide or polypeptides disclosed herein can be used to treat or prevent any disease or disorder in a livestock animal in need thereof. This invention is particularly helpful in the treatment of chronic conditions where repeated dosing is required. Because of the increased half-life of the protein therapeutic, less frequent dosing and/or reduced dose levels may be possible.

In some embodiments, the disease, disorder, condition or symptoms being treated or prevented is an allergic disease, a chronic pain, an acute pain, an inflammatory disease, an autoimmune disease, an endocrine disease, a gastrointestinal disease, a skeletal/musculoskeletal disease, a cardiovascular disease, a neurological disease, a renal disease, a metabolic disease, a immunological disease, a genetic/inherited disease, a fertility related disorder, an infectious disease or a cancer. In certain embodiments, the disease or disorder being treated or prevented is atopic dermatitis, allergic dermatitis, food allergy, osteoarthritic pain, perioperative pain, dental pain, cancer pain, arthritis, anemia, obesity, or diabetes.

Antibodies may not only be used to treat or prevent disease but also to modulate normal biological function, for example, to manage fertility or behavior.

Diagnosis

The polypeptide or polypeptides disclosed herein can also be used for various diagnostic purposes, for example, to determine whether the livestock animal has any particular disease or disorder. In some embodiments, the polypeptide or polypeptides may comprise a binding domain. The binding domain can specifically bind to a protein, subunit, domain, motif, and/or epitope as described herein (e.g., a maker for cancer cells). In some embodiments, the polypeptide or polypeptides further comprises a labeling group. In general, label groups fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labelling group is coupled to the antibody via spacer arms of various lengths to reduce potential steric hindrance. Various methods for labelling proteins are known in the art and may be used in performing the present invention.

In some embodiments, the labeling group is a probe, a dye (e.g., a fluorescent dye), or a radioactive isotope (e.g., $^{3}$H, $^{14}$C, $^{22}$Na, $^{36}$Cl, $^{35}$S, $^{33}$P, or $^{125}$I).

Specific labels can also include optical dyes, including, but not limited to, chromophores, phosphors and fluorophores, with the latter being specific in many instances. Fluorophores can be either "small molecule" fluores, or proteinaceous fluores.

The fluorescent label can be any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malachite green, stilbene, Lucifer Yellow, CASCADE BLUEJ®, Texas Red, IAEDANS, EDANS, BODIPY FL, LC Red 640, Cy 5, Cy 5.5, LC Red 705, Oregon green, the ALEXA FLUOR® dyes (ALEXA FLUOR® 350, ALEXA FLUOR® 430, ALEXA FLUOR® 488, ALEXA FLUOR® 546, ALEXA FLUOR® 568, ALEXA FLUOR® 594, ALEXA FLUOR® 633, ALEXA FLUOR® 660, ALEXA FLUOR® 680), CASCADE BLUE®, CASCADE YELLOW® and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in Molecular Probes Handbook by Richard P. Haugland, which is incorporated by reference in its entirety.

Suitable proteinaceous fluorescent labels also include, but are not limited to, green fluorescent protein, including a Renilla, Ptilosarcus, or Aequorea species of green fluorescent protein (GFP, Chalfie et al., 1994, Science 263:802-805), enhanced GFP (EGFP, Clontech Laboratories, Inc., GENBANK® Accession Number U55762), blue fluorescent protein (BFP, Quantum Biotechnologies, Inc. 1801 de Maisonneuve Blvd. West, 8th Floor, Montreal, Quebec, Canada H3H1J9; Stauber, 1998, Biotechniques 24:462-471; Heim et al., 1996, Curr. Biol. 6:178-182), enhanced yellow fluorescent protein (EYFP, Clontech Laboratories, Inc.), luciferase (Ichiki et al., 1993, J. Immunol. 150:5408-5417), R galactosidase (Nolan et al., 1988, Proc. Natl. Acad. Sci. U.S.A. 85:2603-2607) and Renilla (WO92/15673, WO95/07463, WO98/14605, WO98/26277, WO99/49019, U.S. Pat. Nos. 5,292,658, 5,418,155, 5,683,888, 5,741,668, 5,777,079, 5,804,387, 5,874,304, 5,876,995, 5,925,558). All of the above-cited references in this paragraph are expressly incorporated herein by reference in the entirety.

Assays

FcγRI and FcγRIII Binding:

Binding to FcγRI and FcγRIII is a measure of the ability of an antibody to mediate antibody-dependent cellular cytotoxicity (ADCC). In order to assess this property for an antibody an assay to measure binding of the antibody to FcγRI and FcγRIII can be conducted using methods known in the art.

C1q Binding:

Binding to the first component of complement, C1q, is a measure of the ability of an antibody to mediate complement-dependent cytotoxicity (CDC). In order to assess this property for an antibody, an assay to measure binding of the antibody to C1q can be conducted using methods known in the art.

Half-Life:

Methods of measuring half-life of an antibody are well known in the art. See, e.g., Booth et al., MAbs, 10(7):1098-1110 (2018). As an example, the half-life of an antibody can be measured by injection of the antibody into the species from which the Fc is derived (target species) and measuring levels of the antibody in the serum over a certain period of time. Alternatively a transgenic mouse model could be used that is null for murine FcRn alpha chain and express the target species FcRn alpha transgene. The target species FcRn alpha chain could either be paired with mouse β2-microglobulin protein or the mouse β2-microglobulin gene could be substituted with the target species β2-microglobulin gene thereby forming a native FcRn alpha chain—β2-microglobulin heterodimer protein.

EXAMPLES

Example 1: Generation of NNK Saturation Mutagenesis Libraries at Selected Positions and Analysis of Individual Variants The wild-type (wt) sequences of the CH2 and CH3 domains of porcine, bovine, equine, ovine and caprine IgG (as shown in SEQ ID NOs:1 to 27) are synthesized and used as templates for NNK mutagenesis. The NNK saturation mutagenesis method is an effective strategy to generate all 20 possible amino acids at a desired position (Hogrefe et al., Biotechniques. 33: 1158-1165 [2002]; the content of which is incorporated herein by reference in its entirety). Individual NNK libraries at positions 250, 252, 254, 256, 286, 309, 311, 426, 428, 434 and 436 (EU numbering) are generated. NNK (N=A/C/G/T, K=G/T) primers at the specified position are used with the QuikChange Site-Directed Mutagenesis Kit (Agilent). The PCR-product is subcloned into the GenScript FASEBA plasmid, transformed into $E.\ coli$ and sequenced verified for the presence of the variant. Downstream of the CH2 domain is the SASA (single-domain antibody against serum albumin) tag (Zhang, J.; Wu, S.; Liu, J. Methods and systems for increasing protein stability. Patent application no: US 2013/0129727 A1; the content of which is incorporated herein by reference in its entirety), which has pM affinity for albumin. The SASA antibody enables the capture of the Fc to the sensor chip surface described below. The PelB (pectate lyase B) signal peptide is at the N-terminus to facilitate secretion of the Fc into the medium. The expression of CH2-CH3 protein is regulated by the Lac promoter. The supernatants from conditioned medium are analyzed for binding to the FcRn of the target livestock animal/species at pH 6.0 for variants using surface plasmon resonance (SPR).

The supernatants from multiple individual transformants from each library are assayed for binding to the FcRn of the livestock animal/species at pH 6.0 using the BIACORE™ method, as described below.

For the SPR analyses using the BIACORE™ 8K, bovine serum albumin (BSA) is immobilized to CM5 sensor chip. The sensor chip surface of flow cells 1 and 2 are activated by freshly mixed 50 mmol/L N-Hydroxysuccinimide and 200 mmol/L 1-ethyl-3-(3-dimethylaminopropyl) carbodiimide hydrochloride for 420s (10 μL/min). Afterwards, BSA diluted in 10 mM sodium acetate (pH 4.5) is injected into the flow cell 2 to achieve conjugation, while flow cell 1 is set as blank. After the amine coupling reaction, the remaining active coupling sites on chip surface are blocked with 420s injection of 1 mM ethanolamine hydrochloride. The running buffer for the binding experiment is HBS-EP (10 mM HEPES, 500 mM NaCl, 3 mM EDTA, 0.05% TWEEN® 20, pH 5.5) and run at 25° C. Supernatants from the variants are injected over chip surface and captured via the SASA tag onto the immobilized BSA for 60 sec. FcRn of the livestock animal/species at 200 nM is injected for 120 sec and the dissociation is complete with running buffer for 120 sec. The flow rate for the immobilization phase of BSA is 10 □l/min and the flow rate for the association and dissociation phase is 30 □□l/min. All of the data is processed using the BIACORE™ 8K evaluation software version 1.1. The results will show that the IgG Fc variants tested possess increased binding affinity for an FcRn of the corresponding livestock animal/species at pH 6.0 when compared to wild type IgG Fc of the same livestock animal/species.

Example 2: Scanning Mutagenesis of IgG Fc

A phage display library approach is used to identify IgG1 Fc variants that possess increased affinity to an FcRn of the same livestock animal or species at pH 6.0. The IgG Fc (comprising the CH2+CH3 domains of SEQ ID NO:1-27) are synthesized by Twist Bioscience to produce multiple variants with amino acid mutations (substitutions) at one or more positions. At each of the mutated positions, eight possible amino acids are substituted. These amino acids are arginine and lysine (positively charged side chain), aspartic acid and glutamic acid (negatively charged side chain), threonine and glutamine (polar uncharged side chain), and leucine and valine (hydrophobic side chain). The Fc DNA library is designed to have an average of two variants per Fc molecule. The number of combinations of modifications can be calculated using the formula: $nCr=n!/r!*(n-r)!$, where n represents the number of sites, and r represents the number of variants per molecule. The Fc variants with the desired site-specific mutations are printed as mutagenic oligonucleotides on Twist's silicon-based platform.

The oligonucleotides are then assembled to create a full-length Fc gene fragment pool using assembly PCR. The assembled Fc gene fragment pool is then cloned into the pADL-22c phagemid vector from Antibody Design Labs into the Sfi cut-sites. The cloned DNA library is transformed into electrocompetent TG1 $E.\ coli$ cells to create an experimental diversity of typically >10m variants. The phagemid transformed $E.\ coli$ cells are then co-transfected with M13K07 helper phage to generate a phage pool that is used for protein-based panning. The library is resuspended into 20 mM MES buffer, pH 6.0, 0.05% TWEEN® 20 and 3% milk.

The quality of the library is determined by picking 96 random phage clones and sequenced by the Sanger method.

For the first phage selection, a Protein A capture step is used to eliminate any Fc variants that have lost Protein A binding. For this selection, the phage library is captured onto Protein A beads and washed with phosphate-buffered saline (PBS), pH 7.4. The phage are eluted with 0.1M glycine, pH 2.7 and the pH is immediately neutralized with 1 M Tris-HCl, pH 7.5. The neutralized phage is precipitated with polyethylene glycol/NaCl and centrifuged. The pelleted phage are resuspended in 20 mM MES, pH 6.0, 0.05% TWEEN® 20, 3% milk.

The next phage selections are based on the protocol described by Borrok et al., 2015, $J\ Biol.\ Chem.$, 290:4282, the content of which is incorporated herein by reference in its entirety. Briefly, NUNC™ 96 multi-well plates are coated with Neutravidin and then blocked with 5% bovine serum albumin, PBS, pH 7.4. Biotinylated FcRn of the target livestock animal or species is immobilized in the well at a concentration of about 0.30 μg/ml in PBS, pH 6.0. The phage library in PBS, pH 6.0 is incubated with the immobilized FcRn and then washed with PBS, pH 6.0, 0.05% TWEEN® 20, 0.3 M NaCl. The phage is eluted with PBS, pH 7.4 by incubating at 37° C. for 30 minutes. The eluted phage are depleted with about 0.30 μg/ml of the FcRn of the same livestock animal or species at pH 7.4. The unbound phage is amplified in TG1 cells.

The clones are then sequenced by next generation sequencing using the Illumina MISEQ™.

Unique variants may be reformatted into IgG and miniprep plasmid DNA transfected into EXPI293™ cells with EXPIFECTAMINE™ 293 transfection reagent. The Ig variants can then be purified from the conditioned medium with Protein A chromatography and formulated into 43 mM sodium citrate, 130 mM sodium bicarbonate, pH 6.0.

For determining the affinities of the IgG variants to the FcRn of the corresponding livestock animal/species, a CARTERRA® instrument can be used to determine the binding kinetics. With this approach, the antibodies (~5 μg/ml) are typically amine-coupled to the HC30M sensor chip by EDC/NHS activation, followed by ethanolamine HCl quenching.

Different concentrations (333 nM, 111 nM, 37 nM, 12.3 nM, 4.1 nM, 1.37 nM, 0.45 nM) of FcRn is flowed over the sensor chip in HBSTE (10 mM HEPES, 150 mM NaCl, 3 mM EDTA, 0.05% TWEEN® 20), 0.5% bovine serum albumin, pH 6.0 to determine the kinetics at pH 6.0. This same strategy can be used to determine the binding kinetics to FcRn at pH 7.4 except the pH of the HBSTE buffer is adjusted to 7.4.

A list of the amino acid substitutions that increase the binding of the IgG Fc variant to their corresponding FcRN of the same livestock animal/species is provided in Table 6, below:

TABLE 6

Summary of the amino acid substitutions for livestock animal IgG Fc variants that increase binding affinity to FcRn of the corresponding livestock animal

| EU Number | Pig[11] | Cattle[3] | Horse[7] | Sheep[3] | Goat[3] | Amino acid substitution(s) |
|---|---|---|---|---|---|---|
| 250 | T, I | T | T, A, V | T, S | T, S | Q, E |
| 252 | M | T, M | M, K | M, T | T, M | Y, W, F |
| 254 | S | S, T | T, S | S, T | S, T | T, R, K, H * |
| 256 | T | T | T, M, K | T | T, K | A, D, E |
| 286 | T | T | T, S | T | T | Y, F, W, L, D, E |
| 309 | Q | Q | Q | Q | Q | D, E, V |
| 311 | Q, E | Q | Q, K | Q, D | Q, D, K | V, K, R, L, H ** |
| 426 | A, V | V, A | G, A, V | V | V, A | Y, F, H |
| 428 | M, H | M | M | M | M | L, Y, F *** |
| 434 | N, H | N | N, H | N | N | A, H, F, S, W, Y |
| 436 | Y, T | Y | Y, F, V | Y | Y | H |

[n] denotes the number of different IgG subclasses identified in that species
* not T at that position for ovine or caprine IgG Fc
** not K at this position for equine IgG4 Fc and IgG7 Fc
*** no substitution at this position for bovine IgG Fc Example 3: Binding Kinetics of IgG Fc Variants to FcRn A set of Fc variants was expressed and purified for porcine, ovine, bovine and equine IgGs. The variable domain for the heavy and light chain for each of the IgGs was previously described by Gearing et al. (2016, J Vet Intern Med, 30:1129). The heavy and light chain constant domains used for the different species IgGs were as follows: for porcine it was IgG1a (GENBANK® AAA52219.1 SEQ ID NO: 1) and the porcine kappa chain (GENBANK® AHB17990.1), for ovine it was IgG1 (GENBANK® X69797, SEQ ID NO: 22) and the ovine kappa chain (GENBANK® AU45094.1), for bovine it was IgG1 (GENBANK® ABE68619.1, SEQ ID NO: 12) and the bovine kappa chain (GENBANK® AEM45004.1), and for equine it was IgG1 (GENBANK® CAC44760.1, SEQ ID NO: 15) and the equine kappa chain (GENBANK® CAA53284.1). The variants were made in the Fc of each species at positions 252, 286, 309, 311, 426, 428, 434, and 436 (FIG. 1) (EU numbering). The synthesized DNAs for each variant and wild-type were subcloned into PCDNA™ 3.4 expression vector (Life Technologies) and expressed in HEK293 cells. The conditioned medium for each variant and wild-type were purified with the resins shown in Table 7 and the purified antibodies were formulated in PBS, pH 7.2. All of the resins were acquired from Cytiva with the exception of ROBOCOLUMN ESHMUNO® A which was purchased from EMD Millipore.

The purity of the antibodies was determined by scanning densitometry of Coomassie blue-stained SDS/PAGE gels and each was >90% (FIGS. 2A-2J, 3A-3J, 4A-4J, 5A-5J).

TABLE 7

Resins for purification of IgG Fc variants and wild-type IgG

| Name | Purification |
|---|---|
| Pig wild-type | PreDictor RoboColumn MabSelect Sure |
| Pig M252Y | PreDictor RoboColumn MabSelect Sure |
| Pig T286E | RoboColumn Eshmuno A 0.6 ml |
| Pig Q309D | PreDictor RoboColumn MabSelect Sure |
| Pig Q309V | PreDictor RoboColumn MabSelect Sure |
| Pig Q311V | PreDictor RoboColumn MabSelect Sure |
| Pig A426Y | PreDictor RoboColumn MabSelect Sure |
| Pig M428Y | PreDictor RoboColumn MabSelect Sure |
| Pig N434Y | PreDictor RoboColumn MabSelect Sure |
| Pig Y436H | PreDictor RoboColumn MabSelect Sure |
| Sheep wild-type | PreDictor RoboColumn MabSelect Sure |
| Sheep T252Y | PreDictor RoboColumn MabSelect Sure |
| Sheep T286E | HiTrap Protein G HP |
| Sheep Q309D | PreDictor RoboColumn MabSelect Sure |
| Sheep Q309V | HiTrap Protein G HP |
| Sheep Q311V | PreDictor RoboColumn MabSelect Sure |
| Sheep V426Y | PreDictor RoboColumn MabSelect Sure |
| Sheep M428Y | RoboColumn Eshmuno A 0.6 ml |
| Sheep N434Y | RoboColumn Eshmuno A 0.6 ml |
| Sheep N436H | HiTrap Protein G HP |
| Cow wild-type | PreDictor RoboColumn MabSelect Sure |
| Cow T252Y | RoboColumn Eshmuno A 0.6 ml |
| Cow T286E | PreDictor RoboColumn MabSelect Sure |
| Cow Q309D | HiTrap Protein G HP |
| Cow Q309V | RoboColumn Eshmuno A 0.6 ml |
| Cow Q311V | RoboColumn Eshmuno A 0.6 ml |
| Cow V426Y | RoboColumn Eshmuno A 0.6 ml |
| Cow M428Y | RoboColumn Eshmuno A 0.6 ml |
| Cow N434Y | RoboColumn Eshmuno A 0.6 ml |
| Cow Y436H | RoboColumn Eshmuno A 0.6 ml |
| Horse wild-type | RoboColumn Eshmuno A 0.6 ml |
| Horse M252Y | RoboColumn Eshmuno A 0.6 ml |
| Horse T286E | RoboColumn Eshmuno A 0.6 ml |
| Horse Q309D | RoboColumn Eshmuno A 0.6 ml |
| Horse Q309V | RoboColumn Eshmuno A 0.6 ml |
| Horse Q311V | RoboColumn Eshmuno A 0.6 ml |
| Horse G426Y | RoboColumn Eshmuno A 0.6 ml |
| Horse M428Y | RoboColumn Eshmuno A 0.6 ml |
| Horse N434Y | RoboColumn Eshmuno A 0.6 ml |
| Horse Y436H | RoboColumn Eshmuno A 0.6 ml |

The FcRn complex consists of a large subunit p51 and beta-2-microglobulin. The Avi-tag sequence (SEQ ID NO: 28, GLNDIFEAQKIEWHE) and an 8× His tag was fused to the C-terminus of the extracellular domain of the large subunit p51 (porcine: GENBANK® E9LK24; ovine: GENBANK® Q8HZV2; bovine: GENBANK® AAF60956.1; equine: GENBANK® XP_023505908.1) and subcloned into PCDNA™ 3.4 expression vector (Life Technologies). The FLAG™ tag (SEQ ID NO: 29, DYKDDDDK) was fused to the C-terminus of the beta-2-microglobulin (porcine: GENBANK® L13854.1; ovine: GENBANK® AY549962.1; bovine: GENBANK® X69084.1; equine: GENBANK® X69083.1) and subcloned into the PCDNA™ 3.4 expression vector. For each species, the large subunit p51 expression vector was co-transfected with the beta-2-microglobulin into HEK293 cells. The FcRn complexes were purified from conditioned medium using HISTRAP™ fast flow chromatography (Cytiva) and the proteins were then formulated into PBS, pH 7.2. The proteins were analyzed by SDS/PAGE and analytical SEC (size exclusion chromatography) using a TSK-GEL® G3000SWxl column. The purity of the proteins was >95% by SDS/PAGE and >95% of the FcRn complex was a heterodimer of the large subunit p51 and beta-2-microglobulin by analytical SEC.

The FcRn binding experiments were completed on a BIACORE™ 8K+system at 25° C. A polyclonal antibody against the His tag was coupled to the CM5 biosensor chip using the His Capture Kit (Cytiva, Cat 28995056) following the manufacturer's instructions. The His-tagged FcRn from the different species were flowed on the anti-His polyclonal biosensor chip at 10 l/min until approximately 100 RU were captured. The different porcine, ovine, bovine and equine IgG variants and wild-type were the analytes for the pig, cow, horse and sheep FcRn proteins biosensor chips, respectively. Five concentrations of IgGs were injected for 90 seconds at 30 l/min with a 30 second dissociation time. For the wild-type IgGs of each species, the concentrations of IgG were 6.2 nM, 18 nM, 55 nM, 167 nM, and 500 nM. For the variant IgGs of each species, the concentrations of IgG were 1.2 nM, 3.7 nM, 11 nM, 33 nM, and 100 nM. The running buffer was 1×PBS-P+(Cytiva, Cat #28995084) adjusted to pH 5.9. The surface was regenerated with 10 mM glycine, pH 1.5 at 30 l/min for 30 seconds. Data were evaluated using Insight Evaluation Software by fitting to a 1:1 kinetic interaction model, or by fitting to steady state affinity.

The kinetic binding data for the porcine IgG variants and wild-type are shown in Table 8 and the sensorgrams for the binding data are shown in FIGS. 6A-6J.

TABLE 8

Porcine IgG Fc variants and FcRn binding kinetics

| Porcine Variant | ka | kd | KD | Method for fitting data | Fold increase over wild-type KD |
|---|---|---|---|---|---|
| Porcine wild-type | | | 3.17E−07 | Steady state affinity | 1-fold |
| Porcine M252Y | 3.07E+05 | 2.99E−02 | 9.72E−08 | 1:1 kinetic interaction model | 3.3-fold |
| Porcine T286E | 4.77E+05 | 4.58E−02 | 9.61E−08 | 1:1 kinetic interaction model | 3.3-fold |
| Porcine Q309D | 2.64E+05 | 2.47E−02 | 9.36E−08 | 1:1 kinetic interaction model | 3.4-fold |
| Porcine Q309V | 2.57E+05 | 8.78E−03 | 3.41E−08 | 1:1 kinetic interaction model | 9.3-fold |
| Porcine Q311V | 2.81E+05 | 2.15E−02 | 7.64E−08 | 1:1 kinetic interaction model | 4.1-fold |
| Porcine A426Y | 3.74E+05 | 3.93E−02 | 1.05E−07 | 1:1 kinetic interaction model | 3.0-fold |
| Porcine M428Y | 3.00E+05 | 2.61E−02 | 8.69E−08 | 1:1 kinetic interaction model | 3.6-fold |
| Porcine N434Y | 7.35E+05 | 5.83E−03 | 7.93E−09 | 1:1 kinetic interaction model | 40-fold |
| Porcine Y436H | | | No binding | | |

The kinetic binding data for the ovine IgG variants and wild-type are shown in Table 9 and the sensorgrams for the binding data are shown in FIGS. 7A-7J.

TABLE 9

Ovine IgG Fc variants and FcRn binding kinetics

| Ovine Variant | ka | kd | KD | Method for fitting data | Fold increase over wild-type KD |
|---|---|---|---|---|---|
| Ovine wild-type | | | 4.97E−07 | Steady state affinity | 1-fold |
| Ovine T252Y | 6.12E+05 | 2.64E−02 | 4.31E−08 | 1:1 kinetic interaction model | 11-fold |
| Ovine T286E | | | No binding | | |
| Ovine Q309D | | | No binding | | |
| Ovine Q309V | 6.28E+05 | 4.98E−02 | 7.93E−08 | 1:1 kinetic interaction model | 6.3-fold |
| Ovine Q311V | 7.08E+05 | 6.57E−02 | 9.27E−08 | 1:1 kinetic interaction model | 5.4-fold |
| Ovine V426Y | | | No binding | | |
| Ovine M428Y | 1.58E+06 | 2.63E−01 | 1.66E−07 | 1:1 kinetic interaction model | 3.0-fold |
| Ovine N434Y | 1.58E+06 | 9.60E−03 | 6.09E−09 | 1:1 kinetic interaction model | 81-fold |
| Ovine Y436H | | | No binding | | |

The kinetic binding data for the bovine IgG variants and wild-type are shown in Table 10 and the sensorgrams for the binding data are shown in FIGS. 8A-8J.

TABLE 10

Bovine IgG Fc variants and FcRn binding kinetics

| Bovine Variant | ka | kd | KD | Method for fitting data | Fold increase over wild-type KD |
|---|---|---|---|---|---|
| Bovine wild-type | 2.25E+05 | 1.14E−01 | 5.05E−07 | 1:1 kinetic interaction model | 1-fold |
| Bovine T252Y | 2.33E+05 | 1.66E−02 | 7.14E−08 | 1:1 kinetic interaction model | 7.1-fold |
| Bovine T286E | | | No binding | | |
| Bovine Q309D | | | No binding | | |
| Bovine Q309V | 5.94E+05 | 7.68E−02 | 1.29E−07 | 1:1 kinetic interaction model | 3.9-fold |
| Bovine Q311V | 5.97E+05 | 1.09E−07 | 1.82E−07 | 1:1 kinetic interaction model | 2.8-fold |
| Bovine V426Y | | | No binding | | |
| Bovine M428Y | | | No binding | | |

TABLE 10-continued

Bovine IgG Fc variants and FcRn binding kinetics

| Bovine Variant | ka | kd | KD | Method for fitting data | Fold increase over wild-type KD |
|---|---|---|---|---|---|
| Bovine N434Y | 1.19E+06 | 1.41E−02 | 1.19E−08 | 1:1 kinetic interaction model | 42-fold |
| Bovine Y436H | 6.77E+05 | 1.52E−01 | 2.24E−07 | 1:1 kinetic interaction model | 2.3-fold |

The kinetic binding data for the equine IgG variants and wild-type are shown in Table 11 and the sensorgrams for the binding data are shown in FIGS. 9A-9J.

TABLE 11

Equine IgG Fc variants and FcRn binding kinetics

| Equine Variant | ka | kd | KD | Method for fitting data | Fold increase over wild-type KD |
|---|---|---|---|---|---|
| Equine wild-type | 1.47E−05 | 2.10E−02 | 1.43E−07 | 1:1 kinetic interaction model | |
| Equine M252Y | 2.33E+05 | 1.66E−02 | 7.14E−08 | 1:1 kinetic interaction model | 2.0-fold |
| Equine T286E | 2.55E+05 | 1.22E−02 | 4.80E−08 | 1:1 kinetic interaction model | 3.0-fold |
| Equine Q309D | 1.51E+05 | 2.17E−02 | 1.44E−07 | 1:1 kinetic interaction model | 1.0-fold |
| Equine Q309V | 1.98E+05 | 4.00E−03 | 2.02E−08 | 1:1 kinetic interaction model | 7.2-fold |
| Equine Q311V | 2.16E+05 | 7.71E−03 | 3.57E−08 | 1:1 kinetic interaction model | 4.0-fold |
| Equine G426Y | 2.69E+05 | 1.41E−02 | 5.23E−08 | 1:1 kinetic interaction model | 2.8-fold |
| Equine M428Y | 2.01E+05 | 3.03E−02 | 1.51E−07 | 1:1 kinetic interaction model | 0.9-fold |
| Equine N434Y | 4.16E+05 | 9.78E−04 | 2.35E−09 | 1:1 kinetic interaction model | 61-fold |
| Equine Y436H | 1.91E+05 | 2.98E−02 | 1.56E−07 | 1:1 kinetic interaction model | 0.9-fold |

Table 12 shows a species comparison of the fold increase of each Fc variant compared to the wild-type Fc.

TABLE 12

Comparison of IgG Fc variants and FcRn binding among different species

| Species | 252Y | 286E | 309D | 309V | 311V | 426Y | 428Y | 434Y | 436H |
|---|---|---|---|---|---|---|---|---|---|
| Porcine | 3.3-fold | 3.3-fold | 3.4-fold | 9.3-fold | 4.1-fold | 3.0-fold | 3.6-fold | 40-fold | No binding |
| Ovine | 11-fold | No binding | No binding | 6.3-fold | 5.4-fold | No binding | 3.0-fold | 81-fold | No binding |
| Bovine | 7.1-fold | No binding | No binding | 3.9-fold | 2.8-fold | No binding | No binding | 42-fold | 2.3-fold |
| Equine | 2.0-fold | 3.0-fold | 1.0-fold | 7.2-fold | 4.0-fold | 2.8-fold | 0.9-fold | 61-fold | 0.9-fold |

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A polypeptide comprising a porcine IgG Fc region variant, or an FcRn-binding region thereof, wherein the polypeptide comprises an amino acid substitution at at least one position selected from the group consisting of:

(i) a position that corresponds to amino acid position 250 of a wild type porcine IgG, wherein:
  (a) the wild type porcine IgG is selected from the group consisting of a porcine IgG1a, IgG1b, IgG2a, IgG2b, IgG4a, IgG4b, IgG6a, and IgG6b, wherein the amino acid substitution is T250Q or T250E; or
  (b) the wild type porcine IgG is selected from the group consisting of a porcine IgG3, IgG5a, or IgG5b, wherein the amino acid substitution is I250Q or I250E;
(ii) a position that corresponds to amino acid position 252 of a wild type animal porcine IgG, wherein the amino acid substitution is selected from the group consisting of M252Y, M252W, and M252F;
(iii) a position that corresponds to amino acid position 254 of a wild type porcine IgG, wherein the amino acid substitution is selected from the group consisting of S254T, S254R, S254K, and S254H;
(iv) a position that corresponds to amino acid position 256 of a wild type porcine IgG, wherein the amino acid substitution is selected from the group consisting of T256A, T256D, and T256E;
(v) a position that corresponds to amino acid position 286 of a wild type porcine IgG, wherein the amino acid substitution is selected from the group consisting of T286Y, T286F, T286W, T286L, T286D, and T286E;
(vi) a position that corresponds to amino acid position 309 of a wild type porcine IgG, wherein the amino acid substitution is selected from the group consisting of Q309V, Q309D, and Q309E;
(vii) a position that corresponds to amino acid position 311 of a wild type porcine IgG, wherein:
  (a) the wild type porcine IgG is selected form the group consisting of a wild type porcine IgG1a, IgG1b, IgG2a, IgG2b, IgG3, IgG4a, IgG4b, IgG6a, and IgG6b, wherein the amino acid substitution is selected from the group consisting of Q311V, Q311K, Q311R, Q311L, and Q311H; or
  (b) the wild type porcine IgG is a wild type porcine IgG5a or IgG5b, wherein the amino acid substitution is selected from the group consisting of E311V, E311K, E311R, E311L, and E311H;
(viii) a position that corresponds to amino acid position 426 of a wild type porcine IgG, wherein:
  (a) the wild type porcine IgG is selected from the group consisting of a wild type porcine IgG1a, IgG1b, IgG2a, IgG2b, IgG3, IgG4a, IgG4b, IgG5a, IgG5b, and IgG6a, wherein the amino acid substitution is selected from the group consisting of A426Y, A426F, and A426H; or
  (b) the wild type porcine IgG is a wild type porcine IgG6b, wherein the amino acid substitution is selected from the group consisting of V426Y, V426F, and V426H;
(ix) a position that corresponds to amino acid position 428 of a wild type animal porcine IgG, wherein:
  (a) the wild type porcine IgG is selected from the group consisting of a wild type porcine IgG1a, IgG1b, IgG2a, IgG2b, IgG3, IgG4a, IgG4b, IgG5a, IgG5b, and IgG6a, wherein the amino acid substitution is selected from the group consisting of M428L, M428Y, and M428F; or
  (b) the wild type porcine IgG is a wild type porcine IgG6b, wherein the amino acid substitution is selected from the group consisting of H428L, H428Y, and H428F;
(x) a position that corresponds to amino acid position 434 of a wild type porcine IgG, wherein:
  (a) the wild type porcine IgG is selected from the group consisting of a wild type porcine IgG1a, IgG1b, IgG2a, IgG2b, IgG3, IgG4a, IgG4b, IgG5a, IgG5b, and IgG6a, wherein the amino acid substitution is selected from the group consisting of N434H, N434F, N434S, N434W, and N434Y; or
  (b) the wild type porcine IgG is a wild type porcine IgG6b, wherein the amino acid substitution is selected from the group consisting of H434A, H434F, H434S, H434W, and H434Y; and
(xi) a position that corresponds to amino acid position 436 of a wild type porcine IgG, wherein:

(a) the wild type porcine IgG is selected from the group consisting of a wild type porcine IgG1a, IgG1b, IgG2a, IgG2b, IgG3, IgG4a, IgG4b, IgG5a, IgG5b, and IgG6a, wherein the amino acid substitution is selected from the group consisting of Y436H; or (b) the wild type porcine IgG is a wild type porcine IgG6b, wherein the amino acid substitution is T436H, wherein the amino acid positions are based on EU numbering, and wherein the polypeptide has increased binding affinity to a porcine FcRn when compared to an Fc domain of the wild type porcine IgG.

2. The polypeptide of claim 1, wherein the polypeptide comprises an amino acid substitution at at least one position selected from the group consisting of:

(i) a position that corresponds to amino acid position 252 of a wild type porcine IgG, wherein the amino acid substitution is M252Y;

(ii) a position that corresponds to amino acid position 286 of a wild type porcine IG, wherein the amino acid substitution is T286E;

(iii) a position that corresponds to amino acid position 309 of a wild type porcine IG, wherein the amino acid substitution is Q309D or Q309V;

(iv) a position that corresponds to amino acid position 311 of a wild type porcine IgG, wherein the wild type porcine IgG is selected form the group consisting of a wild type porcine IgG1 a, IgG1 b, IgG2a, IgG2b, IgG3, IgG4a, IgG4b, IgG6a, and IgG6b, and wherein the amino acid substitution is Q311 V;

(v) a position that corresponds to amino acid position 426 of a wild type porcine IgG, wherein the wild type porcine IgG is selected from the group consisting of a wild type porcine IgG1a, IgG1b, IgG2a, IgG2b, IgG3, IgG4a, IgG4b, IgG5a, IgG5b, and IgG6a, and wherein the amino acid substitution is A426Y;

(vi) a position that corresponds to amino acid position 428 of a wild type porcine IgG, wherein the wild type porcine IgG is selected from the group consisting of a wild type porcine IgG1a, IgG1b, IgG2a, IgG2b, IgG3, IgG4a, IgG4b, IgG5a, IgG5b, and IgG6a, and wherein the amino acid substitution is M428Y; and (vii) a position that corresponds to amino acid position 434 of a wild type porcine IgG, wherein the wild type porcine IgG is selected from the group consisting of a wild type porcine IgG1a, IgG1b, IgG2a, IgG2b, IgG3, IgG4a, IgG4b, IgG5a, IgG5b, and IgG6a, and wherein the amino acid substitution is of N434Y.

3. The polypeptide of claim 1, wherein the wild type porcine IgG Fc is:

(a) a porcine IaG1a Fc comprising the amino acid sequence of SEQ ID NO: 1;

(b) a porcine IgG1b Fc comprising the amino acid sequence of SEQ ID NO: 2;

(c) a porcine IgG2a Fc comprising the amino acid sequence of SEQ ID NO: 3;

(d) a porcine IgG2b Fc comprising the amino acid sequence of SEQ ID NO: 4;

(e) a porcine IgG3 Fc comprising the amino acid sequence of SEQ ID NO: 5;

(f) a porcine IgG4a Fc comprising the amino acid sequence of SEQ ID NO: 6;

(q) a porcine IgG4b Fc comprising the amino acid sequence of SEQ ID NO: 7;

(h) a porcine IgG5a Fc comprising the amino acid sequence of SEQ ID NO: 8;

(i) a porcine IgG5b Fc comprising the amino acid sequence of SEQ ID NO: 9;

(i) a porcine IgG6a Fc comprising the amino acid sequence of SEQ ID NO: 10; or (k) a porcine IgG6b Fc comprising the amino acid sequence of SEQ ID NO: 11.

4. A polypeptide comprising a bovine IgG Fc region variant, or an FcRn-binding region thereof, wherein the polypeptide comprises an amino acid substitution at at least one position selected from the group consisting of:

(i) a position that corresponds to amino acid position 250 of a wild type bovine IgG, wherein the amino acid substitution is T250Q or T250E;

(ii) a position that corresponds to amino acid position 252 of a wild type bovine IgG, wherein:

(a) the wild type bovine IgG is a wild type bovine IgG2, wherein the amino acid substitution is selected from the group consisting of M252Y, M252W, and M252F; or (b) the wild type bovine IgG is a wild type bovine IgG1 or IgG3, wherein the amino acid substitution is selected from the group consisting of T252Y, T252W, and T252F;

(iii) a position that corresponds to amino acid position 254 of a wild type bovine IgG, wherein:

(a) the wild type bovine IgG is a wild type bovine IgG1 or IgG3, wherein the amino acid substitution is selected from the group consisting of S254T, S254R, S254K, and S254H; or (b) the wild type bovine IgG is a wild type bovine IgG2, wherein the amino acid substitution is selected from the group consisting of T254R, T254K, and T254H;

(iv) a position that corresponds to amino acid position 256 of a wild type bovine IgG, wherein the amino acid substitution is selected from the group consisting of T256A, T256D, and T256E;

(v) a position that corresponds to amino acid position 286 of a wild type bovine IgG, wherein the amino acid substitution is selected from the group consisting of T286Y, T286F, T286W, T286L, T286D, and T286E;

(vi) a position that corresponds to amino acid position 309 of a wild type bovine IgG, wherein the amino acid substitution is selected from the group consisting of Q309V, Q309D, and Q309E;

(vii) a position that corresponds to amino acid position 311 of a wild type bovine IgG, wherein the amino acid substitution is selected from the group consisting of Q311V, Q311K, Q311R, Q311L, and Q311H;

(viii) a position that corresponds to amino acid position 426 of a wild type bovine IgG, wherein:

(a) the wild type bovine IgG is a wild type bovine IgG3, wherein the amino acid substitution is selected from the group consisting of A426Y, A426F, and A426H; or (b) the wild type bovine IgG is a wild type bovine IgG1 or IgG2, wherein the amino acid substitution is selected from the group consisting of V426Y, V426F, and V426H;

(ix) a position that corresponds to amino acid position 434 of a wild type bovine IgG, wherein the amino acid substitution is selected from the group consisting of N434H, N434F, N434S, N434W$_1$ and N434Y; and (x) a position that corresponds to amino acid position 436 of a wild type bovine IgG, wherein the amino acid substitution is Y436H, wherein the amino acid positions are based on EU numbering, and wherein the polypeptide has increased binding affinity to a bovine FcRn when compared to an Fc domain of the wild type bovine IgG.

5. The polypeptide of claim 4, wherein the polypeptide comprises an amino acid substitution at at least one position selected from the group consisting of:
   (i) a position that corresponds to amino acid position 252 of a wild type bovine IgG, wherein the wild type bovine IgG is a wild type bovine IgG1 or IgG3, and wherein the amino acid substitution is T252Y;
   (ii) a position that corresponds to amino acid position 309 of a wild type bovine IgG, wherein the amino acid substitution is Q309V;
   (iii) a position that corresponds to amino acid position 311 of a wild type bovine IgG, wherein the amino acid substitution is Q311 V;
   (iv) a position that corresponds to amino acid position 434 of a wild type bovine IgG, wherein the amino acid substitution is N434Y; and
   (v) a position that corresponds to amino acid position 436 of a wild type bovine IgG, wherein the amino acid substitution is Y436H.

6. The polypeptide of claim 4, wherein the wild type bovine IgG Fc is:
   (a) a bovine IaG1 Fc comprising the amino acid sequence of SEQ ID NO: 12;
   (b) a bovine IgG2 Fc comprising the amino acid sequence of SEQ ID NO: 13: or
   (c) a bovine IgG3 Fc comprising the amino acid sequence of SEQ ID NO: 14.

7. A polypeptide comprising an ovine IgG Fc region variant, or an FcRn-binding region thereof, wherein the polypeptide comprises an amino acid substitution at at least one position selected from the group consisting of:
   (i) a position that corresponds to amino acid position 250 of a wild type ovine IgG, wherein:
      (a) the wild type ovine IgG is a wild type ovine IgG2, wherein the amino acid substitution is S250Q or S250E; or
      (b) the wild type ovine IgG is a wild type ovine IgG1 or IgG3, wherein the amino acid substitution is T250Q or T250E;
   (ii) a position that corresponds to amino acid position 252 of a wild type ovine IgG, wherein:
      (a) the wild type ovine IgG is a wild type ovine IgG2, wherein the amino acid substitution is selected from the group consisting of M252Y, M252W, and M252F; or
      (b) the wild type ovine IgG is a wild type ovine IgG1 or IgG3, wherein the amino acid substitution is selected from the group consisting of T252Y, T252W, and T252F;
   (iii) a position that corresponds to amino acid position 254 of a wild type ovine IgG, wherein:
      (a) the wild type ovine IgG is a wild type ovine IgG2, wherein the amino acid substitution is selected from the group consisting of S254R, S254K, and S254H; or
      (b) the wild type ovine IgG is a wild type ovine IgG1 or IgG3, wherein the amino acid substitution is selected from the group consisting of T254R, T254K, and T254H;
   (iv) a position that corresponds to amino acid position 256 of a wild type ovine IgG, wherein the amino acid substitution is selected from the group consisting of T256A, T256D, and T256E;
   (v) a position that corresponds to amino acid position 286 of a wild type ovine IgG, wherein the amino acid substitution is selected from the group consisting of T286Y, T286F, T286W, T286L, T286D, and T286E;
   (vi) a position that corresponds to amino acid position 309 of a wild type ovine IgG, wherein the amino acid substitution is selected from the group consisting of Q309V, Q309D, and Q309E;
   (vii) a position that corresponds to amino acid position 311 of a wild type ovine IgG, wherein:
      (a) the wild type ovine IgG is a wild type ovine IgG1 or IgG3, wherein the amino acid substitution is selected from the group consisting of Q311V, Q311 K, Q311R, Q311L, and Q311H; or
      (b) the wild type ovine IgG is a wild type ovine IgG2, wherein the amino acid substitution is selected from the group consisting of D311V, D311K, D311R, D311L, and D311H;
   (viii) a position that corresponds to amino acid position 426 of a wild type ovine IgG, wherein the amino acid substitution is selected from the group consisting of V426Y, V426F, and V426H;
   (ix) a position that corresponds to amino acid position 428 of a wild type ovine IgG, wherein the amino acid substitution is selected from the group consisting of M428L, M428Y, and M428F;
   (x) a position that corresponds to amino acid position 434 of a wild type ovine IgG, wherein the amino acid substitution is selected from the group consisting of N434H, N434F, N434S, N434W$_1$ and N434Y; and
   (xi) a position that corresponds to amino acid position 436 of a wild type ovine IgG, wherein the amino acid substitution is Y436H,
   wherein the amino acid positions are based on EU numbering, and wherein the polypeptide has increased binding affinity to an ovine FcRn when compared to an Fc domain of the wild type ovine IgG.

8. The polypeptide of claim 7, wherein the polypeptide comprises an amino acid substitution at at least one position selected from the group consisting of:
   (i) a position that corresponds to amino acid position 252 of a wild type ovine IgG, wherein the wild type ovine IgG is a wild type ovine IgG1 or IgG3, and wherein the amino acid substitution is T252Y;
   (ii) a position that corresponds to amino acid position 309 of a wild type ovine IgG, wherein the amino acid substitution is Q309V;
   (iii) a position that corresponds to amino acid position 311 of a wild type ovine IgG, wherein the wild type ovine IgG is a wild type ovine IgG1 or IgG3, and wherein the amino acid substitution is Q311 V;
   (iv) a position that corresponds to amino acid position 428 of a wild type ovine IgG, wherein the amino acid substitution is M428Y; and
   (v) a position that corresponds to amino acid position 434 of a wild type ovine IgG, wherein the amino acid substitution is N434Y.

9. The polypeptide of claim 7, wherein the wild type ovine IgG Fc is:
   (a) an ovine IgG1 Fc comprising the amino acid sequence of SEQ ID NO: 22;
   (b) an ovine IgG2 Fc comprising the amino acid sequence of SEQ ID NO: 23; or
   (c) an ovine IgG2 Fc comprising the amino acid sequence of SEQ ID NO: 24.

10. A polypeptide comprising a caprine IgG Fc region variant, or an FcRn-binding region thereof, wherein the polypeptide comprises an amino acid substitution at at least one position selected from the group consisting of:

(i) a position that corresponds to amino acid position 250 of a wild type caprine IgG, wherein:
  (a) the wild type caprine IgG is a wild type caprine IgG2, wherein the amino acid substitution is S250Q or S250E; or
  (b) the wild type caprine IgG is a wild type caprine IgG1 or IgG3, wherein the amino acid substitution is T250Q or T250E;
(ii) a position that corresponds to amino acid position 252 of a wild type caprine IgG, wherein:
  (a) the wild type caprine IgG is a wild type caprine IgG2, wherein the amino acid substitution is selected from the group consisting of M252Y, M252W, and M252F; or
  (b) the wild type caprine IgG is a wild type caprine IgG1 or IgG3, wherein the amino acid substitution is selected from the group consisting of T252Y, T252W, and T252F;
(iii) a position that corresponds to amino acid position 254 of a wild type caprine IgG, wherein:
  (a) the wild type caprine IgG is a wild type caprine IgG1 or IgG3, wherein the amino acid substitution is selected from the group consisting of S254R, S254K, and S254H; or
  (b) the wild type caprine IgG is a wild type caprine IgG2, wherein the amino acid substitution is selected from the group consisting of T254R, T254K, and T254H;
(iv) a position that corresponds to amino acid position 256 of a wild type caprine IgG, wherein:
  (a) the wild type caprine IgG is a wild type caprine IgG2 or IgG3, wherein the amino acid substitution is selected from the group consisting of T256A, T256D, and T256E; or
  (b) the wild type caprine IgG is a wild type caprine IgG1, wherein the amino acid substitution is selected from the group consisting of K256A, K256D, and K256E;
(v) a position that corresponds to amino acid position 286 of a wild type caprine IgG, wherein the amino acid substitution is selected from the group consisting of T286Y, T286F, T286W, T286L, T286D, and T286E;
(vi) a position that corresponds to amino acid position 309 of a wild type caprine IgG, wherein the amino acid substitution is selected from the group consisting of Q309V, Q309D, and Q309E;
(vii) a position that corresponds to amino acid position 311 of a wild type caprine IgG, wherein:
  (a) the wild type caprine IgG is a wild type caprine IgG1, wherein the amino acid substitution is selected from the group consisting of Q311V, Q311 K, Q311R, Q311L, and Q311H;
  (b) the wild type caprine IgG is a wild type caprine IgG2, wherein the amino acid substitution is selected from the group consisting of D311V, D311K, D311R, D311L, and D311H; or
  (c) the wild type caprine IgG is a wild type caprine IgG3, wherein the amino acid substitution is selected from the group consisting of K311V, K311R, K311L, and K311H;
(viii) a position that corresponds to amino acid position 426 of a wild type caprine IgG, wherein:
  (a) the wild type caprine IgG is a wild type caprine IgG3, wherein the amino acid substitution is selected from the group consisting of A426Y, A426F, and A426H; or
  (b) the wild type caprine IgG is a wild type caprine IgG1 or IgG2, wherein the amino acid substitution is selected from the group consisting of V426Y, V426F, and V426H;
(ix) a position that corresponds to amino acid position 428 of a wild type caprine IG, wherein the amino acid substitution is selected from the group consisting of M428L, M428Y, and M428F;
(x) a position that corresponds to amino acid position 434 of a wild type caprine IG, wherein the amino acid substitution is selected from the group consisting of N434H, N434F, N434S, N434W, and N434Y; and
(xi) a position that corresponds to amino acid position 436 of a wild type caprine IgG, wherein the amino acid substitution is Y436H,
wherein the amino acid positions are based on EU numbering, and wherein the polypeptide has increased binding affinity to a caprine FcRn when compared to an Fc domain of the wild type caprine IgG.

11. The polypeptide of claim 10, wherein the wild type caprine IgG Fc is:
  (a) a caprine IgG IgG1 Fc comprising the amino acid sequence of SEQ ID NO: 25;
  (b) a caprine IgG2 Fc comprising the amino acid sequence of SEQ ID NO: 26; or
  (c) a caprine IgG3 Fc comprising the amino acid sequence of SEQ ID NO: 27.

12. A polypeptide comprising an equine IgG Fc region variant, or an FcRn-binding region thereof, wherein the polypeptide comprises an amino acid substitution at at least one position selected from the group consisting of:
(i) a position that corresponds to amino acid position 250 of a wild type equine IgG, wherein:
  (a) the wild type equine IgG is a wild type equine IgG1 or IgG6, wherein the amino acid substitution is T250Q, or T250E;
  (b) the wild type equine IgG is a wild type equine IgG2, wherein the amino acid substitution is A250Q or A250E; or
  (c) the wild type equine IgG is selected from the group consisting of a wild type equine IgG3, IgG4, IgG5, and IgG7, wherein the amino acid substitution is V250Q or V250E;
(ii) a position that corresponds to amino acid position 252 of a wild type equine IgG, wherein:
  (a) the wild type equine IgG is selected from the group consisting of a wild type equine IgG1, IgG2, IgG3, IgG4, IgG6, and IgG7, wherein the amino acid substitution is M252W; or
  (b) the wild type equine IgG is a wild type equine IgG5, wherein the amino acid substitution is K252W;
(iii) a position that corresponds to amino acid position 254 of a wild type equine IgG, wherein:
  (a) the wild type equine IgG is selected from the group consisting of a wild type equine IgG2, IgG4, IgG5, IgG6, and IgG7, wherein the amino acid substitution is S254R or S254K; or
  (b) the wild type equine IgG is a wild type equine IgG1 or IgG3, wherein the amino acid substitution is T254R or T254K;
(iv) a position that corresponds to amino acid position 256 of a wild type equine IgG, wherein:
  (a) the wild type equine IgG is selected from the group consisting of a wild type equine IgG1, IgG2, IgG4, IgG6, and IgG7, wherein the amino acid substitution is T256A;

(b) the wild type equine IgG is a wild type equine IgG3, wherein the amino acid substitution is M256A; or
(c) the wild type equine IgG is a wild type equine IgG5, wherein the amino acid substitution is K256A;
(v) a position that corresponds to amino acid position 286 of a wild type equine IgG, wherein:
(a) the wild type equine IgG is a wild type equine IgG2, wherein the amino acid substitution is selected from the group consisting of S286Y, S286F, S286W, S286L, S286D, and S286E, 286Y, T286F, T286, T286L, T286D and T286E; or
(b) the wild type equine IgG is selected from the group consisting of a wild type equine IgG1, IgG3, IgG4, IgG5, IgG6, and IgG7, wherein the amino acid substitution is selected from the group consisting of T286Y, T286F, T286W, T286L, T286D, and T286E;
(vi) a position that corresponds to amino acid position 309 of a wild type equine IgG, wherein the amino acid substitution is Q309V or Q309D;
(vii) a position that corresponds to amino acid position 311 of a wild type equine IgG, wherein:
(a) the wild type equine IgG is selected from the group consisting of a wild type equine IgG1, IgG2, IgG3, IgG5, and IgG6, wherein the amino acid substitution is selected from the group consisting of Q311V, Q311K, Q311R, Q311L, and Q311H; or
(b) the wild type equine IgG is a wild type equine IgG4 or IgG7, wherein the amino acid substitution is selected from the group consisting of K311V, K311R, K311L, and K311H;
(viii) a position that corresponds to amino acid position 426 of a wild type equine IgG, wherein:
(a) the wild type equine IgG is selected from the group consisting of a wild type equine IgG2, IgG4, and IgG7, wherein the amino acid substitution is selected from the group consisting of A426Y, A426F, and A426H;
(b) the wild type equine IgG is a wild type equine IgG3 or IgG6, wherein the amino acid substitution is selected from the group consisting of V426Y, V426F, and V426H; or
(c) the wild type equine IgG is a wild type equine IgG1 or IgG5, wherein the amino acid substitution is selected from the group consisting of G426Y, G426F, and G426H;
(ix) a position that corresponds to amino acid position 428 of a wild type equine IgG, wherein the amino acid substitution is M428Y or M428F; and
(x) a position that corresponds to amino acid position 436 of a wild type equine IgG, wherein:
(a) the wild type equine IgG is selected from the group consisting of a wild type equine IgG1, IgG4, IgG5, IgG6, and IgG7, wherein the amino acid substitution is Y436H;
(b) the wild type equine IgG is a wild type equine IgG2, wherein the amino acid substitution is F436H; or
(c) the wild type equine IgG is a wild type equine IgG3, wherein the amino acid substitution is V436H;
wherein the amino acid positions are based on EU numbering, and wherein the polypeptide has increased binding affinity to an equine FcRn when compared to an Fc domain of the wild type equine IgG.

13. The polypeptide of claim 12, wherein the polypeptide comprises an amino acid substitution at at least one position selected from the group consisting of:
(i) a position that corresponds to amino acid position 286 of a wild type equine IgG, wherein the wild type equine IgG is selected from the group consisting of a wild type equine IgG1, IgG3, IgG4, IgG5, IgG6, and IgG7, and wherein the amino acid substitution is T286E
(ii) a position that corresponds to amino acid position 309 of a wild type equine IgG, wherein the amino acid substitution is Q309V;
(iii) a position that corresponds to amino acid position 311 of a wild type equine IgG, wherein the wild type equine IgG is selected from the group consisting of a wild type equine IgG1, IgG2, IgG3, IgG5, and IgG6, and wherein the amino acid substitution is Q311 V; and
(iv) a position that corresponds to amino acid position 426 of a wild type equine IgG, wherein the wild type equine IgG is a wild type equine IgG1 or IgG5, and wherein the amino acid substitution is G426Y.

14. The polypeptide of claim 12, wherein the wild type equine IgG Fc is:
(a) an equine IgG1 Fc comprising the amino acid sequence of SEQ ID NO: 15;
(b) an equine IgG2 Fc comprising the amino acid sequence of SEQ ID NO: 16;
(c) an equine IgG3 Fc comprising the amino acid sequence of SEQ ID NO: 17;
(d) an equine IgG4 Fc comprising the amino acid sequence of SEQ ID NO: 18;
(e) an equine IgG5 Fc comprising the amino acid sequence of SEQ ID NO: 19;
(f) an equine IgG6 Fc comprising the amino acid sequence of SEQ ID NO: 20; or
(g) an equine IgG7 Fc comprising the amino acid sequence of SEQ ID NO: 21.

15. The polypeptide of claim 12, wherein the polypeptide comprises two or more of the at least one amino acid substitutions, wherein the two or more amino acid substitutions are at different positions, and wherein the polypeptide has increased binding affinity to an equine FcRn when compared to (a) an Fc domain of the wild type equine IgG, and (b) a polypeptide comprising only one of the two or more amino acid substitutions.

16. The polypeptide of claim 12, further comprising a binding domain.

17. The polypeptide of claim 16, wherein the binding domain comprises (i) six complementarity determining regions (CDRs) of an immunoglobulin molecule; (ii) a ligand binding domain of an equine receptor protein, (iii) a nanobody, or (iv) an extracellular domain of an equine receptor protein.

18. The polypeptide of claim 16, wherein the binding domain specifically binds to an antigen selected from the group consisting of NGF, TrKA, ADAMTS, IL-1, IL-2, IL-4, IL-4R, Angiotensin type 1 (AT1) receptor, Angiotensin type 2 (AT2) receptor, IL-5, IL-12, IL-13, IL-31, IL-33, CD3, CD20, CD47, CD52, and complement system complex.

19. The polypeptide of claim 12, further comprising a protein selected from the group consisting of EPO, CTLA4, LFA3, VEGFR1/VEGFR3, IL-1R, IL-4R, GLP-1 receptor agonist, and Thrombopoietin binding peptide.

20. The polypeptide of claim 12, wherein the polypeptide binds to an equine FcRn at a higher level at an acidic pH than at a neutral pH.

21. The polypeptide of claim 20, wherein the polypeptide binds to an equine FcRn at a higher level at pH 5.5 than at pH 7.4.

22. The polypeptide of claim 20, wherein the polypeptide binds to an equine FcRn at a higher level at pH 6.0 than at pH 7.4.

23. A pharmaceutical composition comprising (i) the polypeptide of claim 12, and (ii) a pharmaceutically acceptable excipient.

24. A nucleic acid or nucleic acids encoding the polypeptide of claim 12.

25. An expression vector or expression vectors comprising the nucleic acid or nucleic acids of claim 24.

26. A host cell comprising the expression vector or expression vectors of claim 25.

27. A method of making a polypeptide, the method comprising:
   (a) providing the nucleic acid or nucleic acids of claim 24;
   (b) expressing the nucleic acid or nucleic acids in a host cell culture, thereby producing the polypeptide; and
   (c) collecting the polypeptide produced in (b) from the host cell culture.

28. The method of claim 27, further comprising formulating the polypeptide as a pharmaceutical formulation.

* * * * *

UNITED STATES PATENT AND TRADEMARK OFFICE
CERTIFICATE OF CORRECTION

PATENT NO. : 12,103,961 B2
APPLICATION NO. : 17/540044
DATED : October 1, 2024
INVENTOR(S) : William Brondyk et al.

It is certified that error appears in the above-identified patent and that said Letters Patent is hereby corrected as shown below:

In the Specification

Column 42, Table 4, Line 28, EU number 408, replace each "5" with --S--.

In the Claims

Column 111, Line 41, Claim 1, replace "wild type animal porcine IgG" with --wild type porcine IgG--.

Column 112, Line 42, Claim 1, replace "wild type animal porcine IgG" with --wild type porcine IgG--.

Column 113, Line 5, Claim 1, replace "amino acid substitution selected from the group consisting of Y436H;" with --amino acid substitution is Y436H;--.

Column 113, Line 29, Claim 2, replace "IgG1 a and IgG1 b" with --IgG1a and IgG1b--.

Column 113, Line 49, Claim 2, replace "is of N434Y" with --is N434Y--.

Column 113, Line 52, Claim 3, replace "IaG1a" with --IgG1a--.

Column 113, Line 64, Claim 3, replace "(q)" with --(g)--.

Column 114, Line 3, Claim 3, replace "(i)" with --(j)--.

Column 114, Line 62, Claim 4, replace "N434W$_1$" with --N434W,--.

Column 115, Line 24, Claim 6, replace "IaG1" with --IgG1--.

Signed and Sealed this
Thirtieth Day of September, 2025

John A. Squires
*Director of the United States Patent and Trademark Office*

CERTIFICATE OF CORRECTION (continued)
U.S. Pat. No. 12,103,961 B2

Column 116, Line 28, Claim 7, replace "N434W$_1$" with --N434W,--.

Column 118, Line 6, Claim 10, replace "wild type caprine IG" with --wild type caprine IgG--.

Column 119, Line 10-11, Claim 12, replace "and S286E, 286Y, T286F, T286, T286L, T286D and T286E; or" with --and S286E; or--.

SEQUENCE LISTING

```
<160> NUMBER OF SEQ ID NOS: 36

<210> SEQ ID NO 1
<211> LENGTH: 218
<212> TYPE: PRT
<213> ORGANISM: Sus scrofa

<400> SEQUENCE: 1

Gly Cys Glu Val Ala Gly Pro Ser Val Phe Ile Phe Pro Pro Lys Pro
1               5                   10                  15

Lys Asp Thr Leu Met Ile Ser Gln Thr Pro Glu Val Thr Cys Val Val
            20                  25                  30

Val Asp Val Ser Lys Glu His Ala Glu Val Gln Phe Ser Trp Tyr Val
        35                  40                  45

Asp Gly Val Glu Val His Thr Ala Glu Thr Arg Pro Lys Glu Glu Gln
```

```
            50                  55                  60
Phe Asn Ser Thr Tyr Arg Val Val Ser Val Leu Pro Ile Gln His Gln
 65                  70                  75                  80

Asp Trp Leu Lys Gly Lys Glu Phe Lys Cys Lys Val Asn Asn Val Asp
                 85                  90                  95

Leu Pro Ala Pro Ile Thr Arg Thr Ile Ser Lys Ala Ile Gly Gln Ser
                100                 105                 110

Arg Glu Pro Gln Val Tyr Thr Leu Pro Pro Ala Glu Glu Leu Ser
                115                 120                 125

Arg Ser Lys Val Thr Val Thr Cys Leu Val Ile Gly Phe Tyr Pro Pro
            130                 135                 140

Asp Ile His Val Glu Trp Lys Ser Asn Gly Gln Pro Glu Pro Glu Gly
145                 150                 155                 160

Asn Tyr Arg Thr Thr Pro Pro Gln Gln Asp Val Asp Gly Thr Phe Phe
                165                 170                 175

Leu Tyr Ser Lys Leu Ala Val Asp Lys Ala Arg Trp Asp His Gly Glu
                180                 185                 190

Thr Phe Glu Cys Ala Val Met His Glu Ala Leu His Asn His Tyr Thr
                195                 200                 205

Gln Lys Ser Ile Ser Lys Thr Gln Gly Lys
            210                 215

<210> SEQ ID NO 2
<211> LENGTH: 218
<212> TYPE: PRT
<213> ORGANISM: Sus scrofa

<400> SEQUENCE: 2

Gly Cys Glu Val Ala Gly Pro Ser Val Phe Ile Phe Pro Pro Lys Pro
  1               5                  10                  15

Lys Asp Thr Leu Met Ile Ser Gln Thr Pro Glu Val Thr Cys Val Val
                 20                  25                  30

Val Asp Val Ser Lys Glu His Ala Glu Val Gln Phe Ser Trp Tyr Val
             35                  40                  45

Asp Gly Val Glu Val His Thr Ala Glu Thr Arg Pro Lys Glu Glu Gln
 50                  55                  60

Phe Asn Ser Thr Tyr Arg Val Val Ser Val Leu Pro Ile Gln His Gln
 65                  70                  75                  80

Asp Trp Leu Lys Gly Lys Glu Phe Lys Cys Lys Val Asn Asn Val Asp
                 85                  90                  95

Leu Pro Ala Pro Ile Thr Arg Thr Ile Ser Lys Ala Ile Gly Gln Ser
                100                 105                 110

Arg Glu Pro Gln Val Tyr Thr Leu Pro Pro Ala Glu Glu Leu Ser
                115                 120                 125

Arg Ser Lys Val Thr Val Thr Cys Leu Val Ile Gly Phe Tyr Pro Pro
            130                 135                 140

Asp Ile His Val Glu Trp Lys Ser Asn Gly Gln Pro Glu Pro Glu Asn
145                 150                 155                 160

Thr Tyr Arg Thr Thr Pro Pro Gln Gln Asp Val Asp Gly Thr Phe Phe
                165                 170                 175

Leu Tyr Ser Lys Leu Ala Val Asp Lys Ala Arg Trp Asp His Gly Asp
                180                 185                 190

Lys Phe Glu Cys Ala Val Met His Glu Ala Leu His Asn His Tyr Thr
                195                 200                 205
```

```
Gln Lys Ser Ile Ser Lys Thr Gln Gly Lys
    210                 215
```

<210> SEQ ID NO 3
<211> LENGTH: 218
<212> TYPE: PRT
<213> ORGANISM: Sus scrofa

<400> SEQUENCE: 3

```
Ala Cys Glu Ser Pro Gly Pro Ser Val Phe Ile Phe Pro Pro Lys Pro
1               5                   10                  15

Lys Asp Thr Leu Met Ile Ser Arg Thr Pro Gln Val Thr Cys Val Val
            20                  25                  30

Val Asp Val Ser Gln Glu Asn Pro Glu Val Gln Phe Ser Trp Tyr Val
        35                  40                  45

Asp Gly Val Glu Val His Thr Ala Gln Thr Arg Pro Lys Glu Glu Gln
    50                  55                  60

Phe Asn Ser Thr Tyr Arg Val Val Ser Val Leu Pro Ile Gln His Gln
65                  70                  75                  80

Asp Trp Leu Asn Gly Lys Glu Phe Lys Cys Lys Val Asn Asn Lys Asp
                85                  90                  95

Leu Pro Ala Pro Ile Thr Arg Ile Ile Ser Lys Ala Lys Gly Gln Thr
            100                 105                 110

Arg Glu Pro Gln Val Tyr Thr Leu Pro Pro His Ala Glu Glu Leu Ser
        115                 120                 125

Arg Ser Lys Val Ser Ile Thr Cys Leu Val Ile Gly Phe Tyr Pro Pro
    130                 135                 140

Asp Ile Asp Val Glu Trp Gln Arg Asn Gly Gln Pro Glu Pro Glu Gly
145                 150                 155                 160

Asn Tyr Arg Thr Thr Pro Pro Gln Gln Asp Val Asp Gly Thr Tyr Phe
                165                 170                 175

Leu Tyr Ser Lys Phe Ser Val Asp Lys Ala Ser Trp Gln Gly Gly Gly
            180                 185                 190

Ile Phe Gln Cys Ala Val Met His Glu Ala Leu His Asn His Tyr Thr
        195                 200                 205

Gln Lys Ser Ile Ser Lys Thr Pro Gly Lys
    210                 215
```

<210> SEQ ID NO 4
<211> LENGTH: 218
<212> TYPE: PRT
<213> ORGANISM: Sus scrofa

<400> SEQUENCE: 4

```
Ala Cys Glu Ser Pro Gly Pro Ser Val Phe Ile Phe Pro Pro Lys Pro
1               5                   10                  15

Lys Asp Thr Leu Met Ile Ser Arg Thr Pro Gln Val Thr Cys Val Val
            20                  25                  30

Val Asp Val Ser Gln Glu Asn Pro Glu Val Gln Phe Ser Trp Tyr Val
        35                  40                  45

Asp Gly Val Glu Val His Thr Ala Gln Thr Arg Pro Lys Glu Glu Gln
    50                  55                  60

Phe Asn Ser Thr Tyr Arg Val Val Ser Val Leu Pro Ile Gln His Gln
65                  70                  75                  80

Asp Trp Leu Asn Gly Lys Glu Phe Lys Cys Lys Val Asn Asn Lys Asp
                85                  90                  95
```

Leu Pro Ala Pro Ile Thr Arg Ile Ile Ser Lys Ala Lys Gly Gln Thr
            100                 105                 110

Arg Glu Pro Gln Val Tyr Thr Leu Pro Pro His Ala Glu Glu Leu Ser
        115                 120                 125

Arg Ser Lys Val Ser Ile Thr Cys Leu Val Ile Gly Phe Tyr Pro Pro
    130                 135                 140

Asp Ile Asp Val Glu Trp Gln Arg Asn Gly Gln Pro Glu Pro Glu Gly
145                 150                 155                 160

Asn Tyr Arg Thr Thr Pro Pro Gln Gln Asp Val Asp Gly Thr Tyr Phe
            165                 170                 175

Leu Tyr Ser Lys Phe Ser Val Asp Lys Ala Ser Trp Gln Gly Gly Gly
        180                 185                 190

Ile Phe Gln Cys Ala Val Met His Glu Ala Leu His Asn His Tyr Thr
    195                 200                 205

Gln Lys Ser Ile Ser Lys Thr Pro Gly Lys
    210                 215

<210> SEQ ID NO 5
<211> LENGTH: 219
<212> TYPE: PRT
<213> ORGANISM: Sus scrofa

<400> SEQUENCE: 5

Ala Ala Glu Val Leu Gly Ala Pro Ser Val Phe Leu Phe Pro Pro Lys
1               5                   10                  15

Pro Lys Asp Ile Leu Met Ile Ser Arg Thr Pro Lys Val Thr Cys Val
            20                  25                  30

Val Val Asp Val Ser Gln Glu Glu Ala Glu Val Gln Phe Ser Trp Tyr
        35                  40                  45

Val Asp Gly Val Gln Leu Tyr Thr Ala Gln Thr Arg Pro Met Glu Glu
    50                  55                  60

Gln Phe Asn Ser Thr Tyr Arg Val Val Ser Val Leu Pro Ile Gln His
65                  70                  75                  80

Gln Asp Trp Leu Lys Gly Lys Glu Phe Lys Cys Lys Val Asn Asn Lys
            85                  90                  95

Asp Leu Leu Ser Pro Ile Thr Arg Thr Ile Ser Lys Ala Thr Gly Pro
            100                 105                 110

Ser Arg Val Pro Gln Val Tyr Thr Leu Pro Pro Ala Trp Glu Glu Leu
        115                 120                 125

Ser Lys Ser Lys Val Ser Ile Thr Cys Leu Val Thr Gly Phe Tyr Pro
    130                 135                 140

Pro Asp Ile Asp Val Glu Trp Gln Ser Asn Gly Gln Gln Glu Pro Glu
145                 150                 155                 160

Gly Asn Tyr Arg Thr Thr Pro Pro Gln Gln Asp Val Asp Gly Thr Tyr
            165                 170                 175

Phe Leu Tyr Ser Lys Leu Ala Val Asp Lys Val Arg Trp Gln Arg Gly
        180                 185                 190

Asp Leu Phe Gln Cys Ala Val Met His Glu Ala Leu His Asn His Tyr
    195                 200                 205

Thr Gln Lys Ser Ile Ser Lys Thr Gln Gly Lys
    210                 215

<210> SEQ ID NO 6
<211> LENGTH: 218
<212> TYPE: PRT
<213> ORGANISM: Sus scrofa

```
<400> SEQUENCE: 6

Ala Cys Glu Gly Pro Gly Pro Ser Ala Phe Ile Phe Pro Pro Lys Pro
1               5                   10                  15

Lys Asp Thr Leu Met Ile Ser Arg Thr Pro Lys Val Thr Cys Val Val
            20                  25                  30

Val Asp Val Ser Gln Glu Asn Pro Glu Val Gln Phe Ser Trp Tyr Val
        35                  40                  45

Asp Gly Val Glu Val His Thr Ala Gln Thr Arg Pro Lys Glu Glu Gln
    50                  55                  60

Phe Asn Ser Thr Tyr Arg Val Val Ser Val Leu Pro Ile Gln His Gln
65                  70                  75                  80

Asp Trp Leu Asn Gly Lys Glu Phe Lys Cys Lys Val Asn Asn Lys Asp
                85                  90                  95

Leu Pro Ala Pro Ile Thr Arg Ile Ile Ser Lys Ala Lys Gly Gln Thr
            100                 105                 110

Arg Glu Pro Gln Val Tyr Thr Leu Pro Pro Pro Thr Glu Glu Leu Ser
        115                 120                 125

Arg Ser Lys Val Thr Leu Thr Cys Leu Val Thr Gly Phe Tyr Pro Pro
130                 135                 140

Asp Ile Asp Val Glu Trp Gln Arg Asn Gly Gln Pro Glu Pro Glu Gly
145                 150                 155                 160

Asn Tyr Arg Thr Thr Pro Pro Gln Gln Asp Val Asp Gly Thr Tyr Phe
                165                 170                 175

Leu Tyr Ser Lys Leu Ala Val Asp Lys Ala Ser Trp Gln Arg Gly Asp
            180                 185                 190

Thr Phe Gln Cys Ala Val Met His Glu Ala Leu His Asn His Tyr Thr
        195                 200                 205

Gln Lys Ser Ile Phe Lys Thr Pro Gly Lys
    210                 215

<210> SEQ ID NO 7
<211> LENGTH: 208
<212> TYPE: PRT
<213> ORGANISM: Sus scrofa

<400> SEQUENCE: 7

Ala Cys Glu Gly Pro Gly Pro Ser Ala Phe Ile Phe Pro Pro Lys Pro
1               5                   10                  15

Lys Asp Thr Leu Met Ile Ser Arg Thr Pro Lys Val Thr Cys Val Val
            20                  25                  30

Val Asp Val Ser Gln Glu Asn Pro Glu Val Gln Phe Ser Trp Tyr Val
        35                  40                  45

Asp Gly Val Glu Val His Thr Ala Gln Thr Arg Pro Lys Glu Glu Gln
    50                  55                  60

Phe Asn Ser Thr Tyr Arg Val Val Ser Val Leu Leu Ile Gln His Gln
65                  70                  75                  80

Asp Trp Leu Asn Gly Lys Glu Phe Lys Cys Lys Val Asn Asn Lys Asp
                85                  90                  95

Leu Pro Ala Pro Ile Thr Arg Ile Ile Ser Lys Ala Lys Gly Gln Thr
            100                 105                 110

Arg Glu Pro Gln Val Tyr Thr Leu Pro Pro Pro Thr Glu Glu Leu Ser
        115                 120                 125

Arg Ser Lys Val Thr Leu Thr Cys Leu Val Thr Gly Phe Tyr Pro Pro
130                 135                 140
```

-continued

Asp Ile Asp Val Glu Trp Gln Arg Asn Gly Gln Pro Glu Pro Glu Gly
145                 150                 155                 160

Asn Tyr Arg Thr Thr Pro Pro Gln Gln Asp Val Asp Gly Thr Tyr Phe
                165                 170                 175

Leu Tyr Ser Lys Leu Ala Val Asp Lys Ala Ser Trp Gln Arg Gly Asp
            180                 185                 190

Thr Phe Gln Cys Ala Val Met His Glu Ala Leu His Asn His Tyr Thr
        195                 200                 205

<210> SEQ ID NO 8
<211> LENGTH: 218
<212> TYPE: PRT
<213> ORGANISM: Sus scrofa

<400> SEQUENCE: 8

Gly Cys Glu Val Ala Gly Pro Ser Val Phe Ile Phe Pro Pro Lys Pro
1               5                   10                  15

Lys Asp Ile Leu Met Ile Ser Arg Thr Pro Glu Val Thr Cys Val Val
            20                  25                  30

Val Asp Val Ser Lys Glu His Ala Glu Val Gln Phe Ser Trp Tyr Val
        35                  40                  45

Asp Gly Glu Glu Val His Thr Ala Glu Thr Arg Pro Lys Glu Glu Gln
50                  55                  60

Phe Asn Ser Thr Tyr Arg Val Val Ser Val Leu Pro Ile Gln His Glu
65                  70                  75                  80

Asp Trp Leu Lys Gly Lys Glu Phe Glu Cys Lys Val Asn Asn Glu Asp
                85                  90                  95

Leu Pro Gly Pro Ile Thr Arg Thr Ile Ser Lys Ala Lys Gly Val Val
            100                 105                 110

Arg Ser Pro Glu Val Tyr Thr Leu Pro Pro Ala Glu Glu Leu Ser
        115                 120                 125

Lys Ser Ile Val Thr Leu Thr Cys Leu Val Lys Ser Ile Phe Pro Pro
130                 135                 140

Phe Ile His Val Glu Trp Lys Ile Asn Gly Lys Pro Glu Pro Glu Asn
145                 150                 155                 160

Ala Tyr Arg Thr Thr Pro Pro Gln Glu Asp Glu Asp Arg Thr Tyr Phe
                165                 170                 175

Leu Tyr Ser Lys Leu Ala Val Asp Lys Ala Arg Trp Asp His Gly Glu
            180                 185                 190

Thr Phe Glu Cys Ala Val Met His Glu Ala Leu His Asn His Tyr Thr
        195                 200                 205

Gln Lys Ser Ile Ser Lys Thr Gln Gly Lys
    210                 215

<210> SEQ ID NO 9
<211> LENGTH: 217
<212> TYPE: PRT
<213> ORGANISM: Sus scrofa

<400> SEQUENCE: 9

Ile Cys Pro Val Ala Gly Pro Ser Val Phe Ile Phe Pro Pro Lys Pro
1               5                   10                  15

Lys Asp Ile Leu Met Ile Ser Arg Thr Pro Glu Val Thr Cys Val Val
            20                  25                  30

Val Asp Val Ser Lys Glu His Ala Glu Val Gln Phe Ser Trp Tyr Val
        35                  40                  45

Asp Gly Glu Glu Val His Thr Ala Glu Thr Arg Pro Lys Glu Glu Gln
            50                  55                  60

Phe Asn Ser Thr Tyr Arg Val Val Ser Val Leu Pro Ile Gln His Glu
 65                  70                  75                  80

Asp Trp Leu Lys Gly Lys Glu Phe Glu Cys Lys Val Asn Asn Glu Asp
                85                  90                  95

Leu Pro Gly Pro Ile Thr Arg Thr Ile Ser Lys Ala Lys Gly Val Val
            100                 105                 110

Arg Ser Pro Glu Val Tyr Thr Leu Pro Pro Pro Ala Glu Glu Leu Ser
            115                 120                 125

Lys Ser Ile Val Thr Leu Thr Cys Leu Val Lys Ser Phe Phe Pro Pro
130                 135                 140

Phe Ile His Val Glu Trp Lys Ile Asn Gly Lys Pro Glu Pro Glu Asn
145                 150                 155                 160

Ala Tyr Arg Thr Thr Pro Pro Gln Glu Asp Glu Asp Gly Thr Tyr Phe
                165                 170                 175

Leu Tyr Ser Lys Phe Ser Val Glu Lys Phe Arg Trp His Ser Gly Gly
                180                 185                 190

Ile His Cys Ala Val Met His Glu Ala Leu His Asn His Tyr Thr Glu
            195                 200                 205

Lys Ser Val Ser Gln Thr Pro Gly Lys
            210                 215

<210> SEQ ID NO 10
<211> LENGTH: 218
<212> TYPE: PRT
<213> ORGANISM: Sus scrofa

<400> SEQUENCE: 10

Ala Cys Glu Gly Pro Gly Pro Ser Ala Phe Ile Phe Pro Pro Lys Pro
 1                   5                  10                  15

Lys Asp Thr Leu Met Ile Ser Arg Thr Pro Lys Val Thr Cys Val Val
                20                  25                  30

Val Asp Val Ser Gln Glu Asn Pro Glu Val Gln Phe Ser Trp Tyr Val
            35                  40                  45

Asp Gly Val Glu Val His Thr Ala Gln Thr Arg Pro Lys Glu Glu Gln
            50                  55                  60

Phe Asn Ser Thr Tyr Arg Val Val Ser Val Leu Pro Ile Gln His Gln
 65                  70                  75                  80

Asp Trp Leu Asn Gly Lys Glu Phe Lys Cys Lys Val Asn Asn Lys Asp
                85                  90                  95

Leu Pro Ala Pro Ile Thr Arg Ile Ile Ser Lys Ala Lys Gly Gln Thr
            100                 105                 110

Arg Glu Pro Gln Val Tyr Thr Leu Pro Pro Thr Glu Glu Leu Ser
            115                 120                 125

Arg Ser Lys Leu Ser Val Thr Cys Leu Ile Thr Gly Phe Tyr Pro Pro
130                 135                 140

Asp Ile Asp Val Glu Trp Gln Arg Asn Gly Gln Pro Glu Pro Glu Gly
145                 150                 155                 160

Asn Tyr Arg Thr Thr Pro Pro Gln Gln Asp Val Asp Gly Thr Tyr Phe
                165                 170                 175

Leu Tyr Ser Lys Leu Ala Val Asp Lys Ala Ser Trp Gln Arg Gly Asp
                180                 185                 190

Pro Phe Gln Cys Ala Val Met His Glu Ala Leu His Asn His Tyr Thr

```
                195                 200                 205
Gln Lys Ser Ile Phe Lys Thr Pro Gly Asn
    210                 215

<210> SEQ ID NO 11
<211> LENGTH: 214
<212> TYPE: PRT
<213> ORGANISM: Sus scrofa

<400> SEQUENCE: 11

Ala Cys Glu Gly Asn Gly Pro Ser Val Phe Ile Phe Pro Lys Pro
1               5                   10                  15

Lys Asp Thr Leu Met Ile Ser Arg Thr Pro Glu Val Thr Cys Val Val
                20                  25                  30

Val Asp Val Ser Gln Glu Asn Pro Glu Val Gln Phe Ser Trp Tyr Val
                35                  40                  45

Asp Gly Glu Glu Val His Thr Ala Glu Thr Arg Pro Lys Glu Glu Gln
            50                  55                  60

Phe Asn Ser Thr Tyr Arg Val Val Ser Val Leu Pro Ile Gln His Gln
65                  70                  75                  80

Asp Trp Leu Lys Gly Lys Glu Phe Glu Cys Lys Val Asn Asn Lys Asp
                85                  90                  95

Leu Pro Ala Pro Ile Thr Arg Ile Ile Ser Lys Ala Lys Gly Pro Ser
                100                 105                 110

Arg Glu Pro Gln Val Tyr Thr Leu Ser Pro Ser Ala Glu Glu Leu Ser
            115                 120                 125

Arg Ser Lys Val Ser Ile Thr Cys Leu Val Thr Gly Phe Tyr Pro Pro
130                 135                 140

Asp Ile Asp Val Glu Trp Lys Ser Asn Gly Gln Pro Glu Pro Glu Gly
145                 150                 155                 160

Asn Tyr Arg Ser Thr Pro Pro Gln Glu Asp Glu Asp Gly Thr Tyr Phe
                165                 170                 175

Leu Tyr Ser Lys Leu Ala Val Asp Lys Ala Arg Leu Gln Ser Gly Gly
                180                 185                 190

Ile His Cys Ala Val Met His Glu Ala Leu His Asn His Tyr Thr Gln
            195                 200                 205

Lys Ser Ile Ser Lys Thr
    210

<210> SEQ ID NO 12
<211> LENGTH: 217
<212> TYPE: PRT
<213> ORGANISM: Bos taurus

<400> SEQUENCE: 12

Pro Pro Glu Leu Pro Gly Gly Pro Ser Val Phe Ile Phe Pro Pro Lys
1               5                   10                  15

Pro Lys Asp Thr Leu Thr Ile Ser Gly Thr Pro Glu Val Thr Cys Val
                20                  25                  30

Val Val Asp Val Gly His Asp Asp Pro Glu Val Lys Phe Ser Trp Phe
                35                  40                  45

Val Asp Asn Val Glu Val Asn Thr Ala Thr Thr Lys Pro Arg Glu Glu
            50                  55                  60

Gln Phe Asn Ser Thr Tyr Arg Val Val Ser Ala Leu Arg Ile Gln His
65                  70                  75                  80

Gln Asp Trp Thr Gly Gly Lys Glu Phe Lys Cys Lys Val His Asn Glu
```

```
            85                  90                  95
Gly Leu Pro Ala Pro Ile Val Arg Thr Ile Ser Arg Thr Lys Gly Pro
            100                 105                 110

Ala Arg Glu Pro Gln Val Tyr Val Leu Ala Pro Pro Gln Glu Glu Leu
            115                 120                 125

Ser Lys Ser Thr Val Ser Leu Thr Cys Met Val Thr Ser Phe Tyr Pro
            130                 135                 140

Asp Tyr Ile Ala Val Glu Trp Gln Arg Asn Gly Gln Pro Glu Ser Glu
145                 150                 155                 160

Asp Lys Tyr Gly Thr Thr Pro Pro Gln Leu Asp Ala Asp Ser Ser Tyr
                165                 170                 175

Phe Leu Tyr Ser Lys Leu Arg Val Asp Arg Asn Ser Trp Gln Glu Gly
                180                 185                 190

Asp Thr Tyr Thr Cys Val Val Met His Glu Ala Leu His Asn His Tyr
                195                 200                 205

Thr Gln Lys Ser Thr Ser Lys Ser Ala
            210                 215

<210> SEQ ID NO 13
<211> LENGTH: 216
<212> TYPE: PRT
<213> ORGANISM: Bos taurus

<400> SEQUENCE: 13

Cys Val Arg Glu Pro Ser Val Phe Ile Phe Pro Pro Lys Pro Lys Asp
1               5                   10                  15

Thr Leu Met Ile Thr Gly Thr Pro Glu Val Thr Cys Val Val Val Asn
            20                  25                  30

Val Gly His Asp Asn Pro Glu Val Gln Phe Ser Trp Phe Val Asp Asp
        35                  40                  45

Val Glu Val His Thr Ala Arg Thr Lys Pro Arg Glu Glu Gln Phe Asn
    50                  55                  60

Ser Thr Tyr Arg Val Val Ser Ala Leu Pro Ile Gln His Gln Asp Trp
65                  70                  75                  80

Thr Gly Gly Lys Glu Phe Lys Cys Lys Val Asn Ile Lys Gly Leu Ser
                85                  90                  95

Ala Ser Ile Val Arg Ile Ile Ser Arg Ser Lys Gly Pro Ala Arg Glu
            100                 105                 110

Pro Gln Val Tyr Val Leu Asp Pro Pro Lys Glu Glu Leu Ser Lys Ser
            115                 120                 125

Thr Val Ser Val Thr Cys Met Val Ile Gly Phe Tyr Pro Glu Asp Val
            130                 135                 140

Asp Val Glu Trp Gln Arg Asp Arg Gln Thr Glu Ser Glu Asp Lys Tyr
145                 150                 155                 160

Arg Thr Thr Pro Pro Gln Leu Asp Ala Asp Arg Ser Tyr Phe Leu Tyr
                165                 170                 175

Ser Lys Leu Arg Val Asp Arg Asn Ser Trp Gln Arg Gly Gly Thr Tyr
                180                 185                 190

Thr Cys Val Val Met His Glu Ala Leu His Asn His Tyr Met Gln Lys
                195                 200                 205

Ser Thr Ser Lys Ser Ala Gly Lys
            210                 215

<210> SEQ ID NO 14
<211> LENGTH: 217
```

```
<212> TYPE: PRT
<213> ORGANISM: Bos taurus

<400> SEQUENCE: 14

Glu Pro Leu Gly Gly Leu Ser Val Phe Ile Phe Pro Pro Lys Pro Lys
1               5                   10                  15

Asp Thr Leu Thr Ile Ser Gly Thr Pro Glu Val Thr Cys Val Val Val
            20                  25                  30

Asp Val Gly Gln Asp Asp Pro Glu Val Gln Phe Ser Trp Phe Val Asp
        35                  40                  45

Asp Val Glu Val His Thr Ala Arg Thr Lys Pro Arg Glu Glu Gln Phe
    50                  55                  60

Asn Ser Thr Tyr Arg Val Val Ser Ala Leu Arg Ile Gln His Gln Asp
65                  70                  75                  80

Trp Leu Gln Gly Lys Glu Phe Lys Cys Lys Val Asn Asn Lys Gly Leu
                85                  90                  95

Pro Ala Pro Ile Val Arg Thr Ile Ser Arg Thr Lys Gly Gln Ala Arg
            100                 105                 110

Glu Pro Gln Val Tyr Val Leu Ala Pro Pro Arg Glu Glu Leu Ser Lys
        115                 120                 125

Ser Thr Leu Ser Leu Thr Cys Leu Ile Thr Gly Phe Tyr Pro Glu Glu
    130                 135                 140

Ile Asp Val Glu Trp Gln Arg Asn Gly Gln Pro Glu Ser Glu Asp Lys
145                 150                 155                 160

Tyr His Thr Thr Ala Pro Gln Leu Asp Ala Asp Gly Ser Tyr Phe Leu
                165                 170                 175

Tyr Ser Lys Leu Arg Val Asn Lys Ser Ser Trp Gln Glu Gly Asp His
            180                 185                 190

Tyr Thr Cys Ala Val Met His Glu Ala Leu Arg Asn His Tyr Lys Glu
        195                 200                 205

Lys Ser Ile Ser Arg Ser Pro Gly Lys
    210                 215

<210> SEQ ID NO 15
<211> LENGTH: 219
<212> TYPE: PRT
<213> ORGANISM: Equus caballus

<400> SEQUENCE: 15

Ala Pro Glu Leu Leu Gly Gly Pro Ser Val Phe Ile Phe Pro Pro Asn
1               5                   10                  15

Pro Lys Asp Thr Leu Met Ile Thr Arg Thr Pro Glu Val Thr Cys Val
            20                  25                  30

Val Val Asp Val Ser Gln Glu Asn Pro Asp Val Lys Phe Asn Trp Tyr
        35                  40                  45

Met Asp Gly Val Glu Val Arg Thr Ala Thr Thr Arg Pro Lys Glu Glu
    50                  55                  60

Gln Phe Asn Ser Thr Tyr Arg Val Val Ser Val Leu Arg Ile Gln His
65                  70                  75                  80

Gln Asp Trp Leu Ser Gly Lys Glu Phe Lys Cys Lys Val Asn Asn Gln
                85                  90                  95

Ala Leu Pro Gln Pro Ile Glu Arg Thr Ile Thr Lys Thr Lys Gly Arg
            100                 105                 110

Ser Gln Glu Pro Gln Val Tyr Val Leu Ala Pro His Pro Asp Glu Leu
        115                 120                 125
```

```
Ser Lys Ser Lys Val Ser Val Thr Cys Leu Val Lys Asp Phe Tyr Pro
    130                 135                 140

Pro Glu Ile Asn Ile Glu Trp Gln Ser Asn Gly Gln Pro Glu Leu Glu
145                 150                 155                 160

Thr Lys Tyr Ser Thr Thr Gln Ala Gln Gln Asp Ser Asp Gly Ser Tyr
                165                 170                 175

Phe Leu Tyr Ser Lys Leu Ser Val Asp Arg Asn Arg Trp Gln Gln Gly
                180                 185                 190

Thr Thr Phe Thr Cys Gly Val Met His Glu Ala Leu His Asn His Tyr
                195                 200                 205

Thr Gln Lys Asn Val Ser Lys Asn Pro Gly Lys
    210                 215

<210> SEQ ID NO 16
<211> LENGTH: 213
<212> TYPE: PRT
<213> ORGANISM: Equus caballus

<400> SEQUENCE: 16

Gly Pro Ser Val Phe Ile Phe Pro Pro Asn Pro Lys Asp Ala Leu Met
1               5                   10                  15

Ile Ser Arg Thr Pro Val Val Thr Cys Val Val Val Asn Leu Ser Asp
                20                  25                  30

Gln Tyr Pro Asp Val Gln Phe Ser Trp Tyr Val Asp Asn Thr Glu Val
            35                  40                  45

His Ser Ala Ile Thr Lys Gln Arg Glu Ala Gln Phe Asn Ser Thr Tyr
        50                  55                  60

Arg Val Val Ser Val Leu Pro Ile Gln His Gln Asp Trp Leu Ser Gly
65                  70                  75                  80

Lys Glu Phe Lys Cys Ser Val Thr Asn Val Gly Val Pro Gln Pro Ile
                85                  90                  95

Ser Arg Ala Ile Ser Arg Gly Lys Gly Pro Ser Arg Val Pro Gln Val
                100                 105                 110

Tyr Val Leu Pro Pro His Pro Asp Glu Leu Ala Lys Ser Lys Val Ser
            115                 120                 125

Val Thr Cys Leu Val Lys Asp Phe Tyr Pro Pro Asp Ile Ser Val Glu
    130                 135                 140

Trp Gln Ser Asn Arg Trp Pro Glu Leu Glu Gly Lys Tyr Ser Thr Thr
145                 150                 155                 160

Pro Ala Gln Leu Asp Gly Asp Gly Ser Tyr Phe Leu Tyr Ser Lys Leu
                165                 170                 175

Ser Leu Glu Thr Ser Arg Trp Gln Gln Val Glu Ser Phe Thr Cys Ala
                180                 185                 190

Val Met His Glu Ala Leu His Asn His Phe Thr Lys Thr Asp Ile Ser
                195                 200                 205

Glu Ser Leu Gly Lys
    210

<210> SEQ ID NO 17
<211> LENGTH: 219
<212> TYPE: PRT
<213> ORGANISM: Equus caballus

<400> SEQUENCE: 17

Ala Pro Glu Leu Leu Gly Gly Pro Ser Val Phe Ile Phe Pro Pro Lys
1               5                   10                  15
```

```
Pro Lys Asp Val Leu Met Ile Thr Arg Met Pro Glu Val Thr Cys Leu
            20                  25                  30

Val Val Asp Val Ser His Asp Ser Asp Val Leu Phe Thr Trp Tyr
        35                  40                  45

Val Asp Gly Thr Glu Val Lys Thr Ala Lys Thr Met Pro Asn Glu Glu
50                  55                  60

Gln Asn Asn Ser Thr Tyr Arg Val Val Ser Val Leu Arg Ile Gln His
65                  70                  75                  80

Gln Asp Trp Leu Asn Gly Lys Lys Phe Lys Cys Lys Val Asn Asn Gln
                85                  90                  95

Ala Leu Pro Ala Pro Val Glu Arg Thr Ile Ser Lys Ala Thr Gly Gln
            100                 105                 110

Thr Arg Val Pro Gln Val Tyr Val Leu Ala Pro His Pro Asp Glu Leu
        115                 120                 125

Ser Lys Asn Lys Val Ser Val Thr Cys Leu Val Lys Asp Phe Tyr Pro
130                 135                 140

Thr Asp Ile Thr Val Glu Trp Gln Ser Asn Glu His Pro Glu Pro Glu
145                 150                 155                 160

Gly Lys Tyr Arg Thr Thr Glu Ala Gln Lys Asp Ser Asp Gly Ser Tyr
                165                 170                 175

Phe Leu Tyr Ser Lys Leu Thr Val Glu Lys Asp Arg Trp Gln Gln Gly
            180                 185                 190

Thr Thr Phe Thr Cys Val Val Met His Glu Ala Leu His Asn His Val
        195                 200                 205

Met Gln Lys Asn Ile Ser Lys Asn Pro Gly Lys
210                 215

<210> SEQ ID NO 18
<211> LENGTH: 218
<212> TYPE: PRT
<213> ORGANISM: Equus caballus

<400> SEQUENCE: 18

Glu Cys Leu Gln Val Gly Pro Ser Val Phe Ile Phe Pro Pro Lys Pro
1               5                   10                  15

Lys Asp Val Leu Met Ile Ser Arg Thr Pro Thr Val Thr Cys Val Val
            20                  25                  30

Val Asp Val Gly His Asp Phe Pro Asp Val Gln Phe Asn Trp Tyr Val
        35                  40                  45

Asp Gly Val Glu Thr His Thr Ala Thr Thr Glu Pro Lys Gln Glu Gln
50                  55                  60

Phe Asn Ser Thr Tyr Arg Val Val Ser Val Leu Pro Ile Gln His Lys
65                  70                  75                  80

Asp Trp Leu Ser Gly Lys Glu Phe Lys Cys Lys Val Asn Asn Lys Ala
                85                  90                  95

Leu Pro Ala Pro Val Glu Arg Thr Ile Ser Lys Pro Thr Gly Gln Pro
            100                 105                 110

Arg Glu Pro Gln Val Tyr Val Leu Ala Pro His Arg Asp Glu Leu Ser
        115                 120                 125

Lys Asn Lys Val Ser Val Thr Cys Leu Val Lys Asp Phe Tyr Pro Thr
130                 135                 140

Asp Ile Asp Ile Glu Trp Lys Ser Asn Gly Gln Pro Glu Pro Glu Thr
145                 150                 155                 160

Lys Tyr Ser Thr Thr Pro Ala Gln Leu Asp Ser Asp Gly Ser Tyr Phe
                165                 170                 175
```

```
Leu Tyr Ser Lys Leu Thr Val Glu Thr Asn Arg Trp Gln Gln Gly Thr
            180                 185                 190

Thr Phe Thr Cys Ala Val Met His Glu Ala Leu His Asn His Tyr Thr
        195                 200                 205

Glu Lys Ser Val Ser Lys Ser Pro Gly Lys
    210                 215
```

<210> SEQ ID NO 19
<211> LENGTH: 219
<212> TYPE: PRT
<213> ORGANISM: Equus caballus

<400> SEQUENCE: 19

```
Ala Pro Glu Leu Pro Gly Gly Pro Ser Val Phe Ile Phe Pro Pro Lys
1               5                   10                  15

Pro Lys Asp Val Leu Lys Ile Ser Arg Lys Pro Glu Val Thr Cys Val
            20                  25                  30

Val Val Asp Leu Gly His Asp Asp Pro Asp Val Gln Phe Thr Trp Phe
        35                  40                  45

Val Asp Gly Val Glu Thr His Thr Ala Thr Thr Glu Pro Lys Glu Glu
    50                  55                  60

Gln Phe Asn Ser Thr Tyr Arg Val Val Ser Val Leu Pro Ile Gln His
65                  70                  75                  80

Gln Asp Trp Leu Ser Gly Lys Glu Phe Lys Cys Ser Val Thr Asn Lys
                85                  90                  95

Ala Leu Pro Ala Pro Val Glu Arg Thr Thr Ser Lys Ala Lys Gly Gln
            100                 105                 110

Leu Arg Val Pro Gln Val Tyr Val Leu Ala Pro His Pro Asp Glu Leu
        115                 120                 125

Ala Lys Asn Thr Val Ser Val Thr Cys Leu Val Lys Asp Phe Tyr Pro
    130                 135                 140

Pro Glu Ile Asp Val Glu Trp Gln Ser Asn Glu His Pro Glu Pro Glu
145                 150                 155                 160

Gly Lys Tyr Ser Thr Thr Pro Ala Gln Leu Asn Ser Asp Gly Ser Tyr
                165                 170                 175

Phe Leu Tyr Ser Lys Leu Ser Val Thr Ser Arg Trp Lys Gln Gly Glu
            180                 185                 190

Ser Phe Thr Cys Gly Val Met His Glu Ala Val Glu Asn His Tyr Thr
        195                 200                 205

Gln Lys Asn Val Ser His Ser Pro Gly Lys
    210                 215
```

<210> SEQ ID NO 20
<211> LENGTH: 219
<212> TYPE: PRT
<213> ORGANISM: Equus caballus

<400> SEQUENCE: 20

```
Asp Ser Lys Phe Leu Gly Arg Pro Ser Val Phe Ile Phe Pro Pro Asn
1               5                   10                  15

Pro Lys Asp Thr Leu Met Ile Ser Arg Thr Pro Glu Val Thr Cys Val
            20                  25                  30

Val Val Asp Val Ser Gln Glu Asn Pro Asp Val Lys Phe Asn Trp Tyr
        35                  40                  45

Val Asp Gly Val Glu Ala His Thr Ala Thr Thr Lys Ala Lys Glu Lys
    50                  55                  60
```

Gln Asp Asn Ser Thr Tyr Arg Val Val Ser Val Leu Pro Ile Gln His
 65                  70                  75                  80

Gln Asp Trp Arg Arg Gly Lys Glu Phe Lys Cys Lys Val Asn Asn Arg
                 85                  90                  95

Ala Leu Pro Ala Pro Val Glu Arg Thr Ile Thr Lys Ala Lys Gly Glu
            100                 105                 110

Leu Gln Asp Pro Lys Val Tyr Ile Leu Ala Pro His Arg Glu Glu Val
        115                 120                 125

Thr Lys Asn Thr Val Ser Val Thr Cys Leu Val Lys Asp Phe Tyr Pro
    130                 135                 140

Pro Asp Ile Asn Val Glu Trp Gln Ser Asn Glu Pro Glu Pro Glu
145                 150                 155                 160

Val Lys Tyr Ser Thr Thr Pro Ala Gln Leu Asp Gly Asp Gly Ser Tyr
                165                 170                 175

Phe Leu Tyr Ser Lys Leu Thr Val Glu Thr Asp Arg Trp Gln Gln Gly
            180                 185                 190

Glu Ser Phe Thr Cys Val Val Met His Glu Ala Ile Arg His Thr Tyr
        195                 200                 205

Arg Gln Lys Ser Ile Thr Asn Phe Pro Gly Lys
    210                 215

<210> SEQ ID NO 21
<211> LENGTH: 218
<212> TYPE: PRT
<213> ORGANISM: Equus caballus

<400> SEQUENCE: 21

Glu Cys Leu Ser Val Gly Pro Ser Val Phe Ile Phe Pro Pro Lys Pro
 1               5                  10                  15

Lys Asp Val Leu Met Ile Ser Arg Thr Pro Thr Val Thr Cys Val Val
                 20                  25                  30

Val Asp Val Gly His Asp Phe Pro Asp Val Gln Phe Asn Trp Tyr Val
            35                  40                  45

Asp Gly Val Glu Thr His Thr Ala Thr Thr Glu Pro Lys Gln Glu Gln
 50                  55                  60

Asn Asn Ser Thr Tyr Arg Val Val Ser Ile Leu Ala Ile Gln His Lys
 65                  70                  75                  80

Asp Trp Leu Ser Gly Lys Glu Phe Lys Cys Lys Val Asn Asn Gln Ala
                 85                  90                  95

Leu Pro Ala Pro Val Gln Lys Thr Ile Ser Lys Pro Thr Gly Gln Pro
            100                 105                 110

Arg Glu Pro Gln Val Tyr Val Leu Ala Pro His Arg Asp Glu Leu Ser
        115                 120                 125

Lys Asn Lys Val Ser Val Thr Cys Leu Val Lys Asp Phe Tyr Pro Thr
    130                 135                 140

Asp Ile Asp Ile Glu Trp Lys Ser Asn Gly Gln Pro Glu Pro Glu Thr
145                 150                 155                 160

Lys Tyr Ser Thr Thr Pro Ala Gln Leu Asp Ser Asp Gly Ser Tyr Phe
                165                 170                 175

Leu Tyr Ser Lys Leu Thr Val Glu Thr Asn Arg Trp Gln Gln Gly Thr
            180                 185                 190

Thr Phe Thr Cys Ala Val Met His Glu Ala Leu His Asn His Tyr Thr
        195                 200                 205

Glu Lys Ser Val Ser Lys Ser Pro Gly Lys
    210                 215

<210> SEQ ID NO 22
<211> LENGTH: 218
<212> TYPE: PRT
<213> ORGANISM: Ovis aries

<400> SEQUENCE: 22

```
Pro Glu Leu Pro Gly Gly Pro Ser Val Phe Ile Phe Pro Pro Lys Pro
1               5                   10                  15

Lys Asp Thr Leu Thr Ile Ser Gly Thr Pro Glu Val Thr Cys Val Val
            20                  25                  30

Val Asp Val Gly Gln Asp Pro Glu Val Gln Phe Ser Trp Phe Val
        35                  40                  45

Asp Asn Val Glu Val Arg Thr Ala Arg Thr Lys Pro Arg Glu Glu Gln
    50                  55                  60

Phe Asn Ser Thr Phe Arg Val Val Ser Ala Leu Pro Ile Gln His Gln
65                  70                  75                  80

Asp Trp Thr Gly Gly Lys Glu Phe Lys Cys Lys Val His Asn Glu Ala
                85                  90                  95

Leu Pro Ala Pro Ile Val Arg Thr Ile Ser Arg Thr Lys Gly Gln Ala
            100                 105                 110

Arg Glu Pro Gln Val Tyr Val Leu Ala Pro Pro Gln Glu Glu Leu Ser
        115                 120                 125

Lys Ser Thr Leu Ser Val Thr Cys Leu Val Thr Gly Phe Tyr Pro Asp
    130                 135                 140

Tyr Ile Ala Val Glu Trp Gln Lys Asn Gly Gln Pro Glu Ser Glu Asp
145                 150                 155                 160

Lys Tyr Gly Thr Thr Thr Ser Gln Leu Asp Ala Asp Gly Ser Tyr Phe
                165                 170                 175

Leu Tyr Ser Arg Leu Arg Val Asp Lys Asn Ser Trp Gln Glu Gly Asp
            180                 185                 190

Thr Tyr Ala Cys Val Val Met His Glu Ala Leu His Asn His Tyr Thr
        195                 200                 205

Gln Lys Ser Ile Ser Lys Pro Pro Gly Lys
    210                 215
```

<210> SEQ ID NO 23
<211> LENGTH: 215
<212> TYPE: PRT
<213> ORGANISM: Ovis aries

<400> SEQUENCE: 23

```
Val Ser Arg Pro Ser Val Phe Ile Phe Pro Pro Lys Pro Lys Asp Ser
1               5                   10                  15

Leu Met Ile Thr Gly Thr Pro Glu Val Thr Cys Val Val Val Asp Val
            20                  25                  30

Gly Gln Gly Asp Pro Glu Val Gln Phe Ser Trp Phe Val Asp Asn Val
        35                  40                  45

Glu Val Arg Thr Ala Arg Thr Lys Pro Arg Glu Glu Gln Phe Asn Ser
    50                  55                  60

Thr Phe Arg Val Val Ser Ala Leu Pro Ile Gln His Asp His Trp Thr
65                  70                  75                  80

Gly Gly Lys Glu Phe Lys Cys Lys Val His Ser Lys Gly Leu Pro Ala
                85                  90                  95

Pro Ile Val Arg Thr Ile Ser Arg Ala Lys Gly Gln Ala Arg Glu Pro
```

```
            100             105             110
Gln Val Tyr Val Leu Ala Pro Pro Gln Glu Leu Ser Lys Ser Thr
        115                 120                 125
Leu Ser Val Thr Cys Leu Val Thr Gly Phe Tyr Pro Asp Tyr Ile Ala
        130                 135                 140
Val Glu Trp Gln Arg Ala Arg Gln Pro Glu Ser Glu Asp Lys Tyr Gly
145                 150                 155                 160
Thr Thr Thr Ser Gln Leu Asp Ala Asp Gly Ser Tyr Phe Leu Tyr Ser
                165                 170                 175
Arg Leu Arg Val Asp Lys Ser Ser Trp Gln Arg Gly Asp Thr Tyr Ala
                180                 185                 190
Cys Val Val Met His Glu Ala Leu His Asn His Tyr Thr Gln Lys Ser
                195                 200                 205
Ile Ser Lys Pro Pro Gly Lys
        210                 215
```

<210> SEQ ID NO 24
<211> LENGTH: 218
<212> TYPE: PRT
<213> ORGANISM: Ovis aries

<400> SEQUENCE: 24

```
Pro Glu Pro Leu Gly Gly Leu Ser Val Phe Ile Phe Pro Pro Lys Pro
1               5                   10                  15
Lys Asp Thr Leu Thr Ile Ser Gly Thr Pro Glu Val Thr Cys Val Val
                20                  25                  30
Val Asp Val Gly Gln Asp Asp Pro Glu Val Gln Phe Ser Trp Phe Val
            35                  40                  45
Asp Asn Val Glu Val Arg Thr Ala Arg Thr Lys Pro Arg Glu Glu Gln
50                  55                  60
Phe Asn Ser Thr Phe Arg Val Val Ser Ala Leu Pro Ile Gln His Gln
65                  70                  75                  80
Asp Trp Leu Arg Gly Lys Glu Ile Lys Cys Lys Val His Asn Lys Gly
                85                  90                  95
Leu Pro Ala Pro Ile Val Arg Thr Ile Ser Arg Thr Lys Gly Gln Ala
                100                 105                 110
Arg Glu Pro Gln Val Tyr Val Leu Ala Pro Pro Gln Glu Glu Leu Ser
                115                 120                 125
Lys Ser Thr Leu Ser Val Thr Cys Leu Val Thr Gly Phe Tyr Pro Asp
        130                 135                 140
Tyr Ile Ala Val Glu Trp Gln Lys Asn Gly Gln Pro Glu Ser Glu Asp
145                 150                 155                 160
Lys Tyr Gly Thr Thr Thr Ser Gln Leu Asp Ala Asp Gly Ser Tyr Phe
                165                 170                 175
Leu Tyr Ser Arg Leu Arg Val Asp Lys Asn Ser Trp Gln Glu Gly Asp
                180                 185                 190
Thr Tyr Ala Cys Val Val Met His Glu Ala Leu His Asn His Tyr Thr
                195                 200                 205
Gln Lys Ser Ile Ser Lys Pro Pro Gly Lys
        210                 215
```

<210> SEQ ID NO 25
<211> LENGTH: 218
<212> TYPE: PRT
<213> ORGANISM: Capra hircus

<400> SEQUENCE: 25

```
Pro Glu Leu Pro Gly Gly Pro Ser Val Phe Ile Phe Pro Pro Lys Pro
1               5                   10                  15

Lys Asp Thr Leu Thr Ile Ser Gly Lys Pro Glu Val Thr Cys Val Val
            20                  25                  30

Val Asp Val Gly Gln Asp Asp Pro Glu Val Gln Phe Ser Trp Phe Val
        35                  40                  45

Asp Asn Val Glu Val His Thr Ala Arg Thr Lys Pro Arg Glu Glu Gln
    50                  55                  60

Phe Asn Ser Thr Phe Arg Val Val Ser Ala Leu Pro Ile Gln His Gln
65                  70                  75                  80

Asp Trp Thr Gly Gly Lys Glu Phe Lys Cys Lys Val His Asn Glu Gly
                85                  90                  95

Leu Pro Ala Pro Ile Val Arg Thr Ile Ser Arg Thr Lys Gly Gln Ala
            100                 105                 110

Arg Glu Pro Gln Val Tyr Val Leu Ala Pro Pro Gln Glu Glu Leu Ser
        115                 120                 125

Lys Ser Thr Leu Ser Val Thr Cys Leu Val Thr Gly Phe Tyr Pro Asp
    130                 135                 140

Tyr Ile Ala Val Glu Trp Gln Arg Asn Gly Gln Pro Glu Ser Glu Asp
145                 150                 155                 160

Lys Tyr Gly Thr Thr Ser Gln Leu Asp Ala Asp Gly Ser Tyr Phe
                165                 170                 175

Leu Tyr Ser Arg Leu Arg Val Asn Lys Ser Ser Trp Gln Glu Gly Asp
            180                 185                 190

Thr Tyr Ala Cys Val Val Met His Glu Ala Leu His Asn His Tyr Thr
        195                 200                 205

Gln Lys Ser Ile Ser Lys Pro Pro Gly Lys
    210                 215
```

<210> SEQ ID NO 26
<211> LENGTH: 215
<212> TYPE: PRT
<213> ORGANISM: Capra hircus

<400> SEQUENCE: 26

```
Val Arg Gly Pro Ser Val Phe Ile Phe Pro Pro Lys Pro Lys Asp Ser
1               5                   10                  15

Leu Met Ile Thr Gly Thr Pro Glu Val Thr Cys Val Val Val Asp Val
            20                  25                  30

Gly Gln Asp Asp Pro Glu Val Gln Phe Ser Trp Phe Val Asp Asn Val
        35                  40                  45

Glu Val His Thr Ala Arg Thr Lys Pro Arg Glu Glu Gln Phe Asn Ser
    50                  55                  60

Thr Phe Arg Val Val Ser Ala Leu Pro Ile Gln His Asp His Trp Thr
65                  70                  75                  80

Gly Gly Lys Glu Phe Lys Cys Lys Val Asn Asn Lys Ala Leu Pro Ala
                85                  90                  95

Pro Ile Val Arg Thr Ile Ser Arg Asp Lys Gly Gln Ala Arg Glu Pro
            100                 105                 110

Gln Val Tyr Val Leu Ala Pro Pro Gln Glu Glu Leu Ser Lys Ser Thr
        115                 120                 125

Leu Ser Val Thr Cys Leu Val Thr Gly Phe Tyr Pro Asp Tyr Ile Ala
    130                 135                 140
```

```
Val Glu Trp Gln Arg Ala Arg Gln Pro Glu Ser Glu Asp Lys Tyr Gly
145                 150                 155                 160

Thr Thr Thr Ser Gln Leu Asp Ala Asp Gly Ser Tyr Phe Leu Tyr Ser
                165                 170                 175

Arg Leu Arg Val Asp Lys Ser Ser Trp Gln Glu Gly Asp Thr Tyr Ala
            180                 185                 190

Cys Val Val Met His Glu Ala Leu His Asn His Tyr Thr Gln Lys Ser
        195                 200                 205

Ile Ser Lys Pro Pro Gly Lys
    210                 215

<210> SEQ ID NO 27
<211> LENGTH: 218
<212> TYPE: PRT
<213> ORGANISM: Capra hircus

<400> SEQUENCE: 27

Pro Glu Pro Leu Gly Gly Leu Ser Val Phe Ile Phe Pro Pro Lys Pro
1               5                   10                  15

Lys Asp Thr Leu Thr Ile Ser Gly Thr Pro Glu Val Thr Cys Val Val
                20                  25                  30

Val Asp Val Gly Gln Asp Asp Pro Glu Val Gln Phe Ser Trp Phe Met
            35                  40                  45

Asp Asn Val Glu Val His Thr Ala Arg Thr Thr Pro Arg Glu Glu Gln
    50                  55                  60

Phe Asn Ser Thr Phe Arg Val Val Ser Ala Leu Pro Ile Gln His Lys
65                  70                  75                  80

Asp Trp Leu Gln Gly Lys Glu Phe Lys Cys Lys Val His Asn Glu Gly
                85                  90                  95

Leu Pro Ala Pro Ile Ile Arg Thr Ile Ser Arg Ala Lys Gly Gln Ala
            100                 105                 110

Arg Glu Pro Gln Val Tyr Val Leu Ala Pro Pro Arg Glu Glu Leu Ser
        115                 120                 125

Lys Ser Thr Leu Ser Val Thr Cys Leu Ile Thr Gly Phe Tyr Pro Glu
130                 135                 140

Glu Val Asp Val Glu Trp Gln Arg Asp Gly Gln Pro Glu Ser Glu Asp
145                 150                 155                 160

Lys Tyr His Thr Ala Pro Pro Gln Leu Asp Ala Asp Gly Ser Tyr Phe
                165                 170                 175

Leu Tyr Ser Arg Leu Arg Val Asn Lys Ser Ser Trp Gln Glu Gly Asp
            180                 185                 190

Thr Tyr Thr Cys Ala Val Met His Glu Ala Leu Arg Asn His Tyr Lys
        195                 200                 205

Glu Lys Ser Ile Ser Lys Ser Pro Gly Lys
    210                 215

<210> SEQ ID NO 28
<211> LENGTH: 15
<212> TYPE: PRT
<213> ORGANISM: Artificial Sequence
<220> FEATURE:
<223> OTHER INFORMATION: Avi-tag

<400> SEQUENCE: 28

Gly Leu Asn Asp Ile Phe Glu Ala Gln Lys Ile Glu Trp His Glu
1               5                   10                  15
```

```
<210> SEQ ID NO 29
<211> LENGTH: 8
<212> TYPE: PRT
<213> ORGANISM: Artificial Sequence
<220> FEATURE:
<223> OTHER INFORMATION: Flag tag

<400> SEQUENCE: 29

Asp Tyr Lys Asp Asp Asp Asp Lys
1               5

<210> SEQ ID NO 30
<211> LENGTH: 202
<212> TYPE: PRT
<213> ORGANISM: Sus scrofa

<400> SEQUENCE: 30

Val Phe Ile Phe Pro Pro Lys Pro Lys Asp Thr Leu Met Ile Ser Gln
1               5                   10                  15

Thr Pro Glu Val Thr Cys Val Val Val Asp Val Ser Lys Glu His Ala
            20                  25                  30

Glu Val Gln Phe Ser Trp Tyr Val Asp Gly Val Glu Val His Thr Ala
        35                  40                  45

Glu Thr Arg Pro Lys Glu Glu Gln Phe Asn Ser Thr Tyr Arg Val Val
    50                  55                  60

Ser Val Leu Pro Ile Gln His Gln Asp Trp Leu Lys Gly Lys Glu Phe
65                  70                  75                  80

Lys Cys Lys Val Asn Asn Val Asp Leu Pro Ala Pro Ile Thr Arg Thr
                85                  90                  95

Ile Ser Lys Ala Ile Gly Gln Ser Arg Glu Pro Gln Val Tyr Thr Leu
            100                 105                 110

Pro Pro Pro Ala Glu Glu Leu Ser Arg Ser Lys Val Thr Val Thr Cys
        115                 120                 125

Leu Val Ile Gly Phe Tyr Pro Pro Asp Ile His Val Glu Trp Lys Ser
    130                 135                 140

Asn Gly Gln Pro Glu Pro Glu Gly Asn Tyr Arg Thr Thr Pro Pro Gln
145                 150                 155                 160

Gln Asp Val Asp Gly Thr Phe Phe Leu Tyr Ser Lys Leu Ala Val Asp
                165                 170                 175

Lys Ala Arg Trp Asp His Gly Thr Phe Glu Cys Ala Val Met His
            180                 185                 190

Glu Ala Leu His Asn His Tyr Thr Gln Lys
        195                 200

<210> SEQ ID NO 31
<211> LENGTH: 202
<212> TYPE: PRT
<213> ORGANISM: Ovis aries

<400> SEQUENCE: 31

Val Phe Ile Phe Pro Pro Lys Pro Lys Asp Thr Leu Thr Ile Ser Gly
1               5                   10                  15

Thr Pro Glu Val Thr Cys Val Val Val Asp Val Gly Gln Asp Asp Pro
            20                  25                  30

Glu Val Gln Phe Ser Trp Phe Val Asp Asn Val Glu Val Arg Thr Ala
        35                  40                  45

Arg Thr Lys Pro Arg Glu Glu Gln Phe Asn Ser Thr Phe Arg Val Val
    50                  55                  60
```

```
Ser Ala Leu Pro Ile Gln His Gln Asp Trp Thr Gly Gly Lys Glu Phe
 65                  70                  75                  80

Lys Cys Lys Val His Asn Glu Ala Leu Pro Ala Pro Ile Val Arg Thr
                 85                  90                  95

Ile Ser Arg Thr Lys Gly Gln Ala Arg Glu Pro Gln Val Tyr Val Leu
            100                 105                 110

Ala Pro Pro Gln Glu Glu Leu Ser Lys Ser Thr Leu Ser Val Thr Cys
        115                 120                 125

Leu Val Thr Gly Phe Tyr Pro Asp Tyr Ile Ala Val Glu Trp Gln Lys
    130                 135                 140

Asn Gly Gln Pro Glu Ser Glu Asp Lys Tyr Gly Thr Thr Thr Ser Gln
145                 150                 155                 160

Leu Asp Ala Asp Gly Ser Tyr Phe Leu Tyr Ser Arg Leu Arg Val Asp
                165                 170                 175

Lys Ser Asn Trp Gln Glu Gly Asp Thr Tyr Ala Cys Val Val Met His
                180                 185                 190

Glu Ala Leu His Asn His Tyr Thr Gln Lys
                195                 200

<210> SEQ ID NO 32
<211> LENGTH: 202
<212> TYPE: PRT
<213> ORGANISM: Bos taurus

<400> SEQUENCE: 32

Val Phe Ile Phe Pro Pro Lys Pro Lys Asp Thr Leu Thr Ile Ser Gly
 1               5                  10                  15

Thr Pro Glu Val Thr Cys Val Val Asp Val Gly His Asp Asp Pro
                 20                  25                  30

Glu Val Lys Phe Ser Trp Phe Val Asp Asn Val Glu Val Asn Thr Ala
             35                  40                  45

Thr Thr Lys Pro Arg Glu Glu Gln Phe Asn Ser Thr Tyr Arg Val Val
         50                  55                  60

Ser Ala Leu Arg Ile Gln His Gln Asp Trp Thr Gly Gly Lys Glu Phe
 65                  70                  75                  80

Lys Cys Lys Val His Asn Glu Gly Leu Pro Ala Pro Ile Val Arg Thr
                 85                  90                  95

Ile Ser Arg Thr Lys Gly Pro Ala Arg Glu Pro Gln Val Tyr Val Leu
            100                 105                 110

Ala Pro Pro Gln Glu Glu Leu Ser Lys Ser Thr Val Ser Leu Thr Cys
        115                 120                 125

Met Val Thr Ser Phe Tyr Pro Asp Tyr Ile Ala Val Glu Trp Gln Arg
    130                 135                 140

Asn Gly Gln Pro Glu Ser Glu Asp Lys Tyr Gly Thr Thr Pro Pro Gln
145                 150                 155                 160

Leu Asp Ala Asp Ser Ser Tyr Phe Leu Tyr Ser Lys Leu Arg Val Asp
                165                 170                 175

Arg Asn Ser Trp Gln Glu Gly Asp Thr Tyr Thr Cys Val Val Met His
                180                 185                 190

Glu Ala Leu His Asn His Tyr Thr Gln Lys
                195                 200

<210> SEQ ID NO 33
<211> LENGTH: 202
<212> TYPE: PRT
<213> ORGANISM: Equus caballus
```

<400> SEQUENCE: 33

```
Val Phe Ile Phe Pro Pro Asn Pro Lys Asp Thr Leu Met Ile Thr Arg
1               5                   10                  15

Thr Pro Glu Val Thr Cys Val Val Asp Val Ser Gln Glu Asn Pro
            20                  25                  30

Asp Val Lys Phe Asn Trp Tyr Met Asp Gly Val Glu Val Arg Thr Ala
            35                  40                  45

Thr Thr Arg Pro Lys Glu Glu Gln Phe Asn Ser Thr Tyr Arg Val Val
50                  55                  60

Ser Val Leu Arg Ile Gln His Gln Asp Trp Leu Ser Gly Lys Glu Phe
65                  70                  75                  80

Lys Cys Lys Val Asn Asn Gln Ala Leu Pro Gln Pro Ile Glu Arg Thr
                85                  90                  95

Ile Thr Lys Thr Lys Gly Arg Ser Gln Glu Pro Gln Val Tyr Val Leu
            100                 105                 110

Ala Pro His Pro Asp Glu Leu Ser Lys Ser Lys Val Ser Val Thr Cys
            115                 120                 125

Leu Val Lys Asp Phe Tyr Pro Pro Glu Ile Asn Ile Glu Trp Gln Ser
130                 135                 140

Asn Gly Gln Pro Glu Leu Glu Thr Lys Tyr Ser Thr Thr Gln Ala Gln
145                 150                 155                 160

Gln Asp Ser Asp Gly Ser Tyr Phe Leu Tyr Ser Lys Leu Ser Val Asp
                165                 170                 175

Arg Asn Arg Trp Gln Gln Gly Thr Thr Phe Thr Cys Gly Val Met His
            180                 185                 190

Glu Ala Leu His Asn His Tyr Thr Gln Lys
            195                 200
```

<210> SEQ ID NO 34
<211> LENGTH: 202
<212> TYPE: PRT
<213> ORGANISM: Felis catus

<400> SEQUENCE: 34

```
Ile Phe Ile Phe Pro Pro Lys Pro Lys Asp Thr Leu Ser Ile Ser Arg
1               5                   10                  15

Thr Pro Glu Val Thr Cys Leu Val Val Asp Leu Gly Pro Asp Asp Ser
            20                  25                  30

Asp Val Gln Ile Thr Trp Phe Val Asp Asn Thr Gln Val Tyr Thr Ala
            35                  40                  45

Lys Thr Ser Pro Arg Glu Glu Gln Phe Asn Ser Thr Tyr Arg Val Val
50                  55                  60

Ser Val Leu Pro Ile Leu His Gln Asp Trp Leu Lys Gly Lys Glu Phe
65                  70                  75                  80

Lys Cys Lys Val Asn Ser Lys Ser Leu Pro Ser Pro Ile Glu Arg Thr
                85                  90                  95

Ile Ser Lys Ala Lys Gly Gln Pro His Glu Pro Gln Val Tyr Val Leu
            100                 105                 110

Pro Pro Ala Gln Glu Glu Leu Ser Arg Asn Lys Val Ser Val Thr Cys
            115                 120                 125

Leu Ile Lys Ser Phe His Pro Pro Asp Ile Ala Val Glu Trp Glu Ile
            130                 135                 140

Thr Gly Gln Pro Glu Pro Glu Asn Asn Tyr Arg Thr Thr Pro Pro Gln
145                 150                 155                 160
```

```
Leu Asp Ser Asp Gly Thr Tyr Phe Val Tyr Ser Lys Leu Ser Val Asp
            165                 170                 175

Arg Ser His Trp Gln Arg Gly Asn Thr Tyr Thr Cys Ser Val Ser His
            180                 185                 190

Glu Ala Leu His Ser His Thr Gln Lys
            195                 200

<210> SEQ ID NO 35
<211> LENGTH: 202
<212> TYPE: PRT
<213> ORGANISM: Canis familiaris

<400> SEQUENCE: 35

Val Phe Ile Phe Pro Pro Lys Pro Lys Asp Thr Leu Ile Ala Arg
1               5                   10                  15

Thr Pro Glu Val Thr Cys Val Val Asp Leu Asp Pro Glu Asp Pro
            20                  25                  30

Glu Val Gln Ile Ser Trp Phe Val Asp Gly Lys Gln Met Gln Thr Ala
            35                  40                  45

Lys Thr Gln Pro Arg Glu Glu Gln Phe Asn Gly Thr Tyr Arg Val Val
50                  55                  60

Ser Val Leu Pro Ile Gly His Gln Asp Trp Leu Lys Gly Lys Gln Phe
65                  70                  75                  80

Thr Cys Lys Val Asn Asn Lys Ala Leu Pro Ser Pro Ile Glu Arg Thr
                85                  90                  95

Ile Ser Lys Ala Arg Gly Gln Ala His Gln Pro Ser Val Tyr Val Leu
            100                 105                 110

Pro Pro Ser Arg Glu Glu Leu Ser Lys Asn Thr Val Ser Leu Thr Cys
            115                 120                 125

Leu Ile Lys Asp Phe Phe Pro Pro Asp Ile Asp Val Glu Trp Gln Ser
130                 135                 140

Asn Gly Gln Gln Glu Pro Glu Ser Lys Tyr Arg Thr Thr Pro Pro Gln
145                 150                 155                 160

Leu Asp Glu Asp Gly Ser Tyr Phe Leu Tyr Ser Lys Leu Ser Val Asp
            165                 170                 175

Lys Ser Arg Trp Gln Arg Gly Asp Thr Phe Ile Cys Ala Val Met His
            180                 185                 190

Glu Ala Leu His Asn His Tyr Thr Gln Glu
            195                 200

<210> SEQ ID NO 36
<211> LENGTH: 199
<212> TYPE: PRT
<213> ORGANISM: Homo sapiens

<400> SEQUENCE: 36

Val Phe Leu Phe Pro Pro Lys Pro Lys Asp Thr Leu Met Ile Ser Arg
1               5                   10                  15

Thr Pro Glu Val Thr Cys Val Val Asp Val Ser His Glu Asp Pro
            20                  25                  30

Glu Val Lys Phe Asn Trp Tyr Val Asp Gly Val Glu Val His Asn Ala
            35                  40                  45

Lys Thr Lys Pro Arg Glu Glu Gln Tyr Asn Ser Thr Tyr Arg Val Val
50                  55                  60

Ser Val Leu Thr Val Leu His Gln Asp Trp Leu Asn Gly Lys Glu Tyr
65                  70                  75                  80
```

```
Lys Cys Lys Val Ser Asn Lys Ala Leu Pro Ala Pro Ile Glu Lys Thr
            85                  90                  95

Ile Ser Lys Ala Gly Gln Pro Arg Glu Pro Gln Val Tyr Thr Leu Pro
            100                 105                 110

Pro Ser Arg Glu Glu Met Thr Lys Asn Gln Val Ser Leu Thr Cys Leu
            115                 120                 125

Val Lys Gly Phe Tyr Pro Ser Asp Ile Ala Val Glu Trp Glu Ser Asn
    130                 135                 140

Gly Gln Pro Glu Asn Asn Tyr Lys Thr Thr Pro Pro Val Leu Asp Ser
145                 150                 155                 160

Asp Gly Ser Phe Phe Leu Tyr Ser Lys Leu Thr Val Asp Lys Ser Arg
                165                 170                 175

Trp Gln Gln Gly Asn Val Phe Ser Cys Ser Val Met His Glu Ala Leu
                180                 185                 190

His Asn His Tyr Thr Gln Lys
            195
```